US009943604B2

(12) United States Patent
Seth et al.

(10) Patent No.: US 9,943,604 B2
(45) Date of Patent: Apr. 17, 2018

(54) TARGETED THERAPEUTIC NUCLEOSIDES AND THEIR USE

(71) Applicant: Ionis Pharmaceuticals, Inc., Carlsbad, CA (US)

(72) Inventors: Punit P. Seth, Carlsbad, CA (US); Thazha P. Prakash, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/021,995

(22) PCT Filed: Sep. 19, 2014

(86) PCT No.: PCT/US2014/056630
§ 371 (c)(1),
(2) Date: Mar. 15, 2016

(87) PCT Pub. No.: WO2015/042447
PCT Pub. Date: Mar. 26, 2015

(65) Prior Publication Data
US 2016/0354476 A1 Dec. 8, 2016

Related U.S. Application Data

(60) Provisional application No. 61/880,813, filed on Sep. 20, 2013.

(51) Int. Cl.
| | | |
|---|---|---|
| *A01N 43/04* | (2006.01) |
| *A61K 31/70* | (2006.01) |
| *A61K 47/48* | (2006.01) |
| *C07H 19/10* | (2006.01) |
| *C07H 19/20* | (2006.01) |
| *A61K 45/06* | (2006.01) |
| *A61K 31/7072* | (2006.01) |
| *A61K 31/711* | (2006.01) |
| *A61K 31/7115* | (2006.01) |
| *A61K 31/712* | (2006.01) |
| *A61K 31/7125* | (2006.01) |
| *A61K 31/713* | (2006.01) |
| *C12N 15/11* | (2006.01) |
| *A61K 31/7052* | (2006.01) |
| *A61K 31/7068* | (2006.01) |
| *A61K 31/7008* | (2006.01) |
| *A61K 31/706* | (2006.01) |
| *A61K 31/7064* | (2006.01) |

(52) U.S. Cl.
CPC .... *A61K 47/48092* (2013.01); *A61K 31/7072* (2013.01); *A61K 31/711* (2013.01); *A61K 31/712* (2013.01); *A61K 31/713* (2013.01); *A61K 31/7115* (2013.01); *A61K 31/7125* (2013.01); *A61K 45/06* (2013.01); *C07H 19/10* (2013.01); *C07H 19/20* (2013.01); *C12N 15/111* (2013.01); *A61K 31/706* (2013.01); *A61K 31/7008* (2013.01); *A61K 31/7052* (2013.01); *A61K 31/7064* (2013.01); *A61K 31/7068* (2013.01); *C12N 2310/11* (2013.01); *C12N 2310/113* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |

(Continued)

FOREIGN PATENT DOCUMENTS

| | | |
|---|---|---|
| WO | WO 1994/014226 | 6/1994 |
| WO | WO 1997/020563 | 6/1997 |
| WO | WO 2002/043771 | 6/2002 |
| WO | WO 2004/063208 | 7/2004 |
| WO | WO 2004/106356 | 12/2004 |
| WO | WO 2005/021570 | 3/2005 |
| WO | WO 2007/090071 | 8/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |

(Continued)

OTHER PUBLICATIONS

Bobeck et al. Antiviral Therapy (2010), vol. 15, p. 935-950.*

(Continued)

*Primary Examiner* — Patrick T Lewis
(74) *Attorney, Agent, or Firm* — Knobbe, Martens, Olson & Bear, LLP

(57) ABSTRACT

Provided herein are compounds comprising one or more therapeutic nucleosides and one or more targeting groups. In certain embodiments, the compounds further comprise one or more oligonucleotides. In certain embodiments, a targeting group comprises one or more N-Acetylgalactosamine.

16 Claims, No Drawings

(56) References Cited

U.S. PATENT DOCUMENTS

| | | | |
|---|---|---|---|
| 5,750,692 A | 5/1998 | Cook et al. | |
| 5,763,588 A | 6/1998 | Matteucci et al. | |
| 5,830,653 A | 11/1998 | Froehler et al. | |
| 5,994,517 A | 11/1999 | Ts'o et al. | |
| 6,268,490 B1 | 7/2001 | Imanishi et al. | |
| 6,300,319 B1 | 10/2001 | Manoharan | |
| 6,525,191 B1 | 2/2003 | Ramasamy | |
| 6,660,720 B2 | 12/2003 | Manoharan et al. | |
| 6,670,461 B1 | 12/2003 | Wengel et al. | |
| 6,770,748 B2 | 8/2004 | Imanishi et al. | |
| 6,777,395 B2 | 8/2004 | Bhat et al. | |
| 6,794,499 B2 | 9/2004 | Wengel et al. | |
| 6,906,182 B2 | 6/2005 | Ts'o et al. | |
| 7,034,133 B2 | 4/2006 | Wengel et al. | |
| 7,053,207 B2 | 5/2006 | Wengel | |
| 7,105,499 B2 | 9/2006 | Carroll et al. | |
| 7,125,855 B2 | 10/2006 | Bhat et al. | |
| 7,202,224 B2 | 4/2007 | Eldrup et al. | |
| 7,262,177 B2 | 8/2007 | Ts'o et al. | |
| 7,399,845 B2 | 7/2008 | Seth et al. | |
| 7,427,672 B2 | 9/2008 | Imanishi et al. | |
| 7,491,805 B2 | 2/2009 | Vargeese et al. | |
| 7,569,686 B1 | 8/2009 | Bhat et al. | |
| 7,683,036 B2 | 3/2010 | Esau et al. | |
| 7,723,509 B2 | 5/2010 | Manoharan et al. | |
| 7,964,580 B2 | 6/2011 | Sofia et al. | |
| 8,106,022 B2 | 1/2012 | Manoharan et al. | |
| 8,466,159 B2 | 6/2013 | Bernstein et al. | |
| 8,828,956 B2* | 9/2014 | Manoharan | A61K 47/48092 514/42 |
| 2003/0119724 A1 | 6/2003 | Ts'o et al. | |
| 2004/0171570 A1 | 9/2004 | Allerson et al. | |
| 2005/0130923 A1 | 6/2005 | Bhat et al. | |
| 2006/0148740 A1 | 7/2006 | Platenburg | |
| 2006/0183886 A1 | 8/2006 | Tso et al. | |
| 2007/0287831 A1 | 12/2007 | Seth et al. | |
| 2008/0039618 A1 | 2/2008 | Allerson et al. | |
| 2011/0123520 A1 | 5/2011 | Manoharan et al. | |
| 2012/0129154 A1 | 5/2012 | Schofield et al. | |
| 2013/0245094 A1* | 9/2013 | Lee | C12N 15/1068 514/44 A |

FOREIGN PATENT DOCUMENTS

| | | |
|---|---|---|
| WO | WO 2009/067647 | 5/2009 |
| WO | WO 2009/082607 | 7/2009 |
| WO | WO 2009/100320 | 8/2009 |
| WO | WO 2009/143369 | 11/2009 |
| WO | WO 2010/036698 | 4/2010 |
| WO | WO 2010/077578 | 7/2010 |
| WO | WO 2010/101951 | 9/2010 |
| WO | WO 2011/017521 | 2/2011 |
| WO | WO 2011/047312 | 4/2011 |
| WO | WO 2011/115818 | 9/2011 |
| WO | WO 2012/037254 | 3/2012 |
| WO | WO 2012/145674 | 10/2012 |
| WO | WO 2012/145697 | 10/2012 |
| WO | WO 2013/033230 | 3/2013 |
| WO | WO 2014/076195 | 5/2014 |
| WO | WO 2014/179620 | 6/2014 |

OTHER PUBLICATIONS

Albaek et al., Journal of Analogues of a Locked Nucleic Acid with Three-Carbon 2', 4'-Linkages: Synthesis by Ring-Closing Metathesis and Influence on Nucleic Acid Duplex Stability and Structure Org. Chem., (2006) 71, 7731-7740.

Biessen et al., "Novel Hepatotrophic Prodrugs of the antiviral nucleoside 9-(2-phoshonylmethoxyethyl) adenine with improved pharmacokinetics and antiviral activity" (2000) FASEB.

Biessen et al., "Synthesis of Cluster Galactosides with High Affinity for the Hepatic Asialoglycoprotein Receptor" Journal of Med. Chemistry (1995) 38:1538-1546.

Biessen et al., "The Cholesterol Derivative of a Triantennary Galactoside with High Affinity for the Hepatic Asialoglycoprotein Receptor: a Potent Cholesterol Lowering Agent" Journal of Med. Chemistry (1995) 38:1846-1852.

Braasch et al., "Locked nucleic acid (LNA): fine-tuning the recognition of DNA and RNA" Chem. Biol. (2001) 8:1-7.

Chen et al., "The Determination of melatonin in health-caring medicine for specific purposes by high performance liquid chromatography-mass spectrometry" Chinese Chemical Letters, (1998) 9(5), 451-453.

Cho et al., "Efficient synthesis of nucleoside aryloxy phosphoramidate prodrugs utilizing benzyloxycarbonyl protection" Tetrahedron (2011) 67:5487-5493.

Coats et al., "Chutes and Ladders in Hepatitis C nucleoside drug development." Antiviral Research (2014) 119-147.

Duff et al., "Organ and Cell-Specific Antisense Conjugates" Methods Enzymology(2000) 313: 297.

Dupouy et al., "Watson-Crick base-pairing properties of nucleic acid analogues with stereocontrolled alpha and beta torsion angles (alpha, beta-D-CNAs)" Angew. Chemie International Ed., (2006)45, 3623-3627.

Elayadi et al., "Application of PNA and LNA oligomers to chemotherapy" Current Opinions in Invenstigational Drugs (2001) 2:558-561.

Englisch et al., "Chemically Modified Oligonucleotides as Probes and Inhibitors" Angewandte Chemie, International Edition, (1991) 30, 613.

Esau et al., "miR-122 regulation of lipid metabolism revealed by in vivo antisense targeting." Cell Metabolism (2006) 3: 87-98.

Freier et al., Nucleic Acids Research, 1997, 25(22), 4429-4443.

Fried et al., "HBeAg and hepatitis B virus DNA as outcome predictors during therapy with peginterferon alfa-2a for HBeAg-positive chronic hepatitis B" Hepatology(2008) 4(2):428-34.

Frieden et al., "Expanding the design horizon of antisense oligonucleotides with alpha-L-LNA" Nucleic Acids Research (2003) 21:6365-6372.

Fung et al., "Nucleoside/nucleotide analogues in the treatment of chronic hepatitis B" Journal of Antimicrobial Chemotherapy (2011) 66: 2715-2725.

Ganem et al., "Hepatitus B virus infection-natural history and clinical consequences" New England Journal of Medicine(2004) 350: 1118-1129.

Geary et al. "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. (2009) 78(3): 284-91.

Hanessian et al., "Synthesis of chemically and functionally diverse scaffolds from pentaerythritol" Canadian Journal of Chemistry, (1996) 74(9), 1731-1737.

Horn et al., "Chemical synthesis and characterization of branched oligodeoxyribonucleotides (bDNA) for use as signal amplfiers in nucleic acid quantification assays" Nucleic Acids Research ( 1997) 25, 4842-4849.

Jiang et al., "The design and synthesis of highly branched and spherically symmetric fluorinated oils and amphiles" Tetrahedron, (2007)63(19): 3982-3988.

Jin et al., "Use of a-N, N-bis [Carboxymethyl]lysine-Modified Peroxidase in Immunoassays" Analytical Biochemistry (1995) 229, 54-60.

Jordheim et al., "Advances in the development of nucleoside and nucleotide analogues for cancer and viral diseases" Nature Reviews Drug Discovery (2013)12, 447-464.

Kim et al., "Synthesis of Novel Phosphoramidite Building Blocks from Pentaerythritol" Synlett, (2003) 12: 1838-1840.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroschwitz "Polynucleotides"The Concise Encyclopedia of Polymer Science and Engineering, Ed., John Wiley & Sons, (1990) 858-859.

(56) References Cited

OTHER PUBLICATIONS

Kumar et al., "The First Analogues of LNA (Locked Nucleic Acids): Phosphorothioate-LNA and 2'-Thio-LNA" Bioorg. Med. Chem. Lett. (1998) 8:2219-2222.
Lee et al., "New and more efficient multivalent glyco-ligands for asialoglycoprotein receptor of mammalian hepatocytes" Bioorganic & Medicinal Chemistry (2011) 19:2494-2500.
Leumann, "DNA analogues: From supramolecular principles to biological properties" *Bioorganic & Medicinal Chemistry* (2002) 10:841-854.
Liang et al., "Hepatitis B e Antigen—the dangerous endgame of hepatitis B" New England Journal of Medicine (2002) 347: 208-210.
Machida et al., "Bivalent inhibitors for disrupting protein surface-substrate interactions and for dual inhibition of protein prenyltransferases" Journal of American Chem. Society (2011) 133, 958-963.
Maier et al., "Synthesis of Antisense Oligonucleotides Conjugated to a Multivalent Carbohydrate Cluster for Cellular Targeting," Bioconjugate Chemistry, 2003, (14): 18-29.
McGuigan et al., "Phosphorodiamidates as a Promising New Phosphate Prodrug Motif for Antiviral Drig Discovery: Application to Anti-HCV Agents" Journal of Medicinal Chemistry (2011) 8632-8645.
Michailidis et al., "Antiviral therapies: focus on Hepatitis B reverse transcriptase" International Journal of Biochem Cell Biology (2012) 4(7): 1060-1071.
Moucari et al., "Early serum HBsAg drop: a strong predictor of sustained virological response to pegylated interferon alfa-2a in HBeAg-negative patients" (2009) Hepatology 49:1151.
Orum et al., "Locked nucleic acids: A promising molecular family for gene-function analysis and antisense drug development" Current Opinion of Mol. Ther. (2001) 3:239-243.
Pawlotsky "Treatment of Chronic Hepatitis C: Current and Future" Current Topics in Microbiology and Immunology (2013) 321-342.
Pockros "Nucleoside/Nucleotide Analogue Polymerase Inhibitors in Development" Clinical Liver Disease ( 2013)105-110.
Rensen et al., "Design and synthesis of novel N-Acetylgalactosamine-Terminated glycolipids for targeting of lipoproteins to the hepatic asialoglycoprotein receptor" Journal of Med. Chem., (2004) 47, 5798-5808.
Rensen et al., "Determination of the Upper Size Limit for Uptake and Processing of Ligands by the Asialoglycoprotein Receptor on Hepatocytes in Vitro and in Vivo" Journal of Biol. Chem. (2001) 276(40):37577-37584.
Rouchaud et al., "A new and efficient synthesis of derivatives of octahydro-4H-pyrrolo-[1,2-c]pyrido[1',2'-a]imidazole" European Journal of Organic Chemistry, (2011) 12, 2346-2353.
Sambrook et al., "Molecular Cloning, A laboratory Manual," 2nd Edition, Cold Spring Harbor Laboratory Press, 1989.
Sanghvi "Synthesis of Nonionic Oligonucleotide Analogues" Carbohydrate Modifications in Antisense Research ACS Symposium Series (1994) 580: 40-65.
Sanghvi et al., "Heterocyclic Base Modifications in Nucleic Acids and Their Applications in Antisense Oligonucleotides" Antisense Research and Applications (1993) pp. 273-288.
Seeger et al., "Hepatisis B virus Biology" Microbiology and Mol Biology Reviews (2000)64: 51-68.
Shchepinov et al., "Oligonucleotide dendrimers: stable nano-structures" Nucleic Acids Research, (1999) 27, 3035-3041.
Shchepinov et al., "Oligonucleotide dendrimers: synthesis and use as polylabelled DNA probes" Nucleic Acids Research, (1997) 25(22), 4447-4454.
Singh et al., "LNA (locked nucleic acids): synthesis and high-affinity nucleic acid recognition" Chem. Communication, (1998) 4, 455-456.
Singh et al., "Synthesis of 2'-Amino-LNA: A Novel Conformationally Restricted High-Affinity Oligonucleotide Analogue with a Handle" Journal of Organic Chem., (1998) 63, 10035-10039.
Rouchaud et al., "A new and efficient synthesis of derivatives of octahydro-4H-pyrrolo-[1,2-c]pytido[1',2'-a]imidazole" European Journal of Organic Chemistry, (2011) 12, 2346-2353.
Sliedregt et al., "Design and Synthesis of Novel Amphiphilic Dendritic Galactosides for Selective Targeting of Liposomes to the Hepatic Asialoglycoprotein Receptor" Journal of Med. Chem. (1999) 42:609-618.
Sofia et al., "Discovery of a beta-d-2'-deoxy-2'-alpha-fluoro-2'-beta-C-methyluridine nucleotide prodrug (PSI-7977) for the treatment of Hepatitis C virus." Journal of Medicinal Chemistry (2010) vol. 53 No. 19: 7202-18; PubChem CID 73425384.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Tober et al., "Self-Metathesis of polyol allyl ethers towards carbohydrate-based oligohydroxy derivatives" European Journal of Organic Chemistry, (2013) 3, 566-577.
Valentijn et al., "Solid-phase synthesis of lysine based cluster galactosides with high affinity for the Asialoglycoprotein Receptor" Tetrahedron, (1997) 53(2), 759-770.
Valette et al., "Decomposition Pathways and in Vitro HIV Inhibitory Effects of IsoddA Pronucleotides: Toward a Rational Approach for Intracellular Delivery of Nucleoside 5'-Monophosphates" Journal of Medicinal Chemistry (1996) 39:1981-1990.
Vincent et al., "Mechanisms of single-stranded phosphorothioate modified antisense oligonucleotide accumulation in hepatocytes." Nucleic Acids Res. (2011) 39(11): 4795-807.
Wahlestedt et al., "Potent and nontoxic antisense oligonucleotides containing locked nucleic acids" PNAS (2000) 97:5633-5638.
Weber et al., "Design and Synthesis of P2-P1 Linked Macrocyclic Human Renin Inhibitors" Journal of Med. Chemistry, (1991) 34, 2692.
Zhou et al., "Fine Tuning of Electrostatics around the Internucleotidic Phosphate through Incorporation of Modified 2', 4'-Carbocyclic-LNAs and -ENAs Leads to Significant Modulation of Antisense Properties" Journal of Organic Chemistry, (2009) 74, 118-134.
International Search Report for Application PCT/US14/56630 dated Dec. 24, 2014.

* cited by examiner

TARGETED THERAPEUTIC NUCLEOSIDES AND THEIR USE

SEQUENCE LISTING

The present application is being filed along with a Sequence Listing in electronic format. The Sequence Listing is provided as a file entitled CORE0119USASEQ_ST25.txt, created on Mar. 14, 2016, which is 8 Kb in size. The information in the electronic format of the sequence listing is incorporated herein by reference in its entirety.

BACKGROUND OF THE INVENTION

Certain therapeutic nucleosides are known in the art. For example, certain modified nucleosides possess antiviral activity. For example, certain such nucleosides inhibit viral polymerases, such as Hepatitis C Virus (HCV) NS5b polymerase. See e.g., U.S. Pat. No. 7,105,499.

In certain instances, certain chemical moieties, when attached to a parent compound, enhance entry of such parent compound into a cell. In certain such instances, entry is particularly increased for a particular cell type. For example, it has been reported that N-acetyl galactoseamine (GalNAc), when attached through certain linkers to an siRNA compound can increase uptake of such siRNA compound into liver cells.

Antisense compounds have been described previously. The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC).

Chemical modifications increasing potency of therapeutic nucleosides and/or antisense compounds allow administration of lower doses, which reduces the potential for toxicity, as well as decreasing overall cost of therapy.

SUMMARY OF THE INVENTION

In certain embodiments, the present disclosure provides therapeutic agents comprising at least one therapeutic nucleoside and at least one targeting group. Certain such therapeutic agents also comprise one or more oligomeric compound, such as an antisense compound. Certain therapeutic agents are represented by the formula:

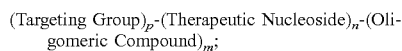
(Targeting Group)$_p$-(Therapeutic Nucleoside)$_n$-(Oligomeric Compound)$_m$;

wherein
p is 0-10;
n is from 1-50; and
m is 0 or 1;
provided that if n is 1 and m is 0, then p is not 0.
In such embodiments, the targeting group may be attached to any position of at least one target nucleoside. Such attachment may be through a cleavable moiety, such as a cleavable bond or a cleavable nucleoside. In embodiments comprising more than one therapeutic nucleoside (i.e., where n is >1) such therapeutic nucleosides may be linked together by cleavable moieties, such as cleavable bonds or cleavable nucleosides. The therapeutic nucleoside may attach to either the 3' or the 5' end of the oligomeric compound and may be attached by a cleavable moiety, such as a cleavable bond or cleavable nucleoside. In certain embodiments, the oligomeric compound is an antisense compound.

Certain therapeutic agents are represented by the formula:

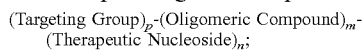
(Targeting Group)$_p$-(Oligomeric Compound)$_m$-(Therapeutic Nucleoside)$_n$;

wherein
p is 0-10;
n is from 1-50; and
m is 0 or 1;
provided that if n is 1 and m is 0, then p is not 0.
In such embodiments, the targeting group may be attached to either the 3' or the 5' end of the oligomeric compound and may be attached by a cleavable moiety, such as a cleavable bond or cleavable nucleoside. The oligomeric compound may attach to any position of at least one therapeutic nucleoside. Such attachment may comprise a cleavable moiety, such as a cleavable bond or cleavable nucleoside. In embodiments comprising more than one therapeutic nucleoside (where n is >1) such therapeutic nucleosides may be linked together by cleavable moieties, such as cleavable bonds or cleavable nucleosides. In certain embodiments, the oligomeric compound is an antisense compound.

In certain embodiments, the therapeutic nucleoside and the oligomeric compound both treat the same disease or condition. In certain such embodiments, the disease or condition is a viral infection. In certain such embodiments, the viral infection comprises infection in the liver. In certain such embodiments, the disease or condition is Hepatitis B infection. In certain embodiments, the disease or condition is Hepatitis C infection.

In certain embodiments, the targeting group comprises a ligand for a cell surface receptor. For example, in certain embodiments, the targeting group comprises at least one N-acetyl galactoseamine, which has been described as a ligand for the asiaglycoprotein receptor. In certain embodiments the targeting group increases uptake of the therapeutic compound (with or without an oligomeric compound) into cells. In certain such embodiments, uptake is particularly increased in certain cells or cell-types. For example, cells that express a receptor that is recognized by a ligand of the targeting group. Asiaglycoprotein receptors are expressed on hepatocytes, so compounds comprising GalNac ligands are preferentially taken up by hepatocytes. In certain embodiments, once inside a cell, the targeting group is cleaved from the one or more therapeutic nucleosides. Further, in certain embodiments comprising more than one therapeutic nucleoside, such therapeutic nucleosides are cleaved from one another. Thus, after uptake and cleavage, free individual therapeutic nucleosides are present in the cell. In certain embodiments, compounds further comprise an oligomeric compound. Such oligomeric compound may be single-stranded or double-stranded and may be an antisense compound, such as a RISC compound or RNase H compound; an siRNA, ssRNA, snRNA, or ASO.

In embodiments comprising more than one therapeutic nucleoside, the targeting group may be absent. That is, in certain embodiments, the invention provides 2-50 linked therapeutic nucleosides. In certain such embodiments, the therapeutic nucleosides are linked by cleavable bonds. In certain embodiments, such 2-50 linked therapeutic nucleosides lacking a targeting group are bound to an oligomeric compound, such as an antisense compound.

Certain therapeutic agents of the present invention are characterized as follows:
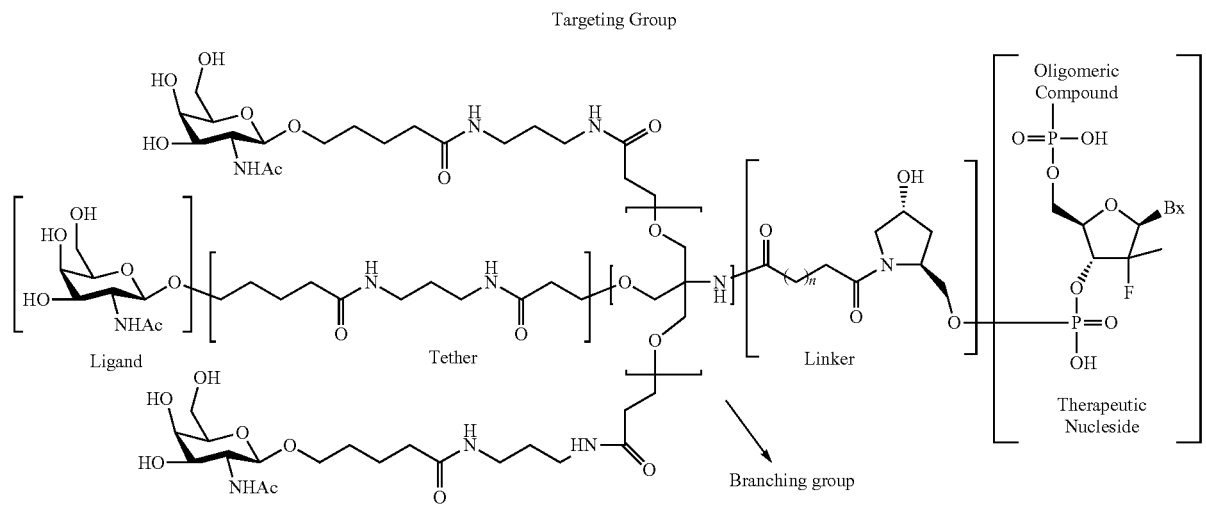
In certain embodiments, therapeutic agents are provided having the structure:
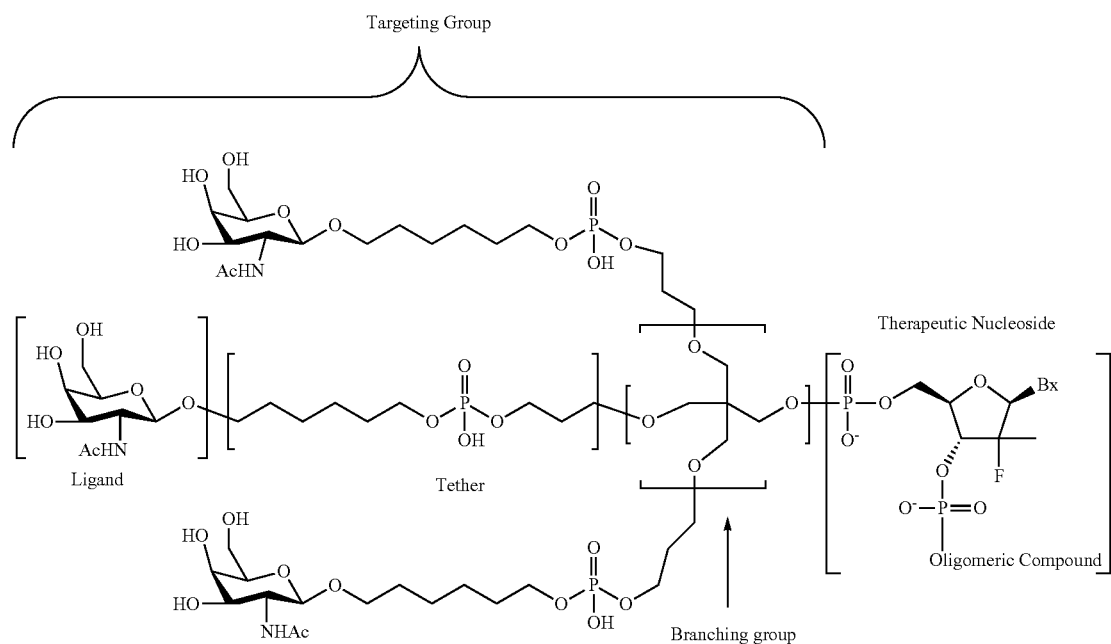
In certain embodiments, therapeutic agents are provided having the structure:

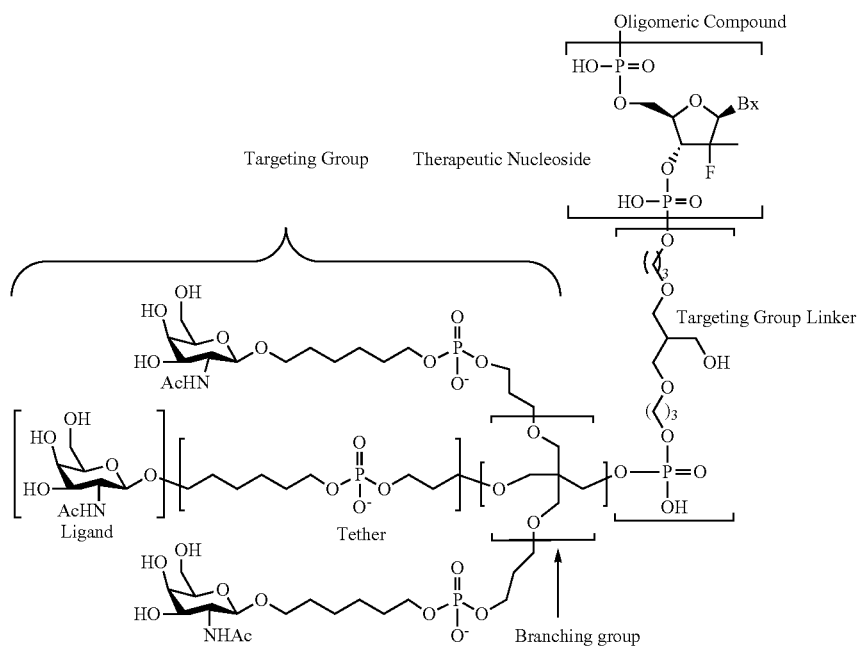

The present disclosure provides the following non-limiting numbered embodiments:

Embodiment 1

A compound comprising a targeting group and at least one therapeutic nucleoside.

Embodiment 2

The compound of embodiment 1, wherein the targeting group comprises at least one cell-targeting ligand.

Embodiment 3

The compound of embodiment 1, wherein the targeting group comprises 1-4 cell-targeting ligands.

Embodiment 4

The compound of embodiment 3 comprising 3 cell-targeting ligands.

Embodiment 5

The compound of any of embodiments 1-4, wherein each cell-targeting ligand is N-acetylgalactosamine.

Embodiment 6

The compound of embodiment 5, wherein the N-acetylgalactosamine is attached to the compound via the galactose C1 oxygen.

Embodiment 7

The compound of any of embodiments 1-6, wherein the targeting group comprises a targeting group linker.

Embodiment 8

The compound of embodiment 7, wherein the targeting group linker comprises one or more groups selected from among: phosphate, amide, ether, ester, pyrrolidine, disulfide, and methylene.

Embodiment 9

The compound of embodiment 8, wherein the targeting group linker comprises a structure selected from among:

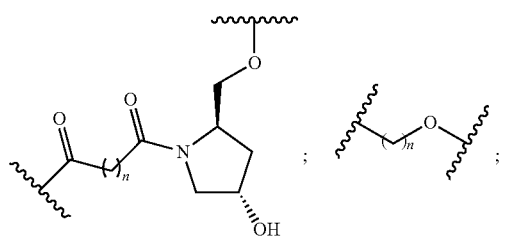

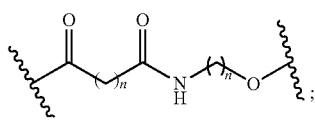

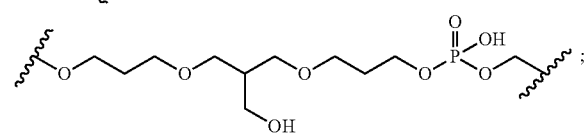

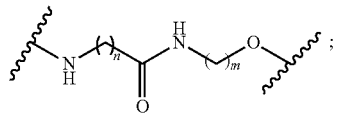

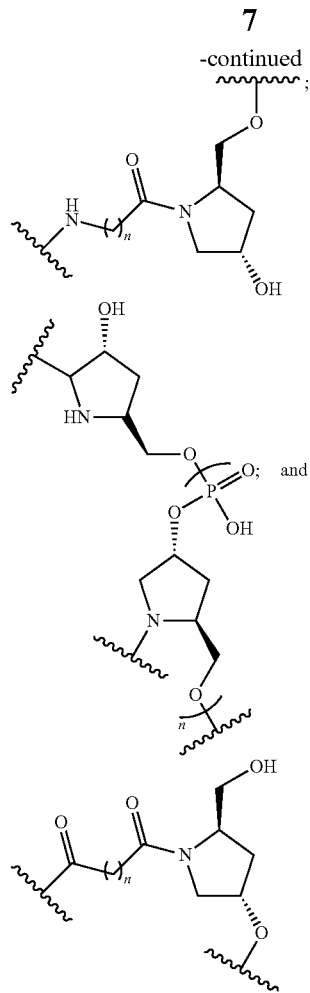

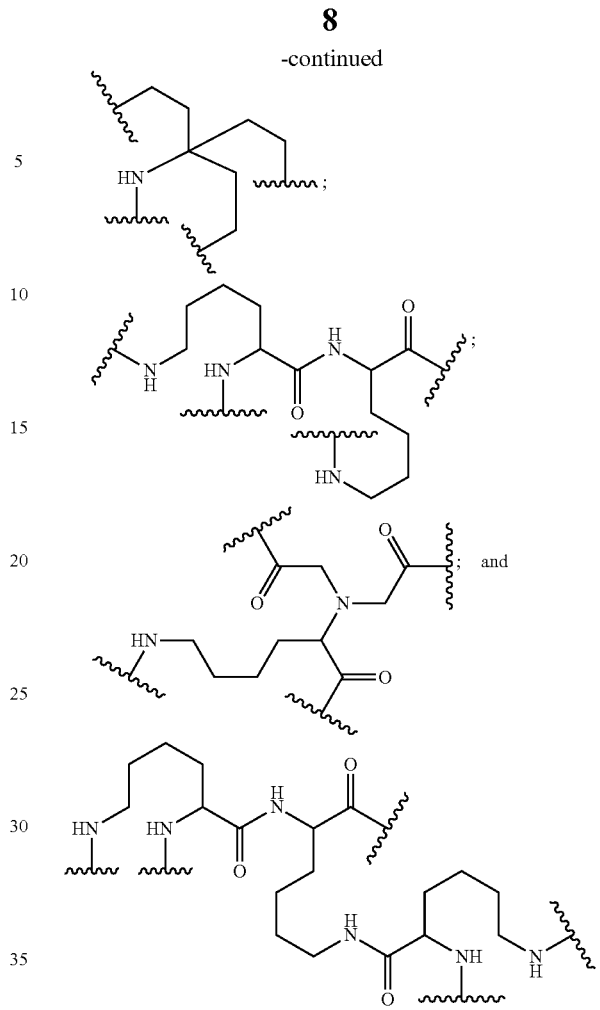

wherein n and m are independently selected from 1, 2, 3, 4, 5, 6, 7, 8, 9, or 10.

Embodiment 10

The compound of any of embodiments 1-9, wherein the targeting group comprises a branching group.

Embodiment 11

The compound of embodiment 10, wherein the branching group comprises one or more groups selected from among: amino acid, amino alcohol, alkoxy, and amine.

Embodiment 12

The compound of embodiment 10 or 11, wherein the branching group has a structure selected from among:

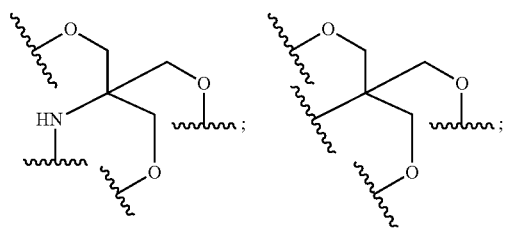

Embodiment 13

The compound of any of embodiments 1-12, wherein the targeting group comprises at least one tether.

Embodiment 14

The compound of embodiment 13, wherein at least one tether comprises one or more groups selected from among: amino acid, amide, methylene, phosphate, carbonyl, and piperidine.

Embodiment 15

The compound of embodiment 14, wherein at least one tether has a structure selected from among:

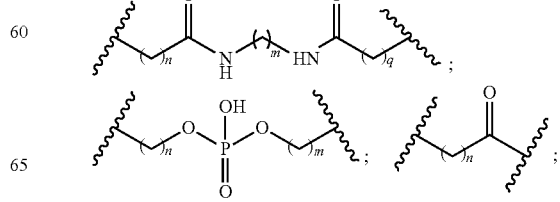

-continued

[chemical structures]

wherein n, m, and q are independently selected from 1, 2, 3, 4, 5, 6, 7, 8, 9, or 10.

Embodiment 16

The compound of any of embodiments 1-15, wherein the targeting group comprises a cleavable moiety.

Embodiment 17

The compound of embodiment 16, wherein the cleavable moiety is a non-therapeutic nucleoside.

Embodiment 18

The compound of embodiment 17, wherein the cleavable non-therapeutic nucleoside is attached to the targeting group linker via a cleavable bond.

Embodiment 19

The compound of embodiment 17 or 18, wherein the non-therapeutic nucleoside comprises a 2' substituent selected from among: H, OH, MOE, F, and OMe.

Embodiment 20

The compound of any of embodiments 1-19, wherein the targeting group comprises a group comprises a structure represented by formula I below:

$$(A-B)_n-C-D-(E)_m$$

wherein:
A is a cell-targeting ligand;
B is a tether;
C is a branching group;
D is a targeting group linker;
E is a cleavable moiety;
n is 1, 2, 3, 4, or 5; and
m is 0 or 1.

Embodiment 21

The compound of any of embodiments 1-20, wherein the targeting group increases potency of the therapeutic nucleoside.

Embodiment 22

The compound of any of embodiments 1-20, wherein the targeting group increases in delivery or uptake of the therapeutic nucleoside in liver cells.

Embodiment 23

The compound of embodiment 22, wherein the liver cells are hepatocytes.

Embodiment 24

The compound of embodiment 22 or 23, wherein the cells are in an animal.

Embodiment 25

The compound of any of embodiments 1-24, wherein at least one therapeutic nucleoside comprises a modified or unmodified pyrimidine nucleobase.

Embodiment 26

The compound of any of embodiments 1-25, wherein at least one therapeutic nucleoside comprises a modified or unmodified purine nucleobase.

Embodiment 27

The compound of any of embodiments 1-26, wherein at least one therapeutic nucleoside comprises a modified furanosyl ring.

Embodiment 28

The compound of embodiment 27, wherein the modified furanosyl ring of the at least one therapeutic nucleoside comprises a 2' or 3' substituent independently selected from hydrogen, halogen, hydroxyl, amino, alkyl, alkenyl, alkynyl, alkoxy, $CF_3$, and ester.

Embodiment 29

The compound of any of embodiments 27-28, wherein the modified furanosyl ring of the at least one therapeutic nucleoside comprises a 5' substituent independently selected from hydrogen, hydroxyl, ester, phosphate, phosphate ester, and phosphoramidate.

Embodiment 30

The compound of any of embodiments 27-29, wherein the modified furanosyl ring of the at least one therapeutic nucleoside comprises a 4' substituent comprising an azido group.

Embodiment 31

The compound of any of embodiments 27-30, wherein the modified furanosyl ring of the at least one therapeutic nucleoside comprises a 2' substituent that is other than H or OH.

Embodiment 32

The compound of embodiment 31, wherein at least one 2' substituent of the modified furanosyl ring of at least one therapeutic nucleoside is selected from F and methyl.

Embodiment 33

The compound of embodiment 32, wherein neither 2' substituent is H or OH.

Embodiment 34

The compound of any of embodiments 27-33, wherein the 2' substituents are methyl and hydroxyl.

Embodiment 35

The compound of any of embodiments 27-33, wherein the 2' substituents are methyl and fluoro.

Embodiment 36

The compound of embodiment 35, wherein absolute configuration of the chiral center at the 2' position is R.

Embodiment 37

The compound of any of embodiments 27-36, wherein the 3' substituents of the modified furanosyl ring of at least one therapeutic nucleoside are hydrogen and hydroxyl.

Embodiment 38

The compound of any of embodiments 27-37, wherein the 5' substituents of the modified furanosyl ring of at least one therapeutic nucleoside comprise OP(O)R$_1$R$_2$, wherein R$_1$ and R$_2$ are each independently hydroxyl, phenoxy, naphthalenoxy, OiPr, NHbenzyl, NHCH(CH$_3$)C(O)OiPr, and NHCH(CH$_3$)C(O)OCH$_2$t-butyl.

Embodiment 39

The compound of any of embodiments 1-38, wherein the therapeutic nucleoside comprises the following structure:

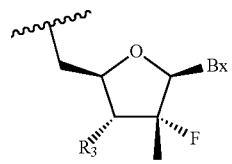

wherein R$_3$ is hydroxyl or the targeting group; and
Bx is a modified or unmodified nucleobase.

Embodiment 40

The compound of embodiment 39, wherein the therapeutic nucleoside comprises the following structure:

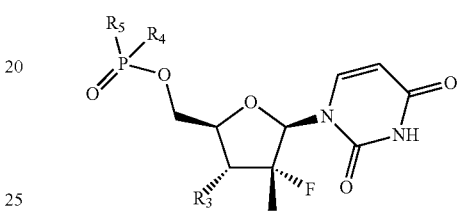

wherein R$_3$ is hydroxyl or the targeting group; and
R$_4$ and R$_5$ are each independently selected from phenoxy, NHCH(CH$_3$)C(O)OiPr, alkoxy, alkylamino, hydroxyl, an internucleoside linking group linking the therapeutic nucleoside to another nucleoside or to an oligomeric compound, and the targeting group;
provided that at least one of R$_3$, R$_4$, and R$_5$ is a targeting group.

Embodiment 41

The compound of any of embodiments 1-38, wherein the therapeutic nucleoside comprises the following structure:

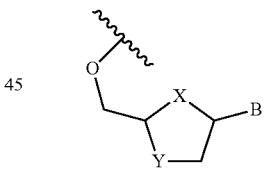

wherein B is a modified or unmodified nucleobase;
X is O or CCH$_2$;
Y is S or CR$_6$R$_7$; and
R$_6$ and R$_7$ are each independently selected from hydrogen, hydroxyl, O-L-valinyl ester, and the targeting group.

Embodiment 42

The compound of embodiment 41, wherein the modified or unmodified nucleobase is selected from among: adenine, uracil, cytosine, 5-methylcytosine, guanine, thymine, and 5-fluorocytosine.

Embodiment 43

The compound of any of embodiments 1-42, wherein at least one therapeutic nucleoside comprises an acyclic sugar surrogate.

Embodiment 44

The compound of embodiment 43, wherein the therapeutic nucleoside comprising an acyclic sugar surrogate comprises a purine nucleobase linked to a phosphonate via the sugar surrogate.

Embodiment 45

The compound of embodiment 44, wherein the targeting group is attached to the phosphonate.

Embodiment 46

The compound of any of embodiments 1-45, wherein at least one therapeutic nucleoside is an antiviral nucleoside.

Embodiment 47

The compound of embodiment 46, wherein the at least one anti-viral nucleoside inhibits a viral polymerase.

Embodiment 48

The compound of embodiment 46 or 47, wherein at least one antiviral nucleoside is an anti-HCV nucleoside.

Embodiment 49

The compound of embodiment 46 or 47, wherein the at least one antiviral nucleoside is an anti-HBV nucleoside.

Embodiment 50

The compound of any of embodiments 1-49, wherein the compound comprises one therapeutic nucleoside.

Embodiment 51

The compound of any of embodiments 1-49, wherein the compound comprises 2-50 therapeutic nucleosides.

Embodiment 52

The compound of embodiment 51, wherein the therapeutic nucleosides are all the same as one another.

Embodiment 53

The compound of embodiment 51, wherein at least 2 therapeutic nucleosides are different from one another.

Embodiment 54

The compound of any of embodiments 51-53, wherein at least one internucleoside linkage linking two therapeutic nucleosides to one another is an unmodified phosphodiester internucleoside linkage.

Embodiment 55

The compound of any of embodiments 51-54, wherein each internucleoside linkage linking two therapeutic nucleosides to one another is an unmodified phosphodiester internucleoside linkage.

Embodiment 56

The compound of any of embodiments 1-55, wherein the targeting group is attached to the therapeutic nucleoside by a cleavable bond.

Embodiment 57

The compound of embodiment 56, wherein the cleavable bond is selected from among an amide, a polyamide, an ester, an ether, a phosphodiester, a phosphate ester, a phosphonate, a phosphoramidate, a carbamate, a disulfide, or a peptide.

Embodiment 58

The compound of any of embodiments 1-57, wherein a targeting group is attached to the 3' position of a therapeutic nucleoside.

Embodiment 59

The compound of any of embodiments 1-58, wherein a targeting group is attached to the 5' position of a therapeutic nucleoside.

Embodiment 60

The compound of any of embodiments 1-59 comprising an oligomeric compound.

Embodiment 61

The compound of embodiment 60, wherein the oligomeric compound is single-stranded.

Embodiment 62

The compound of embodiment 60, wherein the oligomeric compound is double-stranded.

Embodiment 63

The compound of any of embodiments 60-62, wherein the oligomeric compound comprises a modified oligonucleotide consisting of 8-30 linked nucleosides.

Embodiment 64

The compound of embodiment 63, wherein the modified oligonucleotide comprises at least one modified nucleoside comprising a modified sugar.

Embodiment 65

The compound of embodiment 64, wherein the modified oligonucleotide comprises at least one modified nucleoside comprising a modification at the 2' position selected from MOE, OMe, cEt, and LNA.

Embodiment 66

The compound of any of embodiments 63-65, wherein the modified oligonucleotide comprises a region of alternating sugar motif, comprising at least three alternating regions of 2'-OMe nucleosides and 2'-F nucleosides, wherein each region consists of 1-4 nucleosides.

Embodiment 67

The compound of any of embodiments 63-65 wherein the modified oligonucleotide is a gapmer.

Embodiment 68

The compound of any of embodiments 63-67, wherein the modified oligonucleotide comprises at least one phosphorothioate internucleoside linkage.

Embodiment 69

The compound of any of embodiments 63-68, wherein the modified oligonucleotide is an antisense compound.

Embodiment 70

The compound of embodiment 69, wherein the antisense compound is an RNase H compound.

Embodiment 71

The compound of embodiment 69, wherein the antisense compound is an RNAi oligomeric compound.

Embodiment 72

The compound of any of embodiments 69-71, wherein the antisense oligomeric compound is complementary to a target viral RNA or a target human RNA that is involved in virus pathogenicity.

Embodiment 73

The compound of embodiment 72, wherein the target RNA is an HCV RNA or a human RNA involved in HCV pathogenicity.

Embodiment 74

The compound of embodiment 73, wherein the target RNA is a transcript of HCV F-transactivated protein 1.

Embodiment 75

The compound of embodiment 72, wherein the target RNA is an HBV RNA or a human RNA involved in HBV pathogenicity.

Embodiment 76

The compound of embodiment 75, wherein the target RNA is a transcript of HBV associated factor, HBV pX associated protein-8, or HBV pre-s2 binding protein.

Embodiment 77

The compound of any of embodiments 69-76, wherein the antisense oligomeric compound is complementary to a target microRNA.

Embodiment 78

The compound of embodiment 77, wherein the target microRNA is miR-122.

Embodiment 79

The compound of embodiment 77, wherein the target microRNA is miR-221 or miR-21.

Embodiment 80

The compound of any of embodiments 60-79, wherein the therapeutic nucleoside is directly linked to the oligomeric compound.

Embodiment 81

The compound of embodiment 80, wherein the therapeutic nucleoside is directly linked to the 3' end of the oligomeric compound.

Embodiment 82

The compound of embodiment 80, wherein the therapeutic nucleoside is directly linked to the 5' end of the oligomeric compound.

Embodiment 83

The compound of any of embodiments 60-82, wherein the therapeutic nucleoside and the oligomeric compound are linked via a phosphate group.

Embodiment 84

The compound of any of embodiments 60-82, wherein the targeting group is directly attached to one end of the oligomeric compound, and the therapeutic nucleoside is directly attached to the opposite end of the oligomeric compound.

Embodiment 85

The compound of any of embodiments 60-82, wherein the targeting group is directly attached to one end of the therapeutic nucleoside, and the oligomeric compound is attached to the opposite end of the therapeutic nucleoside.

Embodiment 86

A compound of any of embodiments 1-85 having the formula:

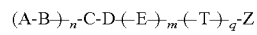

wherein:
A is a cell-targeting ligand;
B is a tether;
C is a branching group;
D is a targeting group linker;
E is a cleavable moiety;
T is a therapeutic nucleoside;
Z is an oligomeric compound;
n is 1, 2, 3, 4, or 5;
m is 0 or 1; and
q is 1-50.

Embodiment 87

A pharmaceutical composition comprising a compound of any of embodiments 1-86 or a pharmaceutically acceptable salt thereof and a pharmaceutically acceptable carrier or diluent.

Embodiment 88

A method of treating an RNA-dependent virus infection comprising administering to a mammal in need of such treatment a therapeutically effective amount of a compound of any of embodiments 1-87.

Embodiment 89

A method of embodiment 88, wherein the RNA-dependent virus is an RNA virus.

Embodiment 90

A method of embodiment 89, wherein the RNA-dependent RNA virus is HCV.

Embodiment 91

A method of embodiment 88, wherein the RNA-dependent virus is a DNA virus.

Embodiment 92

A method of embodiment 91, wherein the RNA-dependent DNA virus is HBV.

Embodiment 93

The use of the compound of any of embodiments 1-87 in the treatment of an RNA-dependent virus infection.

Embodiment 94

The use of the compound of any of embodiments 1-87 in the manufacture of a medicament for the treatment of an RNA-dependent virus infection.

Embodiment 95

The use of embodiment 93 or 94, wherein the RNA-dependent virus is an RNA virus.

Embodiment 96

The use of embodiment 95, wherein the RNA-dependent RNA virus is HCV.

Embodiment 97

The use of embodiment 93 or 94, wherein the RNA-dependent virus is a DNA virus.

Embodiment 98

The use of embodiment 97, wherein the RNA-dependent DNA virus is HBV.

Embodiment 99

A compound comprising at least one therapeutic nucleoside and at least one additional moiety selected from a targeting group and an oligomeric compound.

Embodiment 100

The compound of embodiment 99 comprising a targeting group.

Embodiment 101

The compound of embodiment 100, wherein the targeting group comprises at least one cell-targeting ligand.

Embodiment 102

The compound of embodiment 100, wherein the targeting group comprises 1-4 cell-targeting ligands.

Embodiment 103

The compound of embodiment 102 comprising exactly 1 cell-targeting ligand.

Embodiment 104

The compound of embodiment 102 comprising exactly 2 cell-targeting ligands.

Embodiment 105

The compound of embodiment 102 comprising exactly 3 cell-targeting ligands.

Embodiment 106

The compound of any of embodiments 101-105, wherein each cell-targeting ligand is N-acetylgalactosamine.

Embodiment 107

The compound of embodiment 106, wherein the N-acetylgalactosamine is attached to the compound via the galactose C1 oxygen.

Embodiment 108

The compound of any of embodiments 99-107, wherein the targeting group comprises a targeting group linker.

Embodiment 109

The compound of embodiment 108, wherein the targeting group linker comprises one or more groups selected from among: phosphate, amide, ether, ester, pyrrolidine, disulfide, and methylene.

Embodiment 110

The compound of embodiment 108, wherein the targeting group linker comprises a structure selected from among:

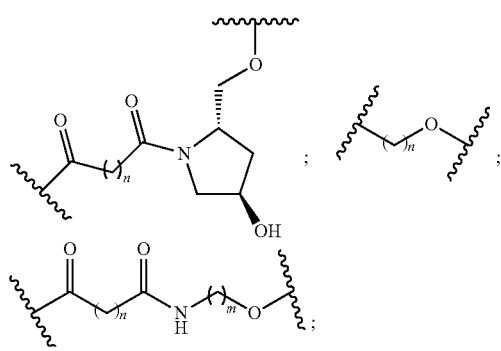

-continued

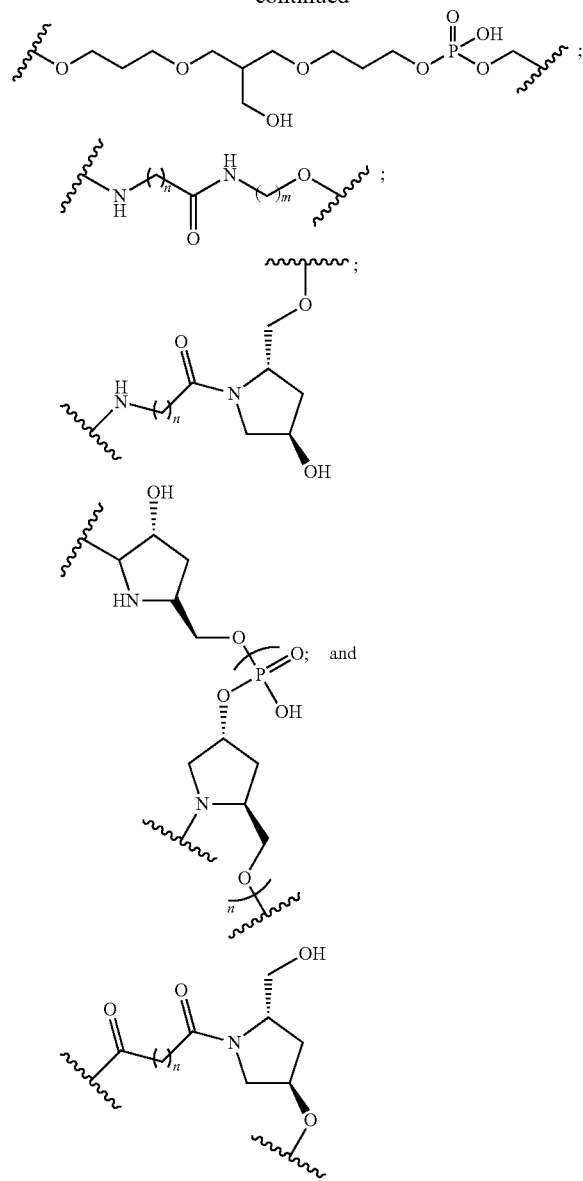

wherein n and m are independently selected from 1, 2, 3, 4, 5, 6, 7, 8, 9, or 10.

Embodiment 111

The compound of embodiment 108, wherein the targeting group linker comprises a structure selected from among:

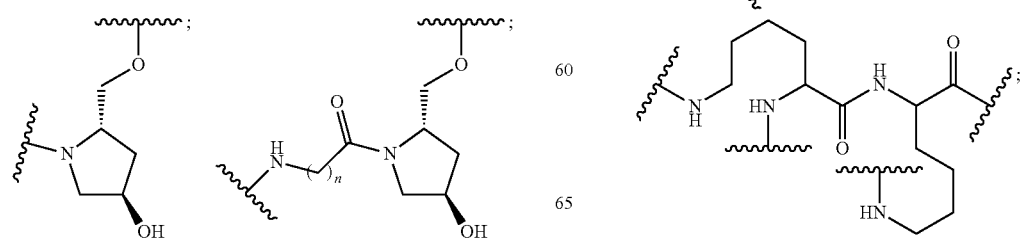

-continued

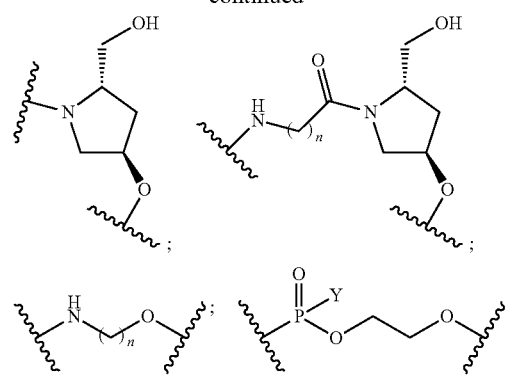

wherein each n is independently selected from 1, 2, 3, 4, 5, 6, 7, 8, 9, or 10.

Embodiment 112

The compound of any of embodiments 99-102 or 104-111, wherein the targeting group comprises a branching group.

Embodiment 113

The compound of embodiment 112, wherein the branching group comprises one or more groups selected from among: amino acid, amino alcohol, alkoxy, and amine.

Embodiment 114

The compound of embodiment 112 or 113, wherein the branching group has a structure selected from among:

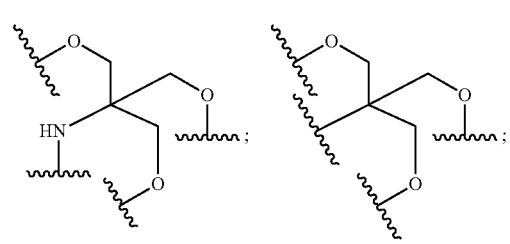

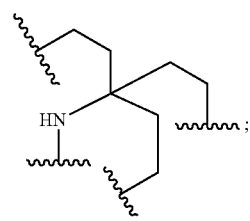

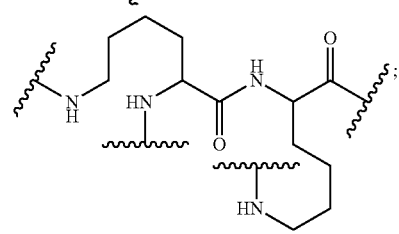

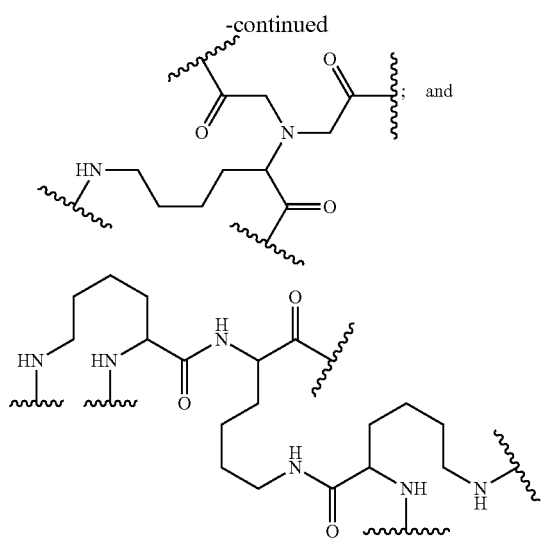

Embodiment 115

The compound of embodiment 112 or 113, wherein the branching group has a structure selected from among:

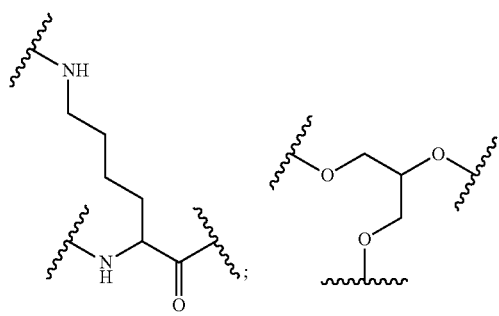 [SMILES: *NCCCCC(N*)C(*)=O ; *OCC(CO*)O*]

Embodiment 116

The compound of any of embodiments 99-115, wherein the targeting group comprises at least one tether.

Embodiment 117

The compound of embodiment 116, wherein the at least one tether comprises one or more groups selected from among: amino acid, amide, methylene, phosphate, carbonyl, and piperidine.

Embodiment 118

The compound of embodiment 116, wherein the at least one tether has a structure selected from among:

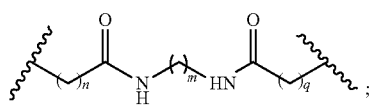

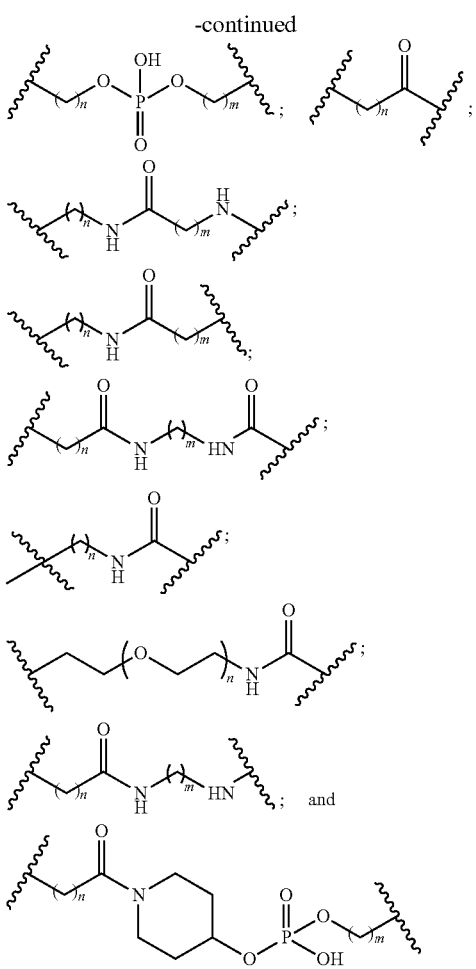

wherein n, m, and q are independently selected from 1, 2, 3, 4, 5, 6, 7, 8, 9, or 10.

Embodiment 119

The compound of embodiment 116, wherein the at least one tether has a structure selected from among:

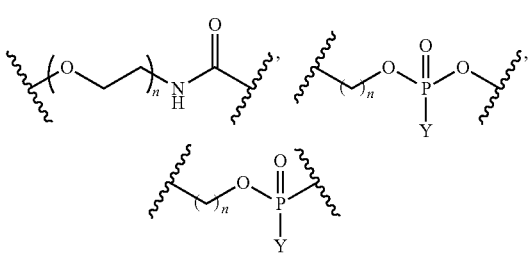

wherein each n is independently selected from 1, 2, 3, 4, 5, 6, 7, 8, 9, or 10.

Embodiment 120

The compound of any of embodiments 99-119, wherein the compound comprises a cleavable moiety.

Embodiment 121

The compound of embodiment 120, wherein the cleavable moiety is a phosphodiester.

Embodiment 122

The compound of embodiment 120, wherein the cleavable moiety is a non-therapeutic nucleoside.

Embodiment 123

The compound of embodiment 122, wherein the cleavable non-therapeutic nucleoside is attached to the targeting group linker via a cleavable bond.

Embodiment 124

The compound of embodiment 122 or 123, wherein the non-therapeutic nucleoside comprises a 2' substituent selected from among: H, OH, MOE, F, and OMe.

Embodiment 125

The compound of any of embodiments 99-124, wherein the targeting group comprises a group comprises a structure represented by formula:

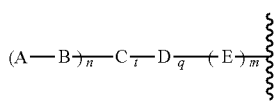

wherein:
A is a cell-targeting ligand;
B is a tether;
C is a branching group;
D is a targeting group linker;
E is a cleavable moiety;
n is 1, 2, 3, 4, or 5;
t is 0 or 1;
q is 0 or 1; and
m is 0 or 1.

Embodiment 126

The compound of any of embodiments 99-125, wherein the targeting group increases potency of the therapeutic nucleoside.

Embodiment 127

The compound of any of embodiments 99-125, wherein the targeting group increases in delivery or uptake of the therapeutic nucleoside in liver cells.

Embodiment 128

The compound of embodiment 127, wherein the liver cells are hepatocytes.

Embodiment 129

The compound of embodiment 127 or 128, wherein the cells are in an animal.

Embodiment 130

The compound of any of embodiments 99-129, wherein at least one therapeutic nucleoside comprises a modified or unmodified pyrimidine nucleobase.

Embodiment 131

The compound of any of embodiments 99-129, wherein at least one therapeutic nucleoside comprises a modified or unmodified purine nucleobase.

Embodiment 132

The compound of any of embodiments 99-131, wherein at least one therapeutic nucleoside comprises a modified furanosyl ring.

Embodiment 133

The compound of embodiment 132, wherein the modified furanosyl ring of the at least one therapeutic nucleoside comprises a 2' or 3' substituent independently selected from hydrogen, halogen, hydroxyl, amino, alkyl, alkenyl, alkynyl, alkoxy, $CF_3$, and ester.

Embodiment 134

The compound of any of embodiments 132-133, wherein the modified furanosyl ring of the at least one therapeutic nucleoside comprises a 5' substituent independently selected from hydrogen, hydroxyl, ester, phosphate, phosphate ester, and phosphoramidate.

Embodiment 135

The compound of any of embodiments 132-134, wherein the modified furanosyl ring of the at least one therapeutic nucleoside comprises a 4' substituent comprising an azido group.

Embodiment 136

The compound of any of embodiments 132-135, wherein the modified furanosyl ring of the at least one therapeutic nucleoside comprises a 2' substituent that is other than H or OH.

Embodiment 137

The compound of embodiment 136, wherein at least one 2' substituent of the modified furanosyl ring of at least one therapeutic nucleoside is selected from F and methyl.

Embodiment 138

The compound of any of embodiments 136-137, wherein neither 2' substituent is H or OH.

Embodiment 139

The compound of any of embodiments 132-137, wherein the 2' substituents are methyl and hydroxyl.

Embodiment 140

The compound of any of embodiments 132-138, wherein the 2' substituents are methyl and fluoro.

Embodiment 141

The compound of embodiment 140, wherein absolute configuration of the chiral center at the 2' position is R.

Embodiment 142

The compound of any of embodiments 132-141, wherein the 3' substituents of the modified furanosyl ring of at least one therapeutic nucleoside are hydrogen and hydroxyl.

Embodiment 143

The compound of any of embodiments 132-142, wherein the 5' substituents of the modified furanosyl ring of at least one therapeutic nucleoside comprise OP(O)$R_1R_2$, wherein $R_1$ and $R_2$ are each independently hydroxyl, phenoxy, naphthalenoxy, OiPr, NHbenzyl, NHCH(CH$_3$)C(O)OiPr, and NHCH(CH$_3$)C(O)OCH$_2$t-butyl.

Embodiment 144

The compound of any of embodiments 99-134, 136-138, or 140-143, wherein the therapeutic nucleoside comprises the following structure:

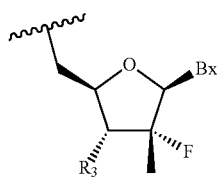

wherein $R_3$ is hydroxyl or the targeting group; and Bx is a modified or unmodified nucleobase.

Embodiment 145

The compound of embodiment 144, wherein the therapeutic nucleoside comprises the following structure:

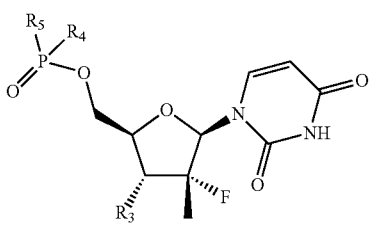

wherein $R_3$ is hydroxyl or the targeting group; and
$R_4$ and $R_5$ are each independently selected from phenoxy, NHCH(CH$_3$)C(O)OiPr, alkoxy, alkylamino, hydroxyl, an internucleoside linking group linking the therapeutic nucleoside to another nucleoside or to an oligomeric compound, and the targeting group;
provided that at least one of $R_3$, $R_4$, and $R_5$ is a targeting group.

Embodiment 146

The compound of any of embodiments 99-132 or 134, wherein the therapeutic nucleoside comprises the following structure:

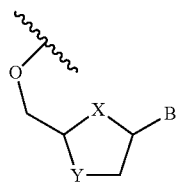

wherein B is a modified or unmodified nucleobase;
X is O or CCH$_2$;
Y is S or CR$_6$R$_7$; and
$R_6$ and $R_7$ are each independently selected from hydrogen, hydroxyl, O-L-valinyl ester, and the targeting group.

Embodiment 147

The compound of embodiment 146, wherein the modified or unmodified nucleobase is selected from among: adenine, uracil, cytosine, 5-methylcytosine, guanine, thymine, and 5-fluorocytosine.

Embodiment 148

The compound of any of embodiments 99-131, wherein at least one therapeutic nucleoside comprises an acyclic sugar surrogate.

Embodiment 149

The compound of embodiment 148, wherein the therapeutic nucleoside comprising an acyclic sugar surrogate comprises a purine nucleobase linked to a phosphonate via the sugar surrogate.

Embodiment 150

The compound of embodiment 149, wherein the targeting group is attached to the phosphonate.

Embodiment 151

The compound of any of embodiments 99-150, wherein at least one therapeutic nucleoside is an antiviral nucleoside.

Embodiment 152

The compound of embodiment 145, wherein the at least one anti-viral nucleoside inhibits a viral polymerase.

Embodiment 153

The compound of embodiment 151 or 152, wherein at least one antiviral nucleoside is an anti-HCV nucleoside.

Embodiment 154

The compound of embodiment 151 or 152, wherein the at least one antiviral nucleoside is an anti-HBV nucleoside.

Embodiment 155

The compound of any of embodiments 99-154, wherein the compound comprises exactly one therapeutic nucleoside.

Embodiment 156

The compound of any of embodiments 99-154, wherein the compound comprises 2-50 therapeutic nucleosides.

Embodiment 157

The compound of embodiment 156, wherein the therapeutic nucleosides are all the same as one another.

Embodiment 158

The compound of embodiment 156, wherein at least 2 therapeutic nucleosides are different from one another.

Embodiment 159

The compound of any of embodiments 156-158, wherein the therapeutic nucleosides are arranged according to the following formula:

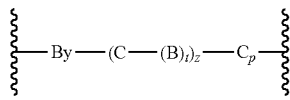

Wherein
each B is independently a cleavable moiety;
each C is independently a therapeutic nucleoside;
y is 0 or 1;
z is 1-50;
each t is independently 0 or 1;
p is 0 or 1;
provided that if z is 1, p is not 0.

Embodiment 160

The compound of embodiment 159, wherein y is 1 and each t is 1.

Embodiment 161

The compound of any of embodiments 159-160, wherein each B comprises a non-therapeutic nucleoside.

Embodiment 162

The compound of any of embodiments 159-160, wherein each B consists of a cleavable bond.

Embodiment 163

The compound of any of embodiments 159-160, wherein each B is a phosphodiester.

Embodiment 164

The compound of any of embodiments 156-163, wherein at least one internucleoside linkage linking two nucleosides to one another is an unmodified phosphodiester internucleoside linkage.

Embodiment 165

The compound of any of embodiments 156-163, wherein each internucleoside linkage linking two nucleosides to one another is an unmodified phosphodiester internucleoside linkage.

Embodiment 166

The compound of any of embodiments 99-165, wherein the targeting group is attached to the therapeutic nucleoside by a cleavable bond.

Embodiment 167

The compound of embodiment 166, wherein the cleavable bond is selected from among an amide, a polyamide, an ester, an ether, a phosphodiester, a phosphate ester, a phosphonate, a phosphoramidate, a carbamate, a disulfide, or a peptide.

Embodiment 168

The compound of any of embodiments 99-167, wherein a targeting group is attached to the 3' position of a therapeutic nucleoside.

Embodiment 169

The compound of any of embodiments 99-167, wherein a targeting group is attached to the 5' position of a therapeutic nucleoside.

Embodiment 170

The compound of any of embodiments 99-169 comprising an oligomeric compound.

Embodiment 171

The compound of embodiment 170, wherein the oligomeric compound is single-stranded.

Embodiment 172

The compound of embodiment 170, wherein the oligomeric compound is double-stranded.

Embodiment 173

The compound of any of embodiments 170-172, wherein the oligomeric compound comprises a modified oligonucleotide consisting of 8-30 linked nucleosides.

Embodiment 174

The compound of embodiment 173, wherein the modified oligonucleotide comprises at least one modified nucleoside comprising a modified sugar.

Embodiment 175

The compound of embodiment 174, wherein the modified oligonucleotide comprises at least one modified nucleoside comprising a modification at the 2' position selected from MOE, OMe, cEt, and LNA.

Embodiment 176

The compound of any of embodiments 173-175, wherein the modified oligonucleotide comprises a region of alternating sugar motif, comprising at least three alternating regions of 2'-OMe nucleosides and 2'-F nucleosides, wherein each region consists of 1-4 nucleosides.

Embodiment 177

The compound of any of embodiments 173-175 wherein the modified oligonucleotide is a gapmer.

Embodiment 178

The compound of any of embodiments 173-177, wherein the modified oligonucleotide comprises at least one phosphorothioate internucleoside linkage.

Embodiment 179

The compound of any of embodiments 173-178, wherein the modified oligonucleotide is an antisense compound.

Embodiment 180

The compound of embodiment 179, wherein the antisense compound is an RNase H compound.

Embodiment 181

The compound of embodiment 179, wherein the antisense compound is an RNAi oligomeric compound.

Embodiment 182

The compound of any of embodiments 179-181, wherein the antisense oligomeric compound is complementary to a target viral RNA or a target human RNA that is involved in virus pathogenicity.

Embodiment 183

The compound of embodiment 182, wherein the target RNA is an HCV RNA or a human RNA involved in HCV pathogenicity.

Embodiment 184

The compound of embodiment 183, wherein the target RNA is a transcript of HCV F-transactivated protein 1.

Embodiment 185

The compound of embodiment 182, wherein the target RNA is an HBV RNA or a human RNA involved in HBV pathogenicity.

Embodiment 186

The compound of embodiment 185, wherein the target RNA is a transcript of HBV associated factor, HBV pX associated protein-8, or HBV pre-s2 binding protein.

Embodiment 187

The compound of any of embodiments 179-186, wherein the antisense oligomeric compound is complementary to a target microRNA.

Embodiment 188

The compound of embodiment 187, wherein the target microRNA is miR-122.

Embodiment 189

The compound of embodiment 187, wherein the target microRNA is miR-221 or miR-21.

Embodiment 190

The compound of any of embodiments 170-189, wherein the therapeutic nucleoside is directly linked to the oligomeric compound.

Embodiment 191

The compound of embodiment 190, wherein the at least one therapeutic nucleoside is directly linked to the 3' end of the oligomeric compound.

Embodiment 192

The compound of embodiment 190, wherein the at least one therapeutic nucleoside is directly linked to the 5' end of the oligomeric compound.

Embodiment 193

The compound of any of embodiments 170-192, wherein the at least one therapeutic nucleoside and the oligomeric compound are linked via a phosphate group.

Embodiment 194

The compound of any of embodiments 170-192, wherein the at least one therapeutic nucleoside and the oligomeric compound are linked via a non-therapeutic nucleoside.

Embodiment 195

The compound of any of embodiments 170-194, wherein the targeting group is directly attached to one end of the oligomeric compound, and the therapeutic nucleoside is directly attached to the opposite end of the oligomeric compound.

Embodiment 196

The compound of any of embodiments 170-194, wherein the targeting group is directly attached to one end of the therapeutic nucleoside, and the oligomeric compound is attached to the opposite end of the therapeutic nucleoside.

Embodiment 197

A compound having the formula:

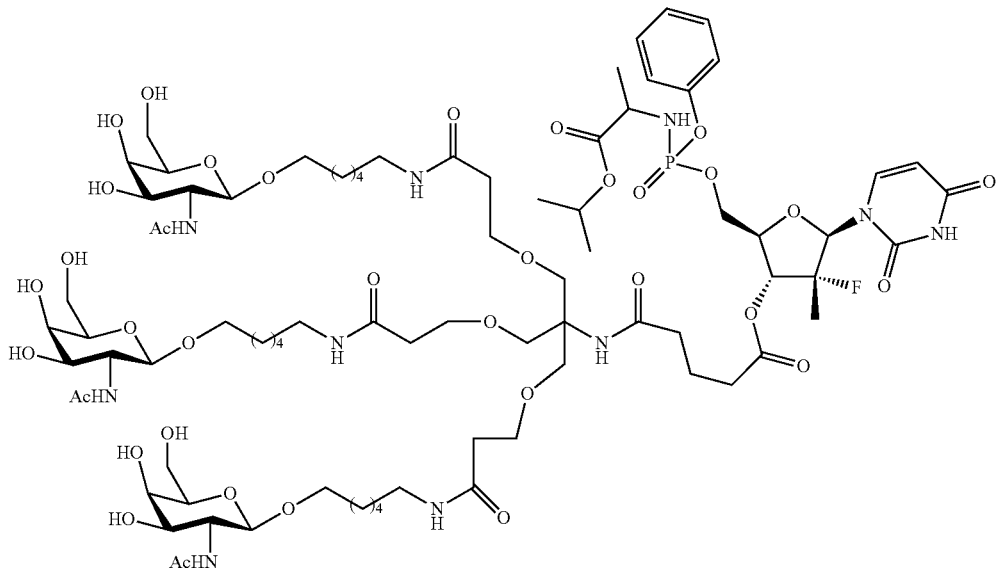

Embodiment 198

A compound having the formula:

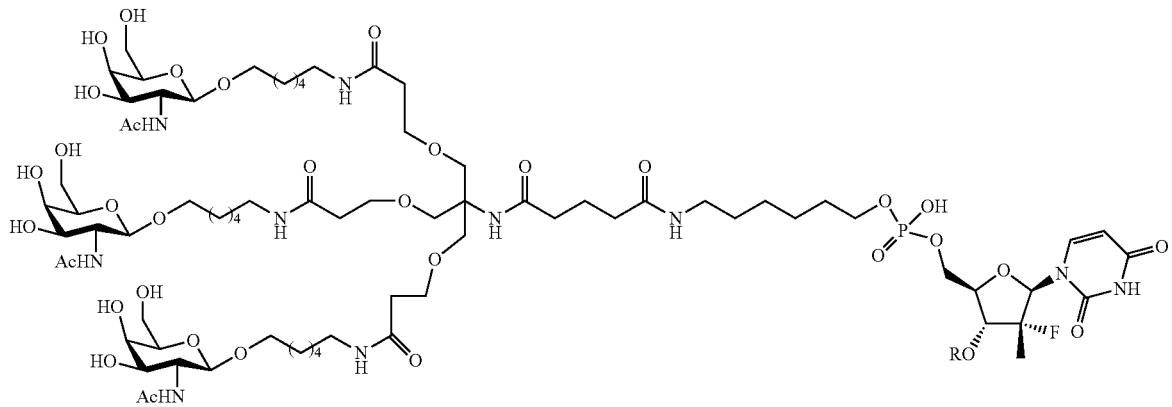

wherein R=H, miR-122, or 1-49 therapeutic nucleosides.

Embodiment 199

A compound of any of embodiments 99-198 having the formula:

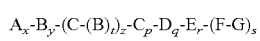

a. wherein
b. A is an oligomeric compound;
c. each B is independently a cleavable moiety
d. each C is independently a therapeutic nucleoside
e. D is a target group linker
f. E is a branching group
g. each F is a tether;
h. each G is a ligand;
i. x is 0 or 1;
j. y is 0 or 1;
k. z is 1-20;
l. each t is independently 0 or 1;
m. p is 0 or 1;
n. q is 0 or 1;
o. r is 0 or 1; and
p. s is 0-5; and
provided that if z is 1, then at least one of x and s is other than 0.

Embodiment 200

A pharmaceutical composition comprising a compound of any of embodiments 99-199 or a pharmaceutically acceptable salt thereof and a pharmaceutically acceptable carrier or diluent.

Embodiment 201

A method of treating an RNA-dependent virus infection comprising administering to a mammal in need of such treatment a therapeutically effective amount of a compound of any of embodiments 99-199.

Embodiment 202

The method of embodiment 201, wherein the RNA-dependent virus is an RNA virus.

Embodiment 203

The method of embodiment 202, wherein the RNA-dependent RNA virus is HCV.

Embodiment 204

The method of embodiment 201, wherein the RNA-dependent virus is a DNA virus.

Embodiment 205

The method of embodiment 204, wherein the RNA-dependent DNA virus is HBV.

Embodiment 206

The use of the compound of any of embodiments 99-199 in the treatment of an RNA-dependent virus infection.

Embodiment 207

The use of the compound of any of embodiments 99-199 in the manufacture of a medicament for the treatment of an RNA-dependent virus infection.

Embodiment 208

The use of embodiment 206 or 207, wherein the RNA-dependent virus is an RNA virus.

Embodiment 209

The use of embodiment 208, wherein the RNA-dependent RNA virus is HCV.

Embodiment 210

The use of embodiment 206 or 207, wherein the RNA-dependent virus is a DNA virus.

Embodiment 211

The use of embodiment 210, wherein the RNA-dependent DNA virus is HBV.

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); both a change in the number of atoms and a replacement of the oxygen; or an acyclic structure. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain such embodiments the 4 to 7 membered ring is a furanosyl. In certain such embodiments, the bridge connects the 2'-carbon and the 4'-carbon of the furanosyl.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means an oligomeric compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

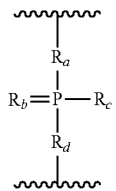

wherein:
R$_a$ and R$_d$ are each, independently, O, S, CH$_2$, NH, or NJ$_1$ wherein J$_1$ is C$_1$-C$_6$ alkyl or substituted C$_1$-C$_6$ alkyl;
R$_b$ is O or S;
R$_c$ is OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino; and
J$_1$ is R$_b$ is O or S.
Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI (—CH$_2$—N(CH$_3$)—O—), amide-3 (—CH$_2$—C(=O)—N(H)—), amide-4 (—CH$_2$—N(H)—C(=O)—), formacetal (—O—CH$_2$—O—), and thioformacetal (—S—CH$_2$—O—). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and CH$_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "targeting group" means a group of atoms which, when bound to a nucleoside or oligomeric compound, modifies one or more properties of such nucleoside or oligomeric compound, including but not limited to pharmacodynamic, pharmacokinetic, binding, absorption, cellular distribution, cellular uptake, and/or clearance properties.

In certain instances, targeting groups are shown herein as radicals, providing a bond for forming covalent attachment to a nucleoside or oligomeric compound such as an oligonucleotide. In certain embodiments, the point of attachment is the oxygen atom of a 3'-hydroxyl group of a nucleoside or of the 3' terminal nucleoside of an oligomeric compound. In certain embodiments, the point of attachment is the oxygen atom of a 5'-hydroxyl group of the nucleoside or of a 5' terminal nucleoside of an oligomeric compound. In certain embodiments, the bond for forming attachment of the targeting group to the nucleoside or oligomeric compound is a cleavable bond. In certain such embodiments, such cleavable bond constitutes all or part of a cleavable moiety.

As used herein, "targeting group linker" or "linker" in the context of a targeting group means a portion of a targeting group comprising any atom or group of atoms and which covalently links (1) an oligomeric compound to another portion of the targeting group or (2) two or more portions of the targeting group to one another.

As used herein, "branching group" means a portion of a targeting group comprising any atom or group of atoms which covalently link a single moiety to two or more separate moieties. In certain embodiments, a branching group links a single oligomeric compound or nucleoside to two or more portions of a targeting group. In certain embodiments, a branching group links a single portion of a targeting group to two or more other portions of the targeting group.

As used herein, "tether" means a portion of a targeting group comprising any atom or group of atoms that covalently links a cell targeting ligand to either (1) an oligomeric compound or nucleoside or (2) another portion of the targeting group.

As used herein, "cell-targeting ligand" means a moiety that binds a cell. In certain embodiments, cell-targeting ligands are selective for one or more particular cell type. In certain embodiments, cell-targeting moieties selectively bind a receptor, such as a cell surface receptor.

As used herein, "cleavable bond" means any chemical bond capable of being split under conditions where such splitting is desired. In certain embodiments, a cleavable bond is split when a compound is administered to an animal and/or after entry into a cell. In certain embodiments, a cleavable bond is selected from among: an amide, a polyamide, an ester, an ether, a phosphodiester, a phosphate ester, a phosphonate, a phosphoramidate, a carbamate, a di-sulfide, or a peptide.

As used herein, "cleavable moiety" means a cleavable bond or group of atoms that comprises one or more cleavable bond. In certain embodiments, a cleavable moiety includes a nucleoside with a cleavable bond linked to the 3' position of the furanosyl ring. In certain embodiments, the cleavable moiety includes a nucleoside with a cleavable bond linked to the 5' position of the furanosyl ring. In certain embodiments, the cleavable moiety includes a nucleoside with cleavable bonds linked to both the 3' and 5' positions of the furanosyl ring. In certain embodiments, the cleavable moiety is a phosphodiester.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "double-stranded" means either a pair of separate oligomeric compounds that are hybridized to one another or a single self-complementary oligomeric compound that forms a hairpin structure. In certain embodiments, a double-stranded oligomeric compound comprises a first and a second oligonucleotide. Such double-stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, "antisense compound" means a compound comprising or consisting of an oligonucleotide at least a portion of which is complementary to a target nucleic acid to which it is capable of hybridizing, resulting in at least one antisense activity. Antisense compounds may be single- or double-stranded. Antisense compounds may comprise non-hybridizing moieties, such as conjugates and/or terminal groups.

As used herein, "antisense activity" means any detectable and/or measurable change attributable to the hybridization of an antisense compound to its target nucleic acid.

As used herein, "gapmer" means an oligonucleotide comprising a gap segment of linked nucleosides that is positioned between 5' and 3' wing segments of linked nucleosides. The gap and wing segments are distinguished by the types of nucleosides they contain. In certain embodiments, the gap contains deoxyribonucleosides. In certain embodiments, the wings contain ribonucleosides and/or 2' modified nucleosides.

As used herein, "RNase H compound" means an antisense compound wherein at least some of the antisense activity of the antisense compound is attributable to hybridization of the antisense compound to a target nucleic acid and subsequent cleavage of the target nucleic acid by RNase H.

As used herein, "RNAi oligomeric compound" means an antisense compound wherein at least some of the antisense activity of the antisense compound is attributable to the RNA Induced Silencing Complex (RISC).

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means an activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid to which an antisense compound is intended to hybridize to result in a desired antisense activity. Antisense compounds have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compounds are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "therapeutic agent" means a compound which is capable of producing a desired result when administered to an animal. Therapeutic agents may be in the most active form when delivered or may be prodrugs or polyprodrugs.

As used herein, "prodrug" means an inactive or less active form of a compound which, when administered to a subject, is metabolized to form the active, or more active, compound. In certain embodiments, a prodrug comprises a targeting group and at least one active compound.

As used herein, "poly-prodrug" means a prodrug comprising more than one active compound.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "therapeutic nucleoside" means a nucleoside that provides a therapeutic benefit when administered to a subject.

As used herein, "non-therapeutic nucleoside" means a nucleoside that does not provide a therapeutic benefit when administered to a subject. In certain embodiments, a prodrug may comprise a non-therapeutic nucleoside. In such embodiments, the presence of the non-therapeutic nucleoside may increase the activity of the active compound, but is not itself directly responsible for the therapeutic activity.

As used herein, the term "therapeutically effective amount" refers to an amount of a pharmaceutical agent that provides a therapeutic benefit to an animal.

As used herein, the term "treatment" or "treating" refers to administering a composition of the invention to effect an alteration or improvement of the disease or condition. Prevention, amelioration, and/or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

As used herein, the term "pharmaceutical agent" refers to a substance that provides a therapeutic benefit when administered to a subject. In certain embodiments, a pharmaceutical agent comprises a prodrug.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "administering" means providing a pharmaceutical agent to an animal, and includes, but is not limited to administering by a medical professional and self-administering.

As used herein, the term "pharmaceutical composition" refers to a mixture of substances suitable for administering to an individual. For example, a pharmaceutical composition may comprise a therapeutic agents and a sterile aqueous solution.

As used herein, the term "animal" refers to a human or non-human animal, including, but not limited to, mice, rats, rabbits, dogs, cats, pigs, and non-human primates, including, but not limited to, monkeys and chimpanzees.

B. Certain Therapeutic Agents

In certain embodiments, the invention provides therapeutic agents comprising at least one therapeutic nucleoside and at least one targeting group. In certain embodiments, the invention provides therapeutic agents comprising at least one therapeutic nucleoside and at least one targeting group and at least one oligomeric compound, such as an antisense compound. In certain embodiments, the invention provides therapeutic agents comprising at least two therapeutic nucleosides. In certain embodiments, the invention provides therapeutic agents comprising at least two therapeutic nucleosides and at least one targeting group. In certain embodiments, the invention provides therapeutic agents comprising at least two therapeutic nucleoside and at least one targeting group and at least one oligomeric compound.

a. Certain Therapeutic Nucleosides

Certain therapeutic nucleosides suitable for use in the present invention have been described. See for example, L. P. Jordheim, D. Durantel, and C. Dumontet, "Advances in the development of nucleoside and nucleotide analogues for cancer and viral diseases" Nature Reviews Drug Discovery 12, 447-464 (2013). Such therapeutic nucleosides include, but are not limited to therapeutic nucleosides for use in treating cancer and viral infections, including but not limited to HIV, HCV, and HBV infections.

i. Certain Antiviral Therapeutic Nucleosides

In certain embodiments, the therapeutic nucleosides used in the present invention are antiviral therapeutic nucleosides. For example, in certain embodiments, the therapeutic nucleoside comprises the following structure:

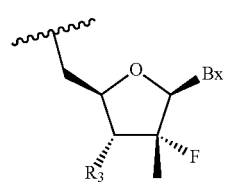

wherein $R_3$ is hydroxyl or a cleavable moiety with additional substituents; and Bx is a modified or unmodified nucleobase.

In certain such embodiments, the therapeutic nucleoside comprises the following structure:

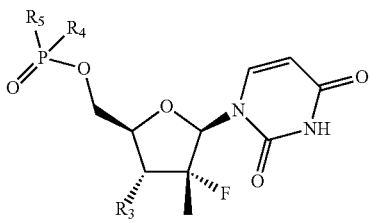

wherein $R_3$ is hydroxyl or the targeting group; and
$R_4$ and $R_5$ are each independently selected from phenoxy, $NHCH(CH_3)C(O)OiPr$, alkoxy, alkylamino, hydroxyl, an internucleoside linking group linking the therapeutic nucleoside to another nucleoside or to an oligomeric compound, and the targeting group;
provided that at least one of $R_3$, $R_4$, and $R_5$ is a targeting group.

In certain embodiments, the therapeutic nucleoside comprises the following structure:

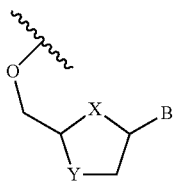

wherein B is a modified or unmodified nucleobase;
X is O or $CCH_2$;
Y is S or $CR_6R_7$; and
$R_6$ and $R_7$ are each independently selected from hydrogen, hydroxyl, O-L-valinyl ester, and the targeting group.

In certain such embodiments, the modified or unmodified nucleobase is selected from among: adenine, uracil, cytosine, 5-methylcytosine, guanine, thymine, and 5-fluorocytosine.

In certain embodiments, a therapeutic nucleoside comprises an acyclic sugar surrogate.

1. Certain Anti-HBV Therapeutic Nucleosides

In certain embodiments, the therapeutic nucleoside can be used to treat HBV infections. In certain embodiments, the therapeutic nucleoside is Telbivudine. In certain embodiments, the therapeutic nucleoside is Entecavir. In certain embodiments, the therapeutic nucleoside is Lamivudine. In certain embodiments, the therapeutic nucleoside is Adefovir dipivoxil. In certain embodiments, the therapeutic nucleoside is Tenofovir disoproxil fumarate. In certain embodiments, the therapeutic nucleoside is Sovaldi. In certain embodiments, a method of treating HBV infection comprises administering a combination of therapeutic nucleosides or a combination of at least one therapeutic nucleoside with at least one non-nucleoside therapeutic agent.

2. Certain Anti-HCV Therapeutic Nucleosides

In certain embodiments, the therapeutic nucleoside can be used to treat HCV infections. In certain embodiments, the therapeutic nucleoside is IDX21437. In certain embodiments, the therapeutic nucleoside is IDX21459. In certain embodiments, the therapeutic nucleoside is Ribavirin. In certain embodiments, the therapeutic nucleoside is Taribavirin. In certain embodiments, the therapeutic nucleoside is Mericitabine. In certain embodiments, the therapeutic nucleoside is ASL-2200. In certain embodiments, the therapeutic nucleoside is Sovaldi. In certain embodiments, a method of treating HCV infection comprises administering a combination of therapeutic nucleosides or a combination of at least one therapeutic nucleoside with at least one non-nucleoside therapeutic agent.

b. Certain Targeting Groups

In certain embodiments, therapeutic agents comprise at least one targeting group. In certain embodiments, such targeting group comprises at least one ligand. In certain embodiments, a targeting group comprises a carbohydrate or carbohydrate cluster. In certain embodiments, a targeting group comprises more than one ligand. In certain such embodiments, the targeting group comprises a branching group to allow attachment of more than one ligand. In certain embodiments, a targeting group is attached to a therapeutic nucleoside by a cleavable moiety, such as a cleavable bond or cleavable nucleoside. In certain such embodiments, such cleavable moiety allows the targeting group to be cleaved from the remainder of the therapeutic agent. In certain embodiments, the cleavable moiety is a cleavable bond. In certain embodiments, the cleavable moiety is a group of atoms comprising at least one cleavable bond. In certain embodiments, the targeting group comprises one or more tether and/or one or more target group linker. In certain such embodiments, such groups are designed to provide suitable separation among functional groups to allow desired interactions, for example interaction of ligands with cell surface receptors. The various portions of targeting groups are discussed separately below. One may use such portions in any combination, including omitting certain portions, to create various targeting groups.

1. Certain Ligands

In certain embodiments, the present disclosure provides targeting group comprising at least one ligand. In certain embodiments, each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamine and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine (GalNAc), 2-acetamido-2-deoxy-D-galactopyranose, 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3, 4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments one or more ligand has a structure selected from among:

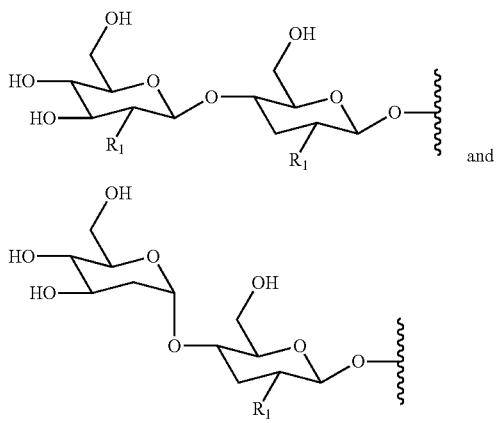

wherein each $R_1$ is selected from OH and $NHCOCH_3$.

In certain embodiments one or more ligand has a structure selected from among:

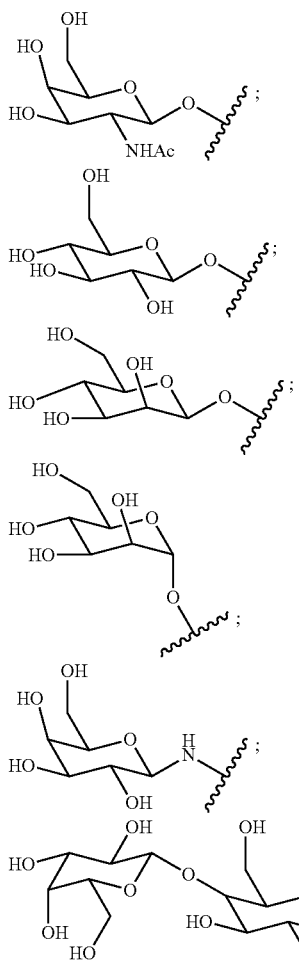

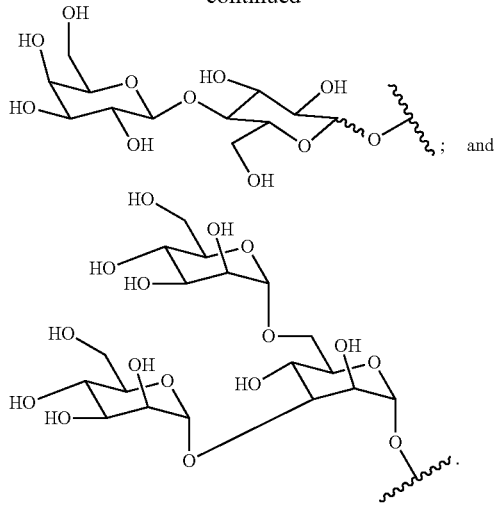

In certain embodiments one or more ligand has a structure selected from among:

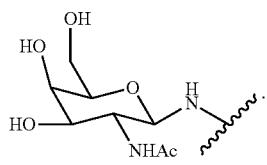

In certain embodiments one or more ligand has a structure selected from among:

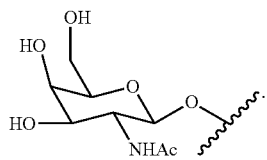

2. Certain Tethers

In certain embodiments, one or more ligand is attached to the remainder of the targeting group through a tether. In certain embodiments, tethers attach a ligand directly to a therapeutic nucleoside. In certain embodiments, a tether attaches a ligand to a branching group or a targeting group linker.

In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

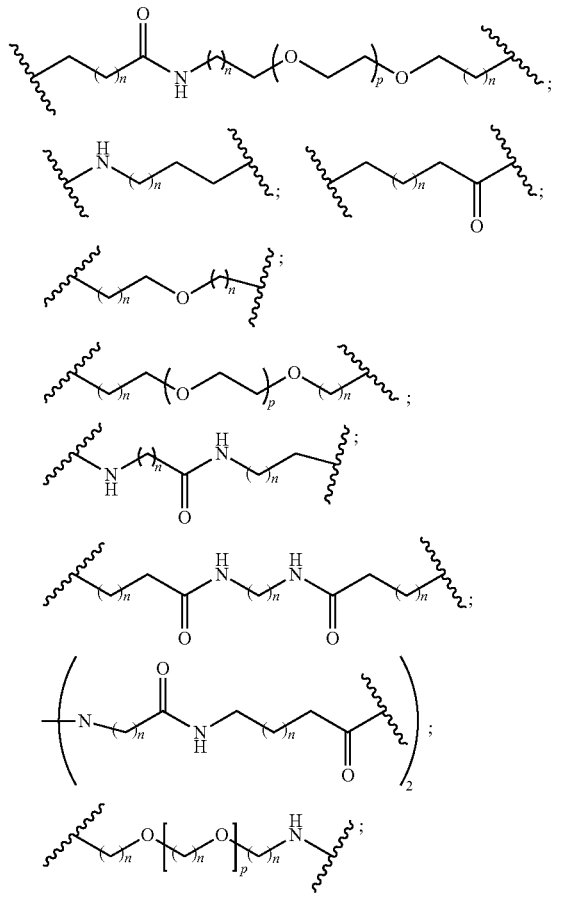

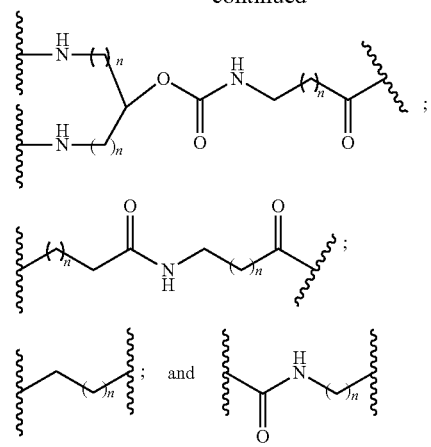

wherein each n is, independently, from 1 to 20; and each p is from 1 to about 6.

In certain embodiments, a tether has a structure selected from among:

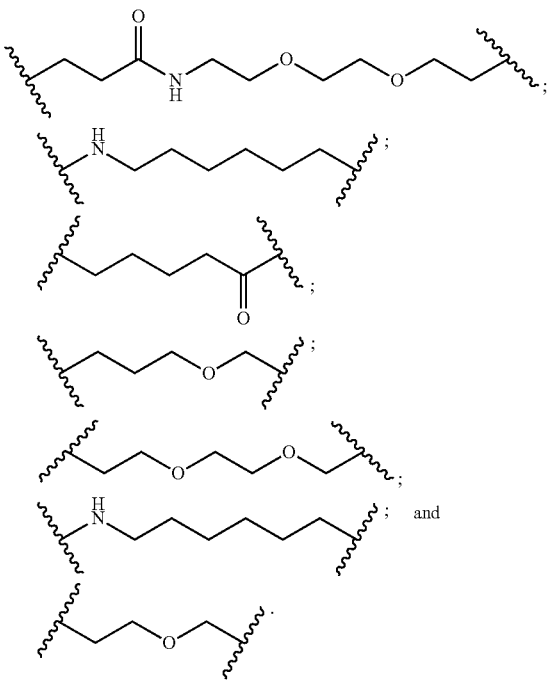

In certain embodiments, a tether has a structure selected from among:

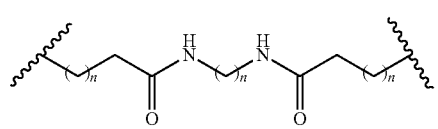

wherein each n is, independently, from 1 to 20.

In certain embodiments, a tether has a structure selected from among:

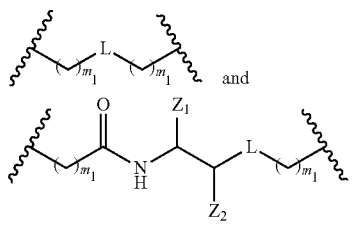 and wherein L is either a phosphorus linking group or a neutral linking group;
$Z_1$ is C(=O)O—$R_2$;
$Z_2$ is H, $C_1$-$C_6$ alkyl or substituted $C_1$-$C_6$ alkyl;
$R_2$ is H, $C_1$-$C_6$ alkyl or substituted $C_1$-$C_6$ alkyl; and
each $m_1$ is, independently, from 0 to 20 wherein at least one $m_1$ is greater than 0 for each tether.

In certain embodiments, a tether has a structure selected from among:

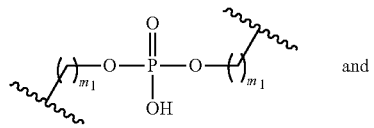

In certain embodiments, a tether has a structure selected from among:

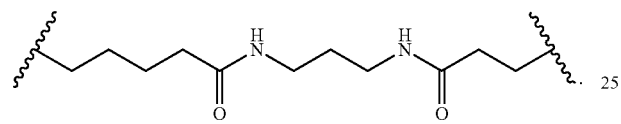 and

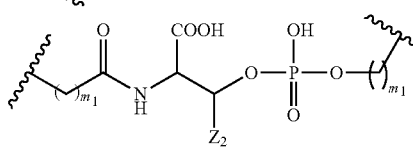

wherein $Z_2$ is H or $CH_3$; and
each $m_1$ is, independently, from 0 to 20 wherein at least one $m_1$ is greater than 0 for each tether.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Branching Groups

In certain embodiments, the targeting groups comprise more than one tethered or untethered ligand. Certain such targeting groups comprise one or more branching groups to accommodate such more that one ligand. In certain embodiments, the branching group attaches two or more tethers or ligands to a target group linker; to a cleavable moiety; or directly to a therapeutic nucleoside.

In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the targeting group does not include a branching group.

In certain embodiments, a branching group has a structure selected from among:

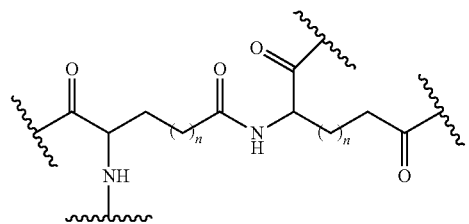;

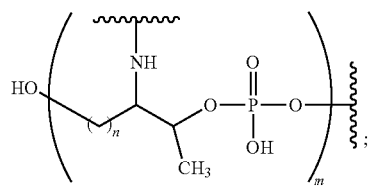;

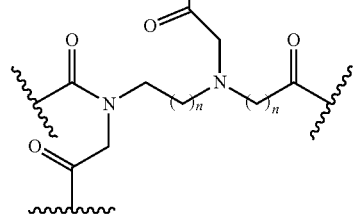;

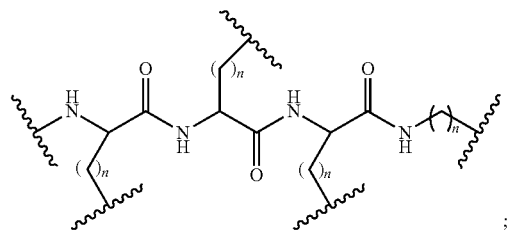;

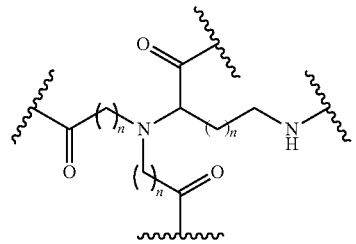;

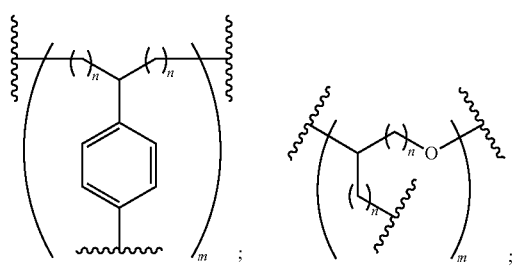;

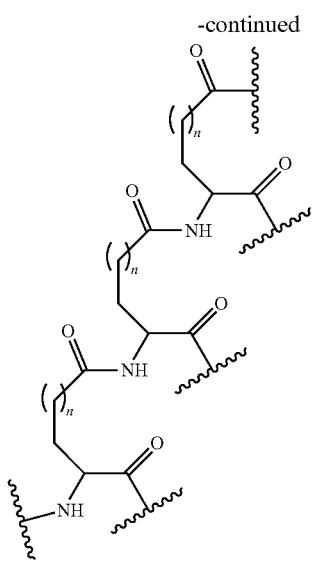
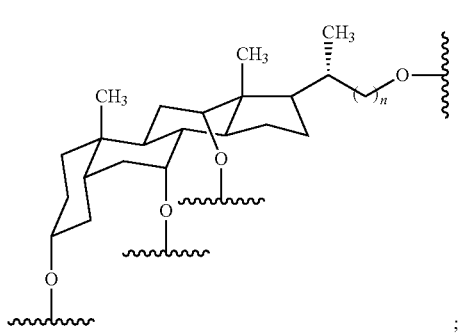
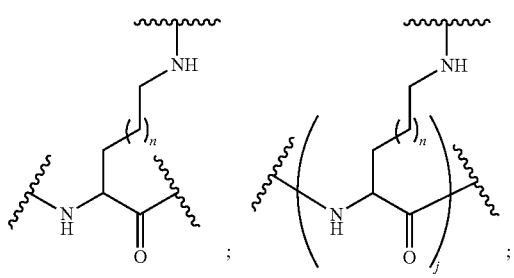
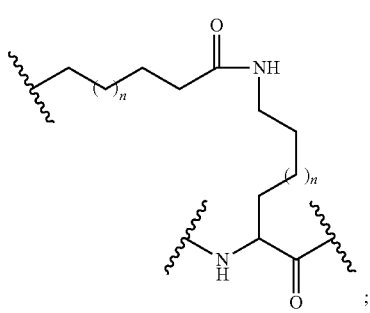
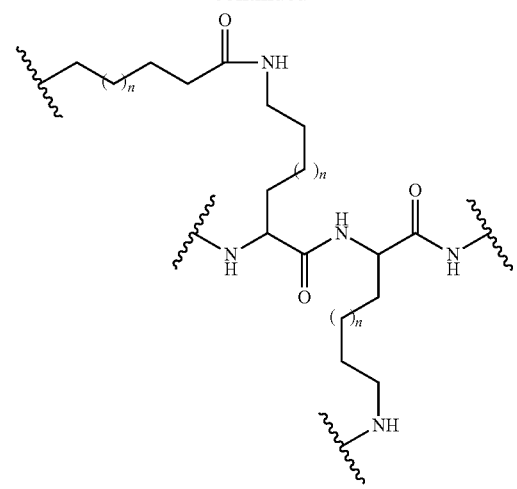
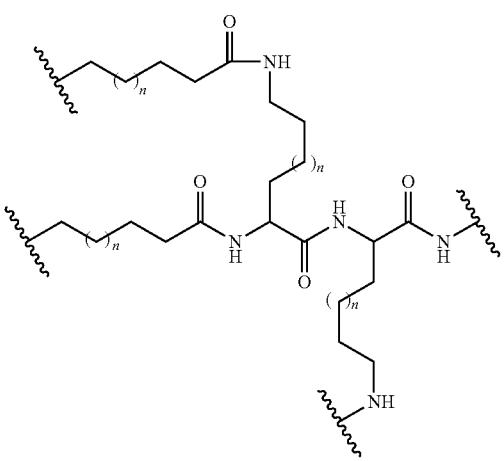
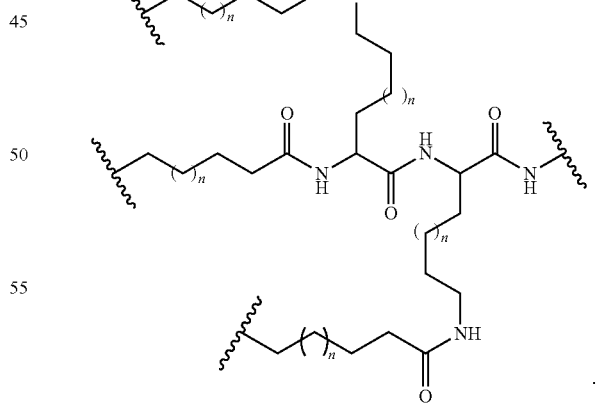
; and
wherein each n is, independently, from 1 to 20;
j is from 1 to 3; and
m is from 2 to 6.
In certain embodiments, a branching group has a structure selected from among:

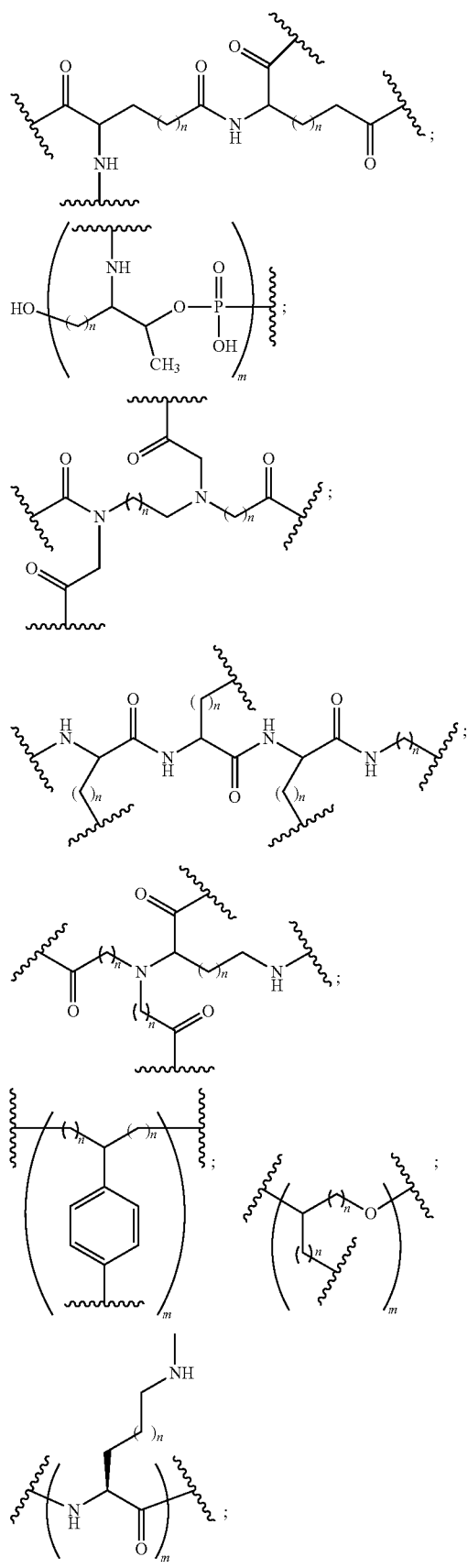
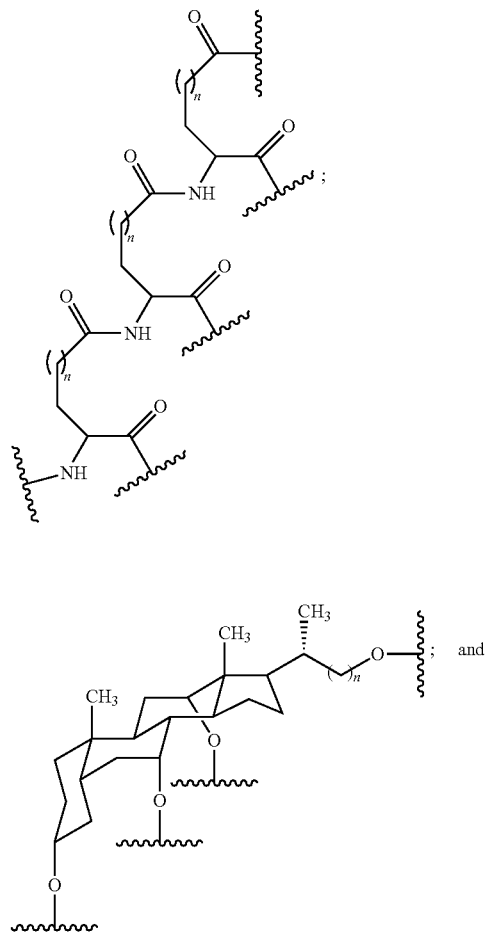
wherein each n is, independently, from 1 to 20; and m is from 2 to 6.
In certain embodiments, a branching group has a structure selected from among:
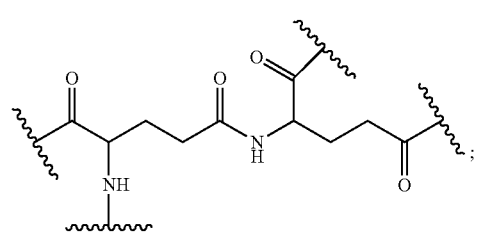

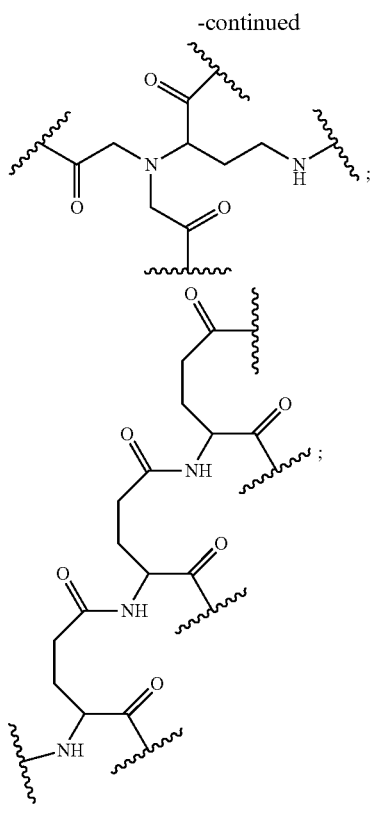
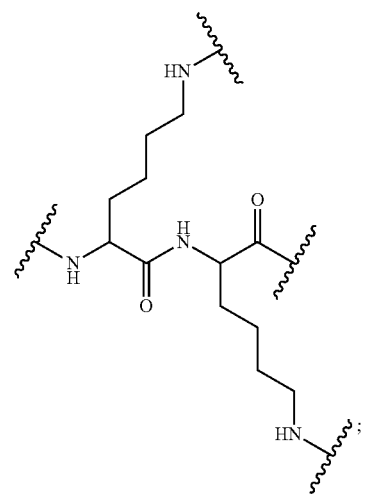
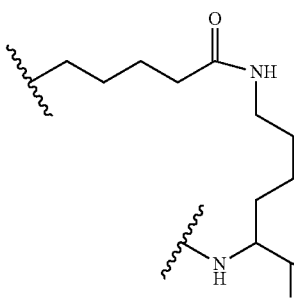
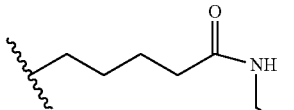
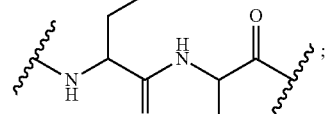
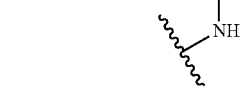

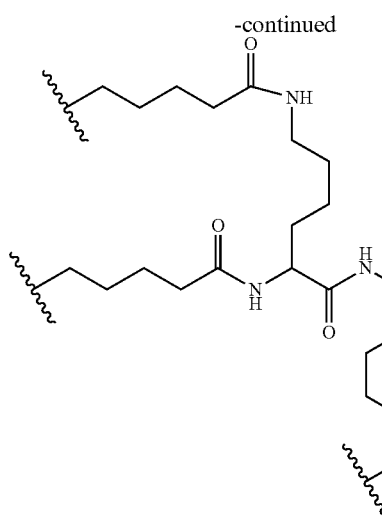

and

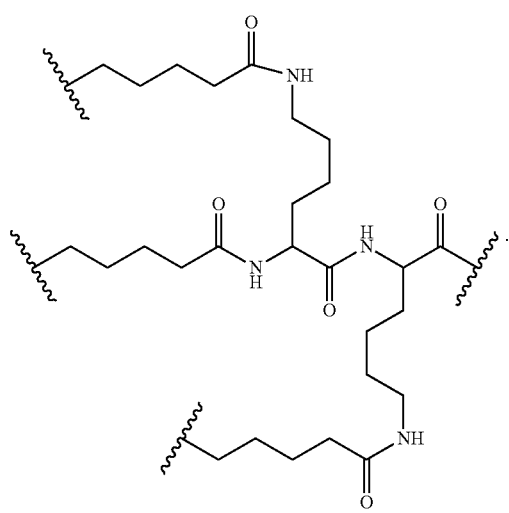 [SMILES: *CCCCC(=O)NCCCCC(NC(=O)C(CCCCNC(=O)CCCC*)NC(=O)CCCC*)C(*)=O]

In certain embodiments, a branching group has a structure selected from among:

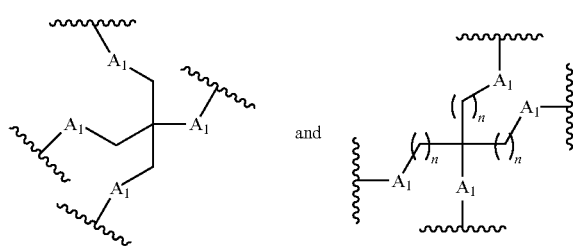

wherein each $A_1$ is independently, O, S, C=O or NH; and each n is, independently, from 1 to 20.

In certain embodiments, a branching group has a structure selected from among:

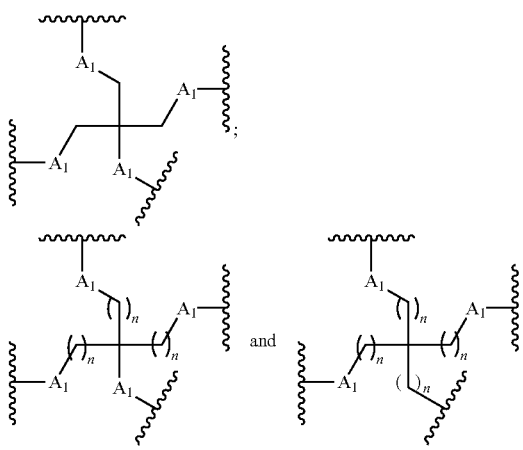

wherein each $A_1$ is independently, O, S, C=O or NH; and each n is, independently, from 1 to 20.

In certain embodiments, a branching group has a structure selected from among:

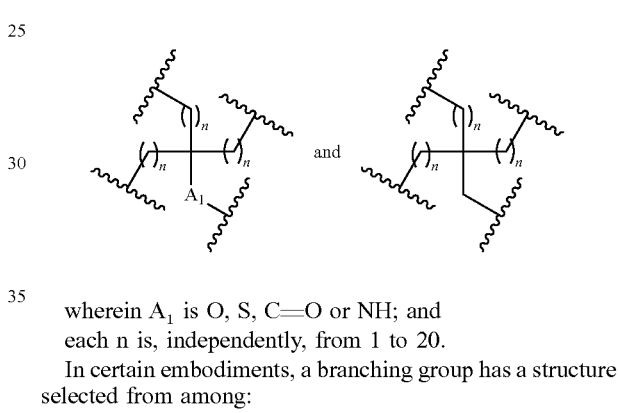

wherein $A_1$ is O, S, C=O or NH; and each n is, independently, from 1 to 20.

In certain embodiments, a branching group has a structure selected from among:

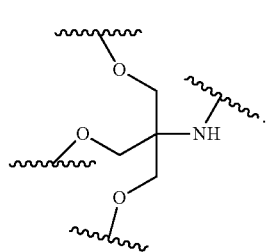 [SMILES: *NC(CO*)(CO*)CO*]

In certain embodiments, a branching group has a structure selected from among:

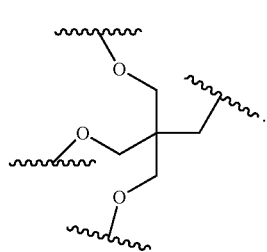 [SMILES: *CC(CO*)(CO*)CO*]

In certain embodiments, a branching group has a structure selected from among:

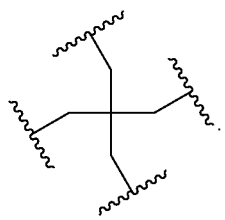 [SMILES: *CC(C*)(C*)C*]

4. Certain Targeting Group Linkers

In certain embodiments, the targeting groups comprise a targeting group linker. In certain such embodiments, the targeting group linker is covalently bound to a branching group and a cleavable moiety. In certain embodiments, the targeting group linker is covalently bound to a branching group and to the therapeutic nucleoside. In certain embodiments, the linker is covalently bound to a cell-targeting moiety. In certain embodiments, the targeting group linker further comprises a covalent attachment to a solid support. In certain embodiments, the targeting group linker further comprises a covalent attachment to a protein binding moiety. In certain embodiments, the targeting group linker further comprises a covalent attachment to a solid support and further comprises a covalent attachment to a protein binding moiety. In certain embodiments, the targeting group linker includes multiple positions for attachment of tethered ligands. In certain embodiments, the targeting group linker includes multiple positions for attachment of tethered ligands and is not attached to a branching group. In certain embodiments, the linker further comprises one or more cleavable bond. In certain embodiments, the targeting group does not include a targeting group linker.

In certain embodiments, the targeting group linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense compound. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the targeting group linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the targeting group linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a targeting group linker has a structure selected from among:

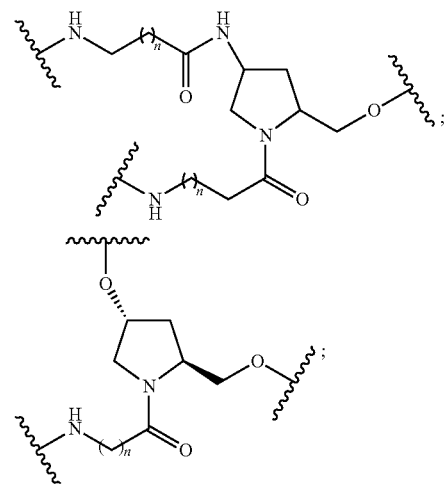

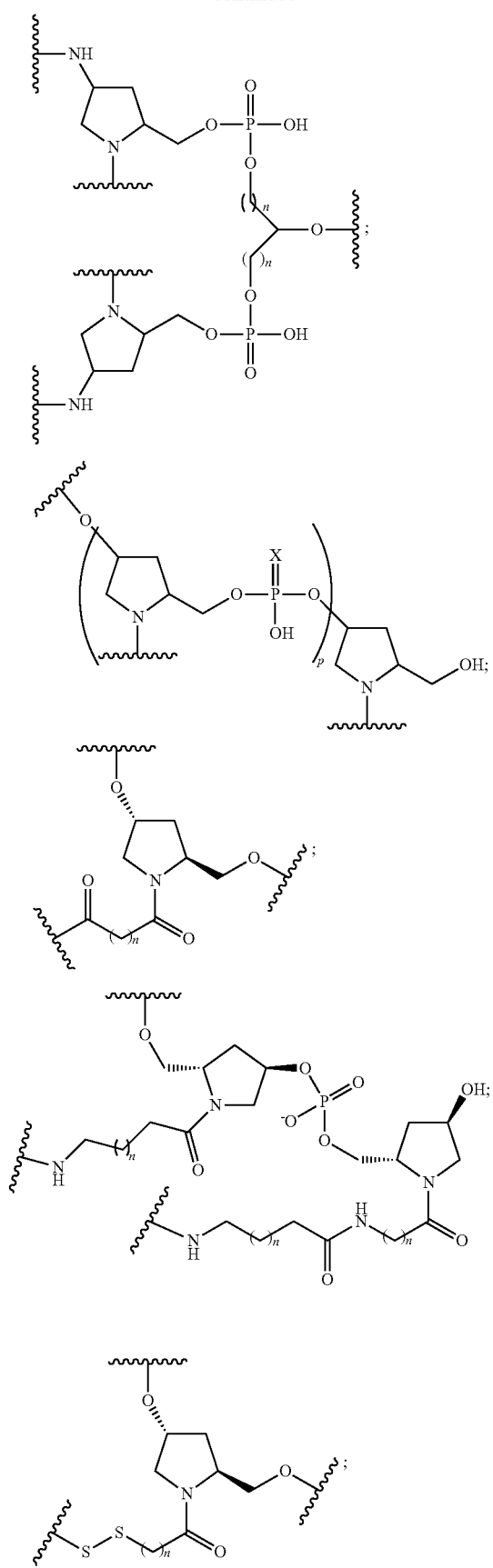
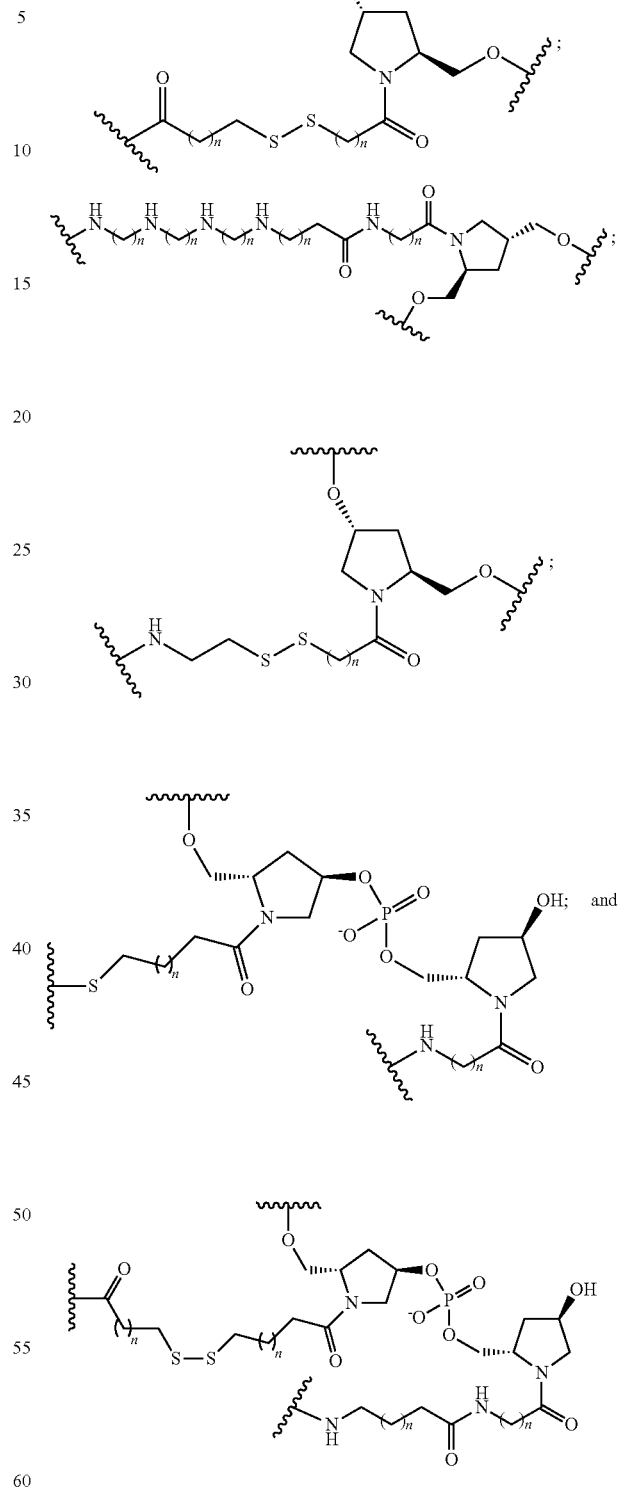
wherein each n is, independently, from 1 to 20; and p is from 1 to 6.
In certain embodiments, a targeting group linker has a structure selected from among:

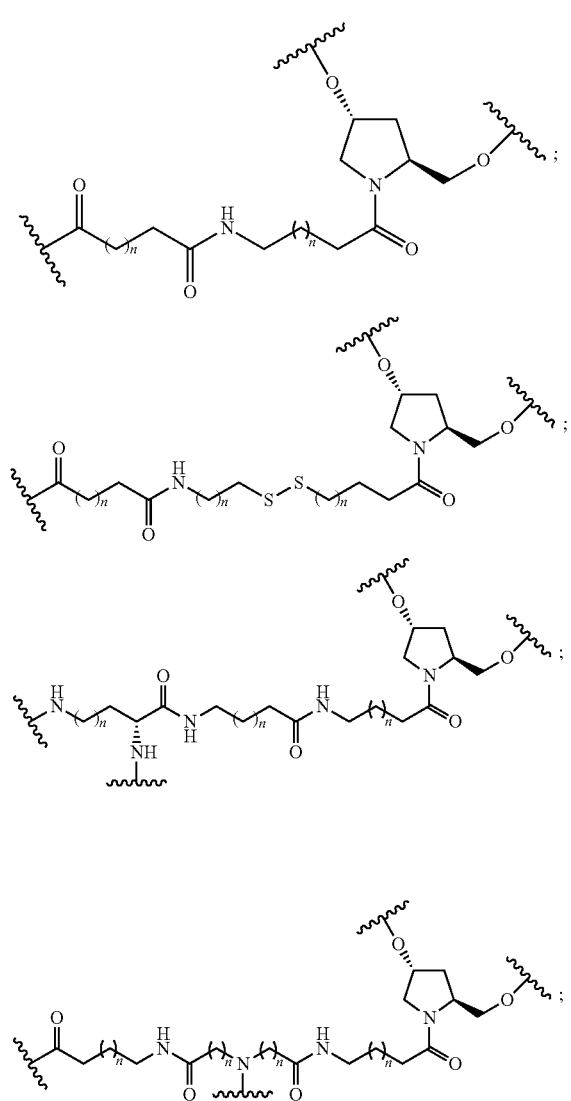
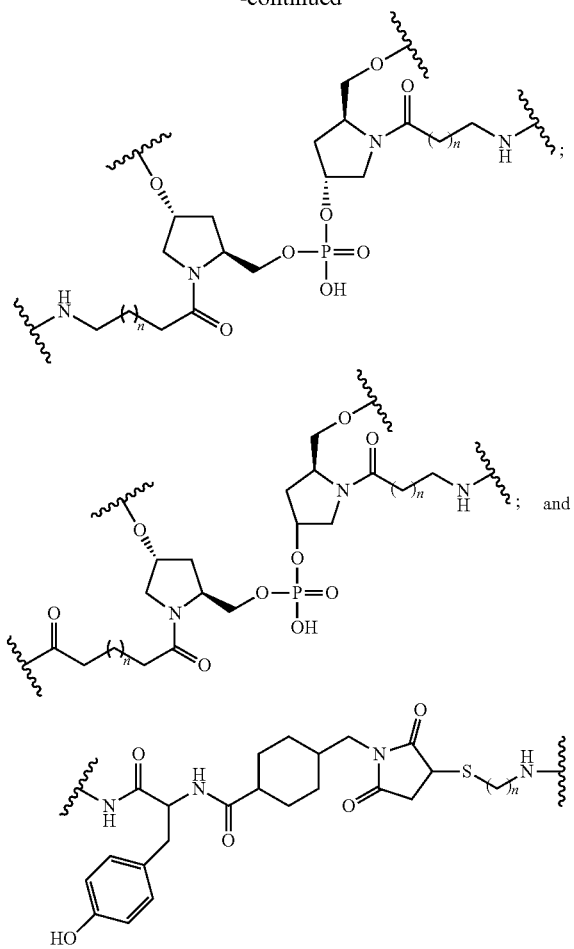
wherein each n is, independently, from 1 to 20.
In certain embodiments, a targeting group linker has a structure selected from among:
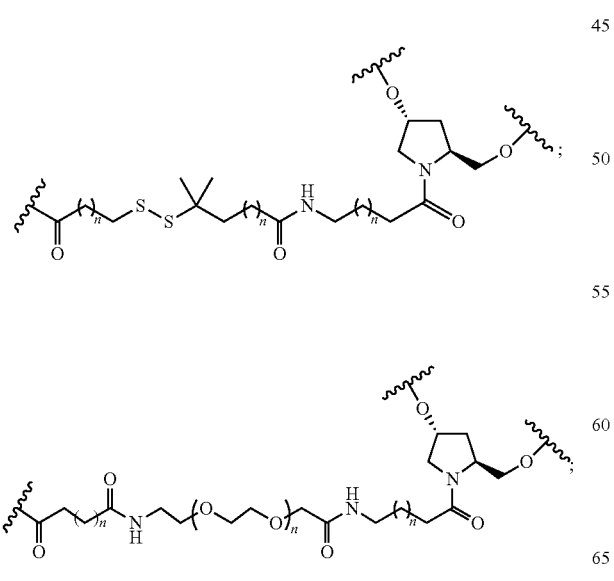
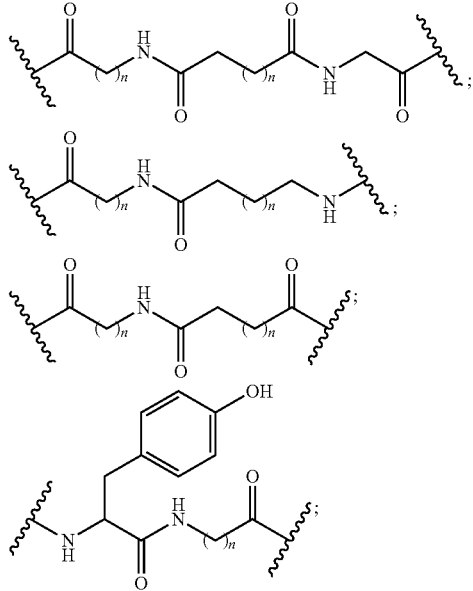

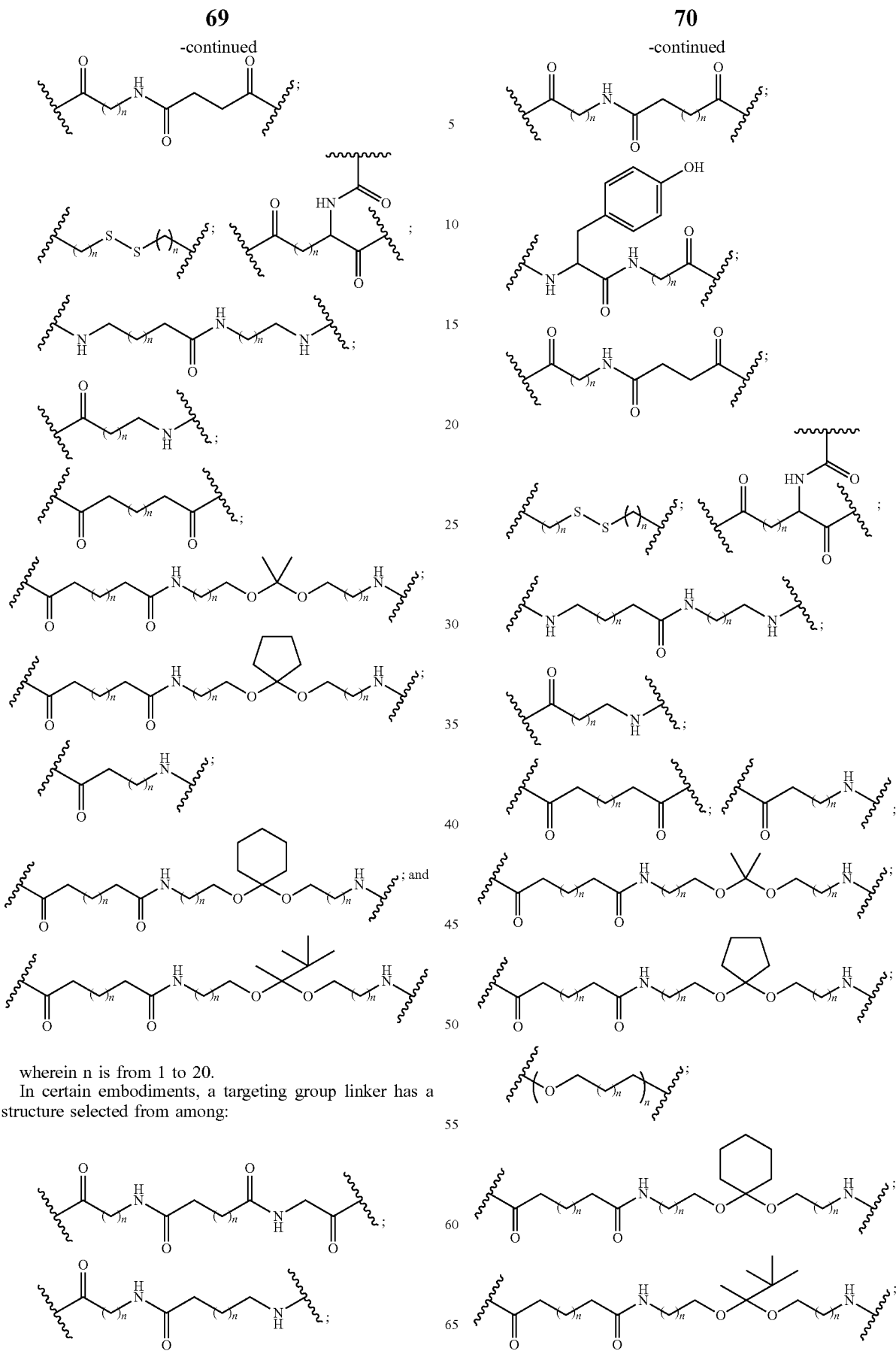
wherein n is from 1 to 20.
In certain embodiments, a targeting group linker has a structure selected from among:

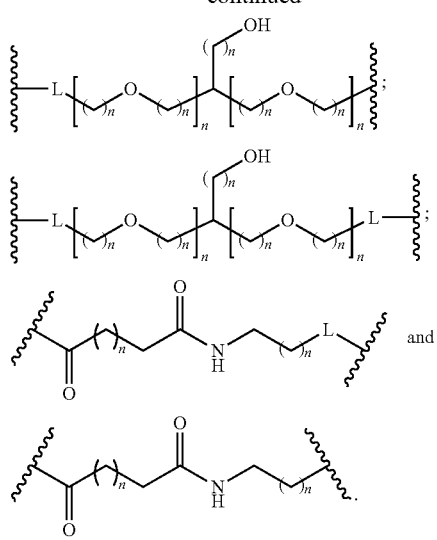
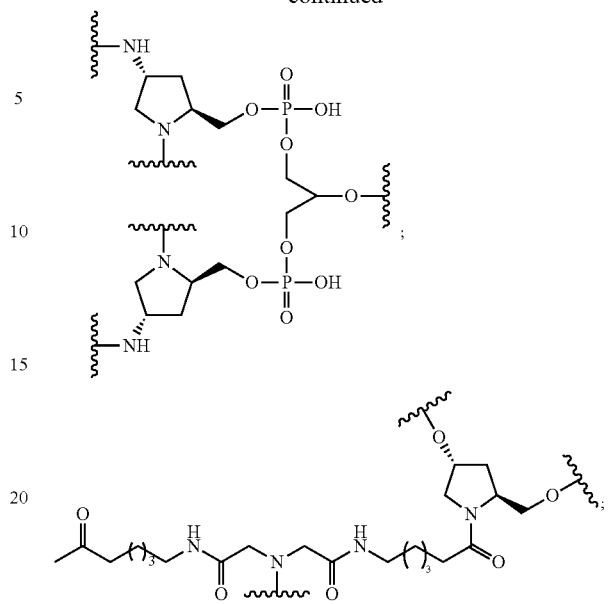
wherein each L is, independently, a phosphorus linking group or a neutral linking group; and
each n is, independently, from 1 to 20.
In certain embodiments, a targeting group linker has a structure selected from among:
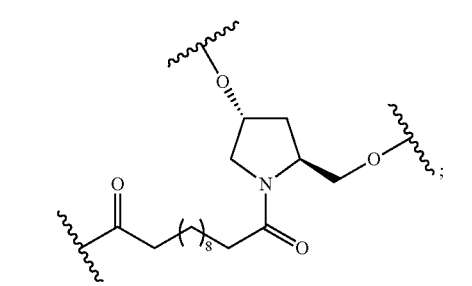
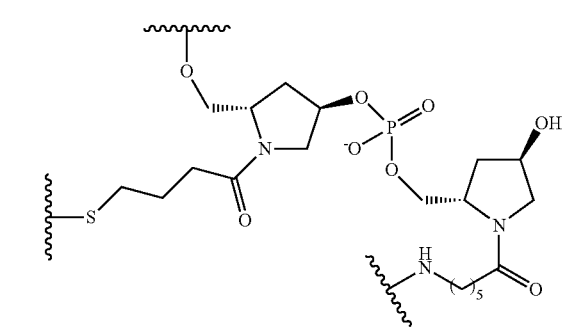
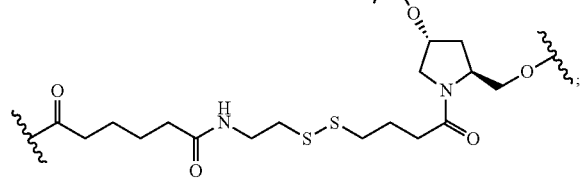
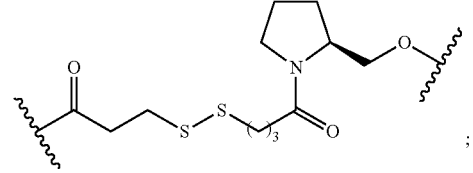
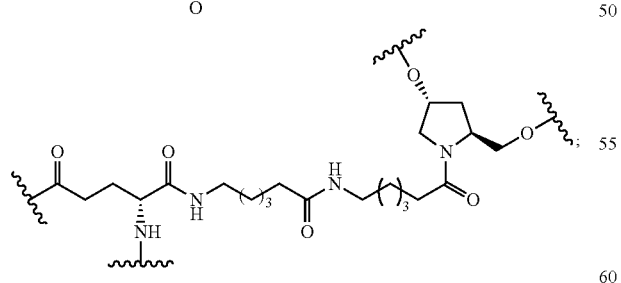
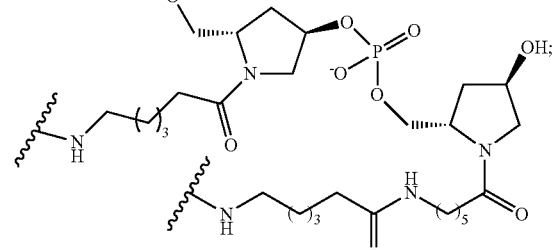
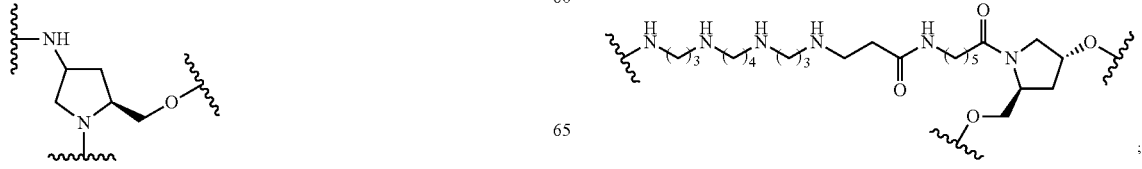

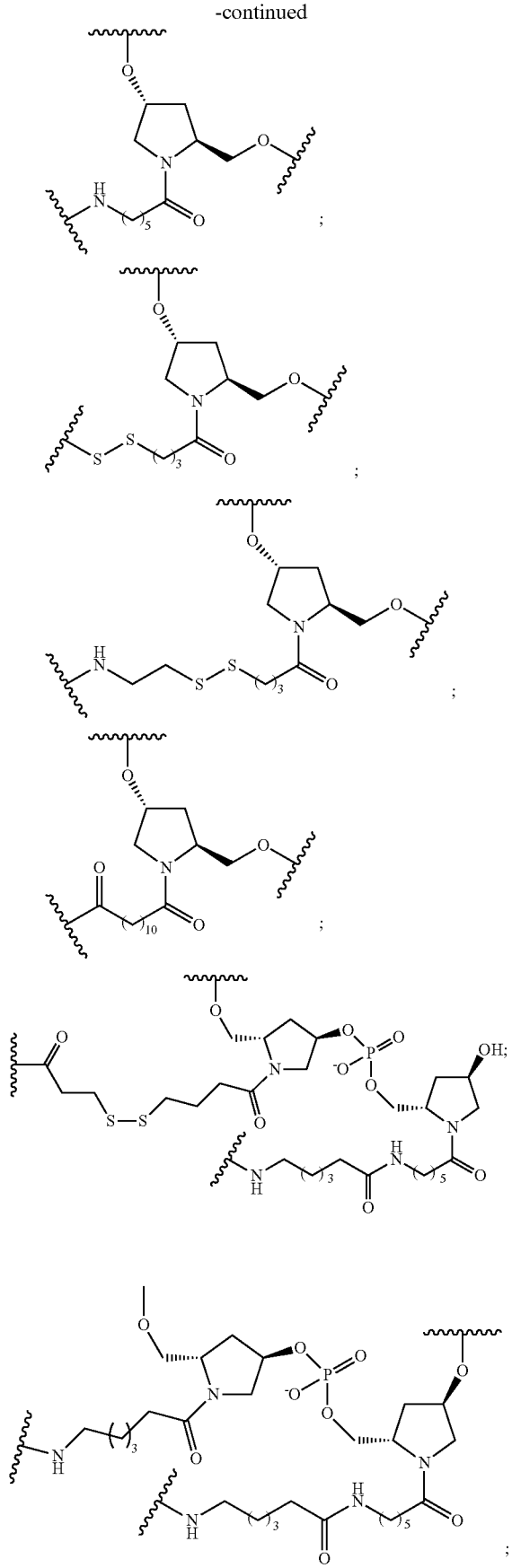
In certain embodiments, a targeting group linker has a structure selected from among:

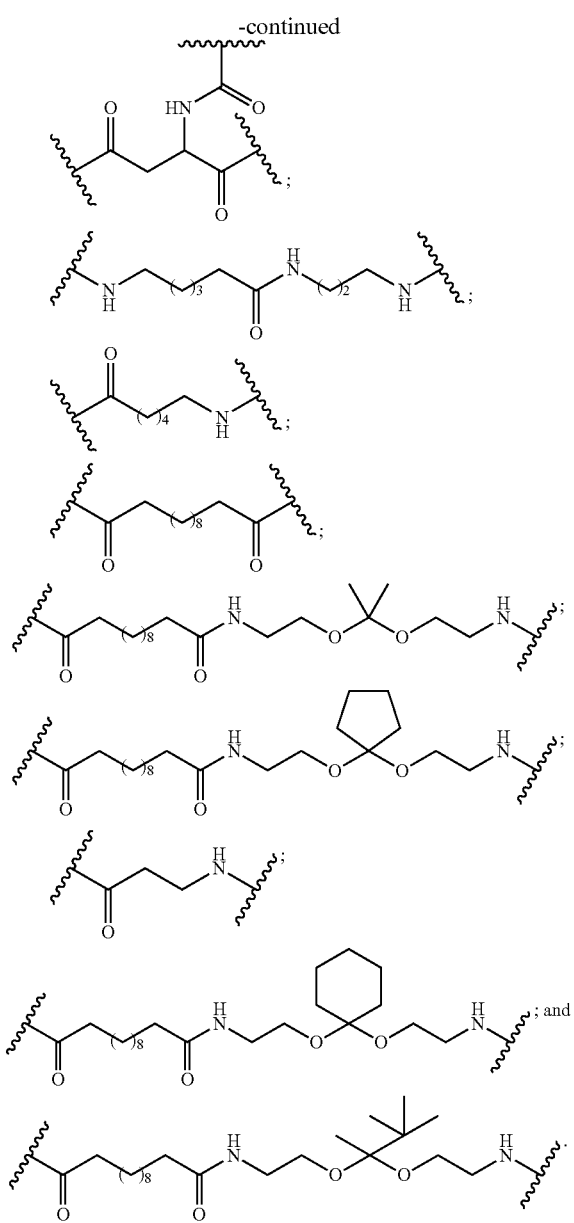
In certain embodiments, a targeting group linker has a structure selected from among:
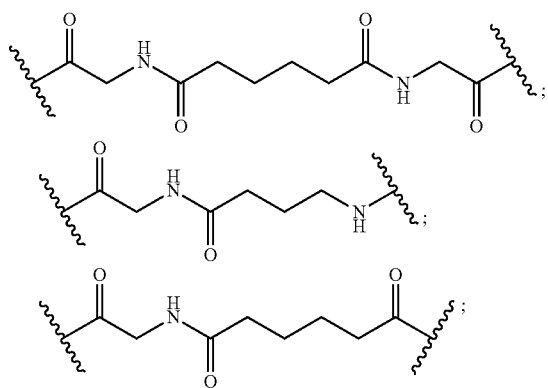
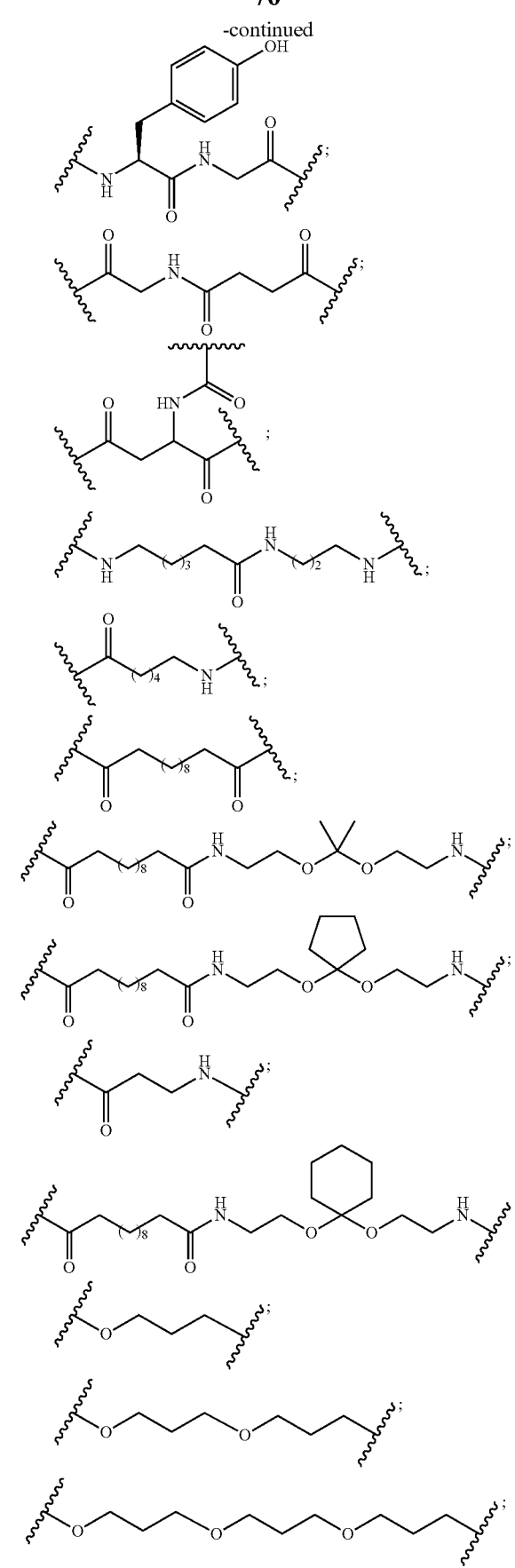

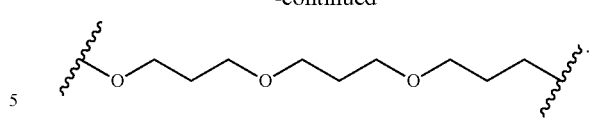

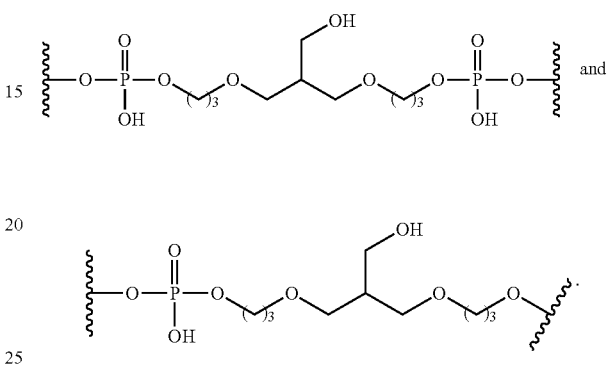

In certain embodiments, a targeting group linker has a structure selected from among:

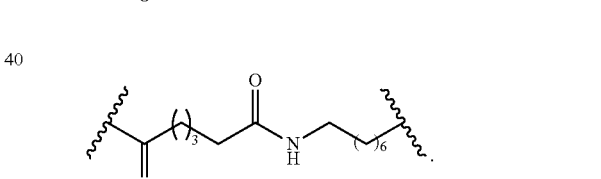

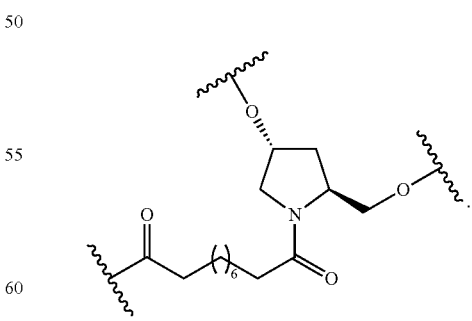

In certain embodiments, a targeting group linker has a structure selected from among:

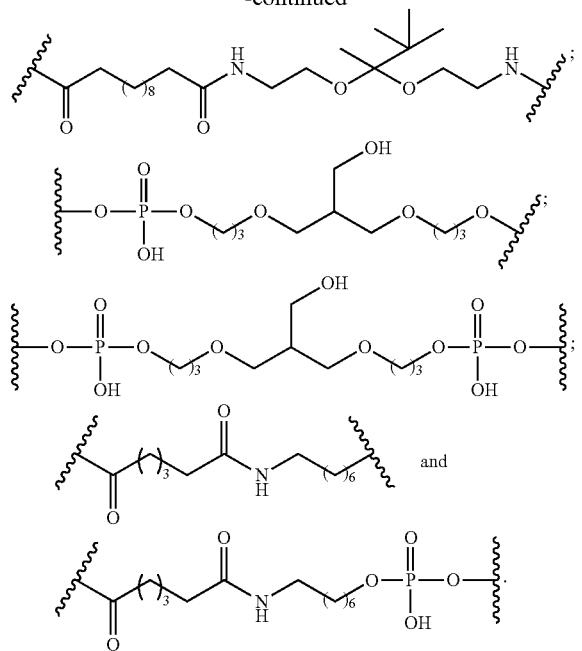

wherein n is from 1 to 20.

In certain embodiments, a targeting group linker has a structure selected from among:

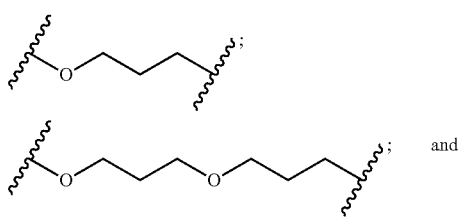

In certain embodiments, a targeting group linker has a structure selected from among:

In certain embodiments, the targeting group linker has the structure:

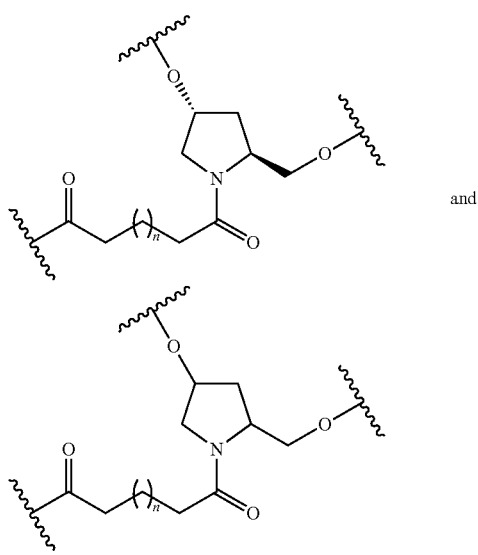

ii. Certain Targeting Groups

In certain embodiments, targeting groups comprise any combination of the structural features above. In certain such embodiments, targeting groups have the following structure:

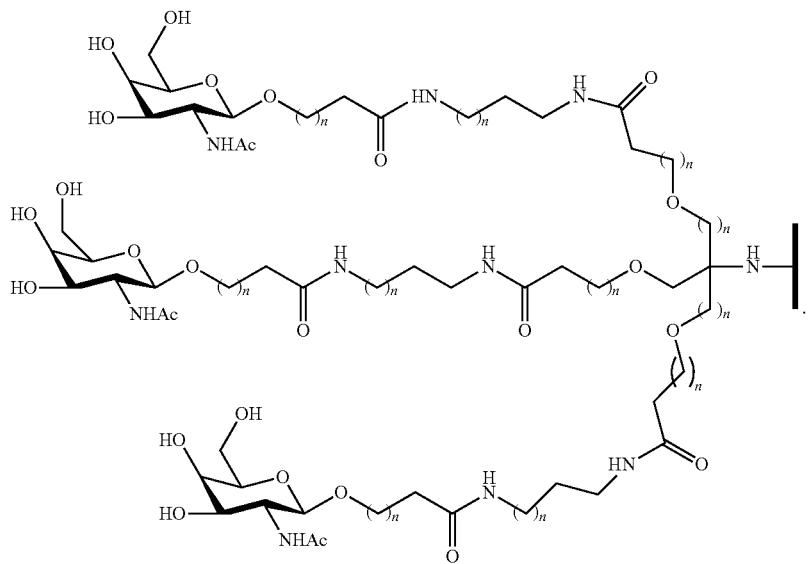
wherein each n is, independently, from 1 to 20.
In certain such embodiments, targeting groups have the following structure:
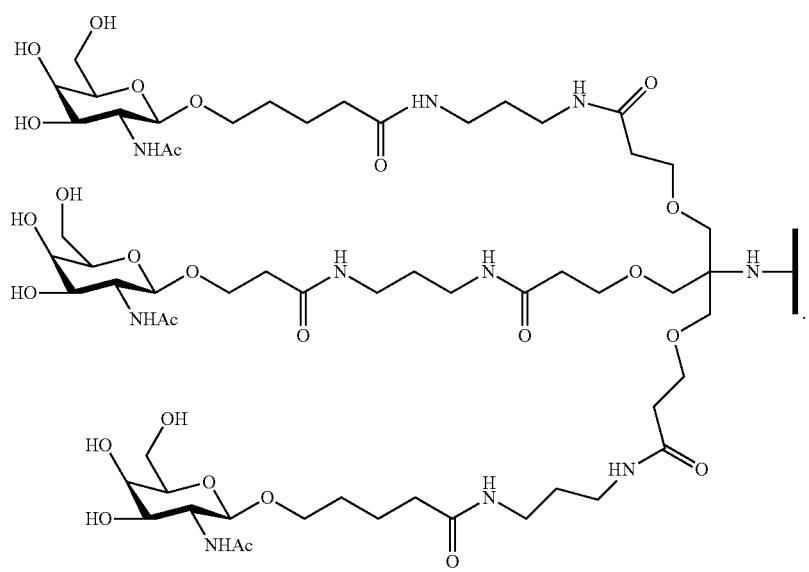
In certain such embodiments, targeting groups have the following structure:

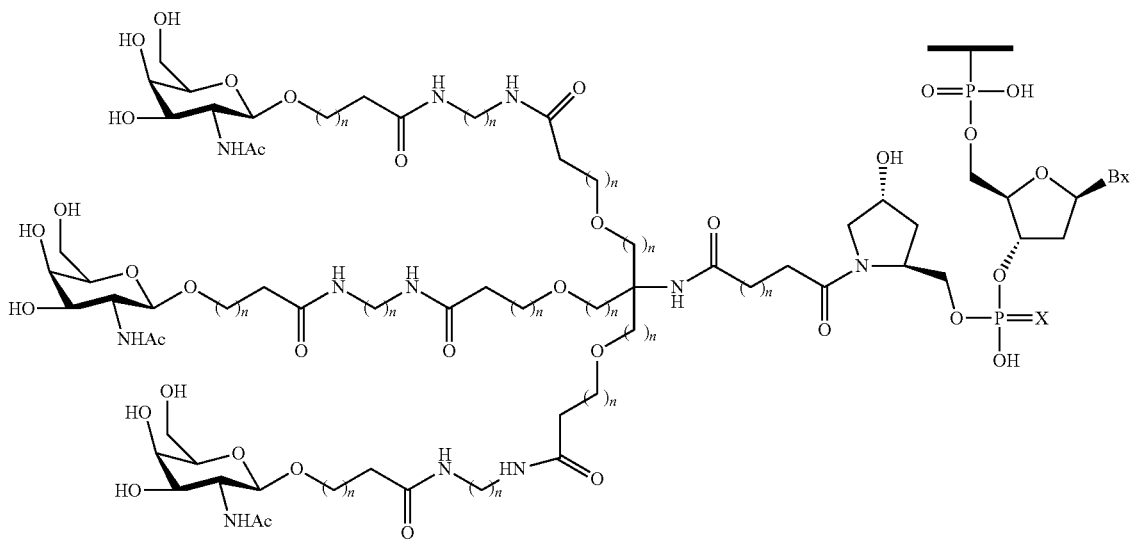
wherein each n is, independently, from 1 to 20;
Z is H or a linked solid support;
Q is an antisense compound;
X is O or S; and
Bx is a heterocyclic base moiety.
In certain such embodiments, targeting groups have the following structure:
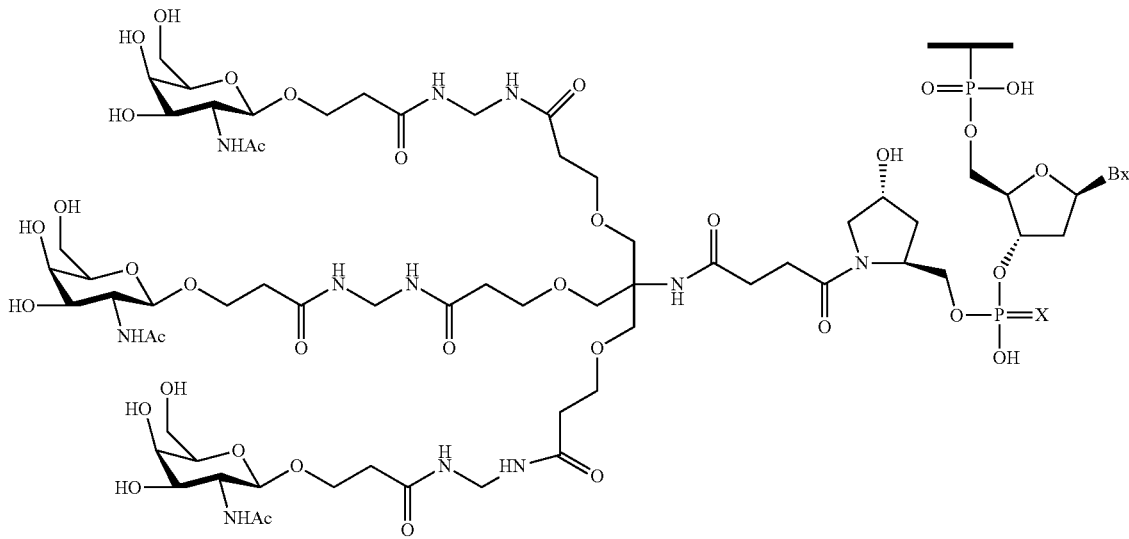
In certain such embodiments, targeting groups have the following structure:

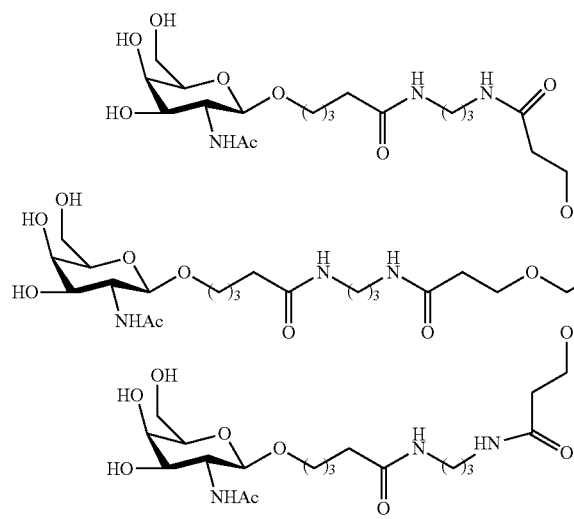
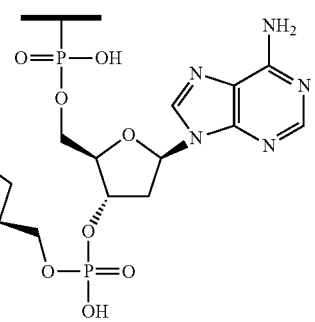
In certain such embodiments, targeting groups have the following structure:
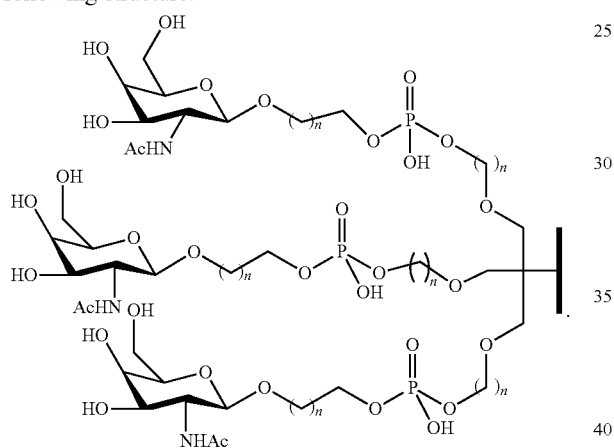
wherein each n is, independently, from 1 to 6.
In certain such embodiments, targeting groups have the following structure:
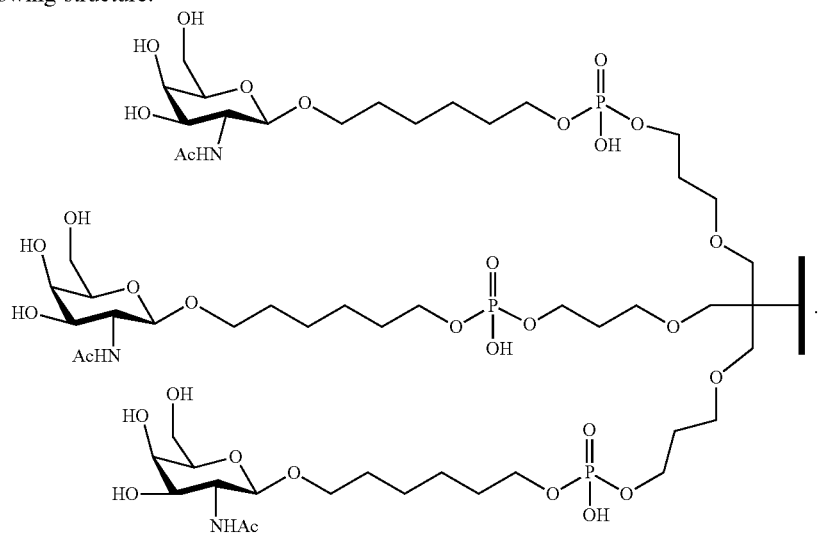

In certain such embodiments, targeting groups have the following structure:
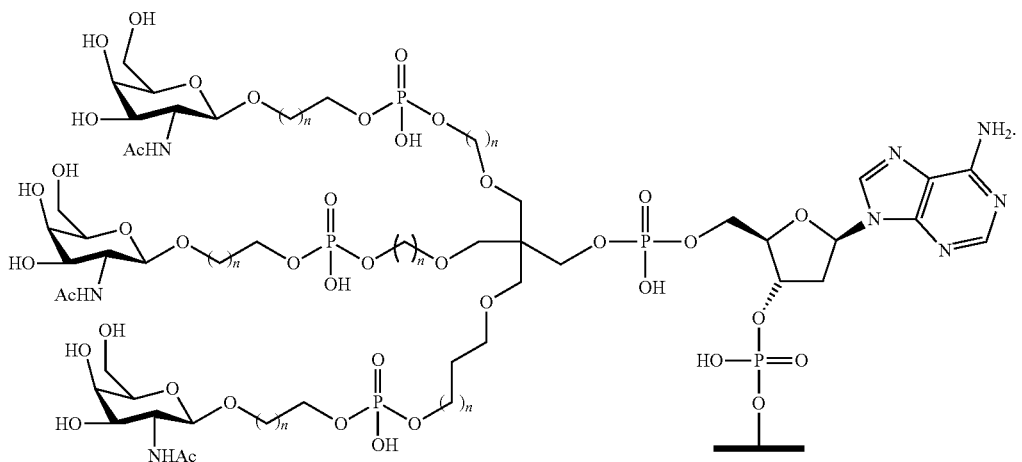
wherein each n is, independently, from 1 to 6.
In certain such embodiments, targeting groups have the following structure:
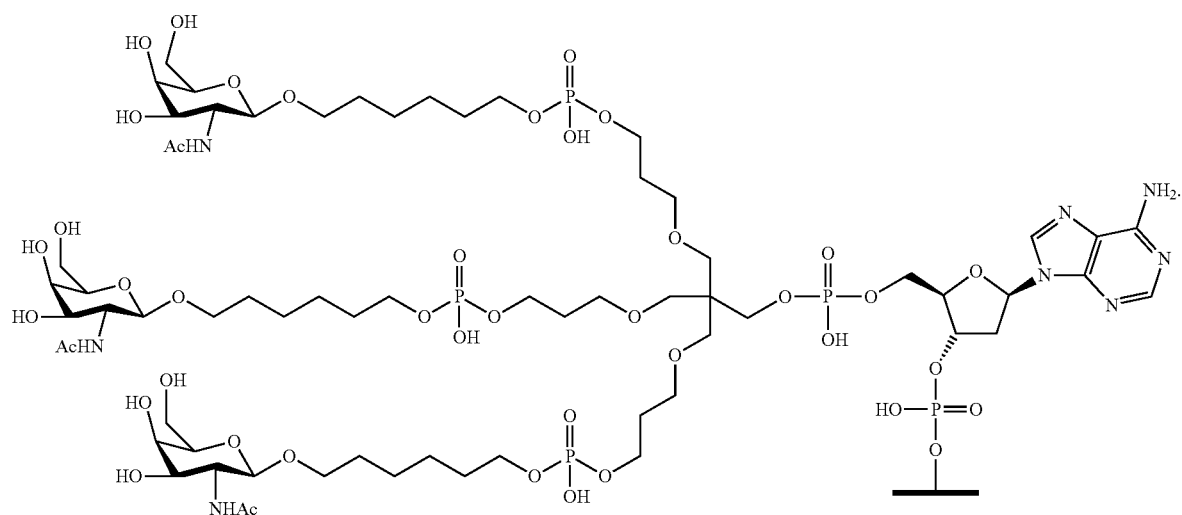
In certain such embodiments, targeting groups have the following structure:

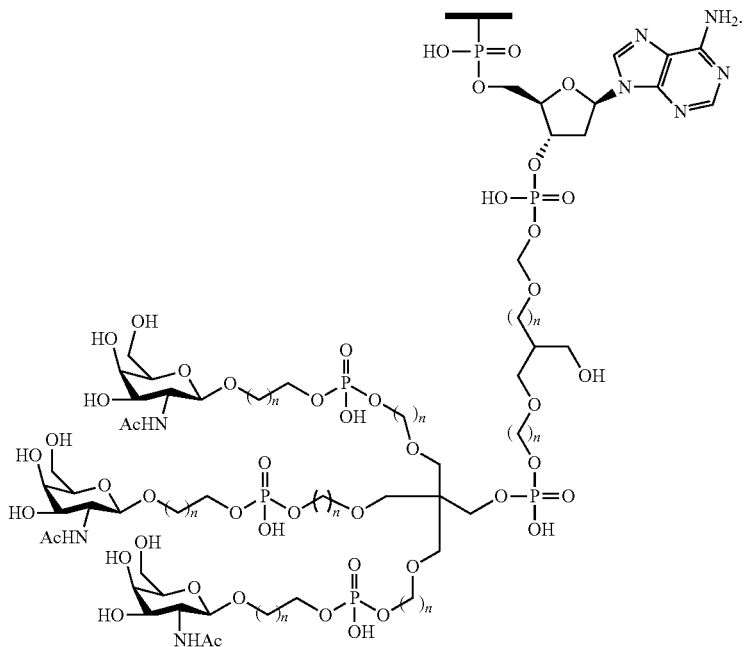

wherein each n is, independently, from 1 to 6.

In certain such embodiments, targeting groups have the following structure:

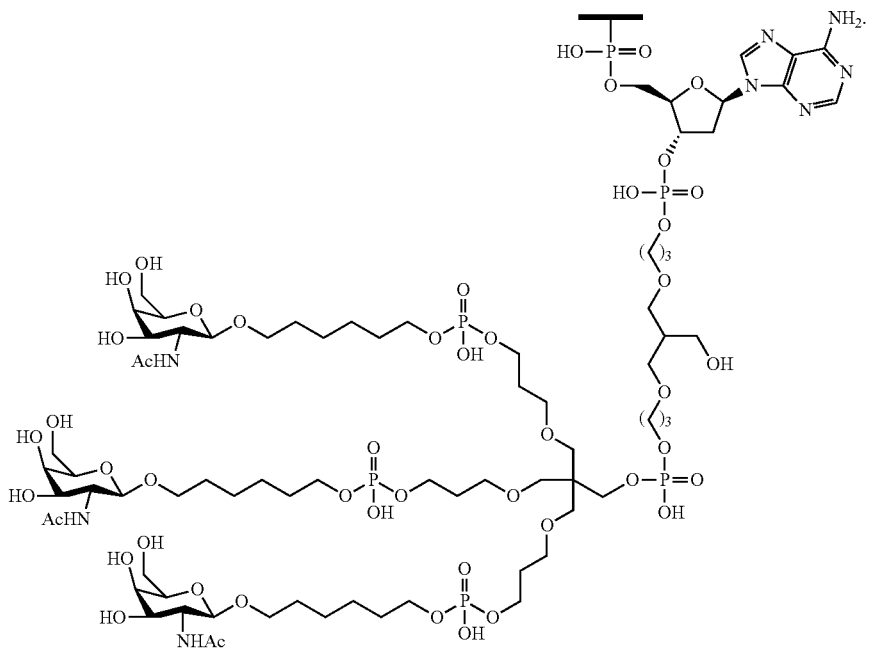

In certain embodiments, targeting groups do not comprise a pyrrolidine.

Additional target groups may be found in the art, sometimes referred to as conjugate groups in the context of oligonucleotides. Representative United States patents, United States patent application publications, and international patent application publications that teach the preparation of certain of the above noted therapeutic agents, target groups, conjugated antisense compounds, tethers, linkers, branching groups, ligands, cleavable moieties as well as other modifications include without limitation, U.S. Pat. No. 5,994,517, U.S. Pat. No. 6,300,319, U.S. Pat. No. 6,660,720, U.S. Pat. No. 6,906,182, U.S. Pat. No. 7,262,177, U.S. Pat. No. 7,491,805, U.S. Pat. No. 8,106,022, U.S. Pat. No. 7,723,509, US 2006/0148740, US 2011/0123520, WO 2013/033230 and WO 2012/037254, each of which is incorporated by reference herein in its entirety.

Representative publications that teach the preparation of certain of the above noted targeting groups, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

c. Certain Cleavable Moieties

In certain embodiments, a therapeutic agent comprises one or more cleavable moieties. In certain embodiments, a targeting group is attached to a therapeutic nucleoside via a cleavable moiety. In certain embodiments, two or more therapeutic nucleosides are joined together by a cleavable moiety. In certain embodiments, a cleavable moiety is a cleavable bond. In certain embodiments, a cleavable moiety comprises a cleavable bond. In certain embodiments a cleavable moiety is a cleavable nucleoside. In certain such embodiments, a cleavable nucleoside is a modified or unmodified nucleoside attached through a cleavable bond, such as a phosphodiester bond.

In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense compound by a phosphodiester linkage and is attached to the linker by a phosphodiester or phosphorothioate linkage. In certain embodiments, the cleavable moiety is 2'-deoxy adenosine that is attached to the 3' position of the antisense compound by a phosphodiester linkage and is attached to the linker by a phosphodiester or phosphorothioate linkage. In certain embodiments, the cleavable moiety is 2'-deoxy adenosine that is attached to the 3' position of the antisense compound by a phosphodiester linkage and is attached to the linker by a phosphodiester linkage.

In certain embodiments, the cleavable moiety is attached to the 3' position of the antisense compound. In certain embodiments, the cleavable moiety is attached to the 5' position of the antisense compound. In certain embodiments, the cleavable moiety is attached to a 2' position of the antisense compound. In certain embodiments, the cleavable moiety is attached to the antisense compound by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage.

In certain embodiments, the cleavable moiety is cleaved after the complex has been administered to an animal only after being internalized by a targeted cell. Inside the cell the cleavable moiety is cleaved thereby releasing the active antisense compound. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

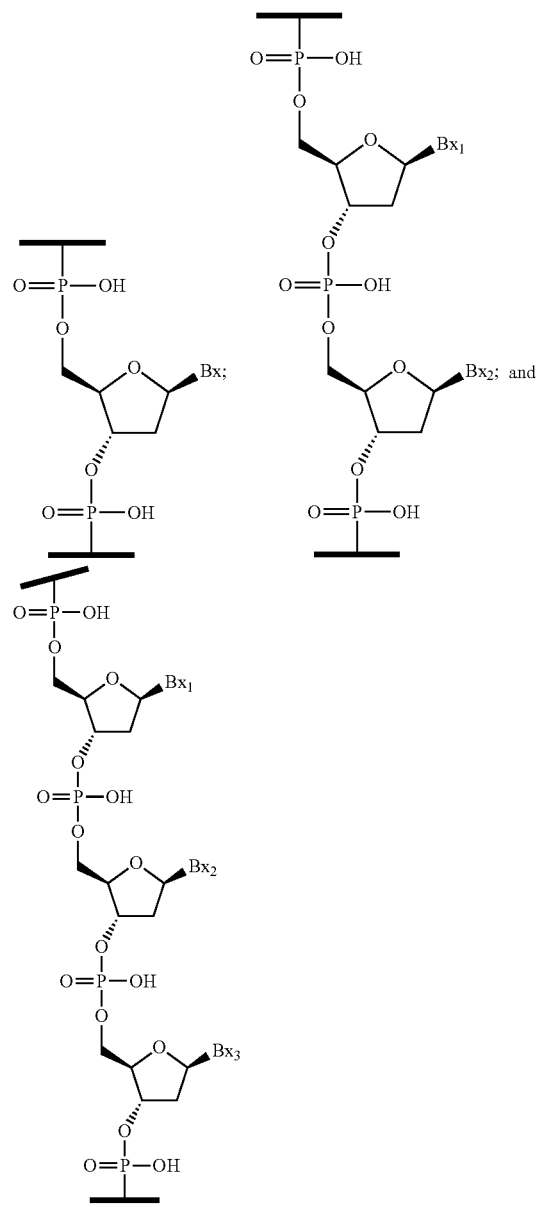

wherein each of Bx, Bx$_1$, Bx$_2$, and Bx$_3$ is independently a heterocyclic base moiety. In certain embodiments, the cleavable moiety has a structure selected from among the following:

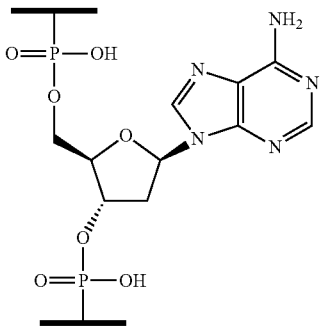

In certain embodiments, the cleavable moiety has the structure:

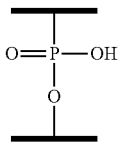

C. Certain Oligomeric Compounds

In certain embodiments, therapeutic agents comprise one or more oligomeric compound. In certain such embodiments, such oligomeric compound comprises or consists of an antisense compound. Such antisense compounds comprise linked nucleosides, each nucleoside comprising a sugar moiety and a nucleobase. The structure of such antisense compounds may be considered in terms of chemical features (e.g., modifications and patterns of modifications) and nucleobase sequence (e.g., sequence of antisense compound, identity and sequence of target nucleic acid).

i. Certain Chemistry Features

In certain embodiments, antisense compound comprise one or more modification. In certain such embodiments, antisense compounds comprise one or more modified nucleosides and/or modified internucleoside linkages. In certain embodiments, modified nucleosides comprise a modified sugar moiety and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N (R)—O— or, —C(R$_a$R$_b$)—O—N(R)—; 4'- CH$_2$-2',4'-(CH$_2$)$_2$-2',4'-(CH$_2$)$_3$-2',4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH₂—N(R)—O-2'-, wherein each R is, independently, H, a protecting group, or $C_1$-$C_{12}$ alkyl; 4'-CH₂—N(R)—O-2', wherein R is H, $C_1$-$C_{12}$ alkyl, or a protecting group (see, U.S. Pat. No. 7,427,672, issued on Sep. 23, 2008); 4'-CH₂—C(H)(CH₃)-2' (see, e.g., Chattopadhyaya, et al., *J. Org. Chem.*, 2009, 74, 118-134); and 4'-CH₂—C(=CH₂)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)₂—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)₂-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH₂—O-2') BNA, (B) β-D-Methyleneoxy (4'-CH₂—O-2') BNA (also referred to as locked nucleic acid or LNA), (C) Ethyleneoxy (4'-(CH₂)₂—O-2') BNA, (D) Aminooxy (4'-CH₂—O—N(R)-2') BNA, (E) Oxyamino (4'-CH₂—N(R)—O-2') BNA, (F) Methyl(methyleneoxy) (4'-CH(CH₃)—O-2') BNA (also referred to as constrained ethyl or cEt), (G) methylene-thio (4'-CH₂—S-2') BNA, (H) methylene-amino (4'-CH2-N(R)-2') BNA, (I) methyl carbocyclic (4'-CH₂—CH(CH₃)-2') BNA, and (J) propylene carbocyclic (4'-(CH₂)₃-2') BNA as depicted below.

(A)

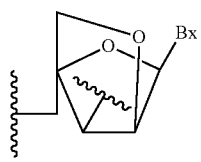

(B)

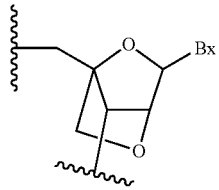

(C)

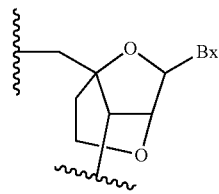

(D)

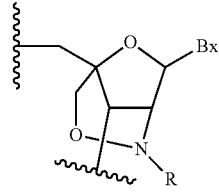

(E)

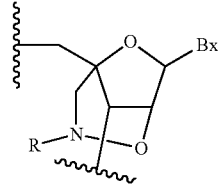

(F)

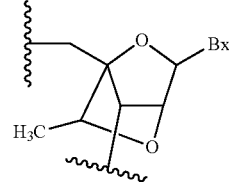

(G)

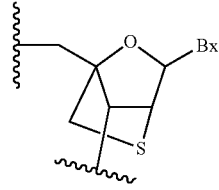

(H)

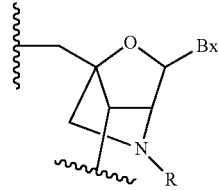

(I)

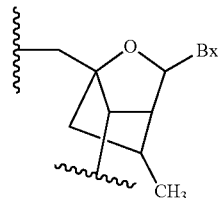

(J)

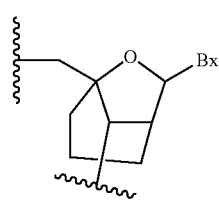

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. No. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense compounds that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VI:

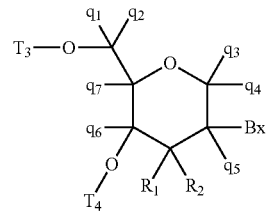

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or 13 such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

4. Certain Motifs

In certain embodiments, antisense compounds comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Compound Chemistry Motifs

In certain embodiments, the chemical structural features of antisense compounds are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense compounds having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessability of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds of therapeutic agents described herein are RNAi compounds. In certain embodiments, antisense compounds of therapeutic agents described herein are ssRNA compounds. In certain embodiments, antisense compounds of therapeutic agents comprise two oligonucleotides which together form an siRNA. In certain embodiments, a targeting group and/or therapeutic nucleoside is attached to the antisense strand in an siRNA compound. In certain embodiments, a targeting group and/or therapeutic nucleoside is attached to the sense strand in an siRNA compound. In certain embodiments, a targeting group and/or therapeutic nucleoside is attached to both the sense strand and the antisense strand of an siRNA.

D. Target Nucleic Acids, Regions and Segments

In certain embodiments, antisense compounds of therapeutic agents target any nucleic acid. In certain embodiments, the target nucleic acid encodes a target protein that is clinically relevant. In such embodiments, modulation of the target nucleic acid results in clinical benefit.

1. Hepatitis B (HBV)

Hepatitis B is a viral disease transmitted parenterally by contaminated material such as blood and blood products, contaminated needles, sexually and vertically from infected or carrier mothers to their offspring. It is estimated by the World Health Organization that more than 2 billion people have been infected worldwide, with about 4 million acute cases per year, 1 million deaths per year, and 350-400 million chronic carriers (World Health Organization: Geographic Prevalence of Hepatitis B Prevalence, 2004. http://www.who.int/vaccines-surveillance/graphics/htmls/hepb-prev.htm).

The virus, HBV, is a double-stranded hepatotropic virus which infects only humans and non-human primates. Viral replication takes place predominantly in the liver and, to a lesser extent, in the kidneys, pancreas, bone marrow and spleen (Hepatitis B virus biology. Microbiol Mol Biol Rev. 64: 2000; 51-68.). Viral and immune markers are detectable in blood and characteristic antigen-antibody patterns evolve over time. The first detectable viral marker is HBsAg, followed by hepatitis B e antigen (HBeAg) and HBV DNA. Titers may be high during the incubation period, but HBV DNA and HBeAg levels begin to fall at the onset of illness and may be undetectable at the time of peak clinical illness (Hepatitis B virus infection—natural history and clinical consequences. N Engl J Med. 350: 2004; 1118-1129). HBeAg is a viral marker detectable in blood and correlates with active viral replication, and therefore high viral load and infectivity (Hepatitis B e antigen—the dangerous end game of hepatitis B. N Engl J Med. 347: 2002; 208-210). The presence of anti-HBsAb and anti-HBcAb (IgG) indicates recovery and immunity in a previously infected individual.

Currently the recommended therapies for chronic HBV infection by the American Association for the Study of Liver Diseases (AASLD) and the European Association for the Study of the Liver (EASL) include interferon alpha (INFα), pegylated interferon alpha-2a (Peg-IFN2a), entecavir, and tenofovir. The nucleoside and nucleobase therapies, entecavir and tenofovir, are successful at reducing viral load, but the rates of HBeAg seroconversion and HBsAg loss are even lower than those obtained using IFNα therapy. Other similar therapies, including lamivudine (3TC), telbivudine (LdT), and adefovir are also used, but for nucleoside/nucleobase therapies in general, the emergence of resistance limits therapeutic efficacy.

Thus, there is a need in the art to discover and develop new anti-viral therapies. Additionally, there is a need for new anti-HBV therapies capable of increasing HBeAg and HBsAg seroconversion rates. Recent clinical research has found a correlation between seroconversion and reductions in HBeAg (Fried et al (2008) Hepatology 47:428) and reductions in HBsAg (Moucari et al (2009) Hepatology 49:1151). Reductions in antigen levels may have allowed immunological control of HBV infection because high levels of antigens are thought to induce immunological tolerance. Current nucleoside therapies for HBV are capable of dramatic reductions in serum levels of HBV but have little impact on HBeAg and HBsAg levels.

Antisense compounds targeting HBV have been previously disclosed in WO2011/047312, WO2012/145674, and WO2012/145697, each herein incorporated by reference in its entirety. Clinical studies are planned to assess the effect of antisense compounds targeting HBV in patients. However, there is still a need to provide patients with additional and more potent treatment options.

Certain Antisense Compounds Targeted to a HBV Nucleic Acid

In certain embodiments, antisense compounds of a therapeutic agent are targeted to a HBV nucleic acid having the sequence of GENBANK® Accession No. U95551.1, incorporated herein as SEQ ID NO: 1. In certain such embodiments, an antisense compound targeted to SEQ ID NO: 1 is at least 90%, at least 95%, or 100% complementary to SEQ ID NO: 1.

In certain embodiments, an antisense compound targeted to SEQ ID NO: 1 comprises an at least 8 consecutive nucleobase sequence of SEQ ID NO: 2. In certain embodiments, an antisense compound targeted to SEQ ID NO: 1 comprises a nucleobase sequence of SEQ ID NO: 2. In the table below "e" represents 2'-MOE modified nucleosides, "d" represents deoxynucleosides (e.g. DNA), and "k" represents cEt modified nucleosides.

TABLE 12

Antisense Compounds targeted to HBV SEQ ID NO: 1

| ISIS No | Target Start Site | Sequence (5'-3') | Motif | SEQ ID NO |
|---|---|---|---|---|
| 505358 | 1583 | GCAGAGGTGAAGCGAAGTGC | eeeeeddddddddddeeeee | 2 |
| 509934 | 1780 | CCAATTTATGCCTACAGCCT | eeedddddddddddeeee | 3 |

TABLE 12-continued

Antisense Compounds targeted to HBV SEQ ID NO: 1

| ISIS No | Target Start Site | Sequence (5'-3') | Motif | SEQ ID NO |
|---|---|---|---|---|
| 510100 | 411 | GGCATAGCAGCAGGATG | eeeeeedddddddddeeee | 4 |
| 552023 | 1266 | AGGAGTTCCGCAGTATGGAT | eeeeeedddddddddeeee | 5 |
| 552024 | 1577 | GTGAAGCGAAGTGCACACGG | eeeeeedddddddddeeee | 6 |
| 552032 | 1585 | GTGCAGAGGTGAAGCGAAGT | eeeeeedddddddddeeee | 7 |
| 552859 | 1583 | AGGTGAAGCGAAGTGC | ekkddddddddddkke | 8 |
| 552925 | 1264 | TCCGCAGTATGGATCG | ekddddddddddeke | 9 |
| 577119 | 1780 | AATTTATGCCTACAGCCT | kdkdkddddddddeeeee | 10 |

HBV Therapeutic Indications

In certain embodiments, the invention provides methods for using a therapeutic agent comprising an antisense compound targeted to a HBV nucleic acid for modulating the expression of HBV in a subject. In certain embodiments, the expression of HBV is reduced.

In certain embodiments, the invention provides methods for using a therapeutic agent comprising an antisense compound targeted to a HBV nucleic acid in a pharmaceutical composition for treating a subject. In certain embodiments, the subject has a HBV-related condition. In certain embodiments, the HBV-related condition includes, but is not limited to, chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, and HBV viremia. In certain embodiments, the HBV-related condition may have which may include any or all of the following: flu-like illness, weakness, aches, headache, fever, loss of appetite, diarrhea, jaundice, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen. In certain embodiments, the subject is at risk for an HBV-related condition. This includes subjects having one or more risk factors for developing an HBV-related condition, including sexual exposure to an individual infected with Hepatitis B virus, living in the same house as an individual with a lifelong hepatitis B virus infection, exposure to human blood infected with the hepatitis B virus, injection of illicit drugs, being a person who has hemophilia, and visiting an area where hepatitis B is common. In certain embodiments, the subject has been identified as in need of treatment for an HBV-related condition.

In certain embodiments, the invention provides methods for using a therapeutic agent comprising an antisense compound targeted to a HBV nucleic acid in the preparation of a medicament.

2. Hepatitis C (HCV)

In certain embodiments, an antisense compound is for the treatment of HCV. In certain embodiments, an antisense compound is targeted to an HCV viral target nucleic acid. In certain embodiments, an antisense compound is targeted to miR122. In certain embodiments, an antisense compound is wholly or partially complementary to the following nucleobase sequence: 5'-uggagugugacaaugguguuug-3'(SEQ ID NO: 11). In certain embodiments, an antisense compound has the following nucleobase sequence: 3'-$c_L c_L t c_L a c_L a c t_L$-$g_L t t a_L c c_L$-5' (SEQ ID NO: 12), wherein a subscript "L" represents an LNA modified nucleobase. In certain embodiments, an antisense compound has the following sequence: 5'ACAAACACCATTGTCACACTCCA-3' (SEQ ID NO: 13).

E. Certain Therapeutic Agents

In certain embodiments, therapeutic agents have the following structure:

$A_x$-$B_y$-(C-$(B)_t)_z$-$C_p$-$D_q$-$E_r$-(F-G)$_s$ wherein
A is an oligomeric compound;
each B is independently a cleavable moiety
each C is independently a therapeutic nucleoside
D is a target group linker
E is a branching group
each F is a tether;
each G is a ligand;
x is 0 or 1;
y is 0 or 1;
z is 1-20;
each t is independently 0 or 1;
p is 0 or 1;
q is 0 or 1;
r is 0 or 1; and
s is 0-5; and
provided that if z is 1, then at least one of x and s is other than 0.

In the above diagram and in similar diagrams herein, the branching group branches as many times as necessary to accommodate the number of tether-ligand groups (indicated by "F-G" in this diagram) as indicated by the subscript (indicated by "s" in this diagram). Thus, where r=1 and s=1, the structure comprises:

E-F-G where r=1 and s=2, the structure comprises:

$$E\begin{matrix}F-G\\F-G\end{matrix}$$

where r=1 and s=3, the structure comprises:

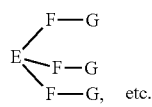

In certain embodiments, A is an antisense compound. In certain embodiments, one or more cleavable moieties is a cleavable bond. In certain embodiments, one or more cleavable moieties is a cleavable nucleoside. In certain such embodiments, the cleavable nucleoside is flanked by one or two cleavable bonds. In certain embodiments, each cleavable nucleoside is flanked by phosphodiester bonds on each side.

In certain embodiments, a therapeutic agent comprises a structure selected from among the following:

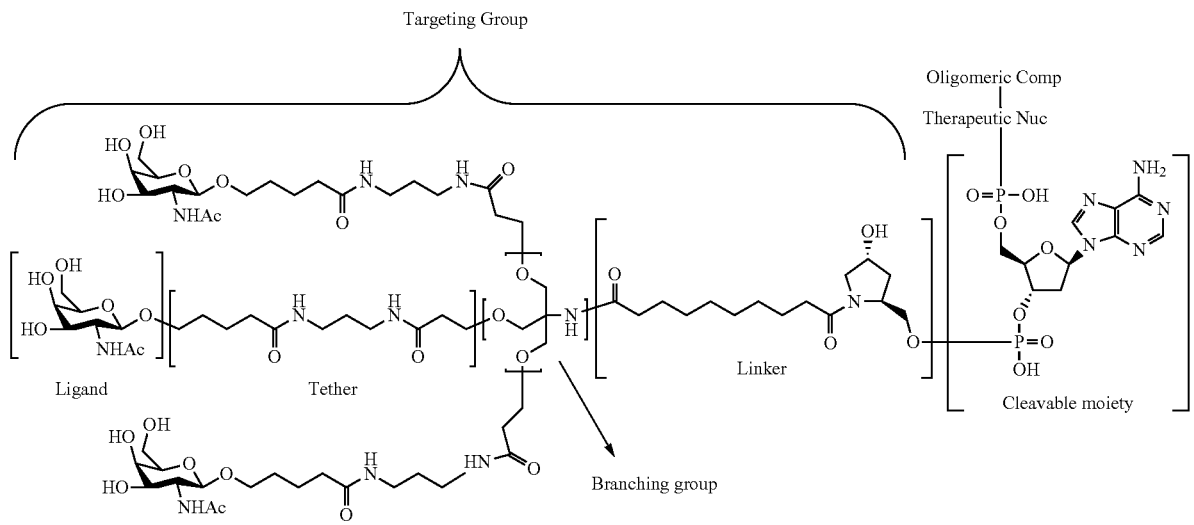

In certain embodiments, a therapeutic agent has a structure selected from among the following:

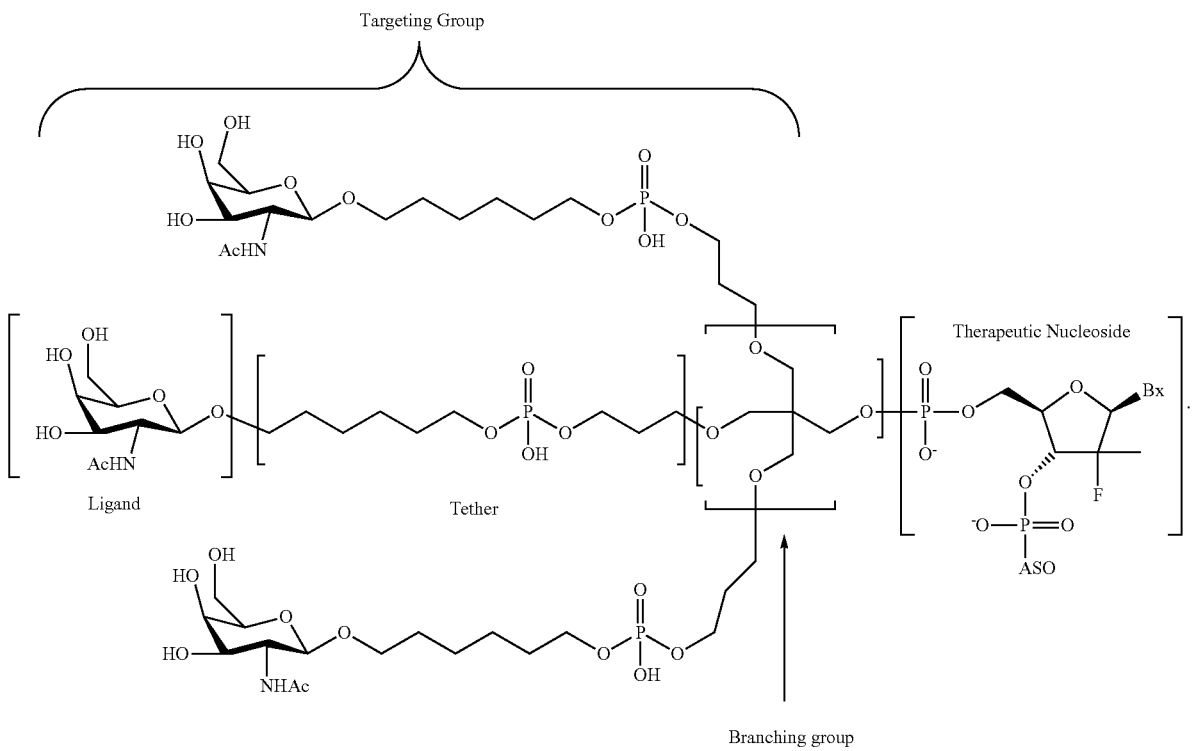

In certain embodiments, a therapeutic agent has a structure selected from among the following:

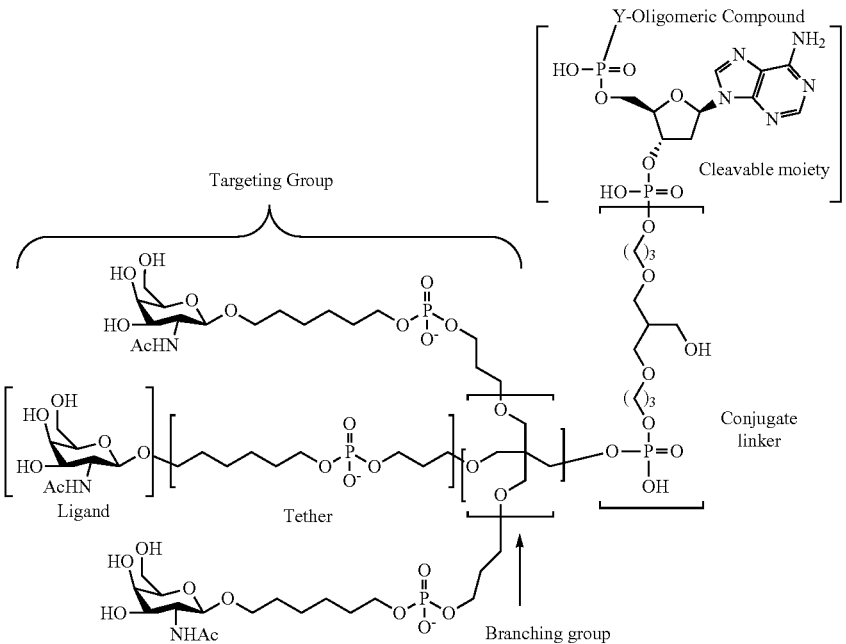

Where Y is at least one therapeutic nucleoside.

F. Certain Uses and Features

In certain embodiments, therapeutic agents are prodrugs. In certain embodiments, therapeutic agents are polyprodrugs.

In certain embodiments, therapeutic agents are a series of linked therapeutic nucleosides. Such linked therapeutic nucleosides may be linked with cleavable moieties, such as cleavable bonds, such as phosphodiester bonds. Such linked therapeutic nucleosides may be linked with cleavable moieties, such as cleavable nucleosides, such as cleavable nucleosides linked with phosphodiester bonds. Thus, the therapeutic agent may comprise or consist of a portion having any of the following formula:

$(TN)_o(TN)_o(TN)_o(TN)_o(TN)_o(TN)_o(TN)_o(TN)$ $(TN)_o(CN)_o(TN)_o(CN)_o(TN)_o(CN)_o(TN)_o(CN)$ where TN represents a therapeutic nucleoside; CN represent a cleavable nucleoside; and o represents a phosphodiester bond. Such compounds could be made to various lengths (e.g., 2 to 50 nucleosides) by increasing or decreasing the number of therapeutic nucleosides and/or the number of cleavable nucleosides. Without being bound by any particular mechanism, such therapeutic nucleosides are expected to cleave into active monomers after administration to an animal. In certain embodiments, such cleavage may occur at least in part after the therapeutic agent has entered a cell. Such a construct may be made using any therapeutic nucleoside, including, but not limited to, those described herein. Such linked therapeutic nucleosides may, in certain embodiments, enter cells more efficiently and result in more potent therapeutic agents than individual therapeutic nucleosides.

In certain embodiments, therapeutic agents comprise at least one targeting group. Such groups, when attached to oligomeric compounds have demonstrated increased uptake into cells or types of cells. Such targeting groups may be attached to a single therapeutic nucleoside or to a linked therapeutic nucleosides. As discussed above, such therapeutic nucleosides may be linked together with cleavable moieties, such as a cleavable bonds and/or cleavable nucleosides. Likewise, a targeting group may be attached to one or more therapeutic nucleoside by a cleavable moiety, such as a cleavable bond or cleavable nucleoside. Certain such therapeutic agents comprise or consist of a portion having the following formula:

$(TG)_o(TN)$ $(TG)_o(TN)_o(TN)_o(TN)_o(TN)_o(TN)_o(TN)_o(TN)$ $(TG)_o(TN)_o(CN)_o(TN)_o(CN)_o(TN)_o(CN)_o(TN)_o(CN)$ $(TG)_o(CN)_o(TN)$ $(TG)_o(CN)_o(TN)_o(TN)_o(TN)_o(TN)_o(TN)_o(TN)_o$
$(TN)$ $(TG)_o(CN)_o(TN)_o(CN)_o(TN)_o(CN)_o(TN)_o(CN)_o(TN)_o$
$(CN)$ where TG represents a targeting group; TN represents a therapeutic nucleoside; CN represent a cleavable nucleoside; and o represents a phosphodiester bond. Such compounds could be made to various lengths (e.g., 2 to 50 nucleosides) by increasing or decreasing the number of therapeutic nucleosides and/or the number of cleavable nucleosides. Further, in certain embodiments targeting groups are attached to more than one nucleoside. Targeting groups may be attached and at any position of any cleavable nucleoside and/or therapeutic nucleoside. Such therapeutic nucleosides linked to a targeting group may, in certain embodiments, enter cells more efficiently and result in more potent therapeutic agents than individual or linked therapeutic nucleosides lacking such targeting group.

In certain embodiments, therapeutic agents comprise at least one oligomeric compound, such an antisense compound. In certain embodiments, antisense compounds modulate the amount or activity of a target nucleic acid. In certain embodiments, antisense compounds result in cleavage, alternate splicing or translational arrest of a target nucleic acid. In certain embodiments, therapeutic agents comprising at least one oligomeric compound comprise or consist of a portion having the following formula:

$(TN)_o(TN)_o(TN)_o(TN)_o(TN)_o(TN)_o(TN)_o(TN)_o(OC)$ $(TN)_o(CN)_o(TN)_o(CN)_o(TN)_o(CN)_o(TN)_o(CN)_o(OC)$ $(TG)_o(TN)_o(OC)$ $(TG)_o(TN)_o(TN)_o(TN)_o(TN)_o(TN)_o(TN)_o(TN)_o(TN)_o$
(OC)

$(TG)_o(TN)_o(CN)_o(TN)_o(CN)_o(TN)_o(CN)_o(TN)_o(CN)_o$
(OC)

$(TG)_o(CN)_o(TN)_o(OC)$ $(TG)_o(CN)_o(TN)_o(TN)_o(TN)_o(TN)_o(TN)_o(TN)_o(TN)_o$
$(TN)_o(OC)$ $(TG)_o(CN)_o(TN)_o(CN)_o(TN)_o(CN)_o(TN)_o(CN)_o(TN)_o$
$(CN)_o(OC)$ $(TN)_o(TN)_o(TN)_o(TN)_o(TN)_o(TN)_o(TN)_o(TN)_o(CN)_o$
(OC)

$(TN)_o(CN)_o(TN)_o(CN)_o(TN)_o(CN)_o(TN)_o(CN)_o(CN)_o$
(OC)

$(TG)_o(TN)_o(CN)_o(OC)$ $(TG)_o(TN)_o(TN)_o(TN)_o(TN)_o(TN)_o(TN)_o(TN)_o(TN)_o$
$(CN)_o(OC)$ $(TG)_o(TN)_o(CN)_o(TN)_o(CN)_o(TN)_o(CN)_o(TN)_o(CN)_o$
$(CN)_o(OC)$ $(TG)_o(CN)_o(TN)_o(CN)_o(OC)$ $(TG)_o(CN)_o(TN)_o(TN)_o(TN)_o(TN)_o(TN)_o(TN)_o(TN)_o$
$(TN)_o(CN)_o(OC)$ $(TG)_o(CN)_o(TN)_o(CN)_o(TN)_o(CN)_o(TN)_o(CN)_o(TN)_o$
$(CN)_o(CN)_o(OC)$ where OC represents an oligomeric compound; TG represents a targeting group; TN represents a therapeutic nucleoside; CN represent a cleavable nucleoside; and o represents a phosphodiester bond. Such compounds could be made to various lengths (e.g., 2 to 50 nucleosides) by increasing or decreasing the number of therapeutic nucleosides and/or the number of cleavable nucleosides. Further, in certain embodiments targeting groups are attached to more than one nucleoside. Targeting groups may be attached at any position of any cleavable nucleoside and/or therapeutic nucleoside. The oligomeric compound typically comprises 10-30 linked nucleosides. The oligomeric compound may be attached at its 5'-end, its 3' end or an internal nucleoside. In certain embodiments, the oligomeric compound is an antisense compound. In certain such embodiments, the antisense compound is complementary to a target nucleic acid, the modulation of which treats a disease or condition. In certain such embodiments, the disease or condition is also treated by the therapeutic nucleoside.

Productive and non-productive uptake of oligonucleotides has been discussed previously (See e.g. Geary, R. S., E. Wancewicz, et al. (2009). "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. 78(3): 284-91; & Koller, E., T. M. Vincent, et al. (2011). "Mechanisms of single-stranded phosphorothioate modified antisense oligonucleotide accumulation in hepatocytes." Nucleic Acids Res. 39(11): 4795-807). Targeting groups described herein may improve productive uptake of oligonucleotides, including, but not limited to linked therapeutic nucleosides, antisense oligonucleotides, and therapeutic agents comprising both one or more therapeutic nucleosides and one or more antisense oligonucleotides.

In certain embodiments, the targeting groups described herein may further improve potency by increasing the affinity of therapeutic agents for a particular type of cell or tissue. In certain embodiments, the targeting groups described herein may further improve potency by increasing recognition of the targeting group by one or more cell-surface receptors. In certain embodiments, the targeting groups described herein may further improve potency by facilitating endocytosis of a therapeutic agent.

In certain embodiments, the cleavable moiety may further improve potency by allowing the targeting group to be cleaved from the remainder of the therapeutic agent after the therapeutic agent has entered a cell. Accordingly, in certain embodiments, therapeutic agents can be administered at doses lower than would be necessary for therapeutic nucleosides and/or antisense oligonucleotides.

G. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Certain compounds, compositions, and methods herein are described as "comprising exactly" or "comprises exactly" a particular number of a particular element or feature. Such descriptions are used to indicate that while the compound, composition, or method may comprise additional other elements, the number of the particular element or feature is the identified number. For example, "a compound comprising exactly one cell-targeting ligand" is a compound that contains one and only one cell-targeting ligand, though it may contain other elements in addition to the one cell-targeting ligand.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: General Method for the Preparation of Phosphoramidites, Compounds 1, 1a and 2

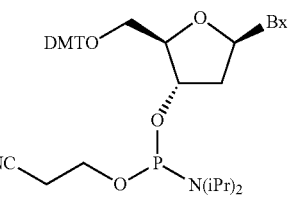

1

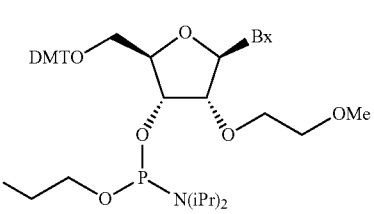

1a

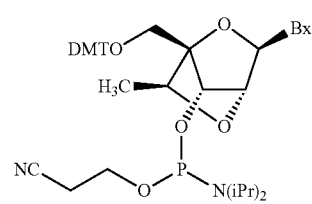

2

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7
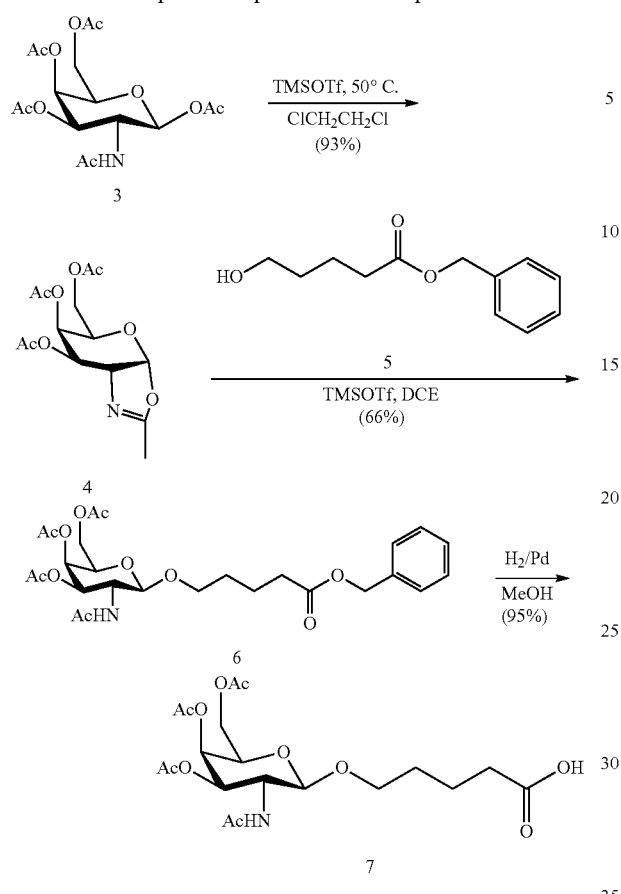
Compounds 3 (2-acetamido-1,3,4,6-tetra-O-acetyl-2-deoxy-β-D galactopyranose or galactosamine pentaacetate) is commercially available. Compound 5 was prepared according to published procedures (Weber et al., *J. Med. Chem.*, 1991, 34, 2692).
Example 3: Preparation of Compound 11
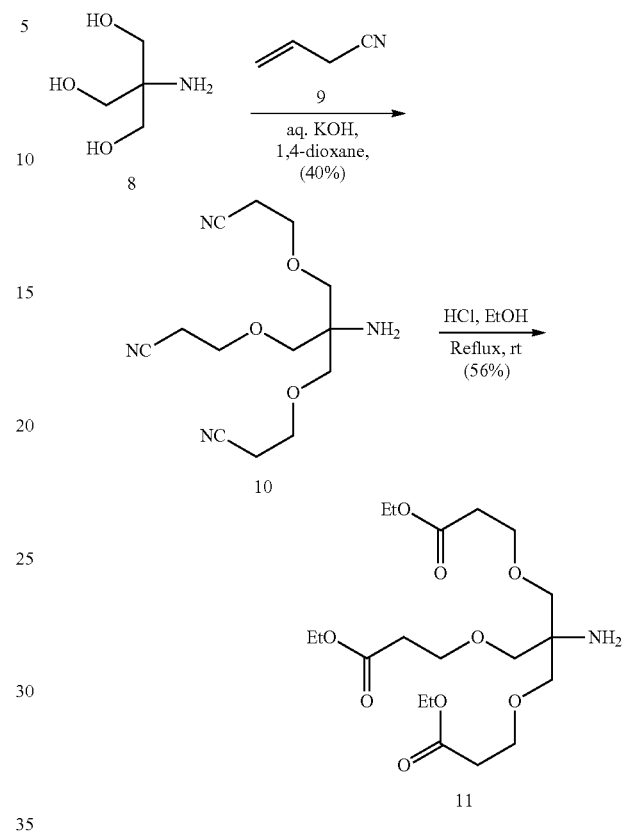
Compounds 8 and 9 are commercially available.
Example 4: Preparation of Compound 18
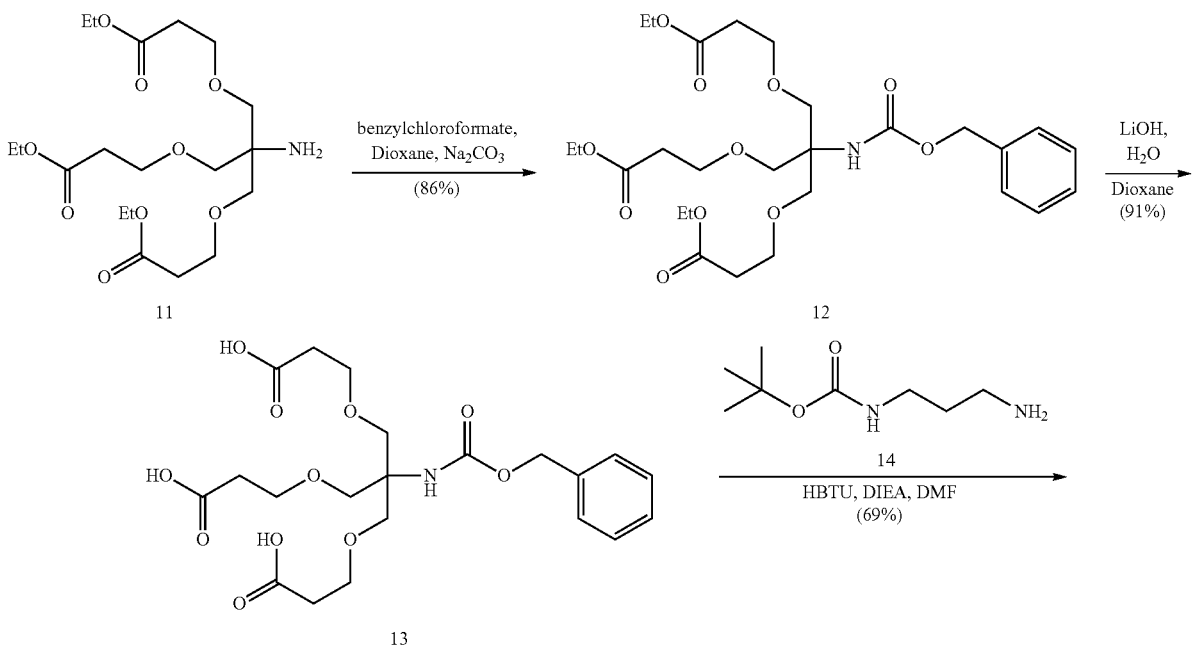

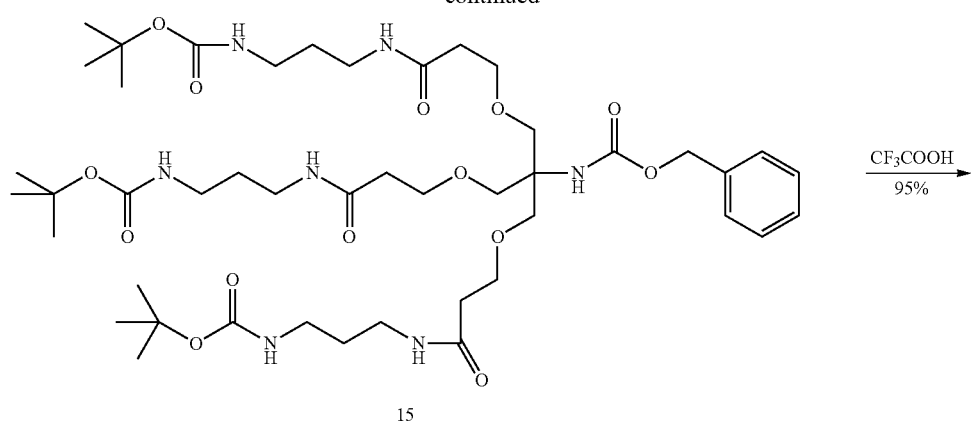
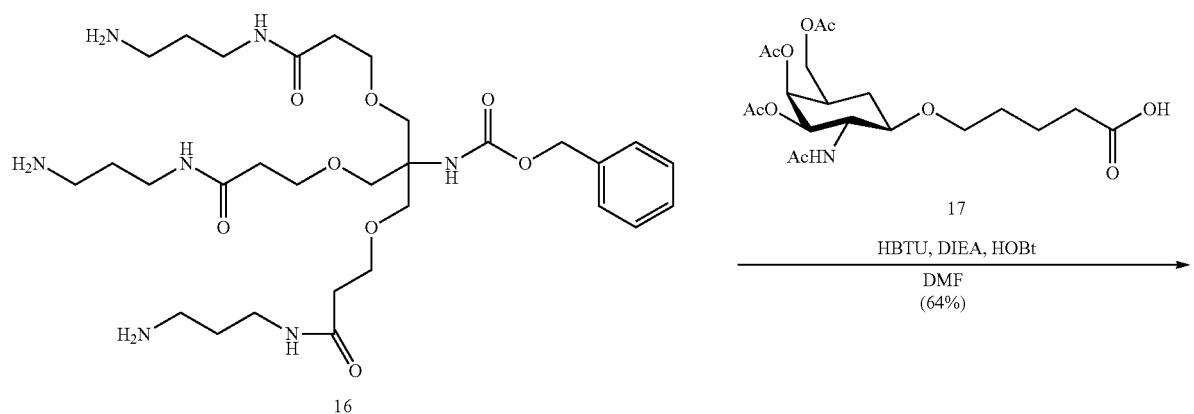
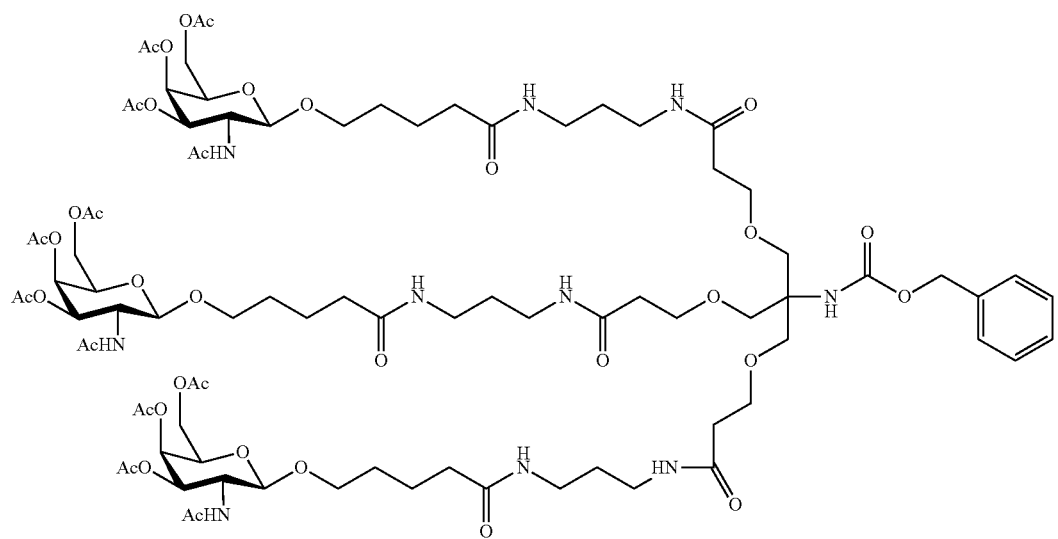

Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5: Preparation of Compound 23
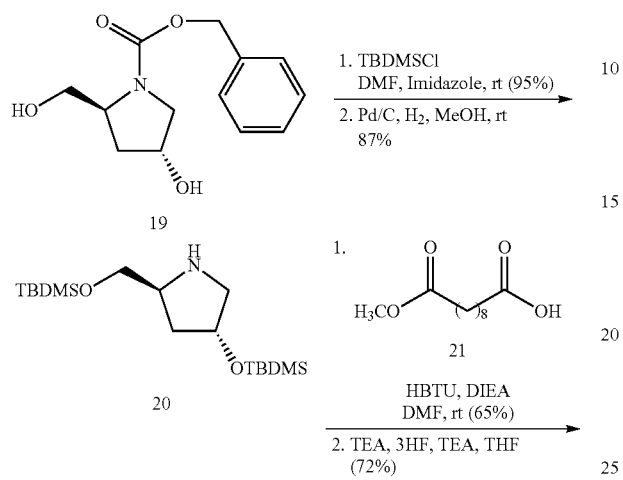
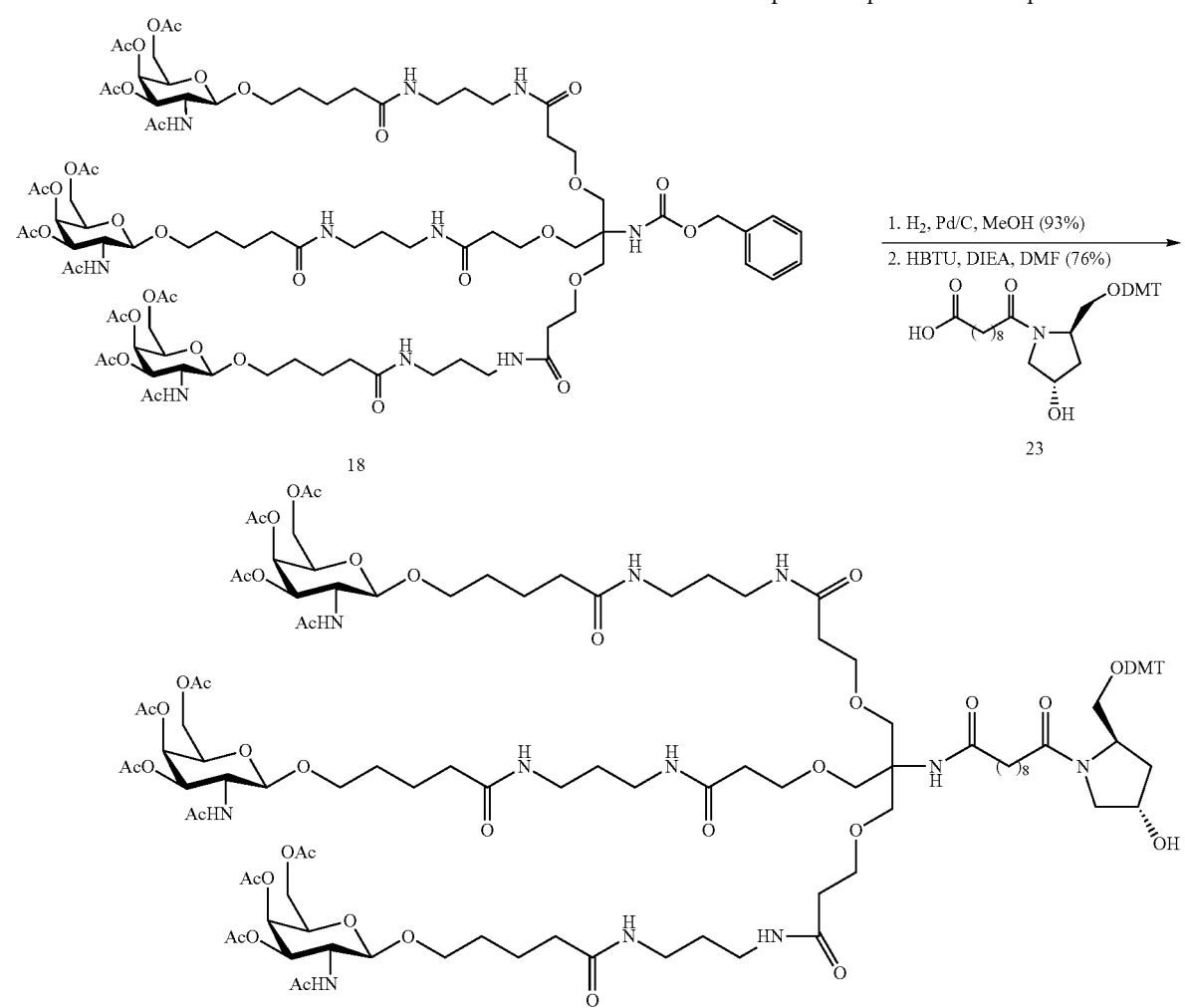
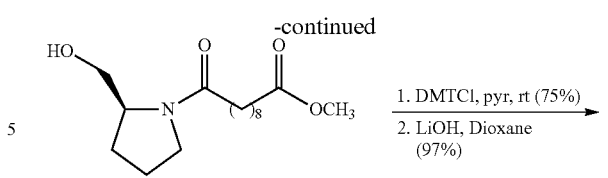
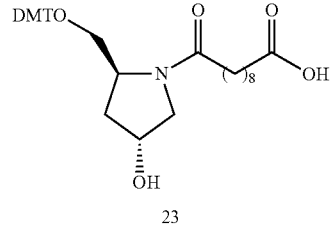
Compounds 19 and 21 are commercially available.
Example 6: Preparation of Compound 24

Compounds 18 and 23 were prepared as per the procedures illustrated in Examples 4 and 5.
Example 7: Preparation of Compound 25
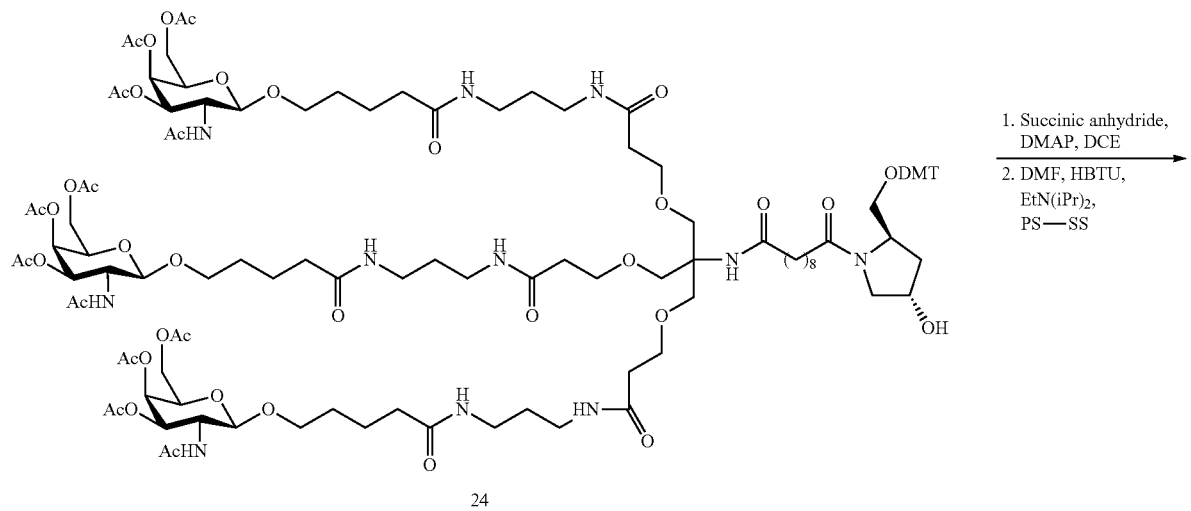
24
1. Succinic anhydride, DMAP, DCE
2. DMF, HBTU, EtN(iPr)$_2$, PS—SS
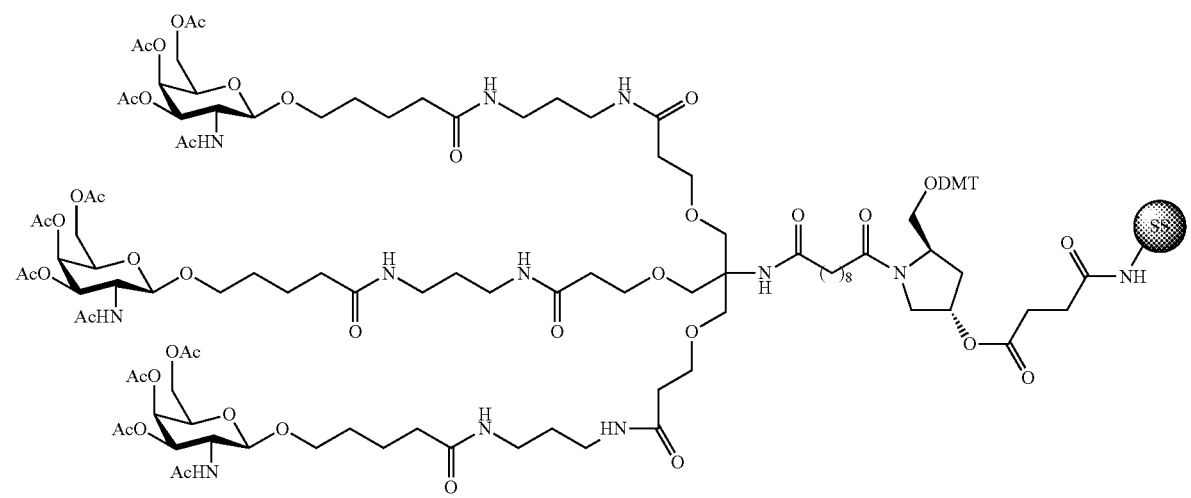
25
Compound 24 was prepared as per the procedures illustrated in Example 6.

Example 8: General Preparation of Therapeutic Agents Comprising GalNAc$_3$-1 at the 5' Terminus
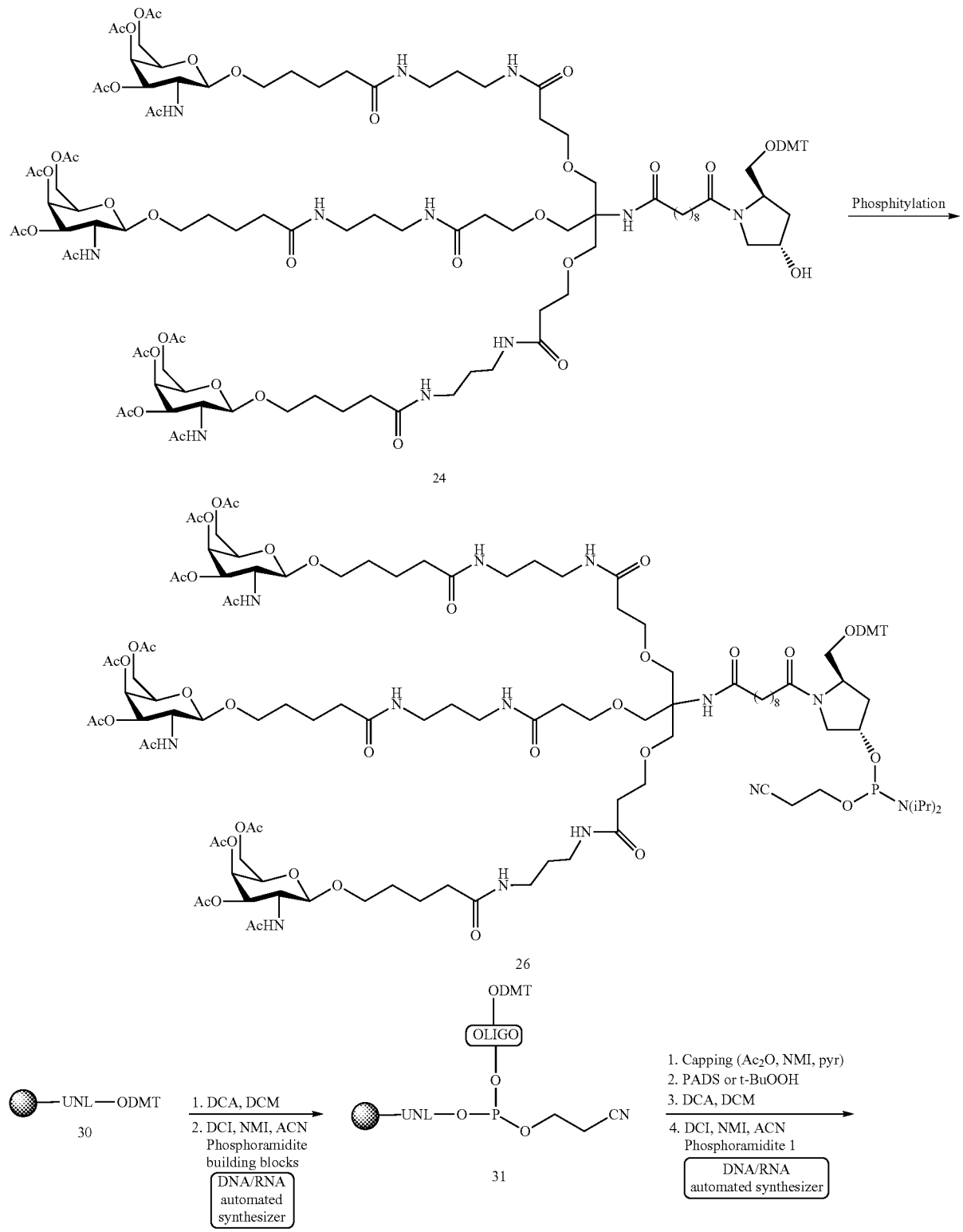

-continued
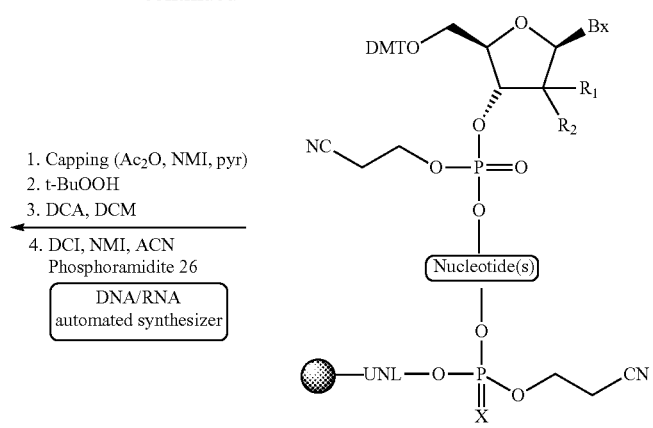
1. Capping (Ac₂O, NMI, pyr)
2. t-BuOOH
3. DCA, DCM
4. DCI, NMI, ACN
   Phosphoramidite 26
   DNA/RNA automated synthesizer
32
X = O, or S
Bx = Heterocylic base
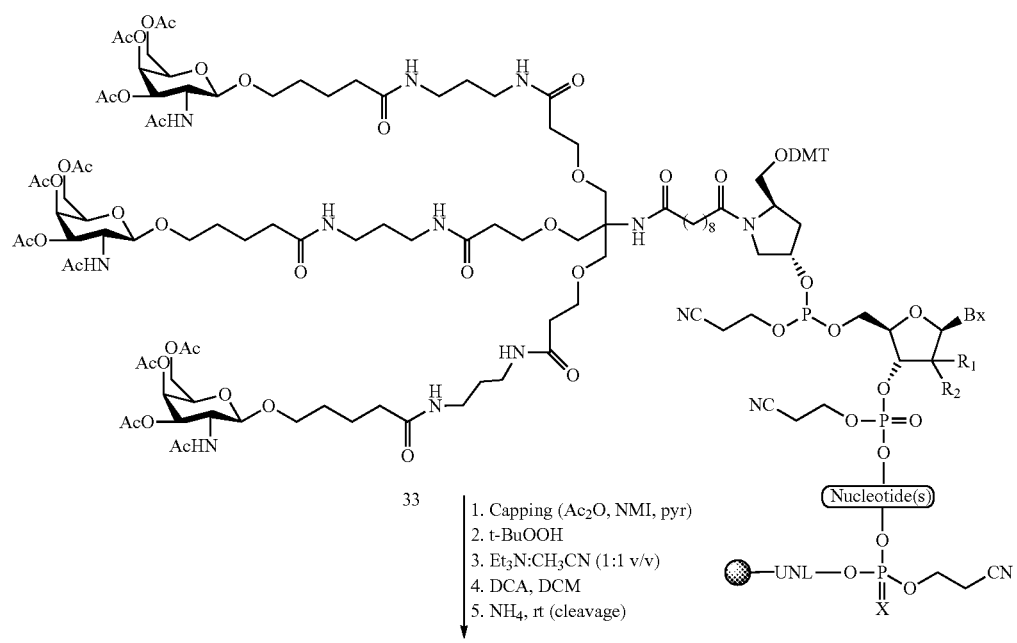
33
1. Capping (Ac₂O, NMI, pyr)
2. t-BuOOH
3. Et₃N:CH₃CN (1:1 v/v)
4. DCA, DCM
5. NH₄, rt (cleavage)

-continued

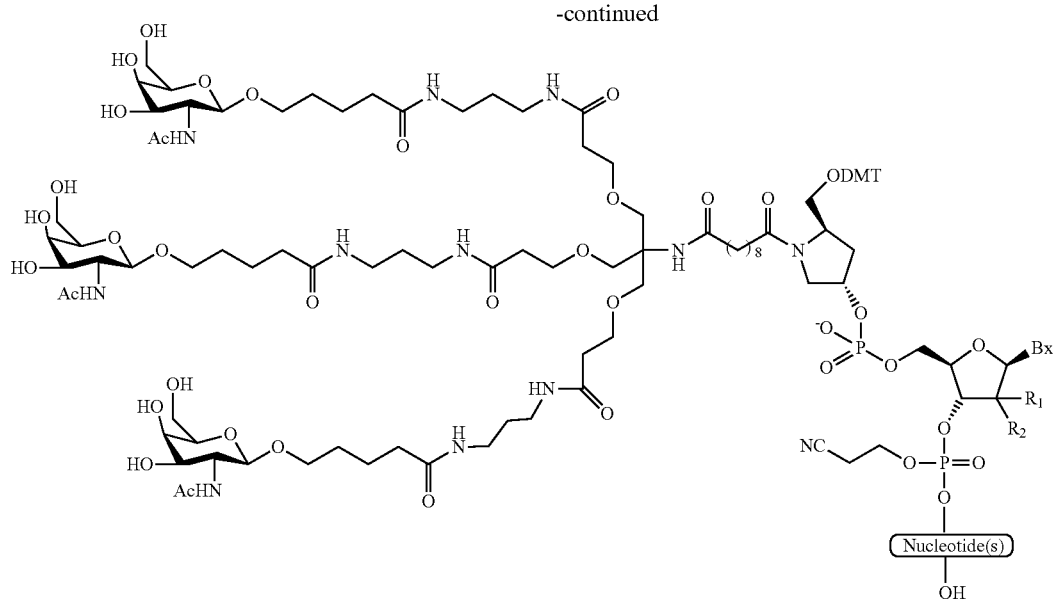

34

Wherein $R_1$ and $R_2$ are independently selected from H, OH, F, Me, and MOE. As used in the scheme above and throughout these examples, "Nucleotide(s)" means one or more therapeutic and/or non-therapeutic nucleotides. Compound 24 is prepared as per the procedures illustrated in Example 6. The Unylinker™ 30 is commercially available. Compound 34 comprising a GalNAc$_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare a compound having a predetermined sequence or composition. The order and quantity of phosphoramidites added to the solid support can be adjusted to prepare gapped oligomeric compounds as described herein. Such gapped oligomeric compounds can have predetermined composition and base sequence as dictated by any given target.

Example 9: General Preparation of Therapeutic Agents Comprising GalNAc$_3$-1 at the 3' Terminus

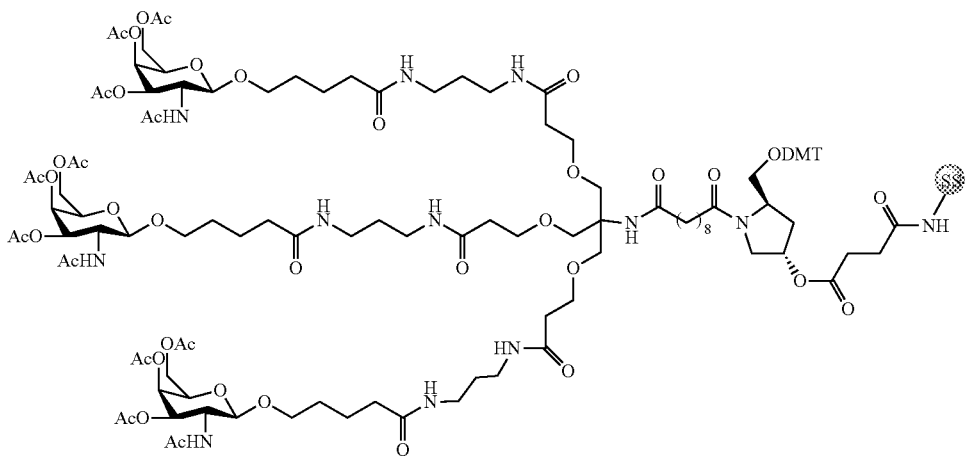

25

1. DCA, DCM
2. DCI, NMI, ACN
   Phosphoramidite
   building block 1
3. Capping
4. t-BuOOH DNA/RNA automated synthesizer

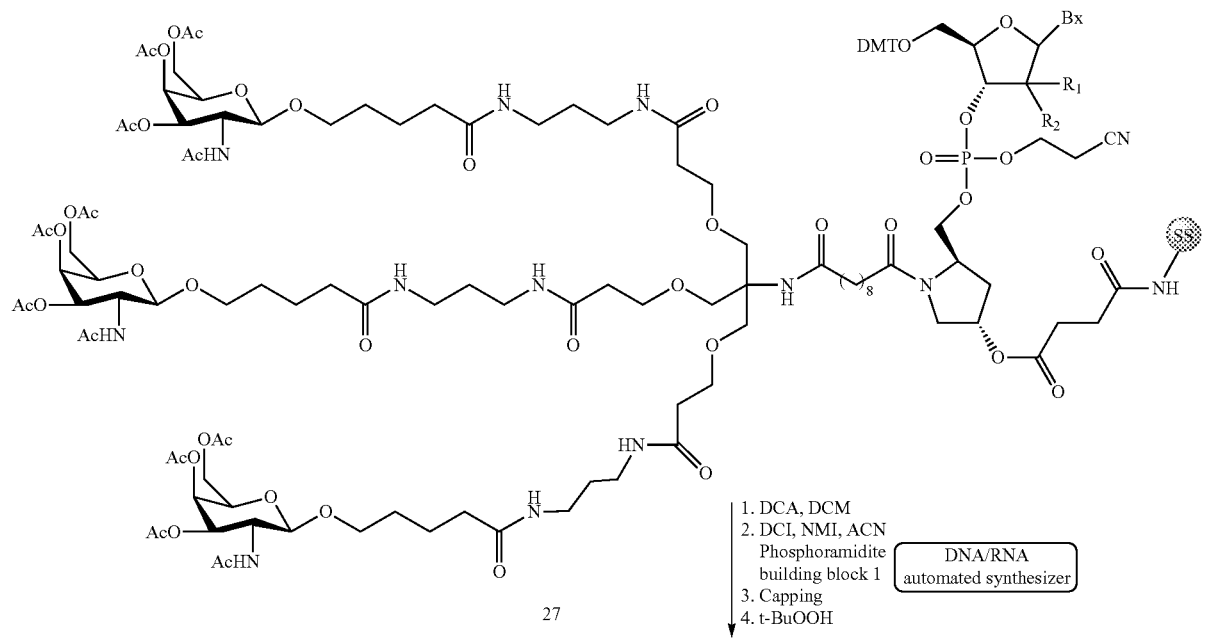
27
1. DCA, DCM
2. DCI, NMI, ACN
   Phosphoramidite building block 1
3. Capping
4. t-BuOOH
DNA/RNA automated synthesizer
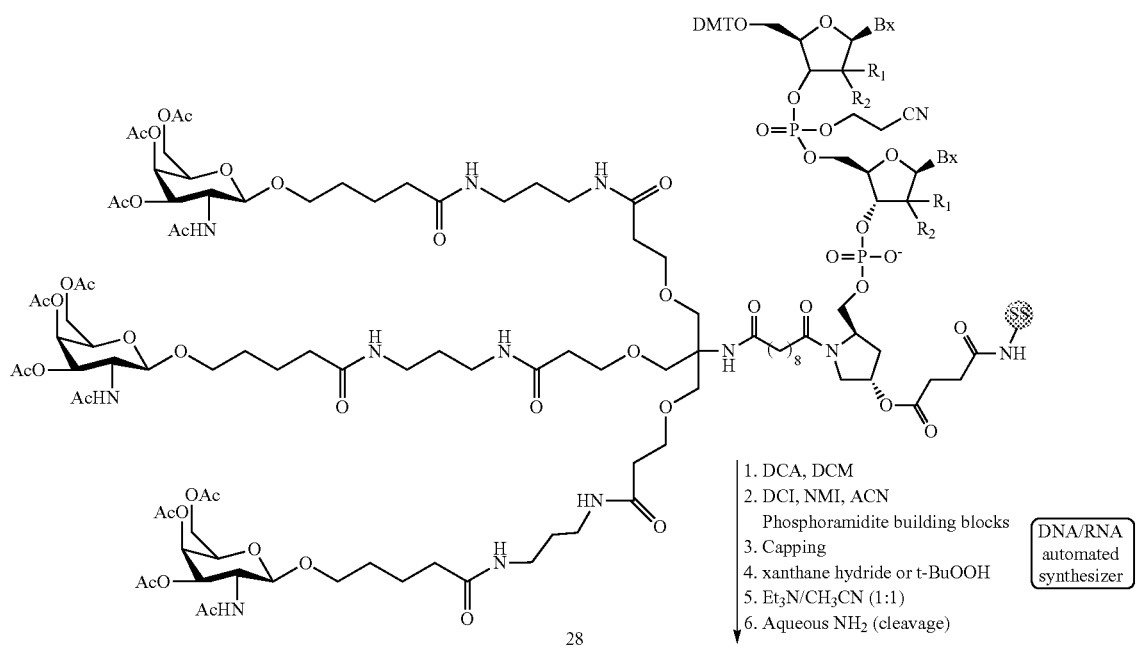
28
1. DCA, DCM
2. DCI, NMI, ACN
   Phosphoramidite building blocks
3. Capping
4. xanthane hydride or t-BuOOH
5. Et₃N/CH₃CN (1:1)
6. Aqueous NH₂ (cleavage)
DNA/RNA automated synthesizer -continued
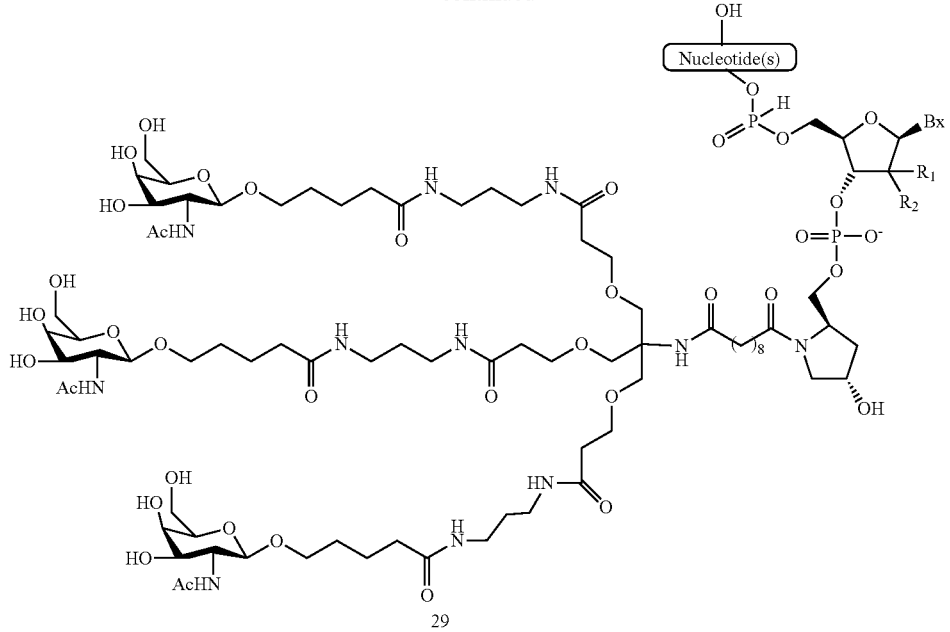
Wherein R₁ and R₂ are independently selected from H, OH, F, Me, and MOE; and GalNAc₃-1 has the structure:
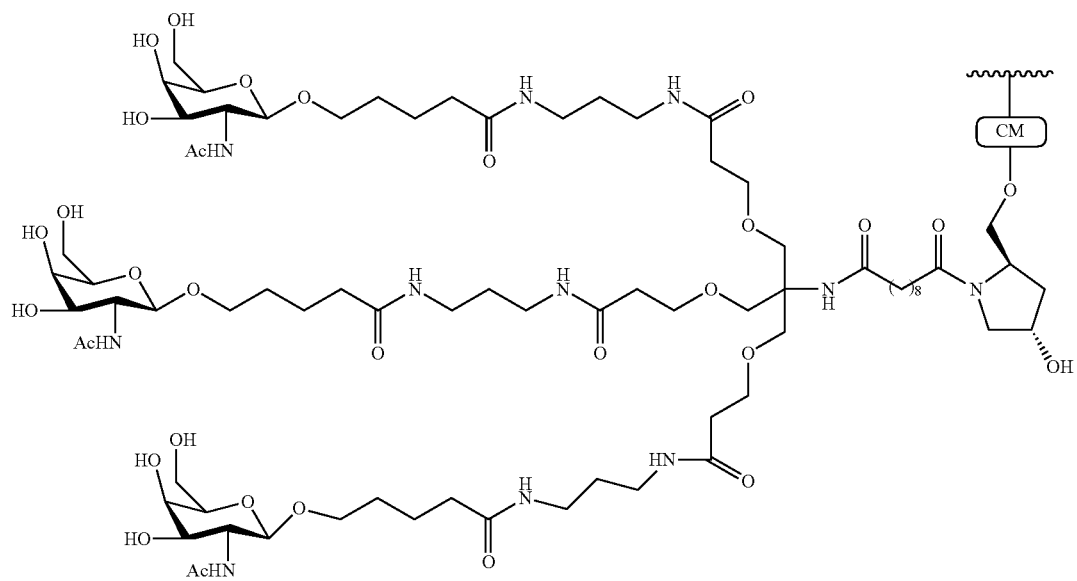
The GalNAc₃ cluster portion of the targeting group GalNAc₃-1 (GalNAc₃-1ₐ) can be combined with any cleavable moiety. Wherein GalNAc₃-1ₐ has the formula:

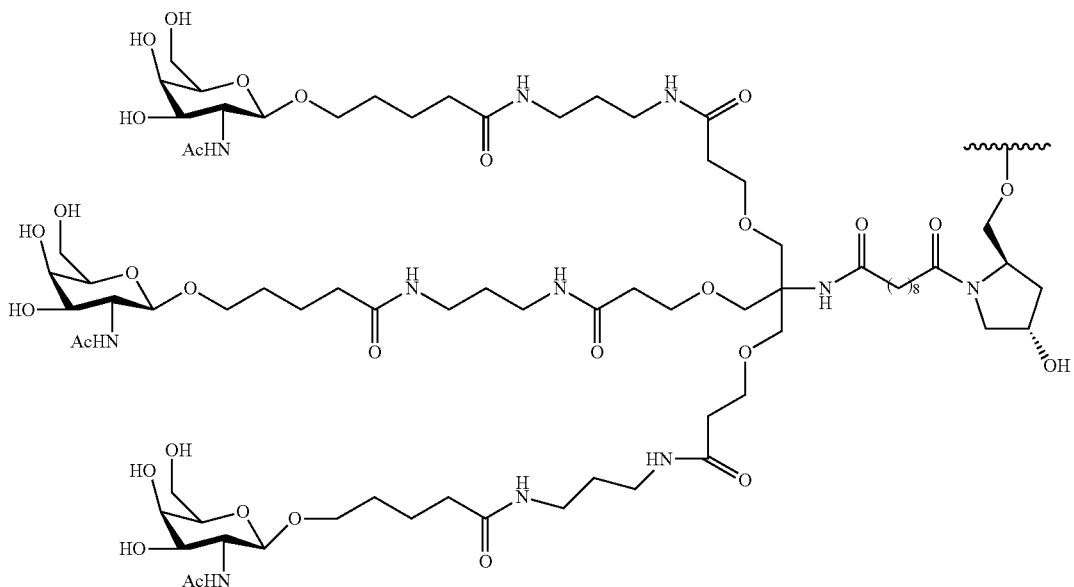

25

The solid support bound protected GalNAc₃-1, Compound 25, was prepared as per the procedures illustrated in Example 7. Compound 29 comprising GalNAc₃-1 at the 3' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a are prepared as per the procedures illustrated in Example 1. The phosphoramidites illustrated are meant to be representative and not intended to be limiting as other phosphoramidite building blocks can be used to prepare compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: Preparation of Compound 39

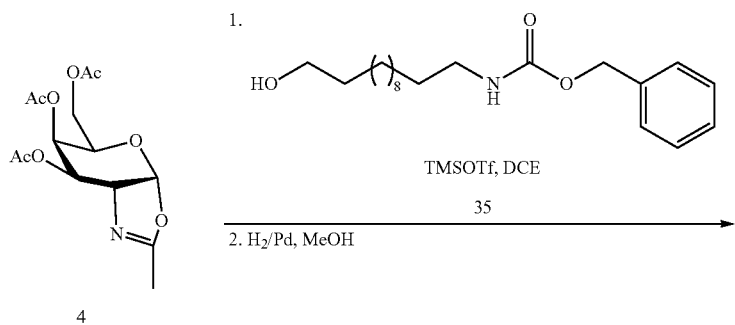

4

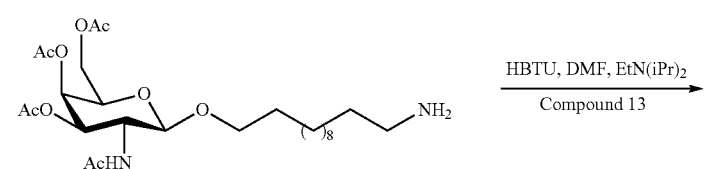

36

-continued
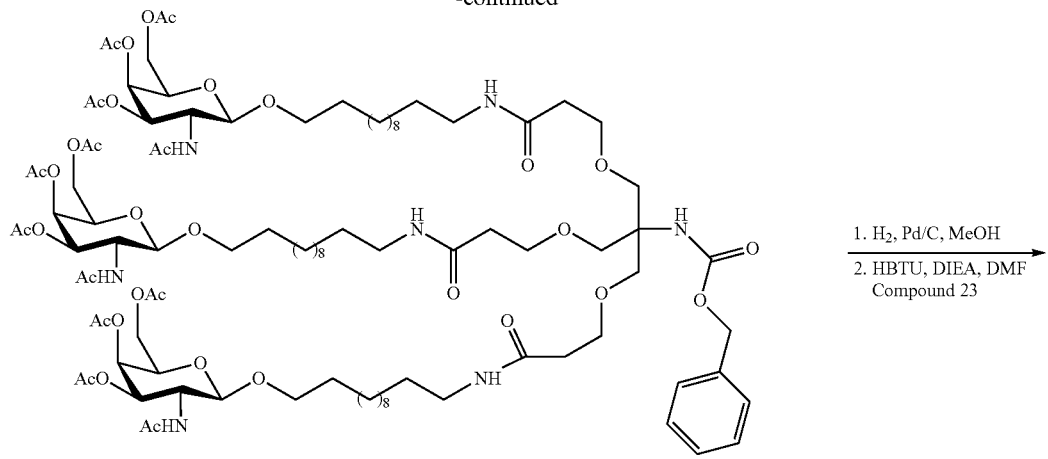
37
1. H₂, Pd/C, MeOH
2. HBTU, DIEA, DMF
   Compound 23
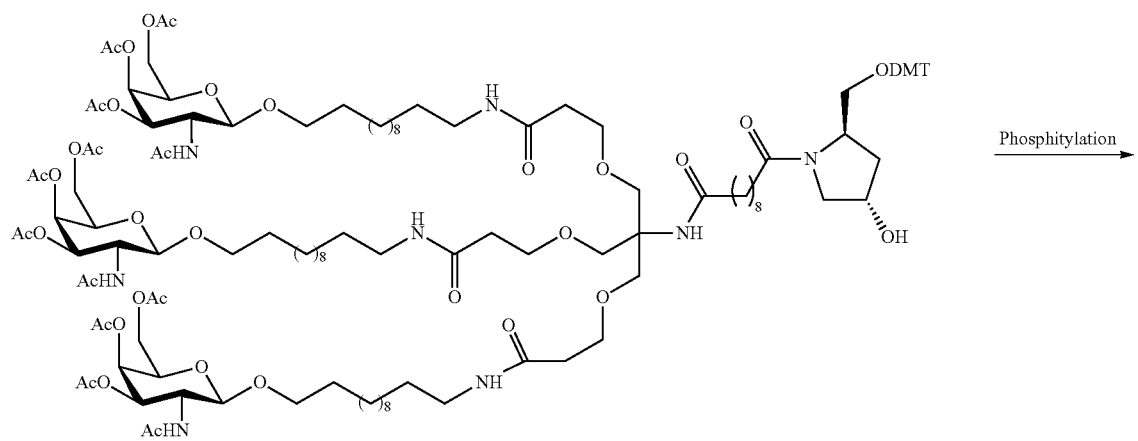
38
Phosphitylation
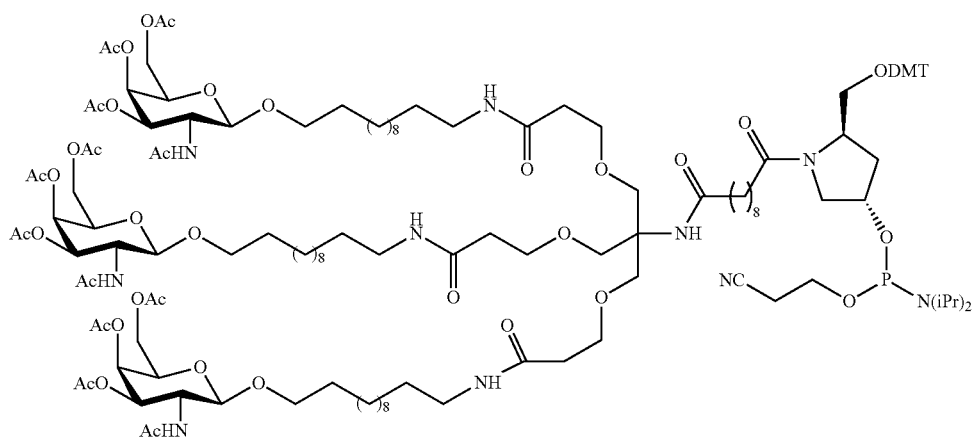
39
Compounds 4, 13 and 23 are prepared as per the procedures illustrated in Examples 2, 4, and 5. Compound 35 is prepared using similar procedures published in Rouchaud et al., *Eur. J. Org. Chem.*, 2011, 12, 2346-2353.

Example 11: Preparation of Compound 40
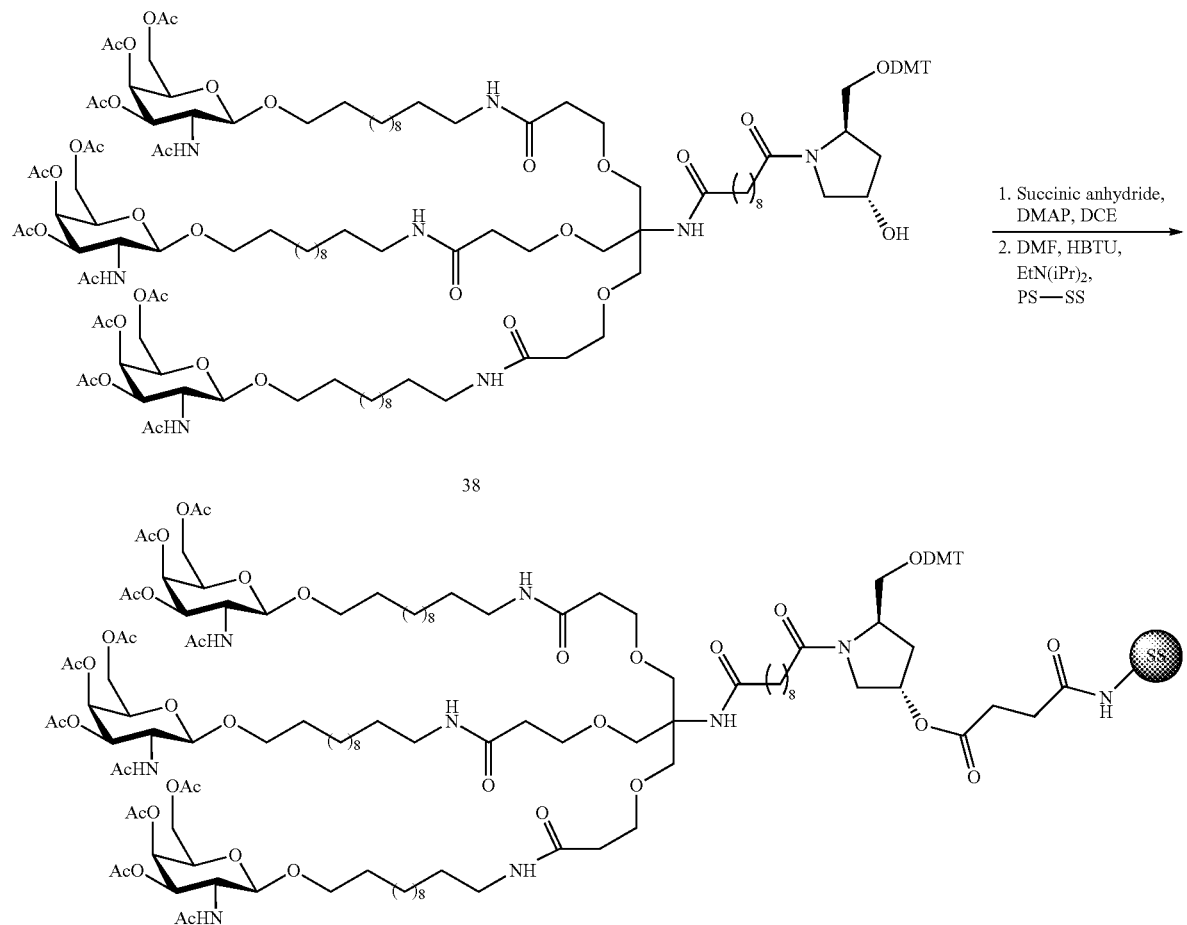
Compound 38 is prepared as per the procedures illustrated in Example 10.
Example 12: Preparation of Compound 44
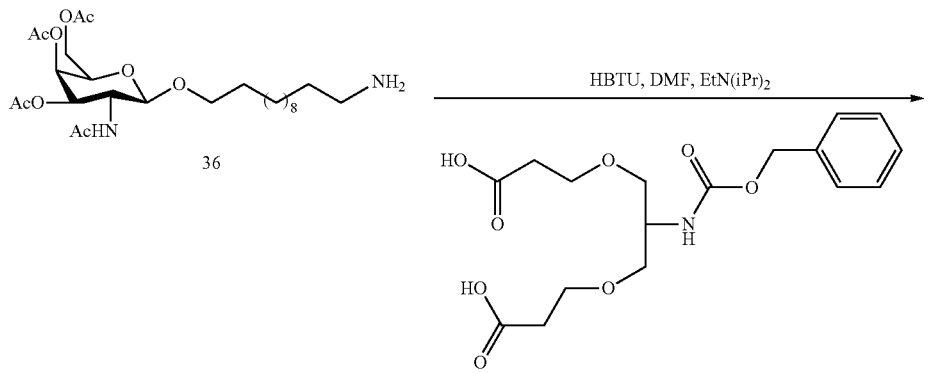

-continued
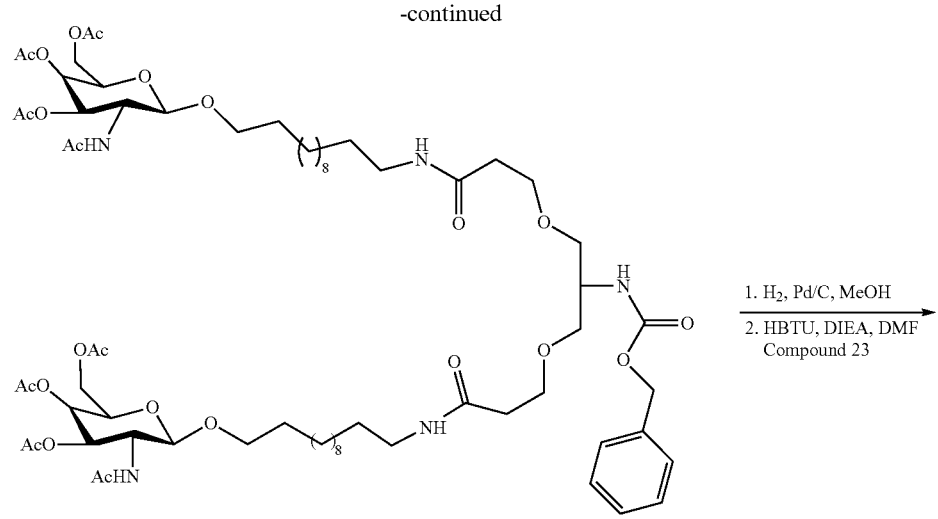
42
1. H₂, Pd/C, MeOH
2. HBTU, DIEA, DMF
   Compound 23
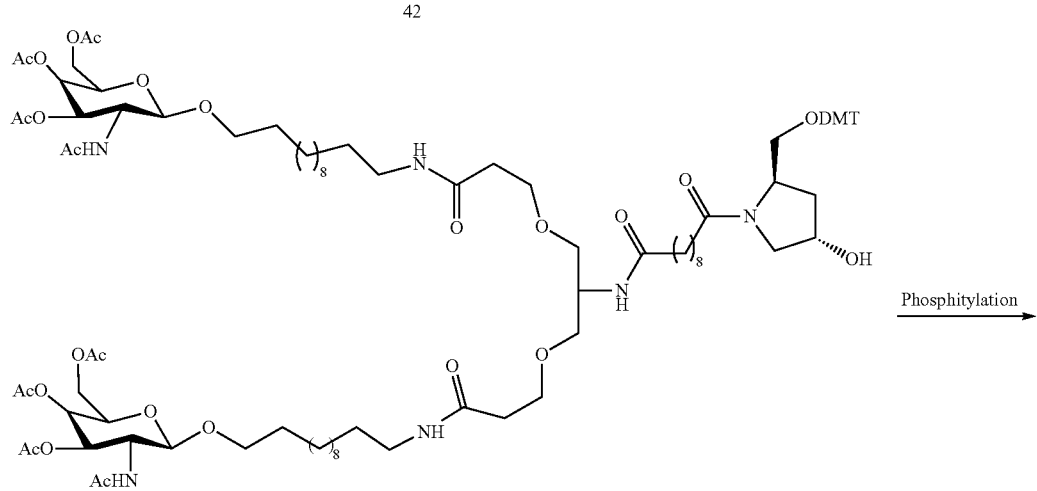
43
Phosphitylation
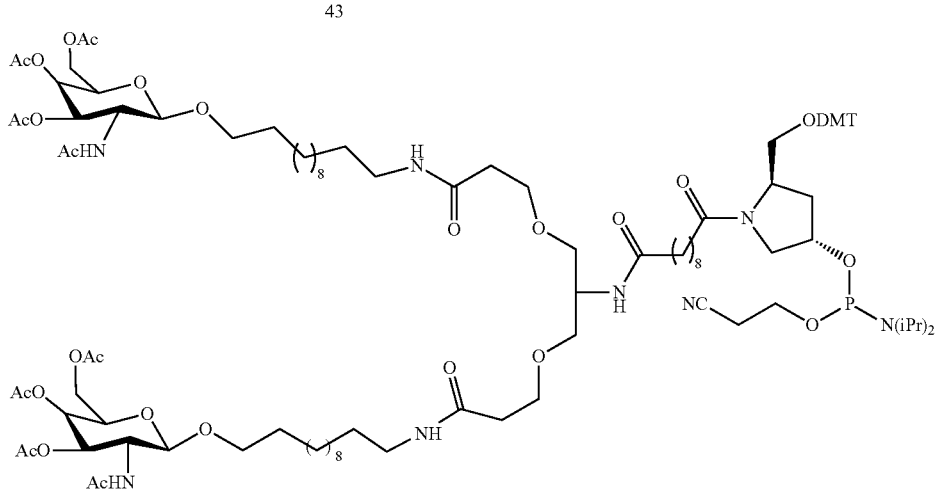
44
Compounds 23 and 36 are prepared as per the procedures illustrated in Examples 5 and 10. Compound 41 is prepared using similar procedures published in WO 2009082607.

Example 13: Preparation of Compound 45
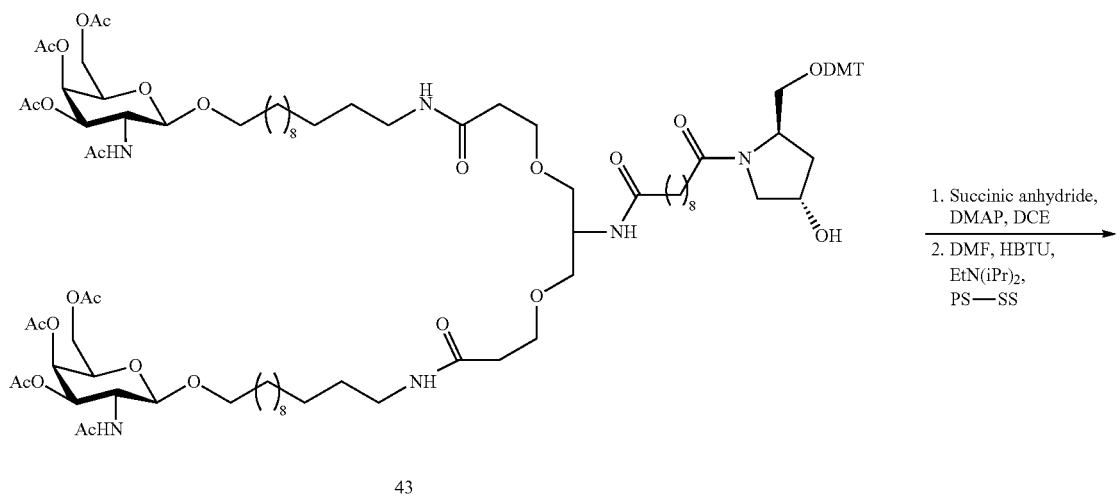
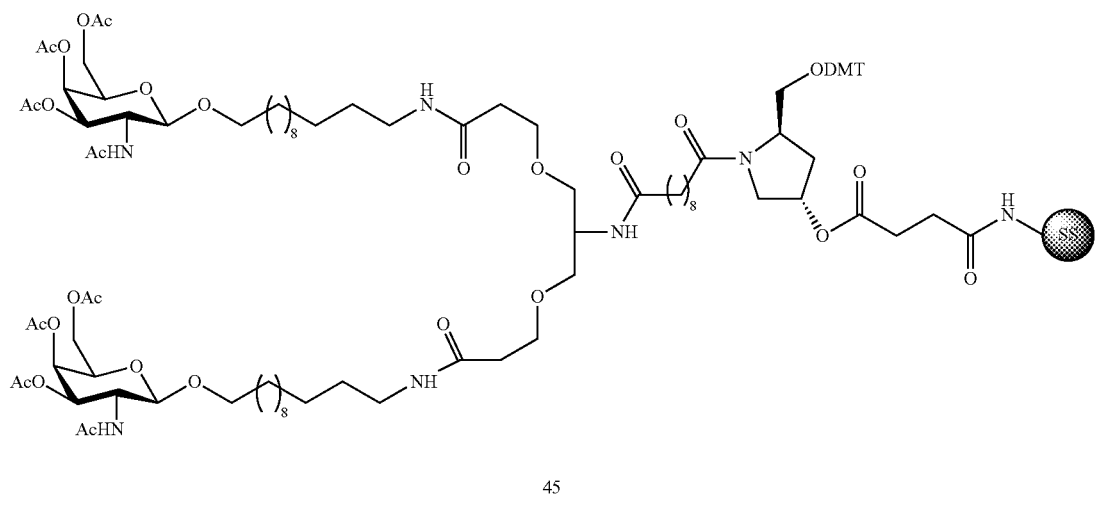
Compound 43 is prepared as per the procedures illustrated in Example 12.
Example 14: Preparation of Compound 47
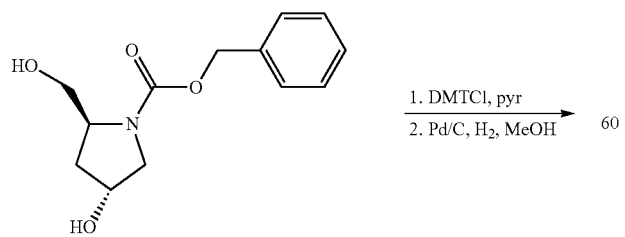
Compound 46 is commercially available.

Example 15: Preparation of Compound 53
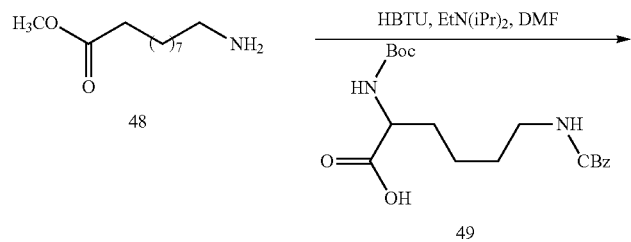
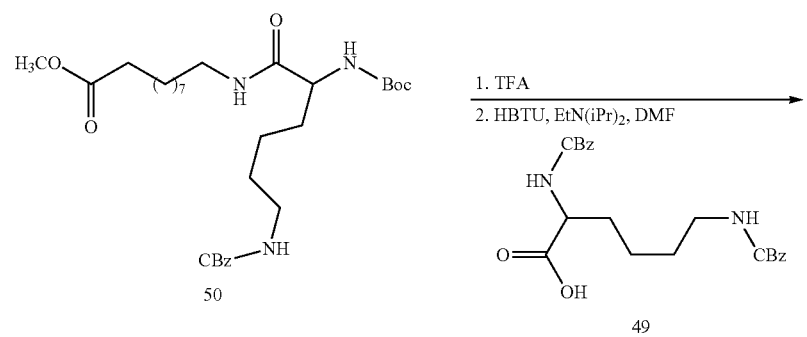
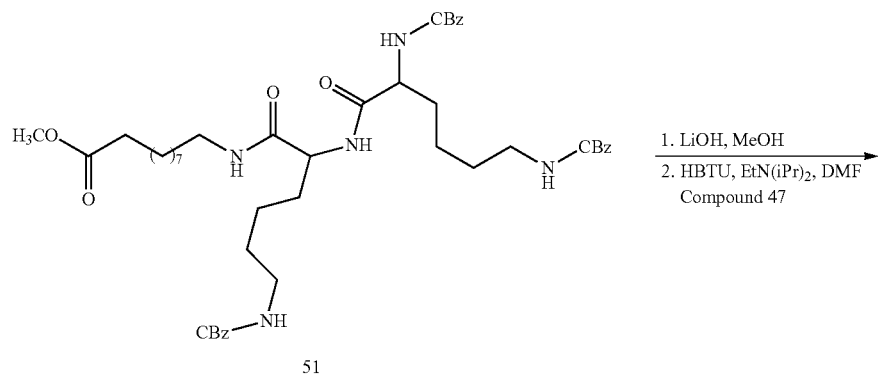
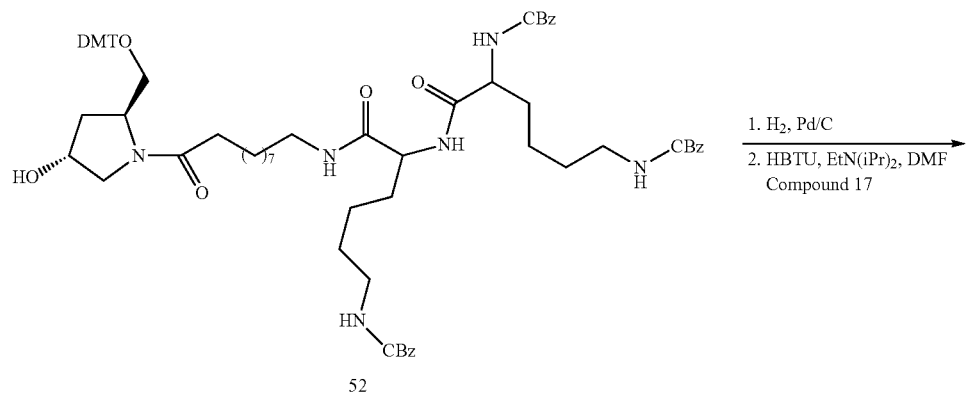

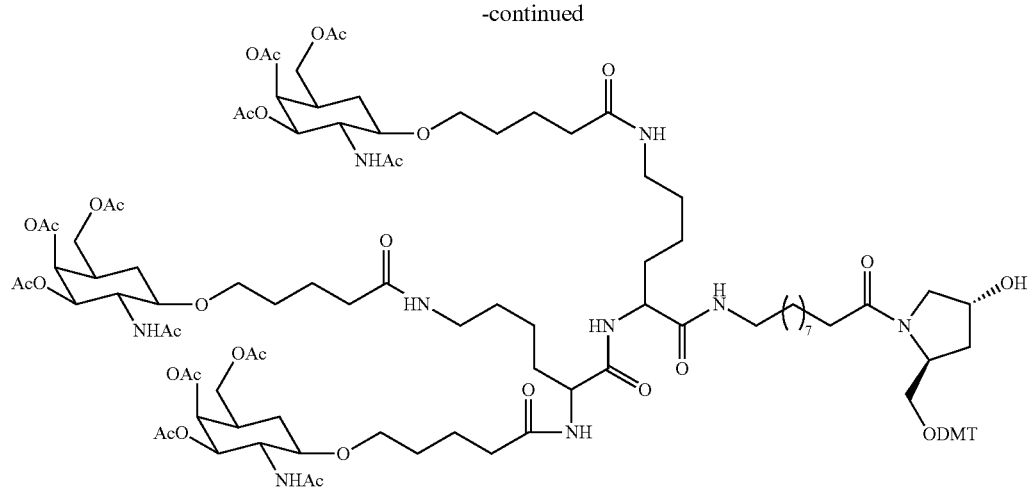
53
Compounds 48 and 49 are commercially available. Compounds 17 and 47 are prepared as per the procedures illustrated in Examples 4 and 14.
Example 16: Preparation of Compound 54
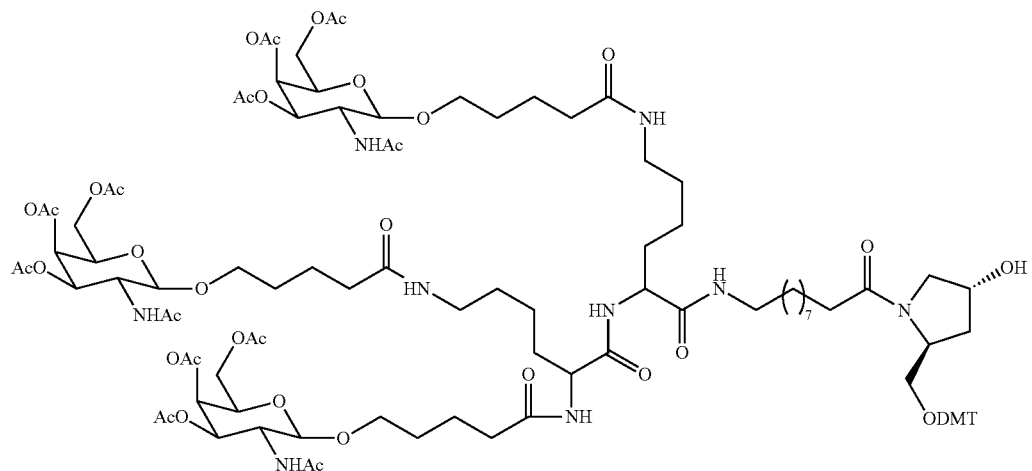
53
↓ Phosphitylation -continued
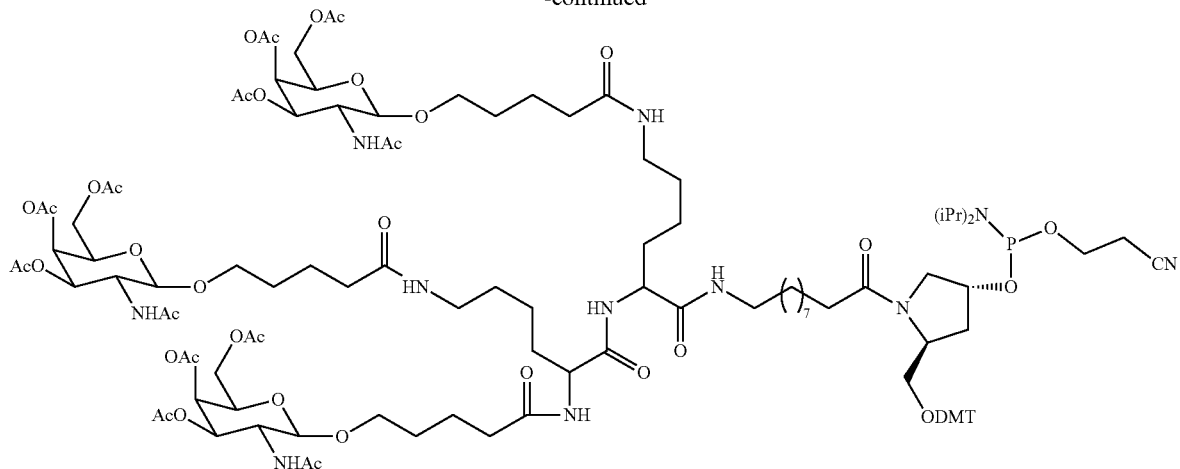
54
Compound 53 is prepared as per the procedures illustrated in Example 15.
Example 17: Preparation of Compound 55
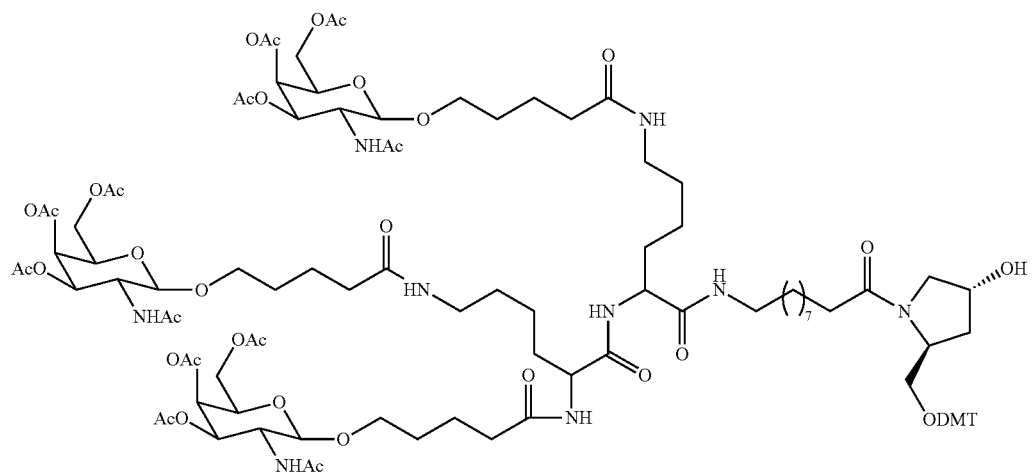
53
1. Succinic anhydride, DMAP, DCE
2. DMF, HBTU, EtN(iPr)₂, PS—SS

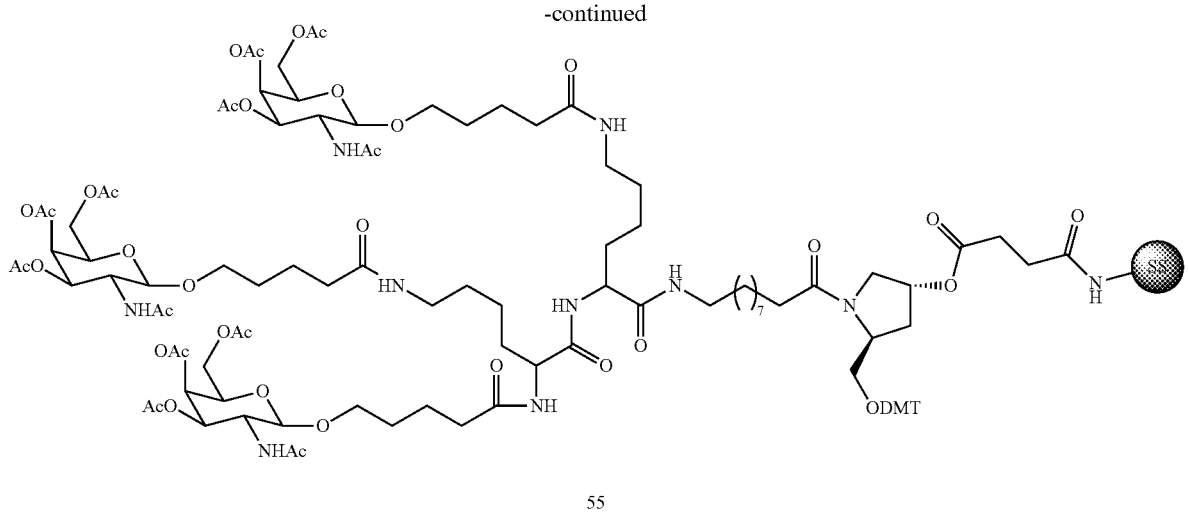

55

Compound 53 is prepared as per the procedures illustrated in Example 15.

Example 18: Compound 56

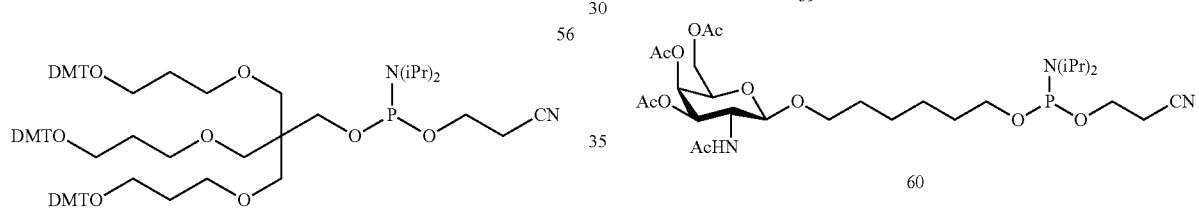

56

Compound 56 is commercially available from Glen Research or is prepared according to published procedures reported by Shchepinov et al., *Nucleic Acids Research*, 1997, 25(22), 4447-4454.

Example 19: Preparation of Compound 60

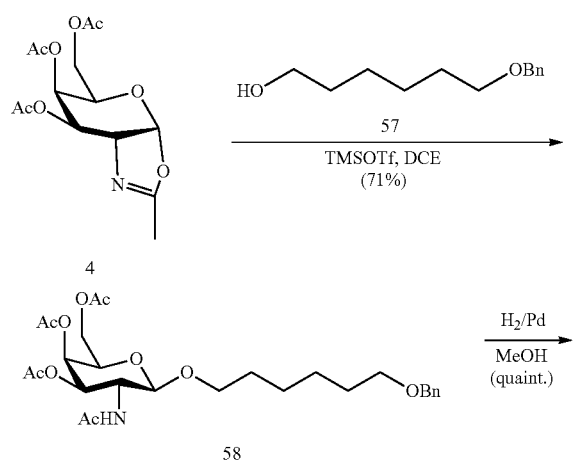

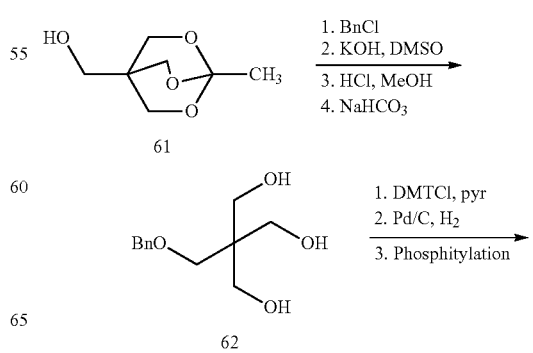

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 20: Preparation of Compound 63

-continued

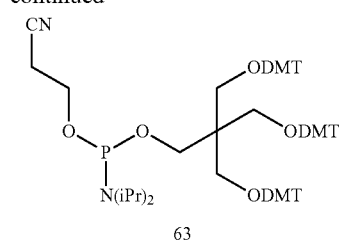

63

Compounds 61 and 62 are prepared using procedures similar to those reported by Tober et al., *Eur. J. Org. Chem.*, 2013, 3, 566-577; and Jiang et al., *Tetrahedron*, 2007, 63(19), 3982-3988.

Alternatively, Compound 63 is prepared using procedures similar to those reported in scientific and patent literature by Kim et al., *Synlett*, 2003, 12, 1838-1840; and Kim et al., published PCT International Application, WO 2004063208.

Example 21: Preparation of Compound 63b

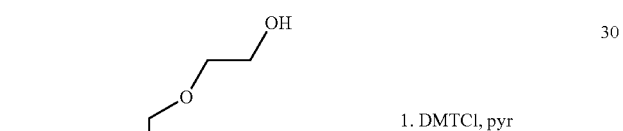

63a

Compound 63a is prepared using procedures similar to those reported by Hanessian et al., *Canadian Journal of Chemistry*, 1996, 74(9), 1731-1737.

Example 22: Preparation of Compound 63d

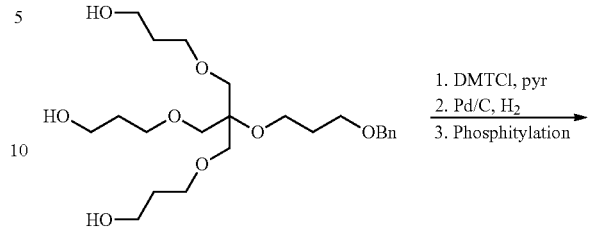

63d

Compound 63c is prepared using procedures similar to those reported by Chen et al., *Chinese Chemical Letters*, 1998, 9(5), 451-453.

Example 23: Preparation of Compound 67

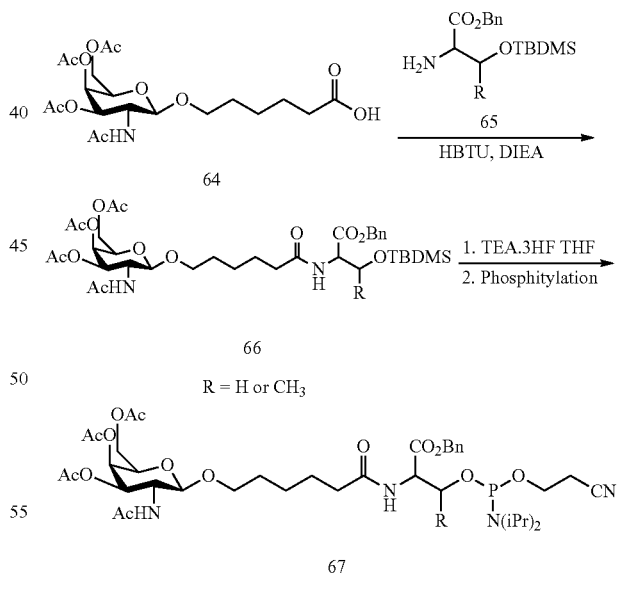

R = H or CH$_3$

67

Compound 64 is prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 24: Preparation of Compound 70

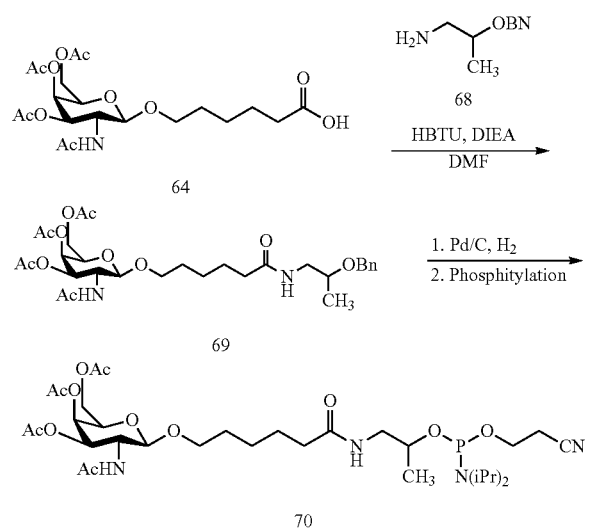

Compound 64 is prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 25: Preparation of Compound 75a

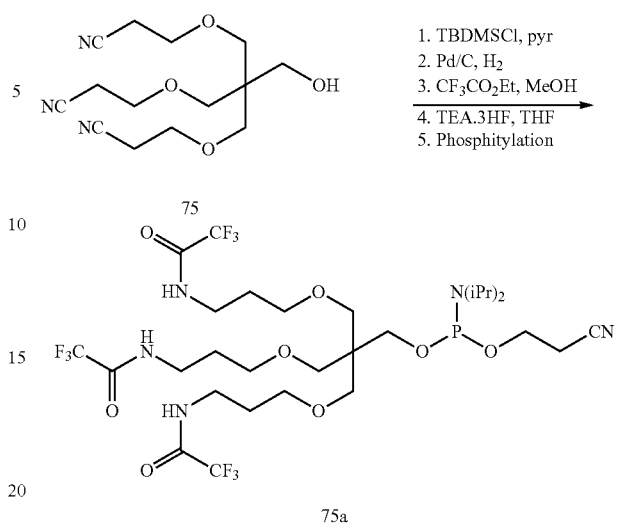

Compound 75 is prepared according to published procedures reported by Shchepinov et al., *Nucleic Acids Research*, 1997, 25(22), 4447-4454.

Example 26: Preparation of Compound 79

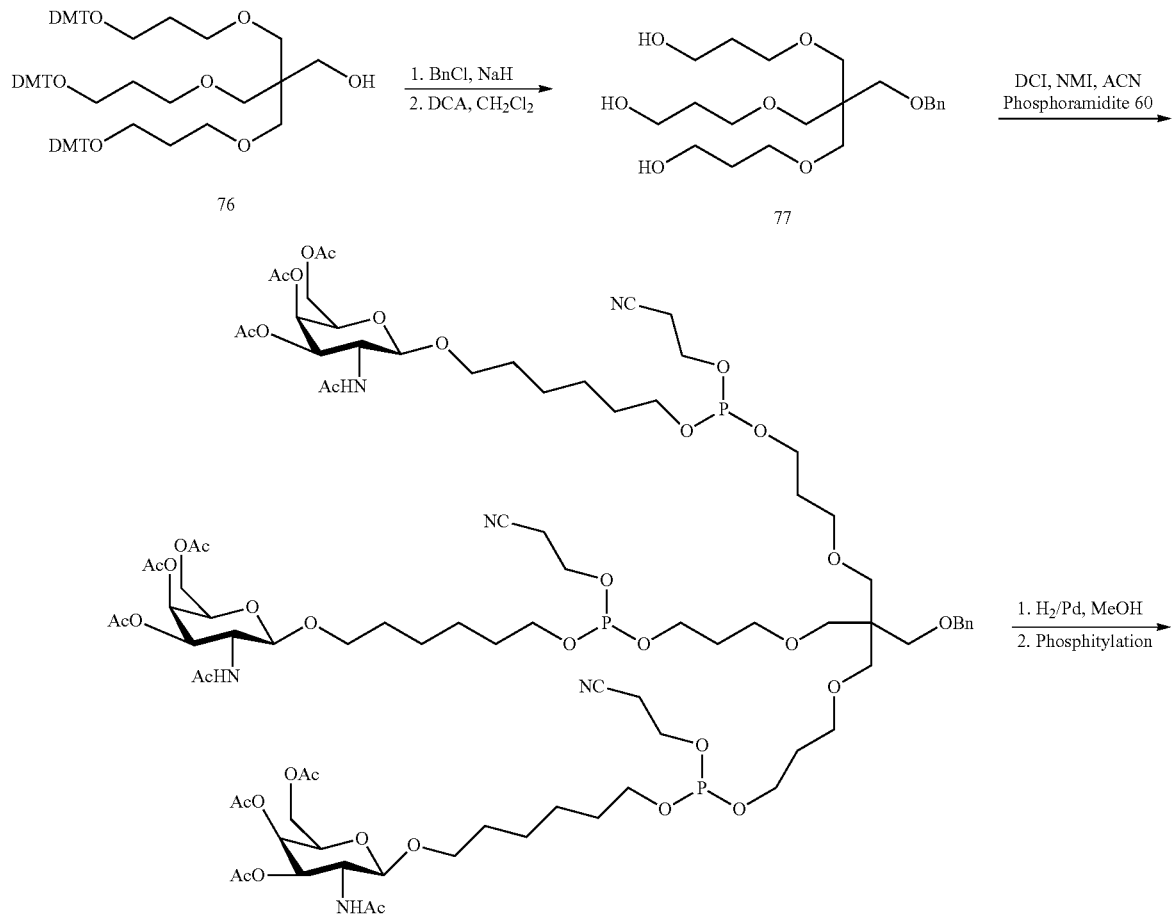

-continued
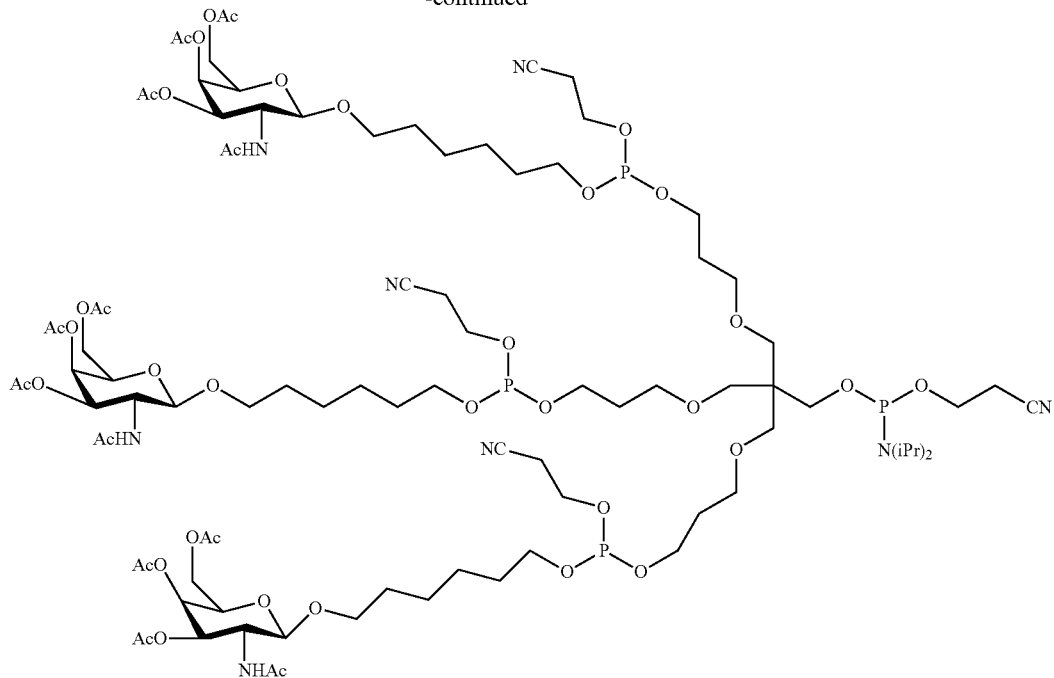
79
Compound 76 is prepared according to published procedures reported by Shchepinov et al., *Nucleic Acids Research*, 1997, 25(22), 4447-4454.
Example 27: Preparation of Compound 79a
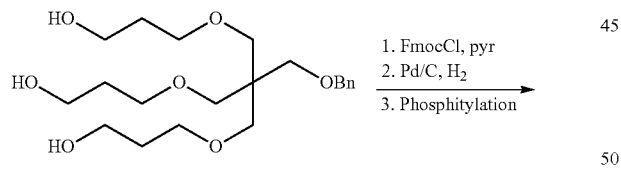
77
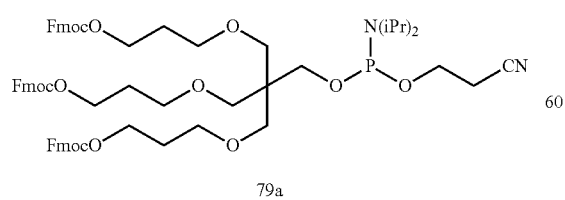
79a
Compound 77 is prepared as per the procedures illustrated in Example 26.

Example 28: General Method for the Preparation of Therapeutic Agents Comprising a Phosphodiester Linked GalNAc$_3$-2 Targeting Group at 5' Terminus Via Solid Support
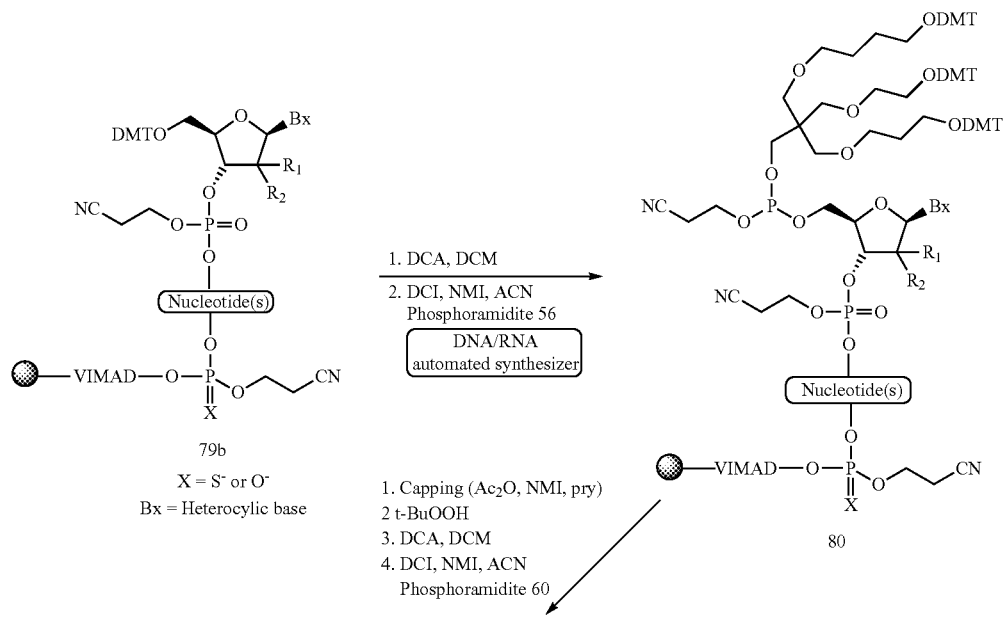
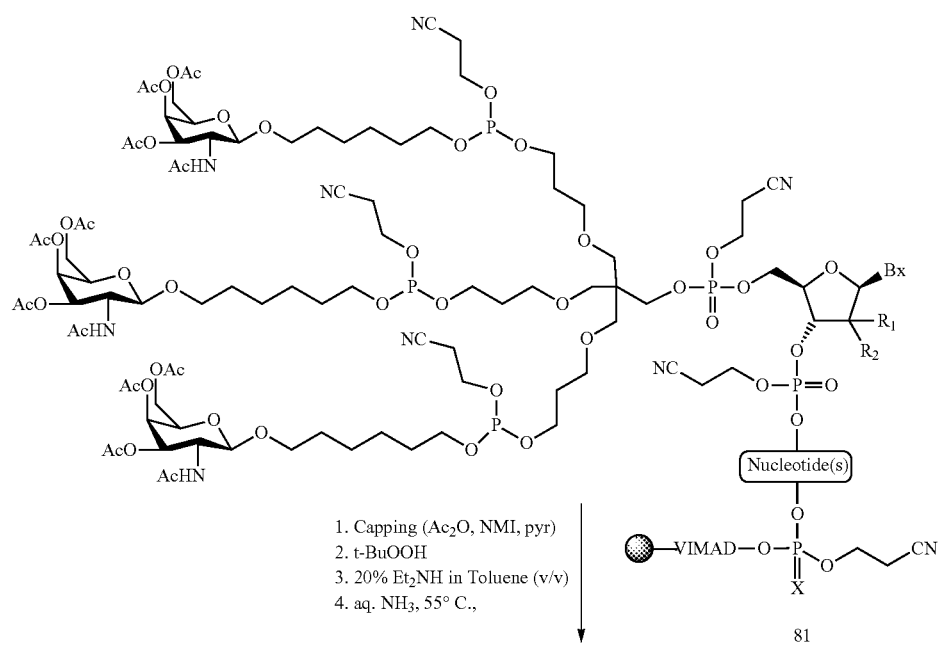

-continued
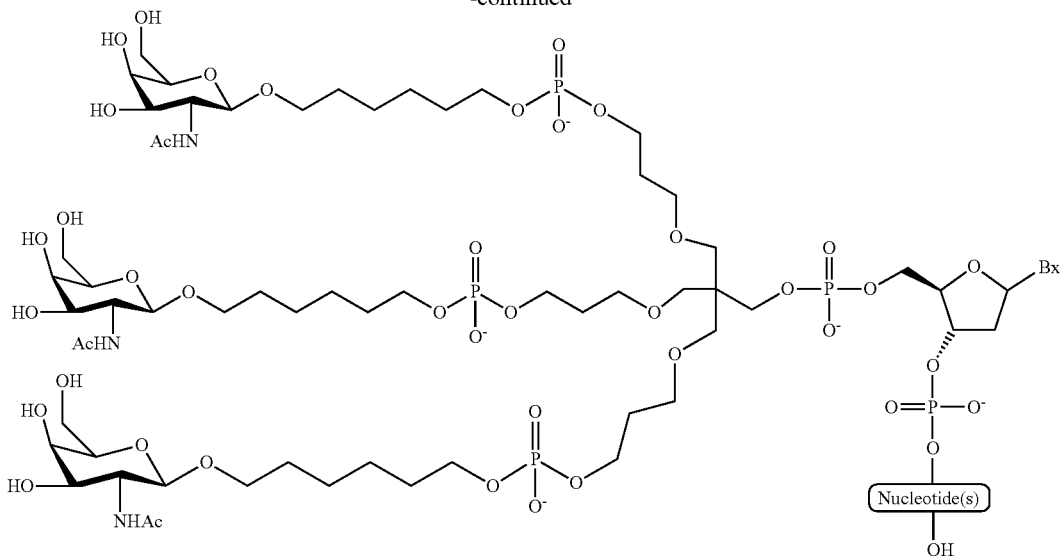
82
wherein GalNAc$_3$-2 has the structure:
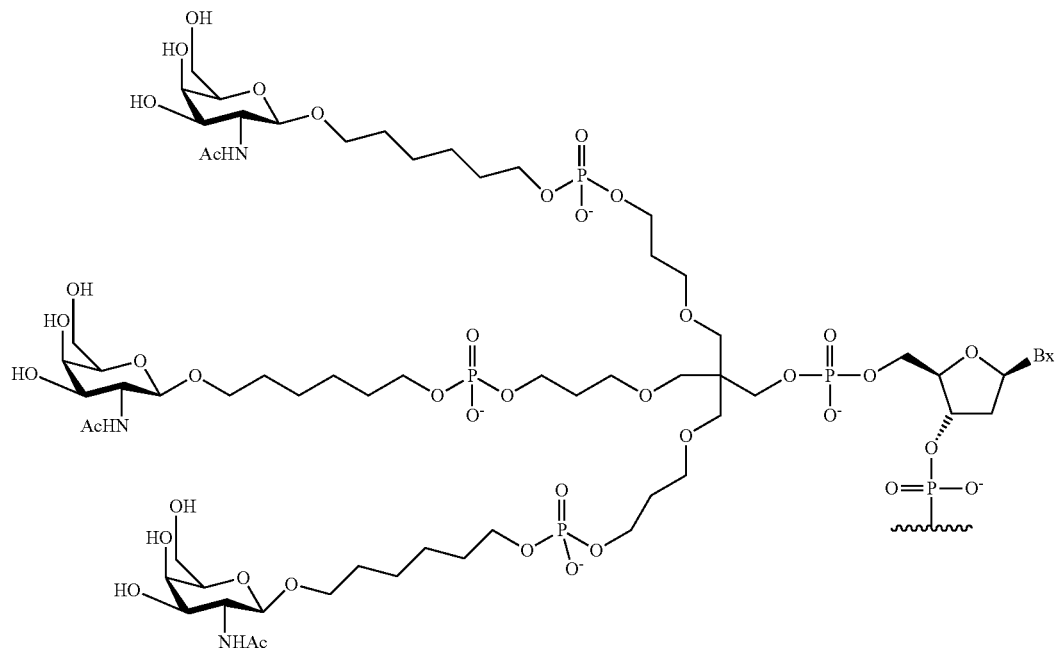
The GalNAc$_3$ cluster portion of the targeting group GalNAc$_3$-2 (GalNAc$_3$-2$_a$) can be combined with any cleavable moiety. Wherein GalNAc$_3$-2$_a$ has the formula:

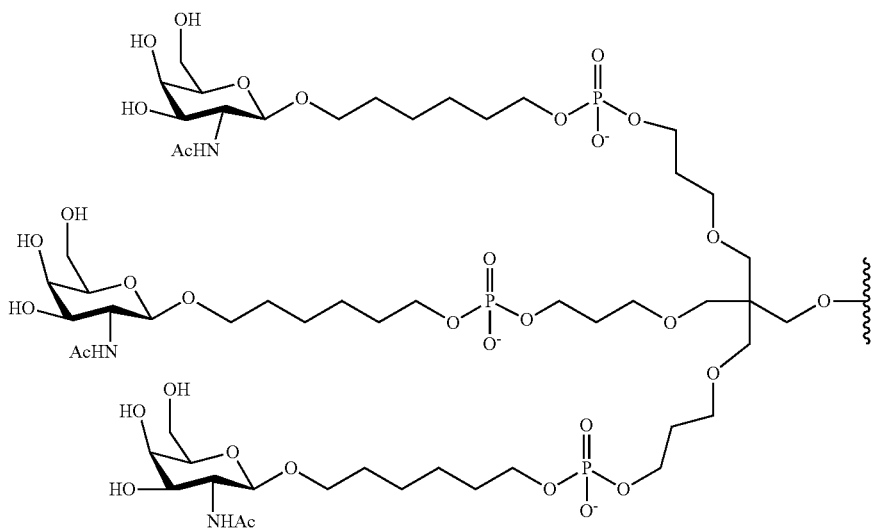

The VIMAD-bound compound 79b is prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 18 and 19, respectively. The phosphoramidites illustrated are meant to be representative and not intended to be limiting as other phosphoramidite building blocks including but not limited those presented in the specification herein can be used to prepare a therapeutic agent having a phosphodiester linked conjugate group at the 5' terminus. The order and quantity of phosphoramidites added to the solid support can be adjusted to prepare the compounds as described herein having any predetermined sequence and composition.

Example 29: General Method for the Preparation of Compound 83h Comprising a GalNAc$_3$-3 Targeting Group at the 5' Terminus (GalNAc$_3$-1 Modified for 5' End Attachment) Via Solid Support

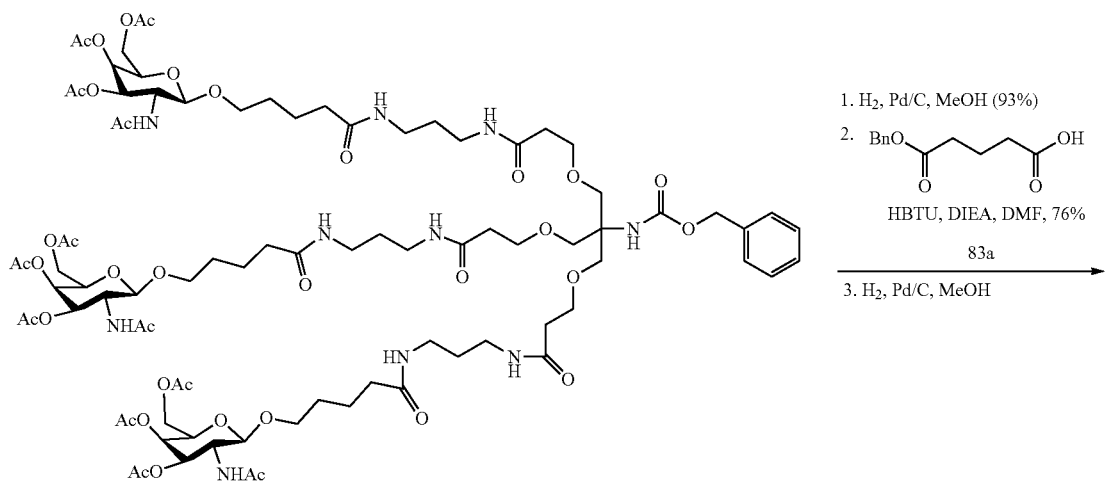

-continued
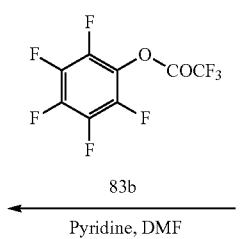
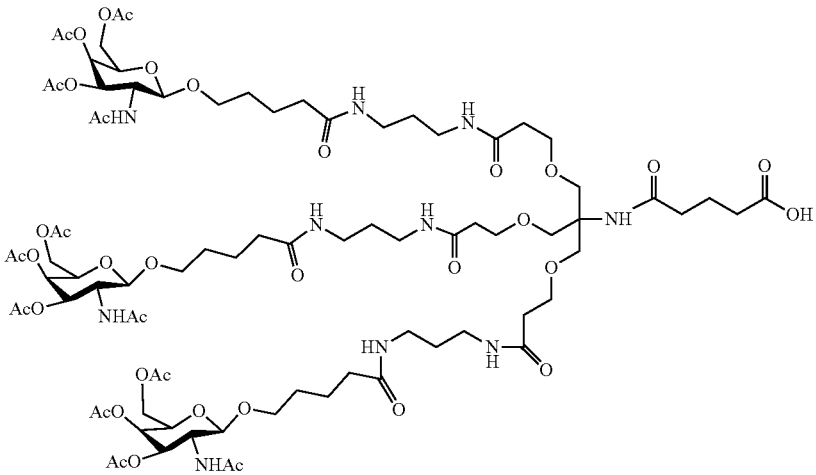
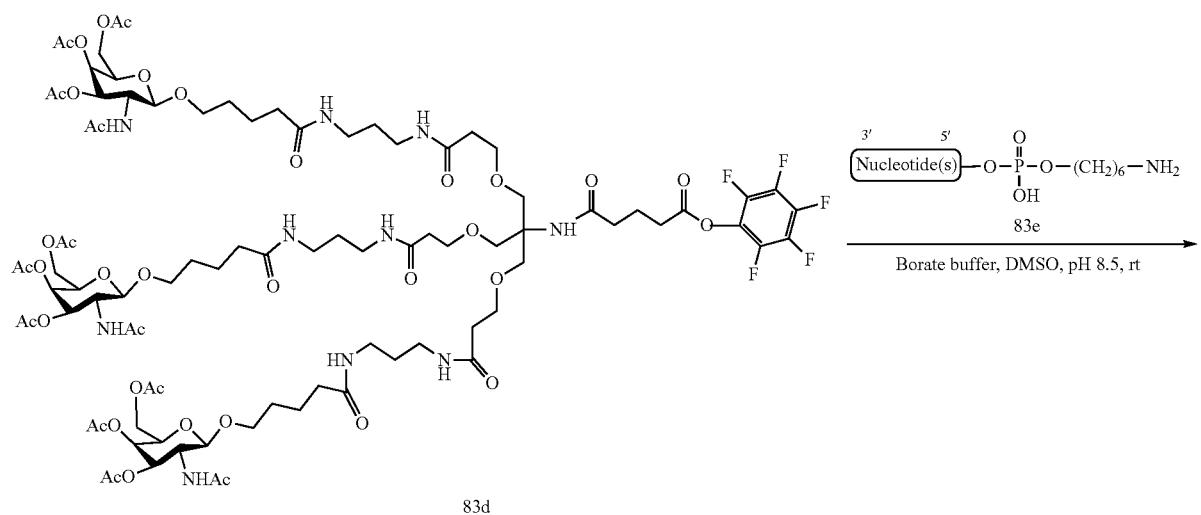
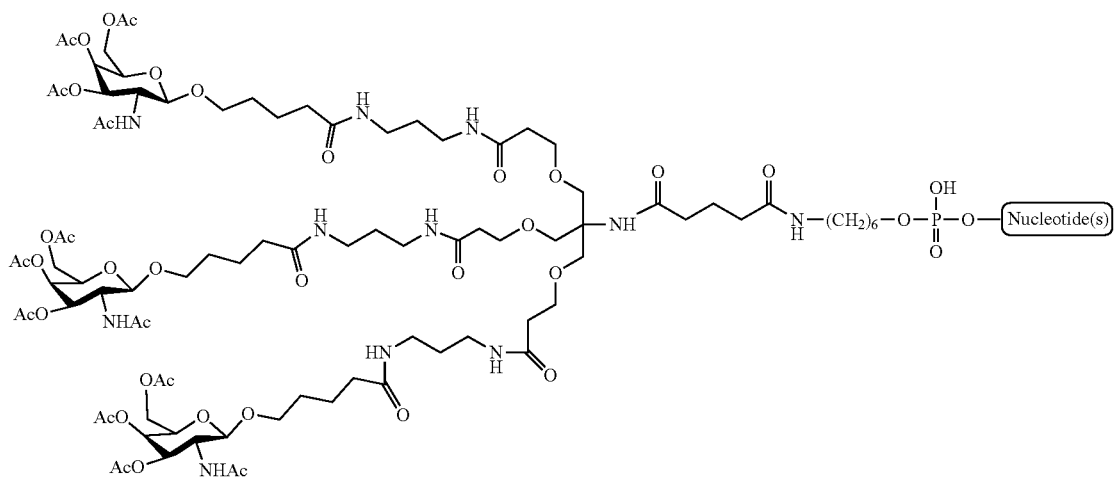

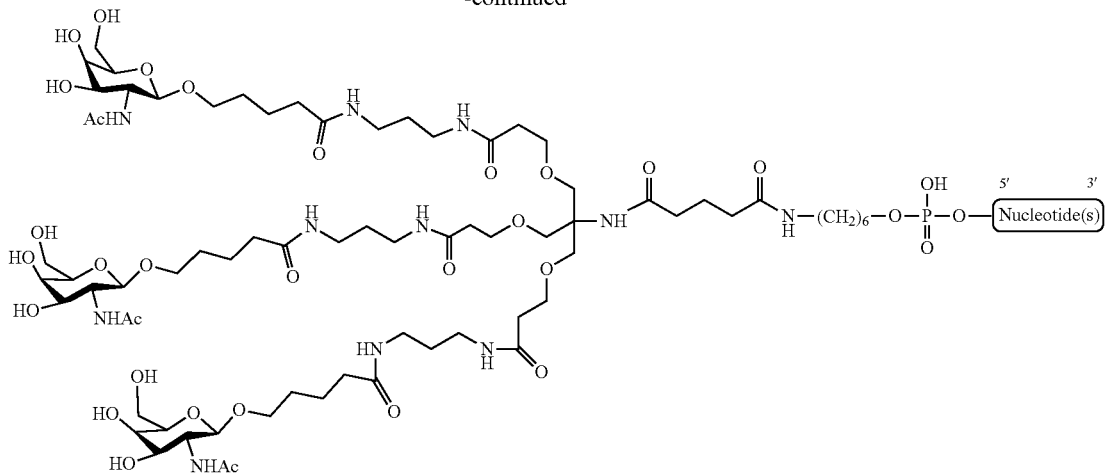

83h

Compound 18 is prepared as per the procedures illustrated in Example 4. Compounds 83a and 83b are commercially available. Compound 83e comprising a phosphodiester linked hexylamine is prepared using standard oligonucleotide synthesis procedures. Treatment of the protected compound with aqueous ammonia will provide the 5'-GalNAc$_3$-3 compound (83h).

Wherein GalNAc$_3$-3 has the structure:

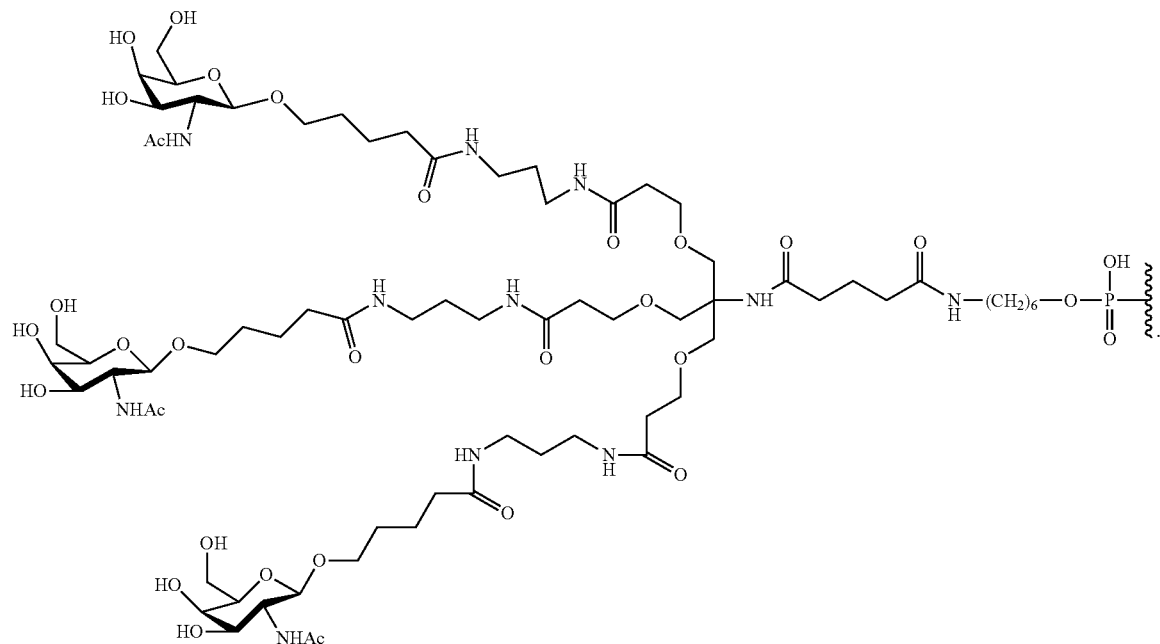

The GalNAc$_3$ cluster portion of the targeting group GalNAc$_3$-3 (GalNAc$_3$-3$_a$) can be combined with any cleavable moiety. Wherein GalNAc$_3$-3$_a$ has the formula:

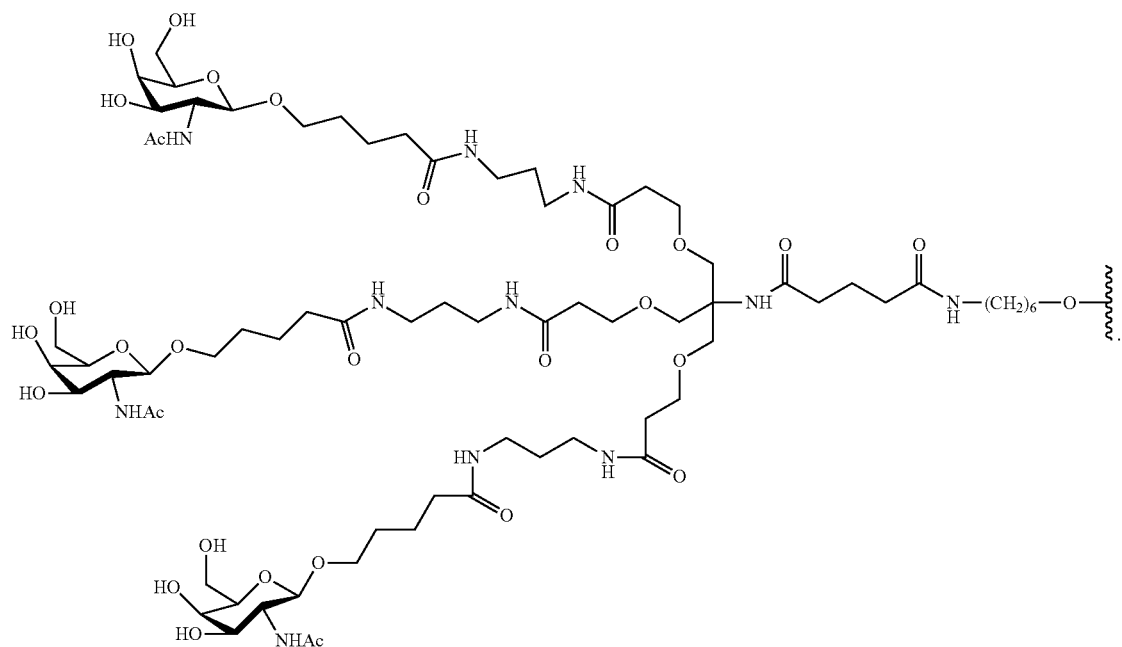
Example 30: General Method for the Preparation of Therapeutic Agent 89 Comprising a Phosphodiester Linked GalNAc$_3$-4 at the 3' Terminus Via Solid Support
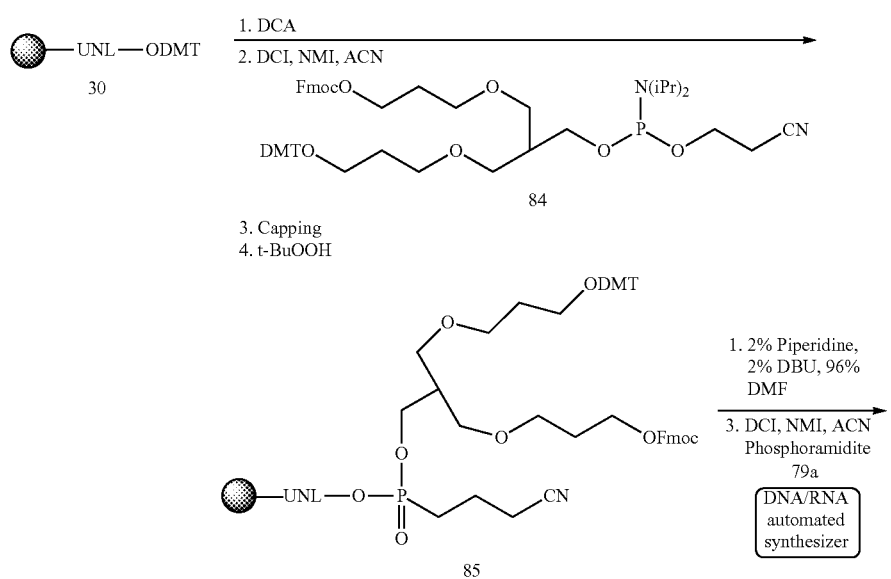

-continued
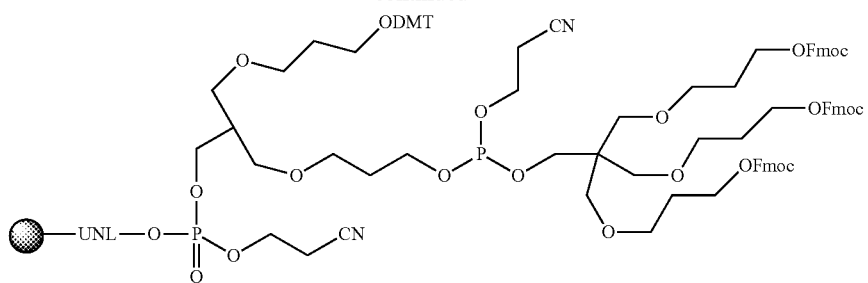
86
1. Capping
2. t-BuOOH
3. 2% Piperidine, 2% DBU, 96% DMF
4. DCI, NMI, ACN Phosphoramidite 60
   DNA/RNA automatedsynthesizer
5. Capping
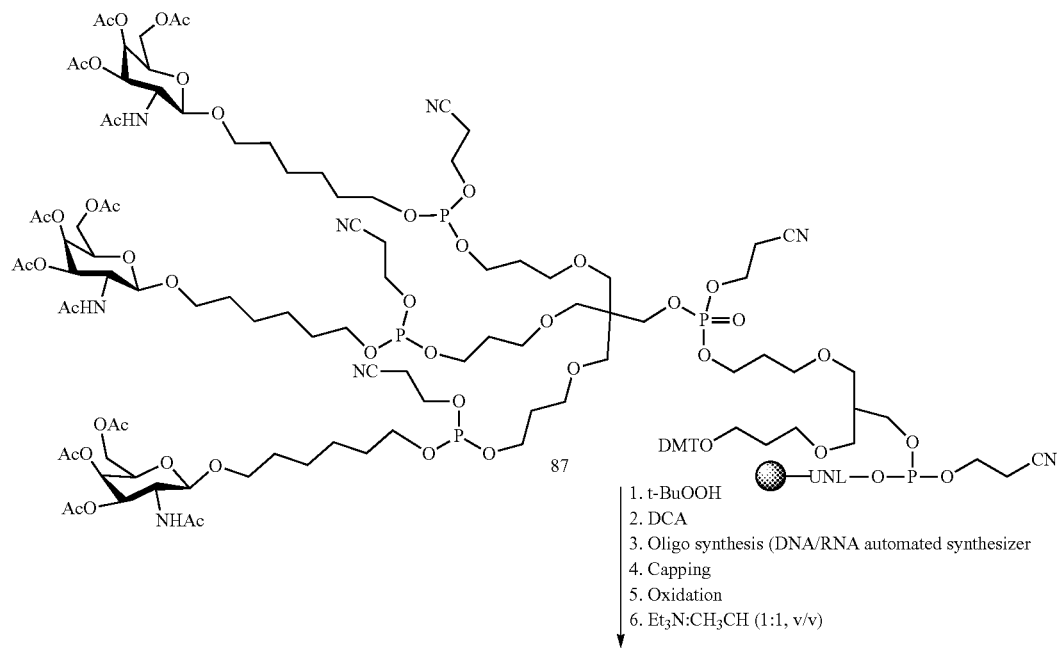
87
1. t-BuOOH
2. DCA
3. Oligo synthesis (DNA/RNA automated synthesizer
4. Capping
5. Oxidation
6. Et₃N:CH₃CH (1:1, v/v)

-continued
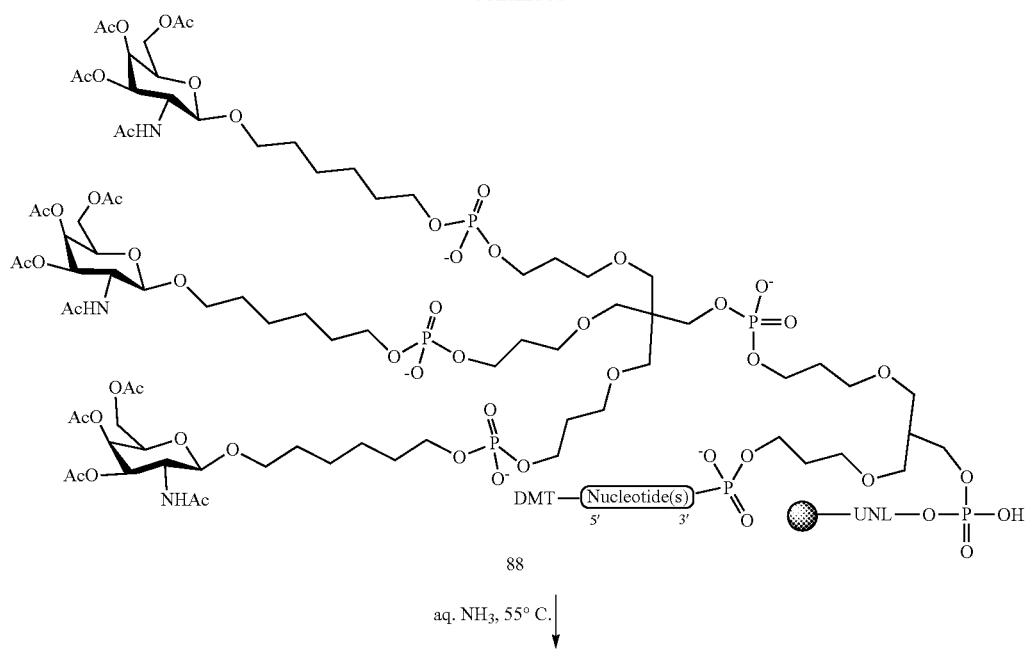
88
aq. NH$_3$, 55° C.
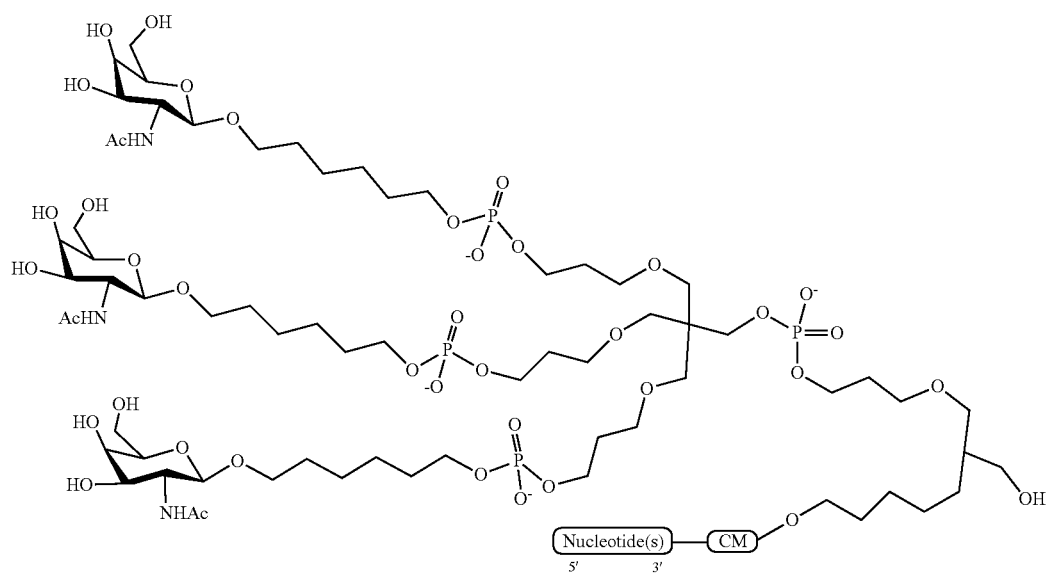
89

Wherein GalNAc₃-4 has the structure:
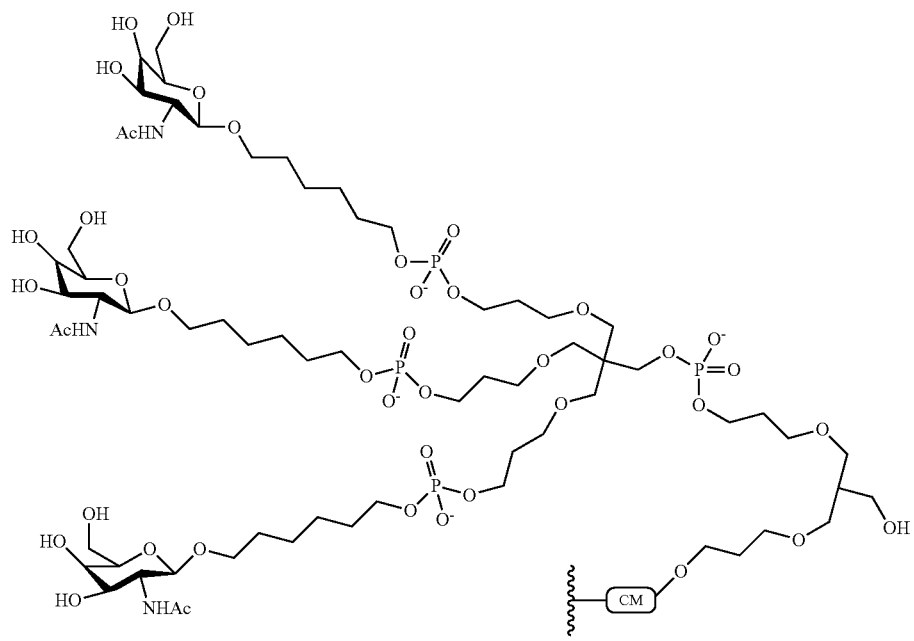
wherein CM is a cleavable moiety. In certain embodiments, cleavable moiety is:
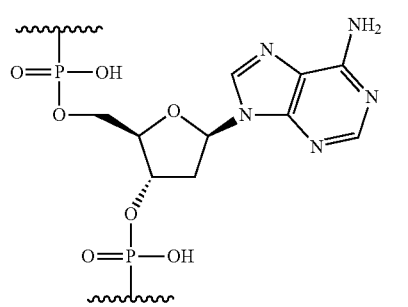 [SMILES: *P(=O)(O)OC[C@H]1O[C@@H](n2cnc3c(N)ncnc32)C[C@@H]1OP(*)(=O)O]
The GalNAc₃ cluster portion of the targeting group GalNAc₃-4 (GalNAc₃-4$_a$) can be combined with any cleavable moiety. Wherein GalNAc₃-4$_a$ has the formula:

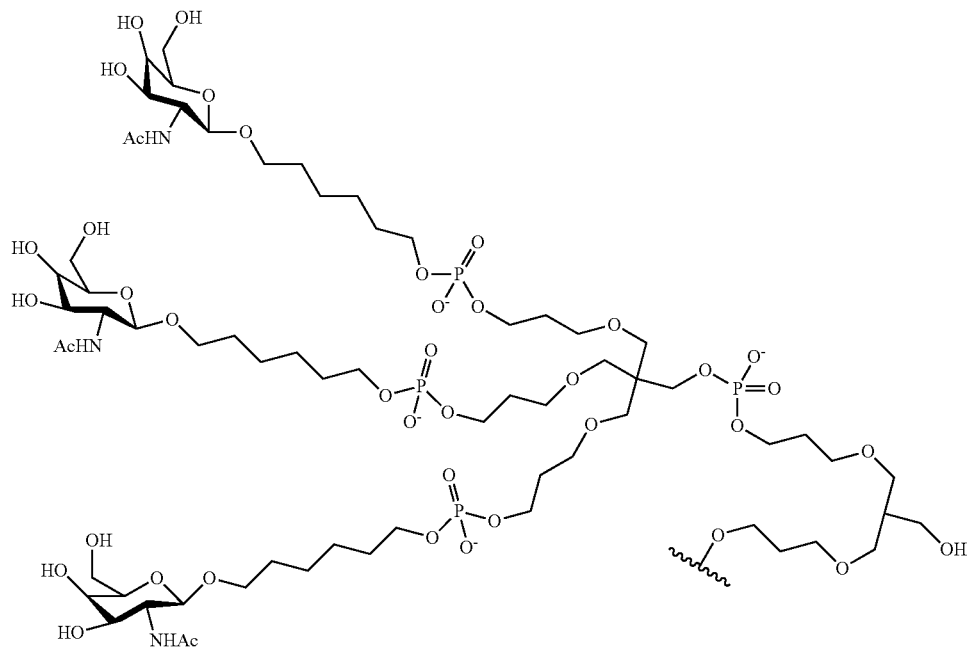

The protected Unylinker functionalized solid support Compound 30 is commercially available. Compound 84 is prepared using procedures similar to those reported in the literature (see Shchepinov et al., *Nucleic Acids Research*, 1997, 25(22), 4447-4454; Shchepinov et al., *Nucleic Acids Research*, 1999, 27, 3035-3041; and Hornet et al., *Nucleic Acids Research*, 1997, 25, 4842-4849).

The phosphoramidite building blocks, Compounds 60 and 79a are prepared as per the procedures illustrated in Examples 19 and 27, respectively. The phosphoramidites illustrated are meant to be representative and not intended to be limiting as other phosphoramidite building blocks can be used to prepare a therapeutic agent having a phosphodiester linked targeting group at the 3' terminus and a predetermined sequence and composition. The order and quantity of phosphoramidites added to the solid support can be adjusted to prepare the compounds as described herein having any predetermined sequence and composition.

Example 31: Preparation of PFP Ester, Compound 110a

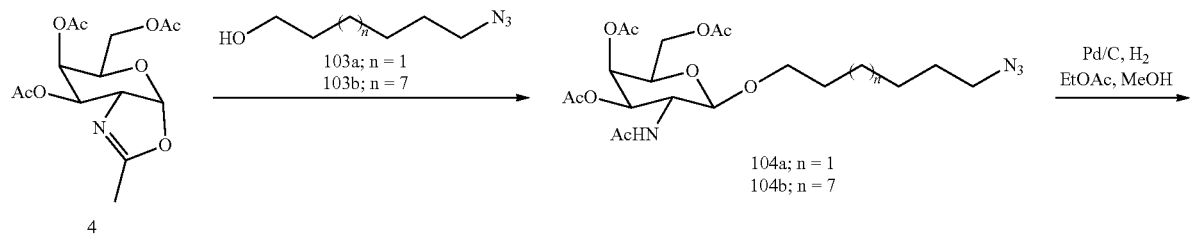

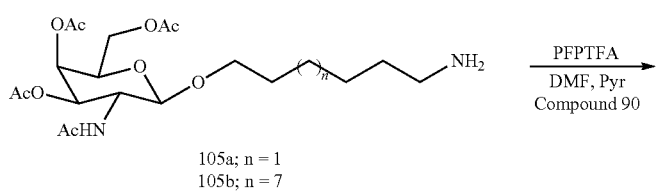

-continued
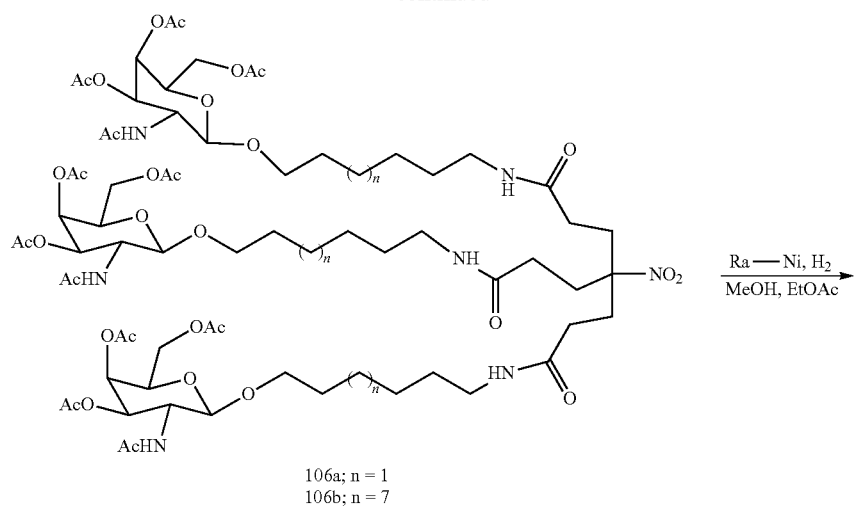
106a; n = 1
106b; n = 7
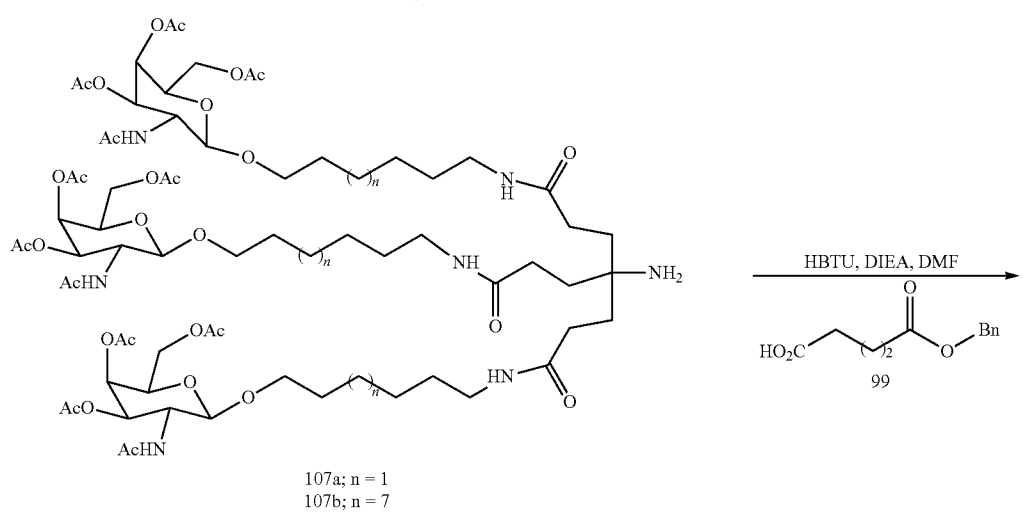
107a; n = 1
107b; n = 7
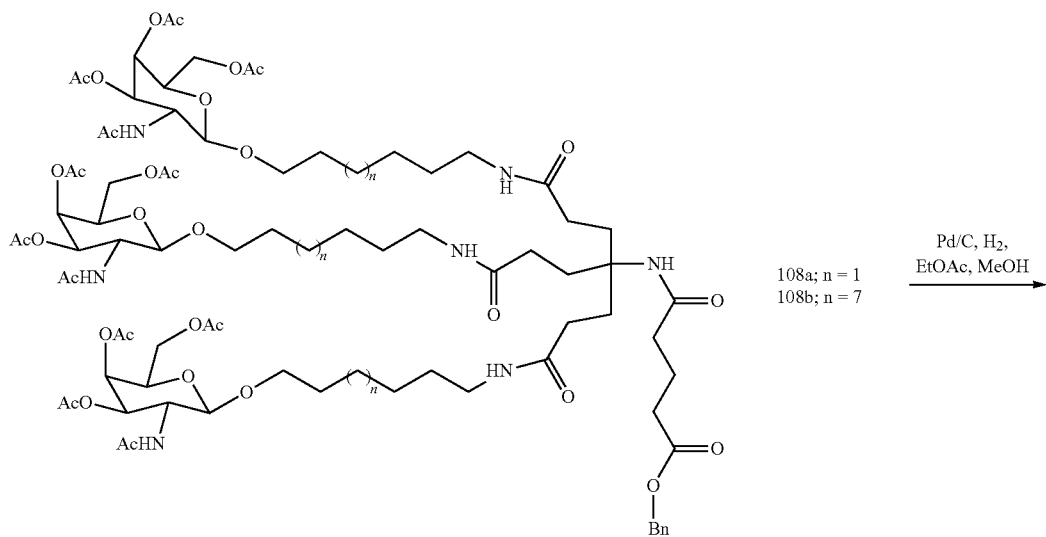
108a; n = 1
108b; n = 7

-continued

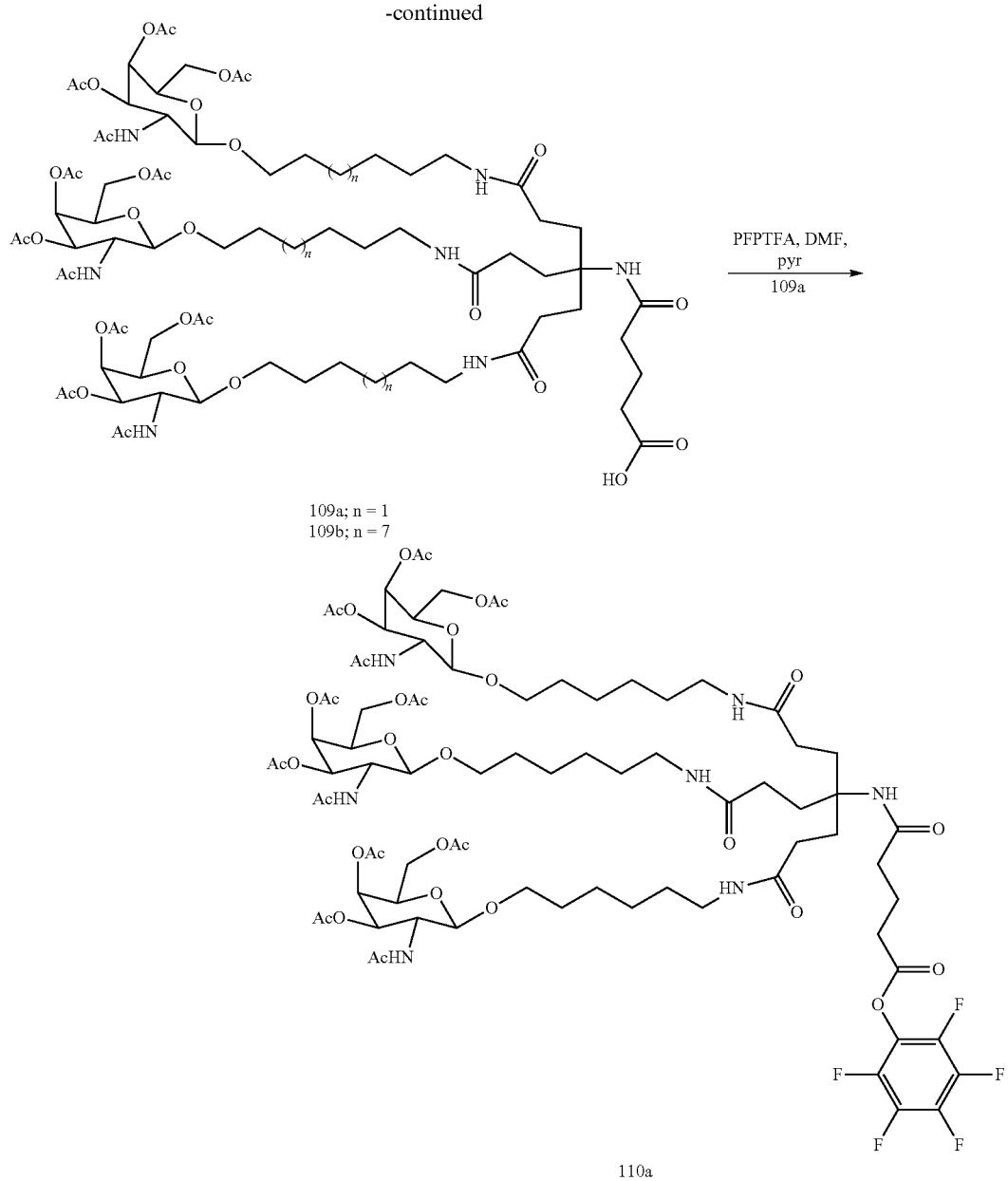

109a; n = 1
109b; n = 7

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%→10% methanol dichloromethane) to give compounds 104a and 104b in >80% yield. LCMS and proton NMR was consistent with the structure.

Compounds 104a and 104b were treated to the same conditions as for compounds 101a-d (Example 33), to give compounds 105a and 105b in >90% yield. LCMS and proton NMR was consistent with the structure.

Compounds 105a and 105b were treated, individually, with compound 90 under the same conditions as for compounds 92a-b, to give compounds 106a (80%) and 106b (20%). LCMS and proton NMR was consistent with the structure.

Compounds 106a and 106b were treated to the same conditions as for compounds 97a-d (Example 33), to give 107a (60%) and 107b (20%). LCMS and proton NMR was consistent with the structure.

Compounds 107a and 107b were treated to the same conditions as for compounds 100a-d (Example 33), to give compounds 108a and 108b in 40-60% yield. LCMS and proton NMR was consistent with the structure.

Compounds 108a (60%) and 108b (40%) were treated to the same conditions as for compounds 101a-d (Example 33), to give compounds 109a and 109b in >80% yields. LCMS and proton NMR was consistent with the structure.

Compound 109a was treated to the same conditions as for compounds 102a-d (Example 33), to give Compound 110a in 30-60% yield. LCMS and proton NMR was consistent with the structure. Alternatively, Compound 110b can be prepared in a similar manner starting with Compound 109b.

Example 32: General Procedure for Conjugation with PFP Esters

A 5'-hexylamino modified (oligo)nucleotide is synthesized and purified using standard solid-phase oligonucleotide procedures. The 5'-hexylamino modified (oligo)nucleotide is dissolved in 0.1 M sodium tetraborate, pH 8.5 (200 µL) and 3 equivalents of a selected PFP esterified GalNAc$_3$ cluster dissolved in DMSO (50 µL) is added. If the PFP ester precipitates upon addition to the ASO solution DMSO is added until all PFP ester is in solution. The reaction is complete after about 16 h of mixing at room temperature. The resulting solution is diluted with water to 12 mL and then spun down at 3000 rpm in a spin filter with a mass cut off of 3000 Da. This process is repeated twice to remove small molecule impurities. The solution is then lyophilized to dryness and redissolved in concentrated aqueous ammonia and mixed at room temperature for 2.5 h followed by concentration in vacuo to remove most of the ammonia. The conjugated (oligo)nucleotide is purified and desalted by RP-HPLC and lyophilized to provide the GalNAc$_3$ conjugated therapeutic agent.

Compound 111 is conjugated to GalNAc$_3$-10. The GalNAc$_3$ cluster portion of the targeting group GalNAc$_3$-10 (GalNAc$_3$-10$_a$) can be combined with any cleavable moiety. In a certain embodiment, the cleavable moiety is —P(=O)(OH)-A$_d$-P(=O)(OH)—. The structure of GalNAc$_3$-10 (GalNAc$_3$-10$_a$-CM-) is shown below:

Example 33: Preparation of Therapeutic Agent 102 Comprising GalNAc$_3$-8

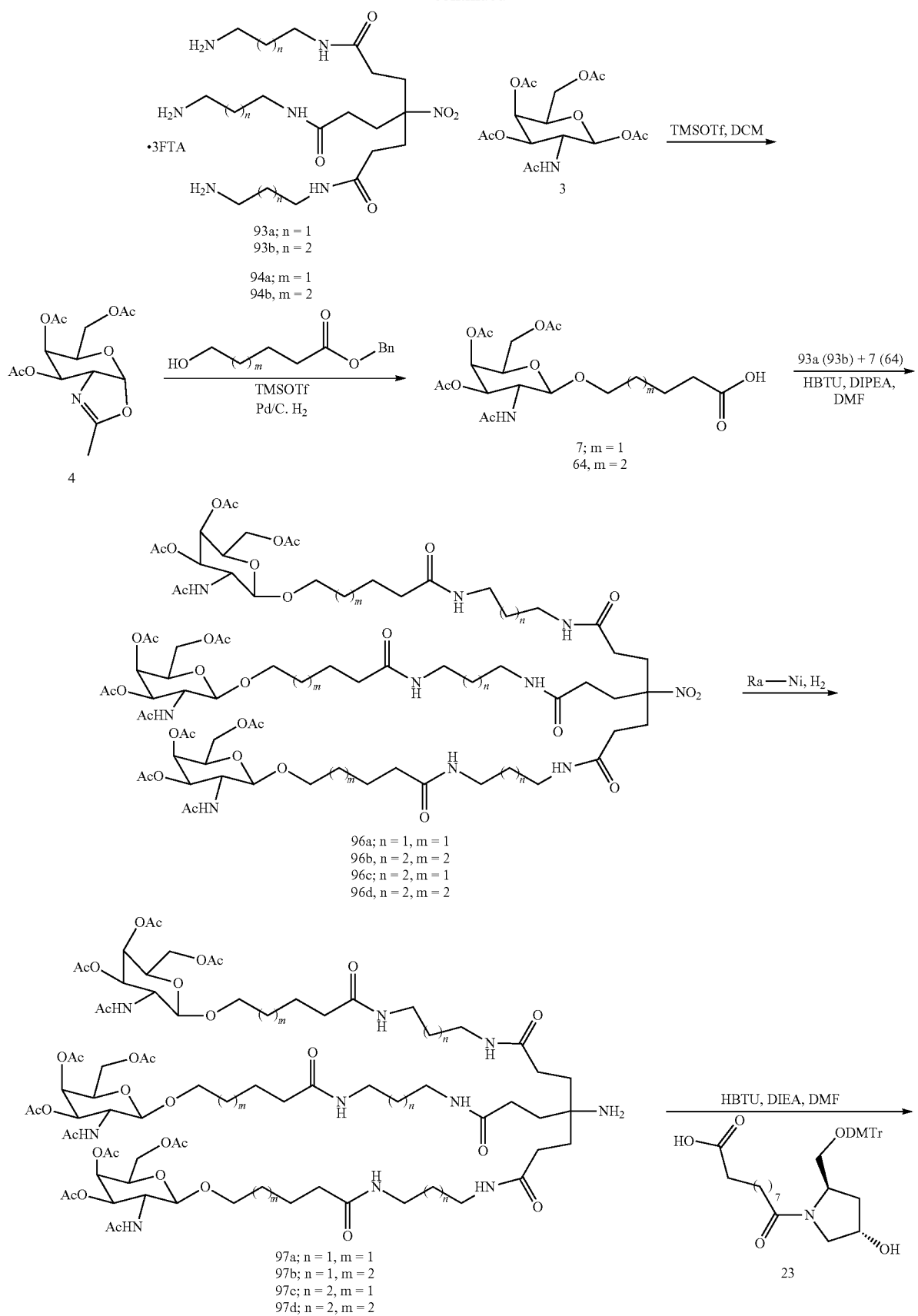

-continued
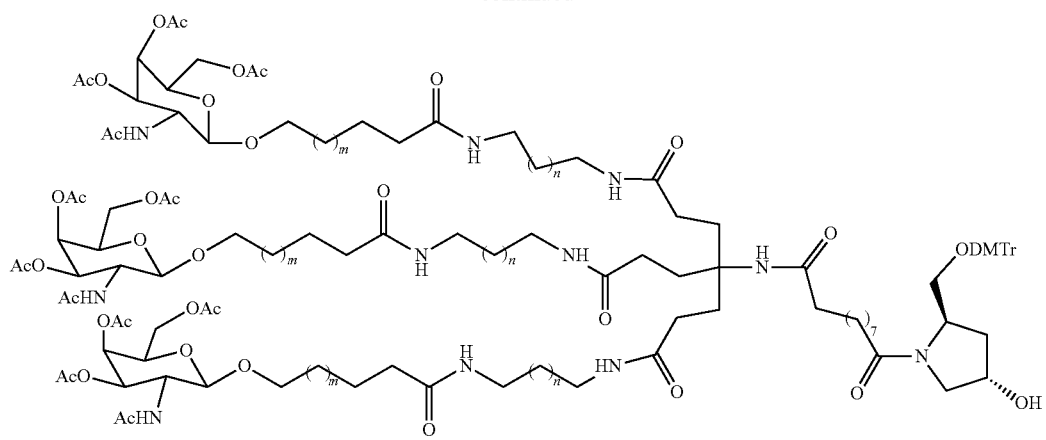
98a; n = 1, m = 1
98b; n = 1, m = 2
98c; n = 2, m = 1
98d; n = 2, m = 2
97a; n = 1, m = 1
97b; n = 1, m = 2
97c; n = 2, m = 1
97d; n = 2, m = 2
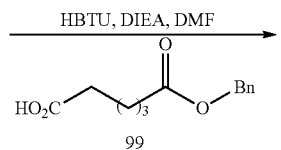
HBTU, DIEA, DMF
99
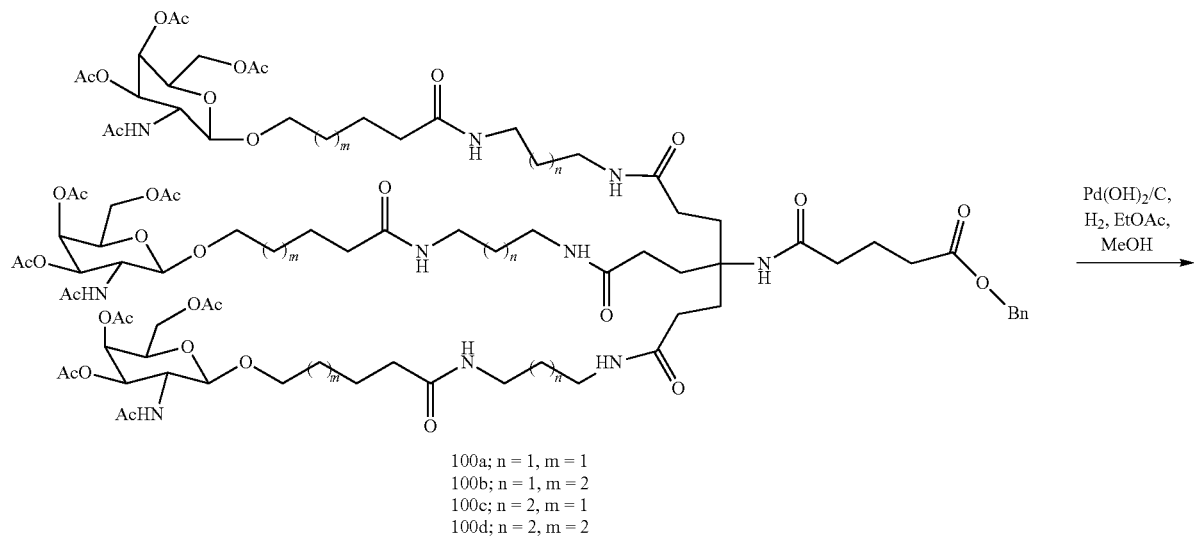
100a; n = 1, m = 1
100b; n = 1, m = 2
100c; n = 2, m = 1
100d; n = 2, m = 2
Pd(OH)$_2$/C, H$_2$, EtOAc, MeOH

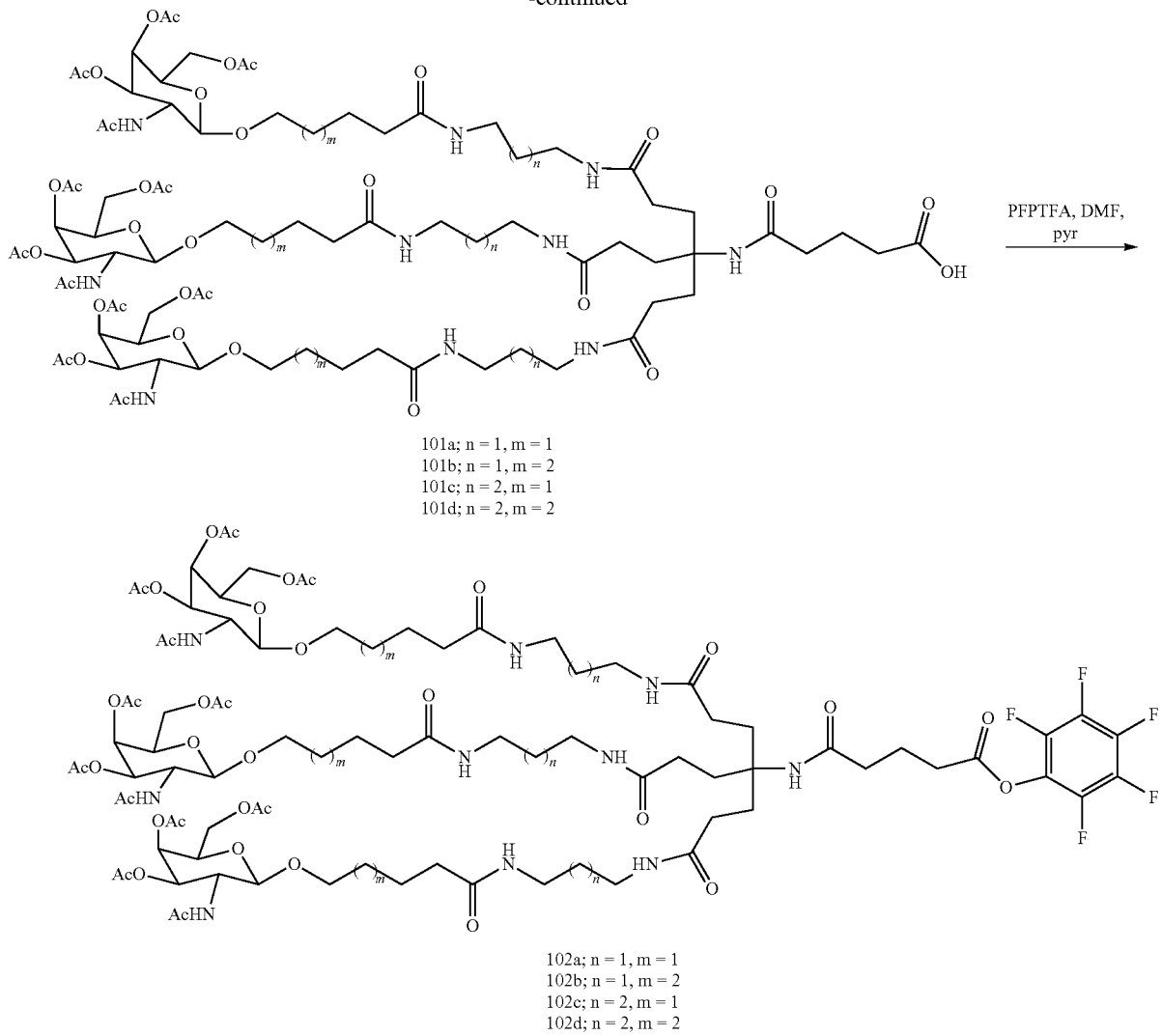

101a; n = 1, m = 1
101b; n = 1, m = 2
101c; n = 2, m = 1
101d; n = 2, m = 2

102a; n = 1, m = 1
102b; n = 1, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→10% methanol dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol dichloromethane) to give compounds 102a-d in an approximate 80% yield. LCMS and proton NMR were consistent with the structure.

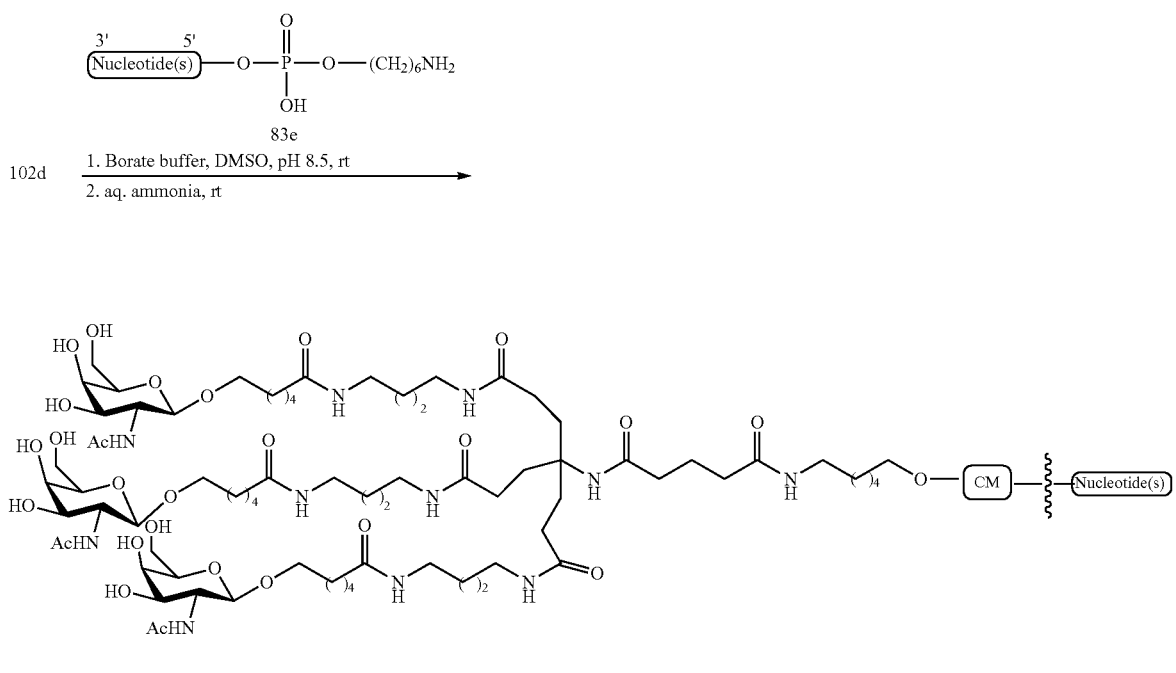

102 sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 100a-d in 40-60% yield. LCMS and proton NMR was consistent with the structure.

Compounds 100a-d (0.16 mmoles), individually, were hydrogenated over 10% Pd(OH)$_2$/C for 3 hours in methanol/

Compound 102, comprising a GalNAc$_3$-8 targeting group, is prepared using the general procedures illustrated in Example 32. The GalNAc$_3$ cluster portion of the targeting group GalNAc$_3$-8 (GalNAc$_3$-8$_a$) can be combined with any cleavable moiety. In certain embodiments, the cleavable moiety is —P(=O)(OH)-A$_d$-P(=O)(OH)—.

The structure of GalNAc$_3$-8 (GalNAc$_3$-8$_a$-CM-) is shown below:

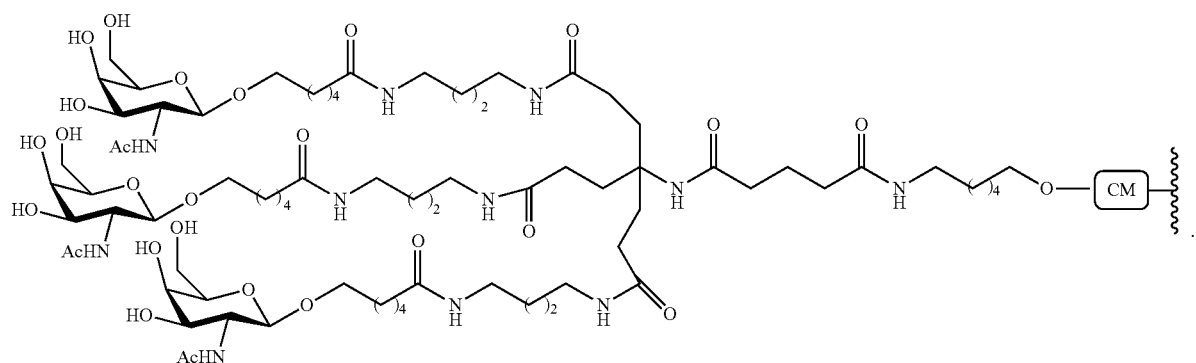
Example 34: Preparation of Therapeutic Agent 119 Comprising GalNAc$_3$-7
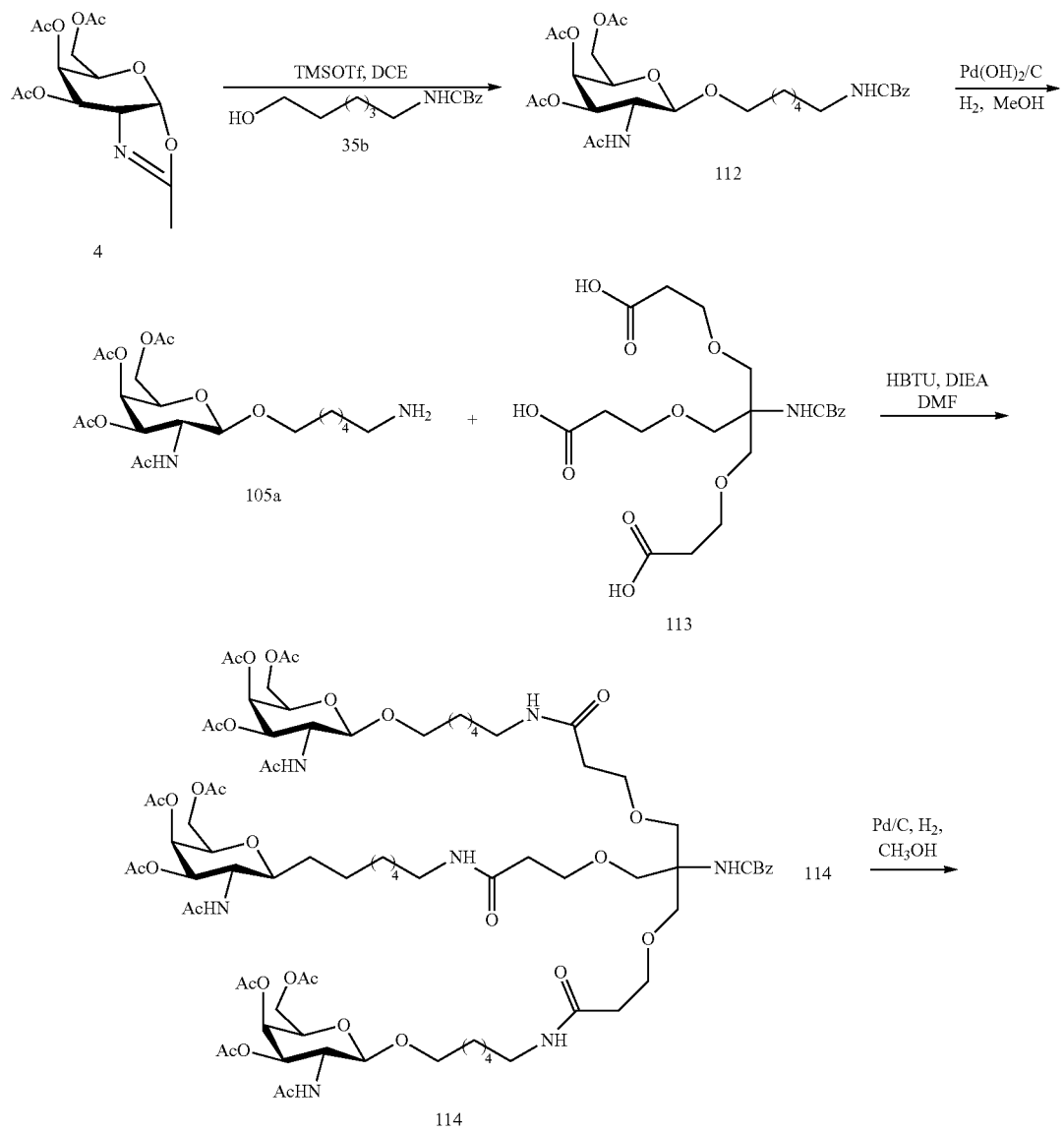

-continued

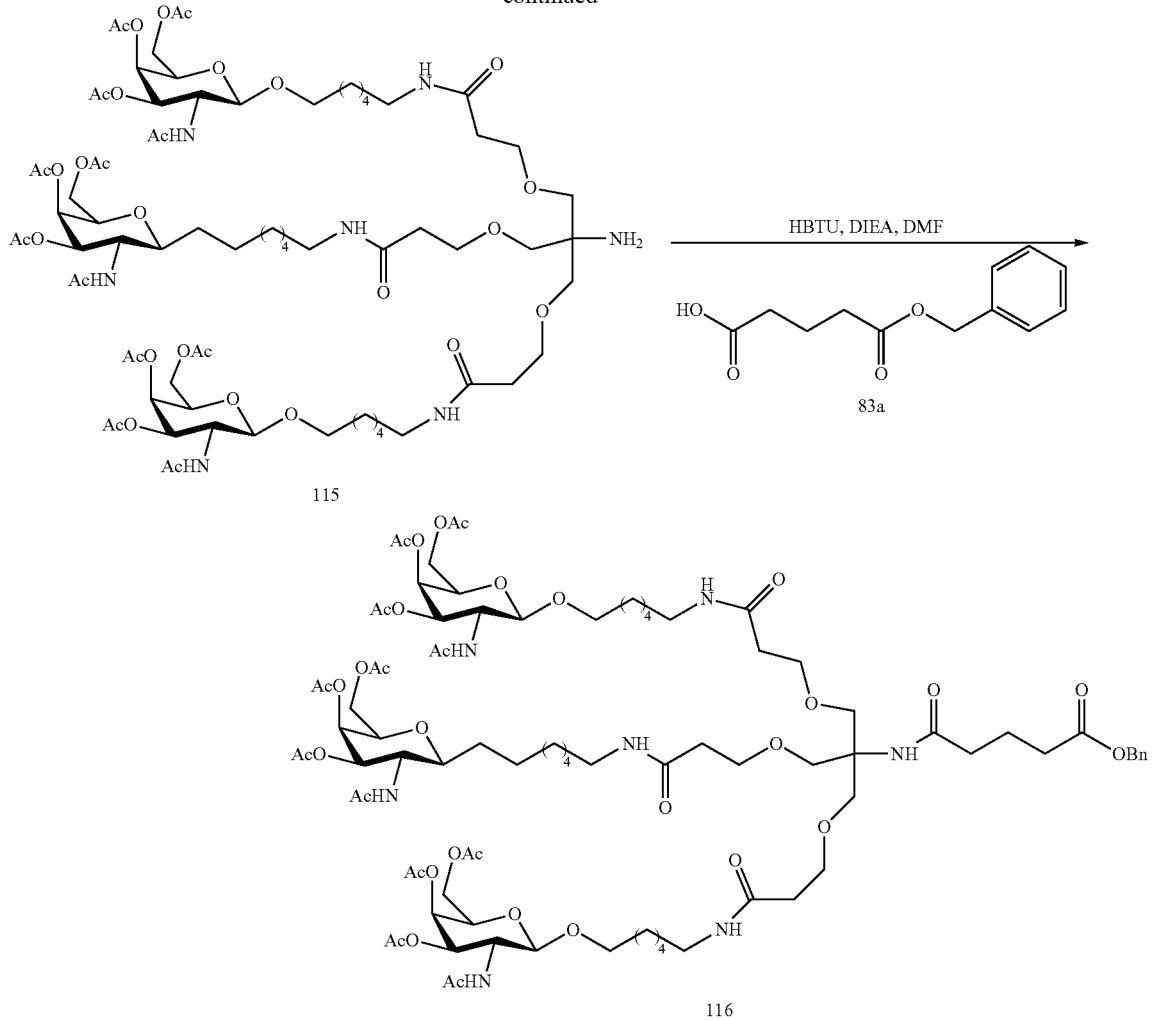

Compound 112 was synthesized following the procedure described in the literature (J. Med. Chem. 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in CH$_2$Cl$_2$ (100 mL) and washed with aqueous saturated NaHCO$_3$ solution (100 mL) and brine (100 mL). The organic phase was separated, dried (Na$_2$SO$_4$), filtered and evaporated. The residue was purified by silica gel column chromatography and eluted with 10 to 20% MeOH in dichloromethane to yield Compound 114 (1.45 g, 30%). The structure was confirmed by LCMS and $^1$H NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1$H NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in CH$_2$Cl$_2$. The organic layer was washed aqueous saturated NaHCO$_3$ solution and brine and dried over anhydrous Na$_2$SO$_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1$H NMR analysis.

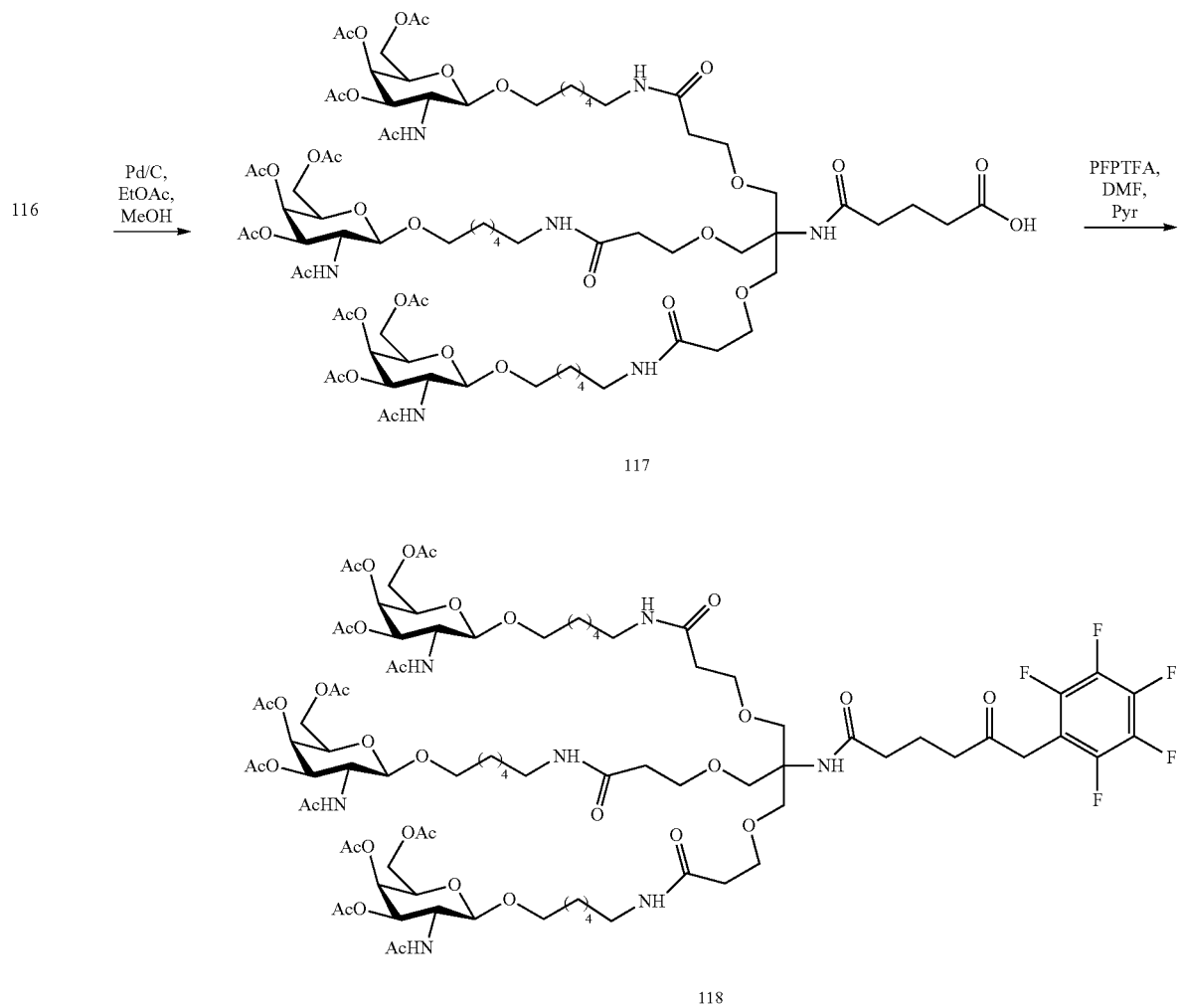

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^1$H NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated NaHCO$_3$ solution. The mixture was extracted with dichloromethane, washed with brine and dried over anhydrous Na$_2$SO$_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1$H and $^1$H and $^{19}$F NMR.

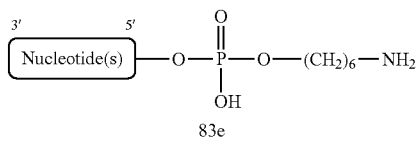

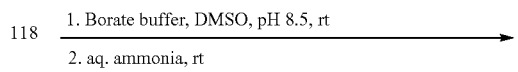

-continued

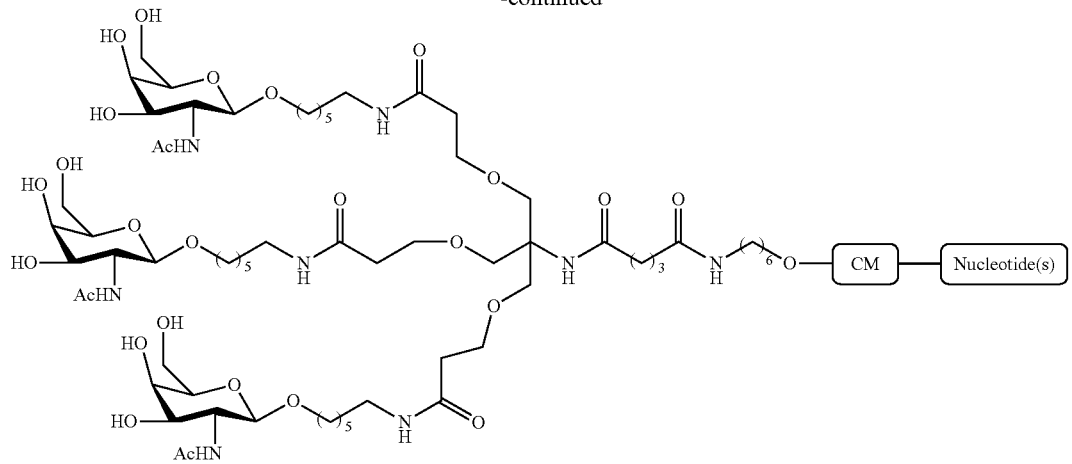

119

Compound 119, comprising a GalNAc$_3$-7 targeting group, is prepared using the general procedures illustrated in Example 32. The GalNAc$_3$ cluster portion of the targeting group GalNAc$_3$-7 (GalNAc$_3$-7$_a$) can be combined with any cleavable moiety. In a certain embodiment, the cleavable moiety is —P(=O)(OH)-A$_d$-P(=O)(OH)—.

The structure of GalNAc$_3$-7 (GalNAc$_3$-7$_a$-CM-) is shown below:

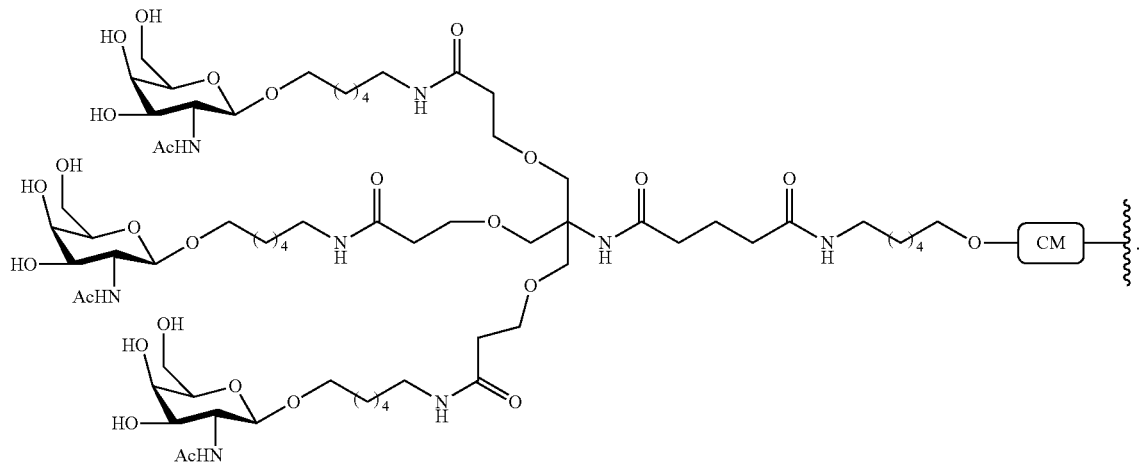

Example 35: Preparation of Therapeutic Agent 132 Comprising GalNAc₃-5

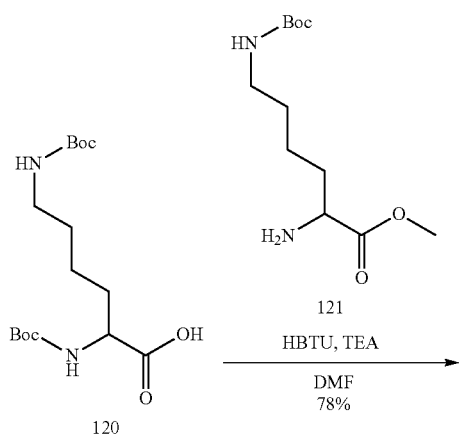

120

121

HBTU, TEA
DMF
78%

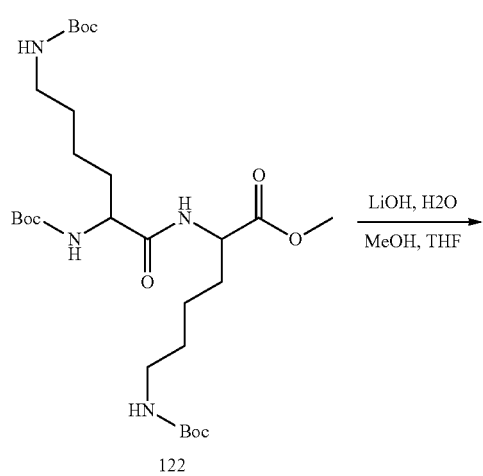

122

LiOH, H2O
MeOH, THF

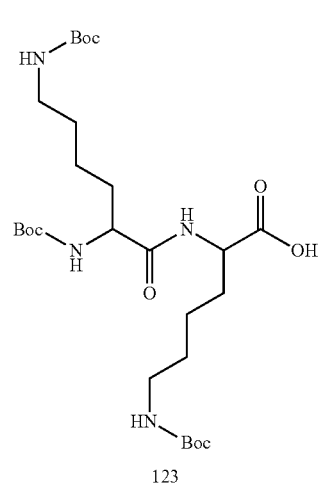

123

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M NaHSO₄ (3×150 mL), aqueous saturated NaHCO₃ solution (3×150 mL) and brine (2×100 mL). Organic layer was dried with Na₂SO₄. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and $^1$H NMR analysis. Mass m/z 589.3 [M+H]⁺.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried (Na₂SO₄), filtered and evaporated to yield Compound 123 (8.42 g). Residual salt is the likely cause of excess mass. LCMS is consistent with structure. Product was used without any further purification. M.W.cal: 574.36; M.W.fd: 575.3 [M+H]⁺.

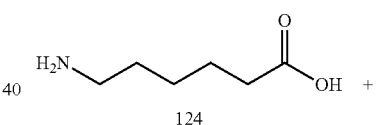

124

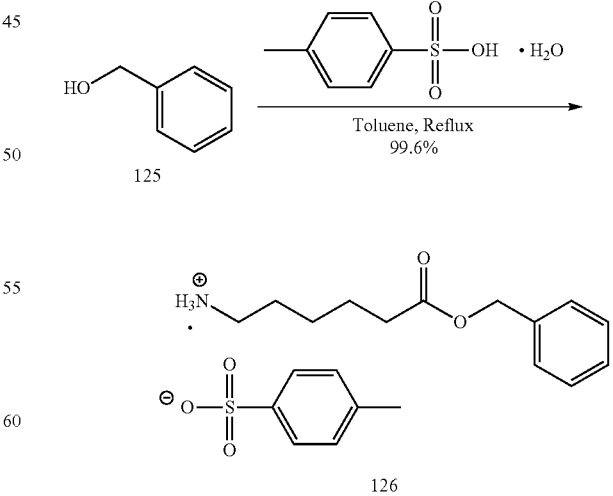

125

126

Compound 126 was synthesized following the procedure described in the literature (*J. Am. Chem. Soc.* 2011, 133, 958-963).

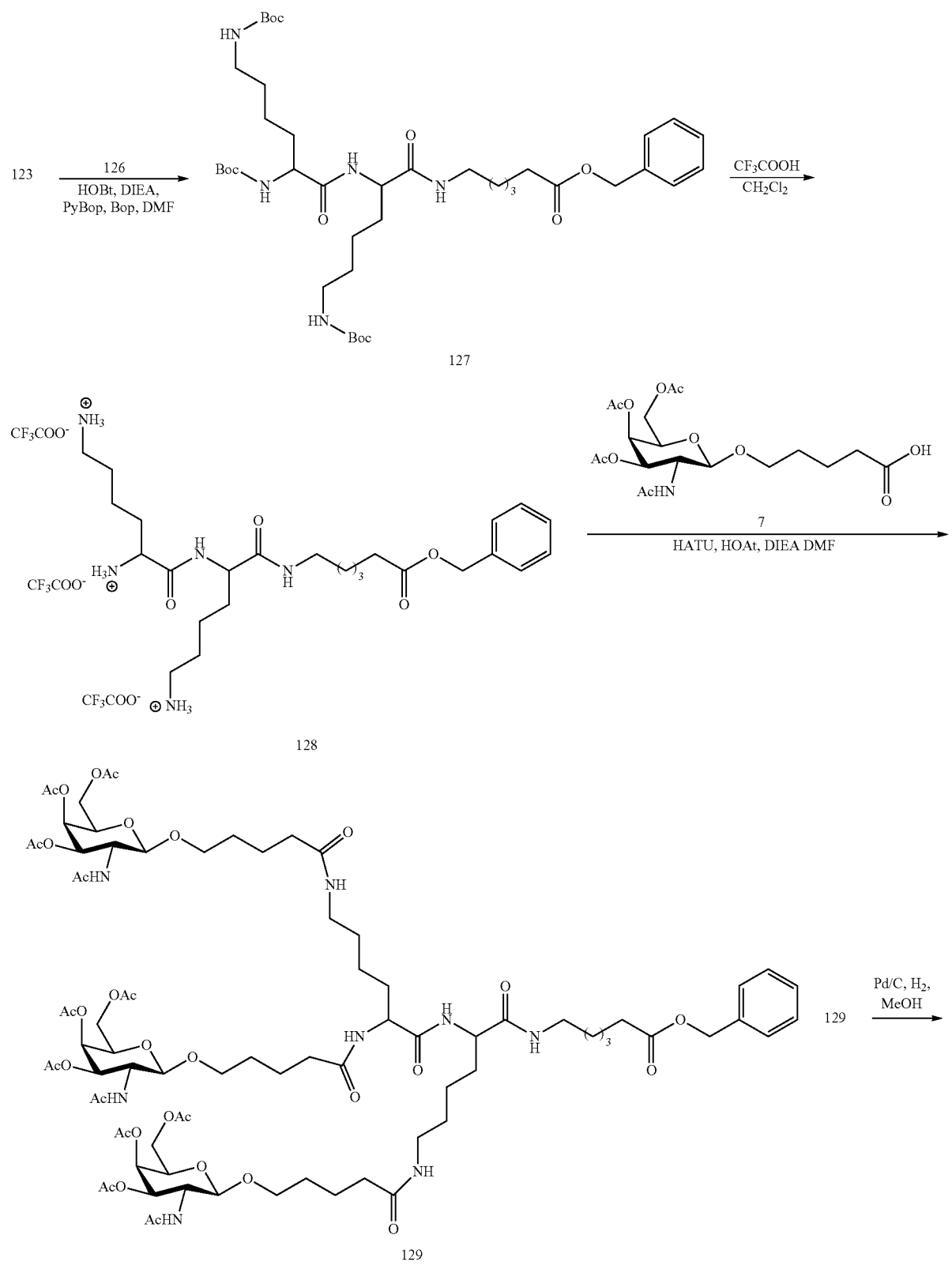

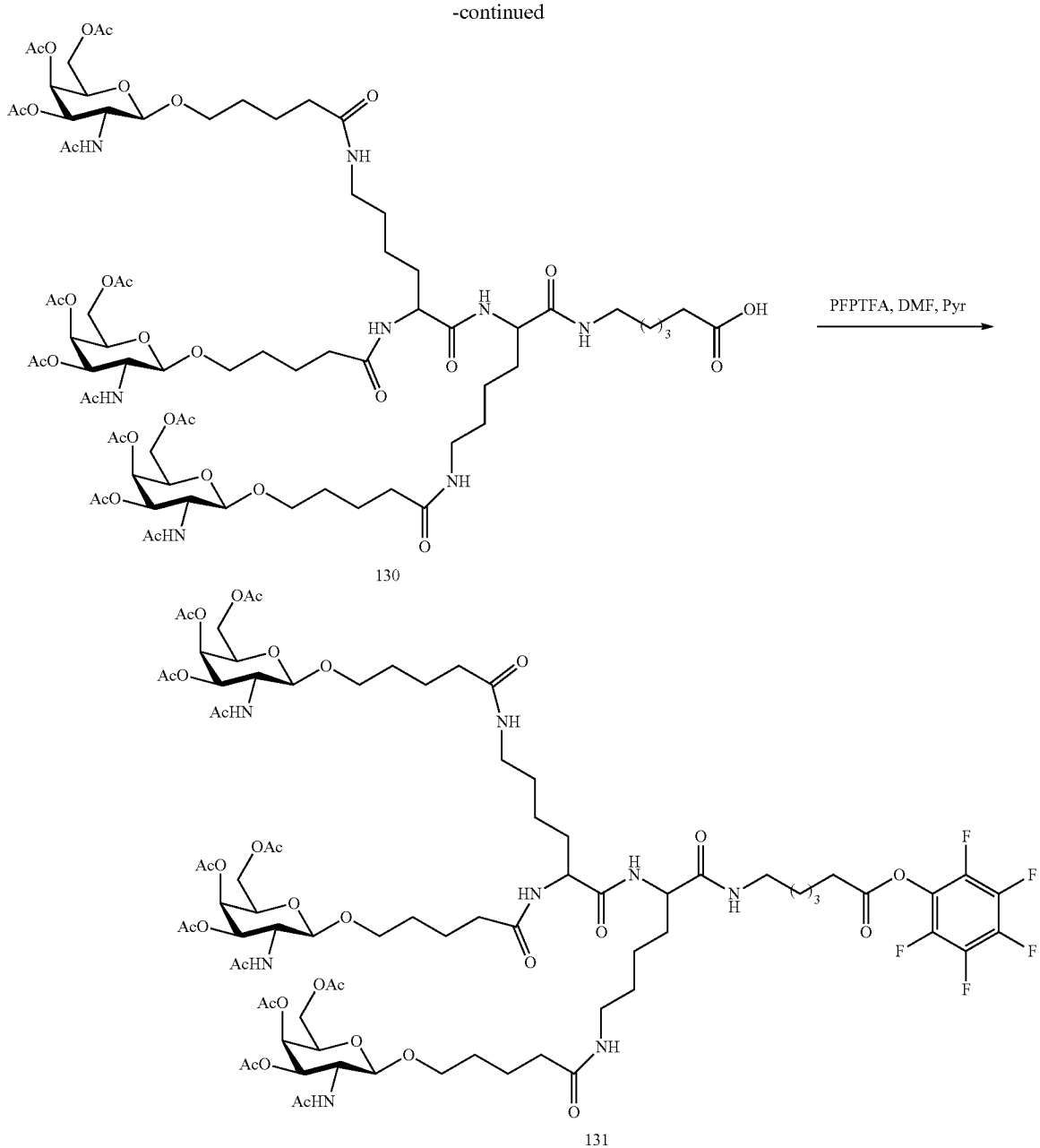

130

131

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M NaHSO$_4$ (3×100 mL), aqueous saturated NaHCO$_3$ (3×100 mL) and brine (2×100 mL). The organic phase separated dried (Na$_2$SO$_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m/z 778.4 [M+H]$^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m/z 478.2 [M+H]$^+$.

Compound 7 (0.43 g, 0.963 mmol), HATU (0.35 g, 0.91 mmol), and HOAt (0.035 g, 0.26 mmol) were combined together and dried for 4 h over P$_2$O$_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M NaHSO$_4$ (3×20 mL), aqueous saturated NaHCO$_3$ (3×20 mL) and brine (3×20 mL). The organic phase was separated, dried over Na$_2$SO$_4$, filtered and concentrated. The residue was purified by silica gel column chromatography using 5-15% MeOH in dichloromethane to yield Compound 129 (96.6 mg). LC MS and $^1$H NMR are consistent with structure. Mass m/z 883.4 [M+2H]$^+$.

LCMS and $^1$H NMR were consistent with structure. The product was used without further purification. Mass m/z 838.3 [M+2H]$^+$.

To a 10 mL pointed round bottom flask were added compound 130 (75.8 mg, 0.046 mmol), 0.37 M pyridine/DMF (200 µL) and a stir bar. To this solution was added 0.7 M pentafluorophenyl trifluoroacetate/DMF (100 µL) drop wise with stirring. The reaction was completed after 1 h as determined by LC MS. The solvent was removed under reduced pressure and the residue was dissolved in CHCl$_3$ (~10 mL). The organic layer was partitioned against NaHSO$_4$ (1 M, 10 mL), aqueous saturated NaHCO$_3$ (10 mL) and brine (10 mL) three times each. The organic phase separated and dried over Na$_2$SO$_4$, filtered and concentrated to yield Compound 131 (77.7 mg). LCMS is consistent with structure. Used without further purification. Mass m/z 921.3 [M+2H]$^+$.

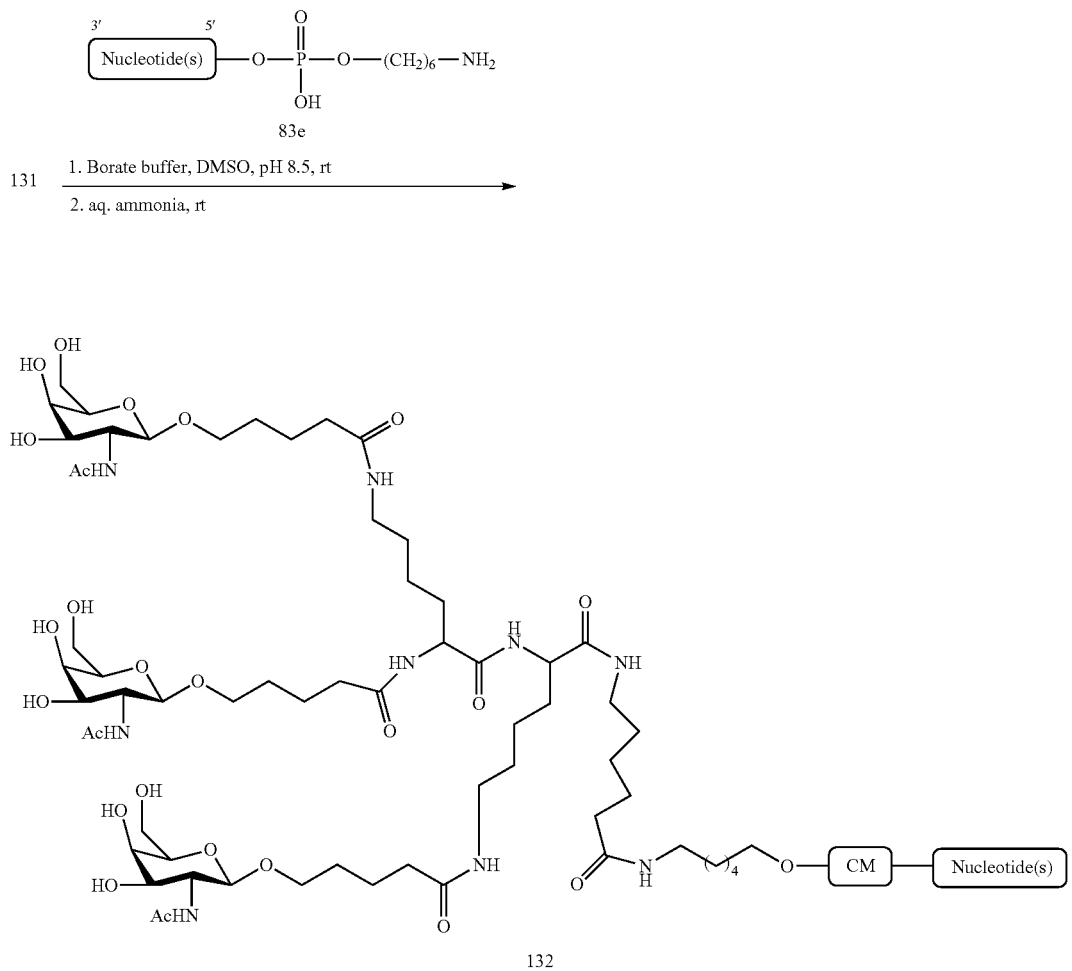

Compound 129 (0.09 g, 0.051 mmol) was dissolved in methanol (5 mL) in 20 mL scintillation vial. To this was added a small amount of 10% Pd/C (0.015 mg) and the reaction vessel was flushed with H$_2$ gas. The reaction mixture was stirred at room temperature under H$_2$ atmosphere for 18 h. The reaction mixture was filtered through a pad of Celite and the Celite pad was washed with methanol. The filtrate washings were pooled together and concentrated under reduced pressure to yield Compound 130 (0.08 g).

Compound 132, comprising a GalNAc$_3$-5 targeting group, is prepared using the general procedures illustrated in Example 32. The GalNAc$_3$ cluster portion of the targeting group GalNAc$_3$-5 (GalNAc$_3$-5$_a$) can be combined with any cleavable moiety. In a certain embodiment, the cleavable moiety is —P(=O)(OH)-A$_d$-P(=O)(OH)—.

The structure of GalNAc$_3$-5 (GalNAc$_3$-5$_a$-CM-) is shown below:

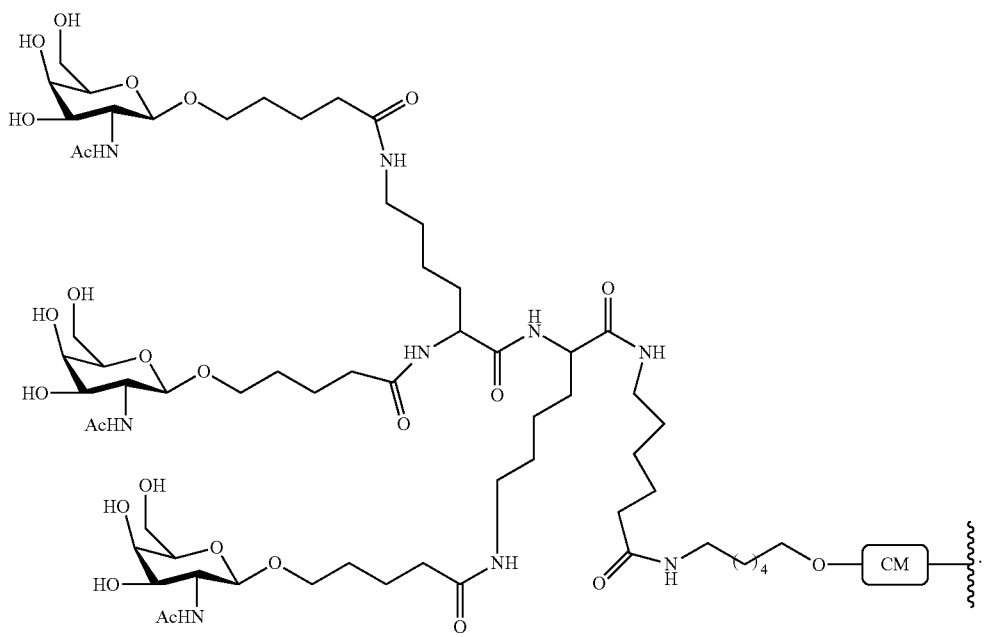
Example 36: Preparation of Therapeutic Agent 144
Comprising GalNAc$_4$-11
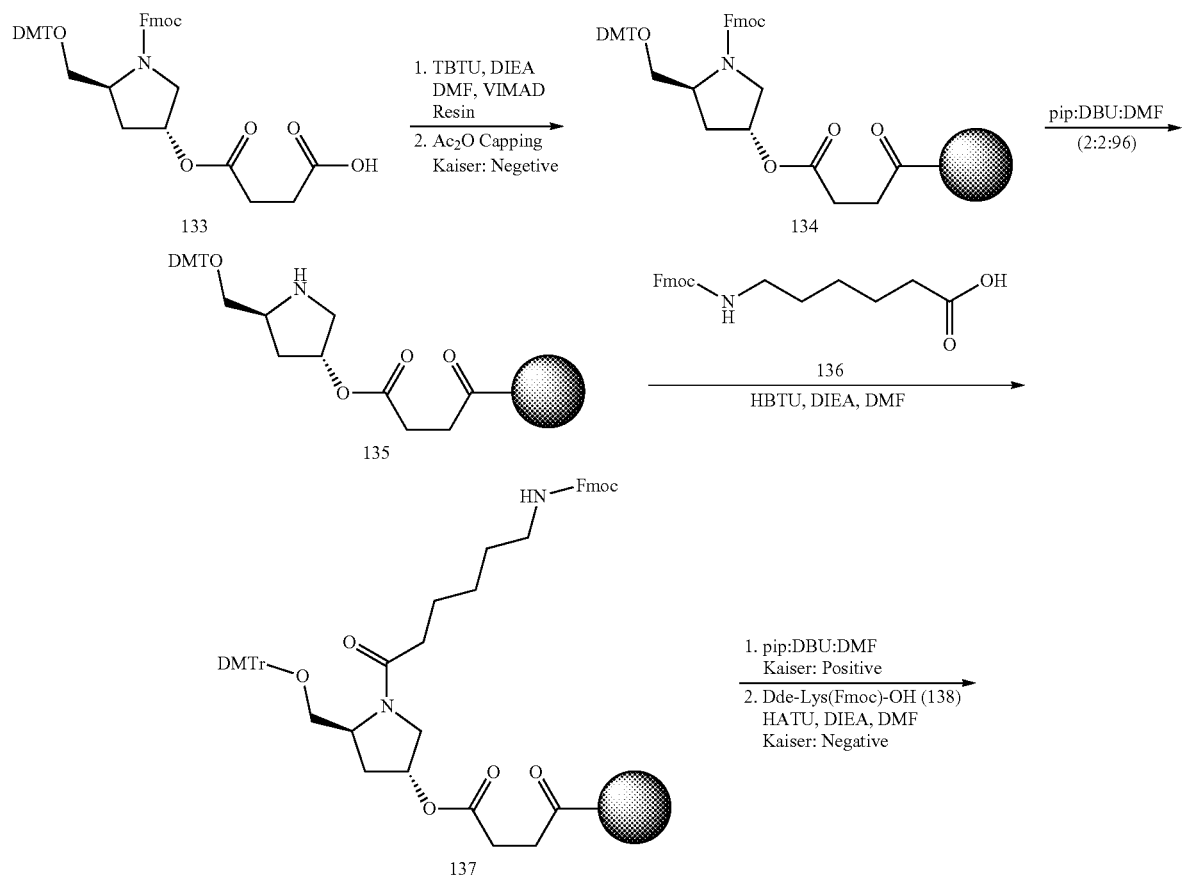

-continued
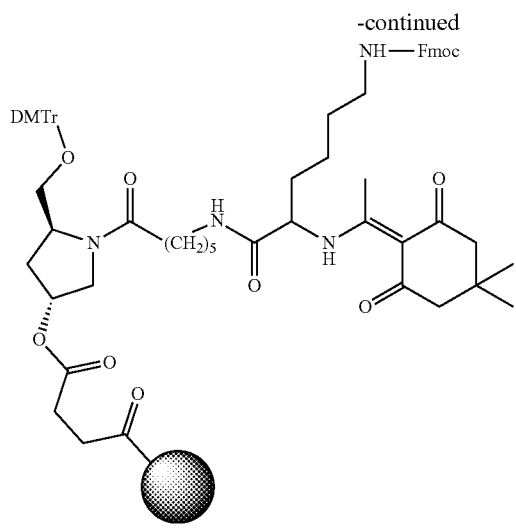
139
1. 2% hydrazine/DMF
   Kaiser: Positive
2. Fmoc-Lys(Fmoc)-OH (140)
   HATU, DIEA, DMF
   Kaiser: Negative
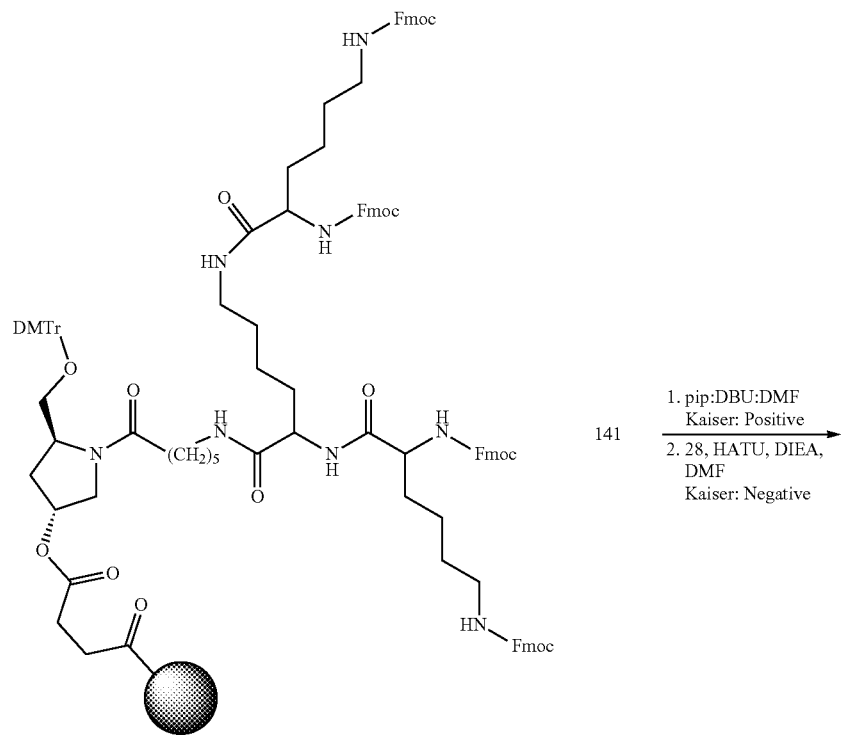
141
1. pip:DBU:DMF
   Kaiser: Positive
2. 28, HATU, DIEA, DMF
   Kaiser: Negative -continued

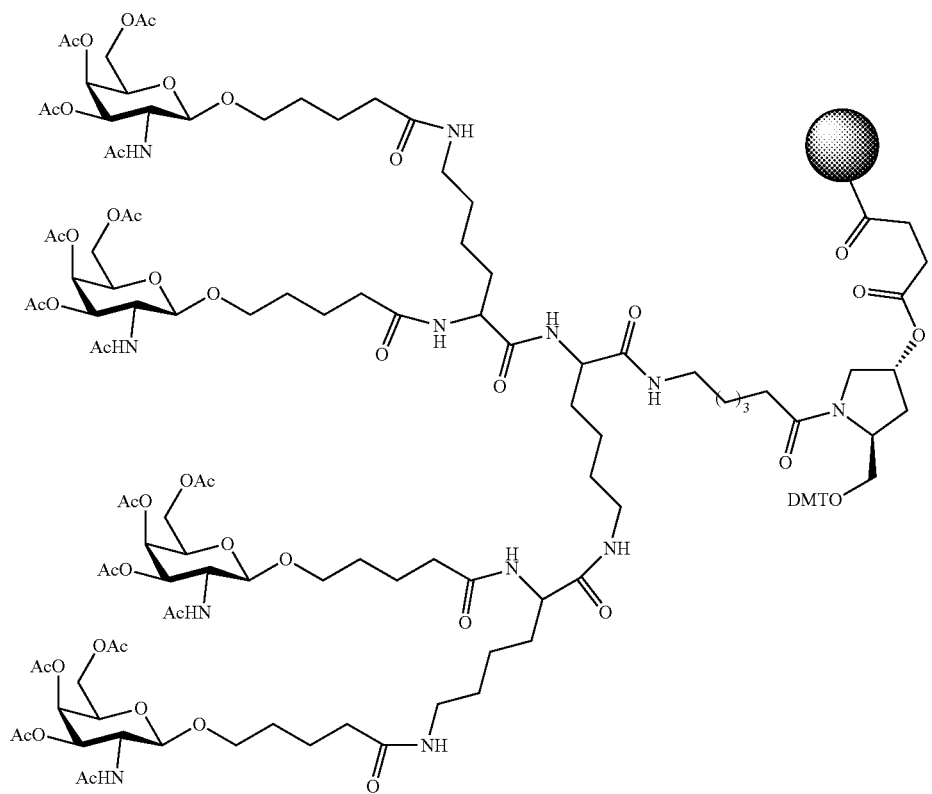

142

Synthesis of Compound 134. To a Merrifield flask was added aminomethyl VIMAD resin (2.5 g, 450 µmol/g) that was washed with acetonitrile, dimethylformamide, dichloromethane and acetonitrile. The resin was swelled in acetonitrile (4 mL). Compound 133 (where from) was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 µmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 $[M+2H]^+$.

The solid support bound compound 142 was synthesized using solid phase peptide synthesis methods.

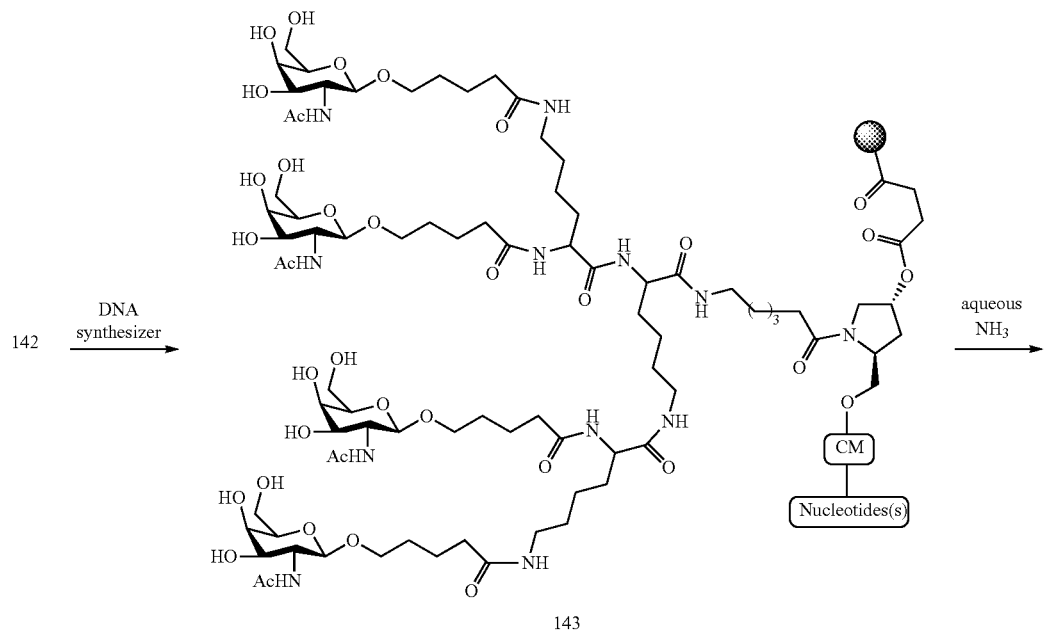
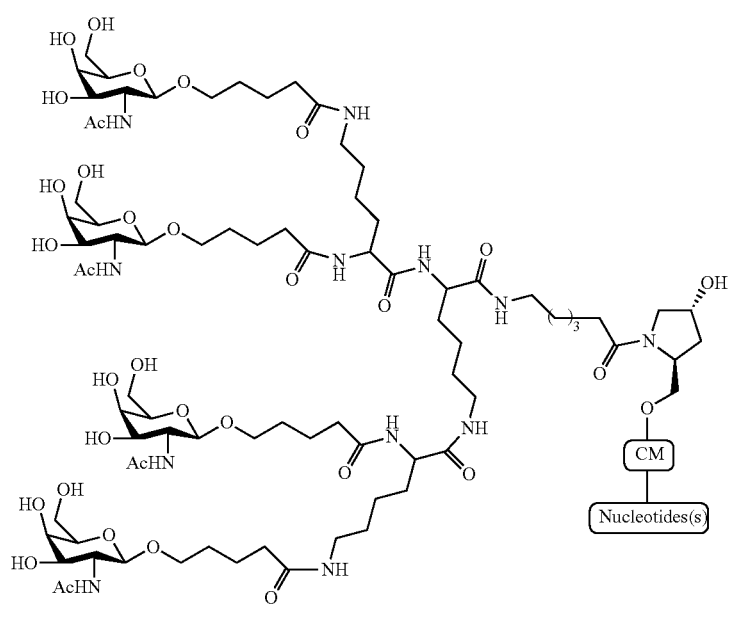
The solid support bound compound 143 is synthesized using standard solid phase synthesis on a DNA synthesizer.
The GalNAc$_4$ cluster portion of the targeting group GalNAc$_4$-11 (GalNAc$_4$-11$_a$) can be combined with any cleavable moiety. In a certain embodiment, the cleavable moiety is —P(=O)(OH)-A$_d$-P(=O)(OH)—.
The structure of GalNAc$_4$-11 (GalNAc$_4$-11$_a$-CM) is shown below:

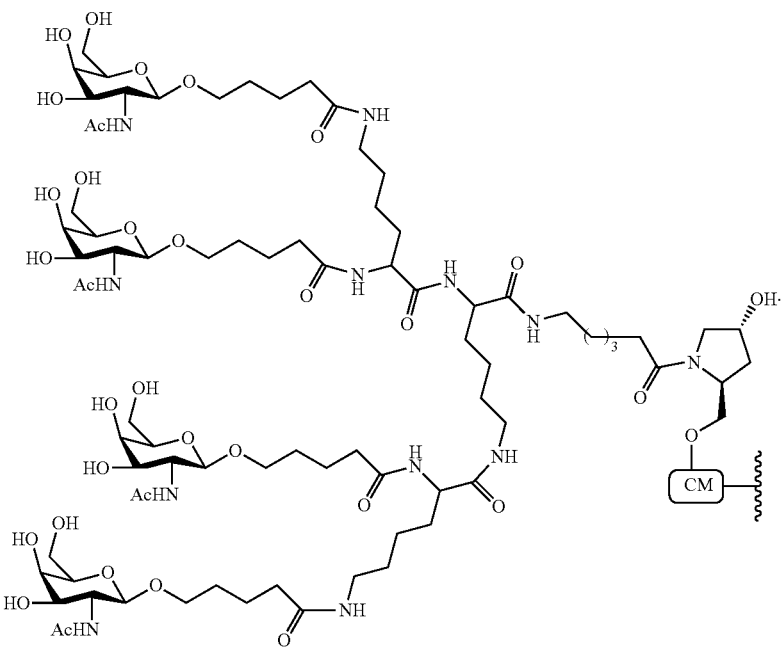
Example 37: Preparation of Therapeutic Agent 155 Comprising GalNAc₃-6
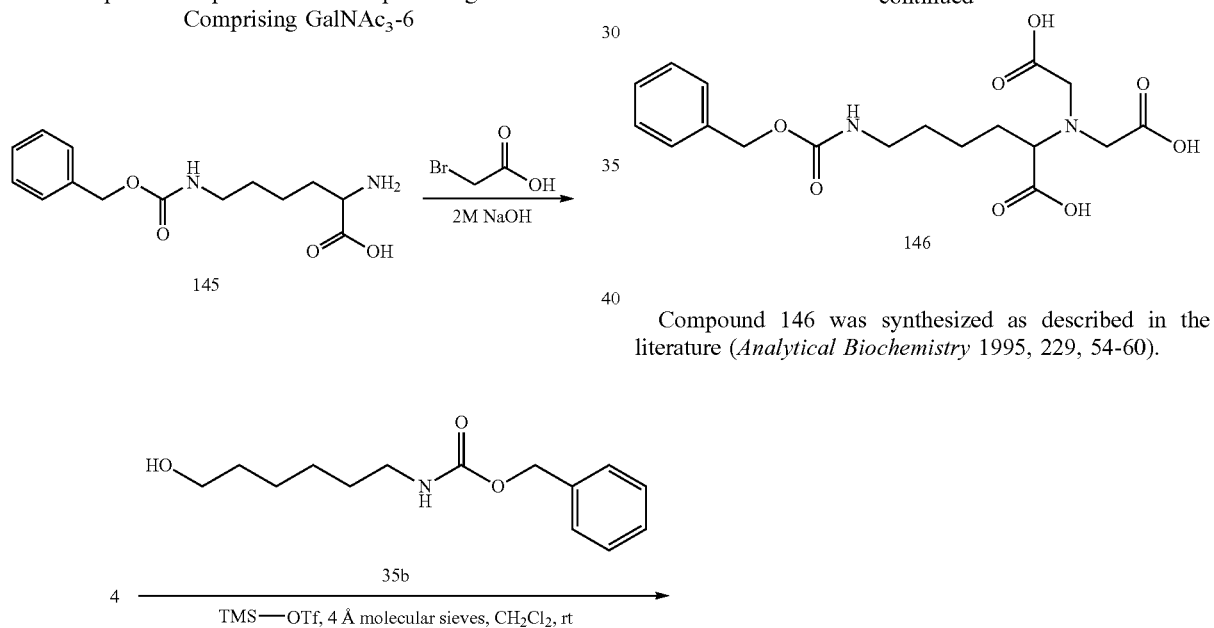
Compound 146 was synthesized as described in the literature (*Analytical Biochemistry* 1995, 229, 54-60).
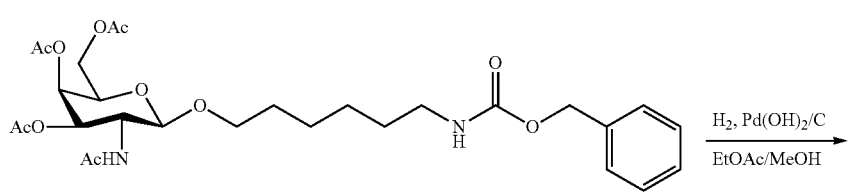

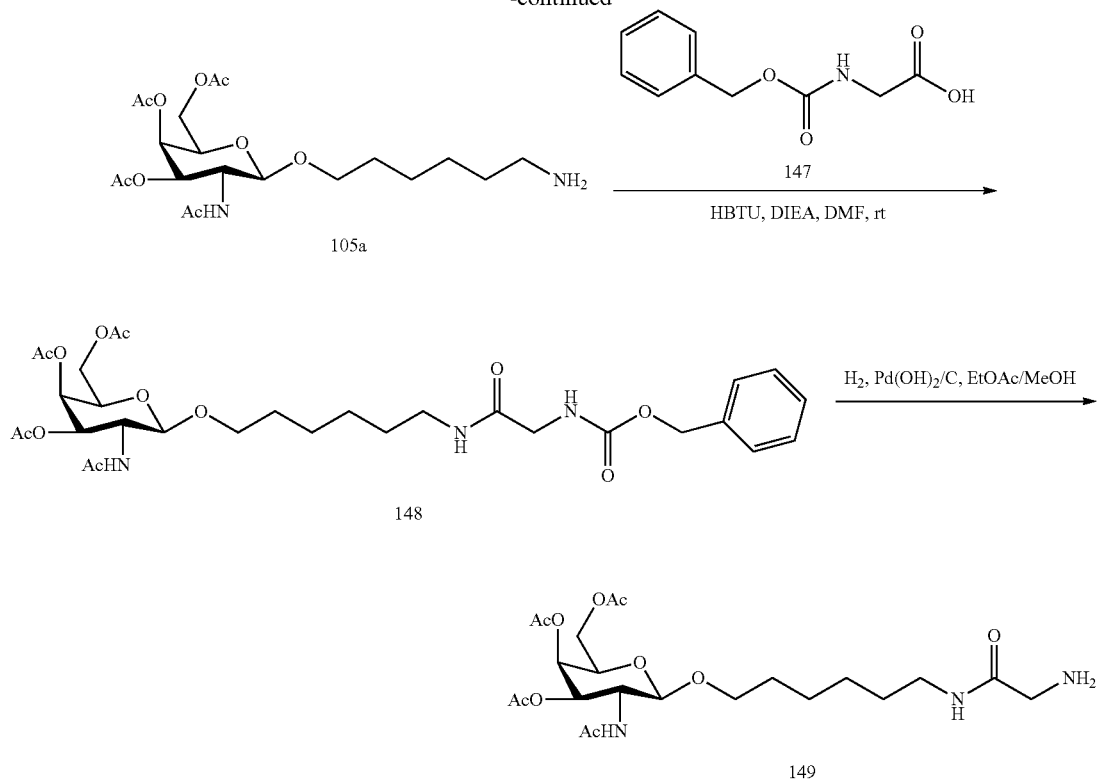

Compound 4 (15 g, 45.55 mmol) and compound 35b (14.3 grams, 57 mmol) were dissolved in $CH_2Cl_2$ (200 ml). Activated molecular sieves (4 Å. 2 g, powdered) was added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous $NaHCO_3$ (500 ml) and crushed ice (~150 g). The organic layer was separated, washed with brine, dried over $MgSO_4$, filtered, and was concentrated to an orange oil under reduced pressure. The crude material was purified by silica gel column chromatography and eluted with 2-10% MeOH in $CH_2Cl_2$ to yield Compound 112 (16.53 g, 63%). LCMS and $^1H$ NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled thru the solution for 30 minutes. Upon completion (TLC 10% MeOH in $CH_2Cl_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous $NaHCO_3$ and brine. The organics phase was separated, dried ($MgSO_4$), filtered, and concentrated to an orange syrup. The crude material was purified by column chromatography 2-5% MeOH in $CH_2Cl_2$ to yield Compound 148 (3.44 g, 73%). LCMS and $^1H$ NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

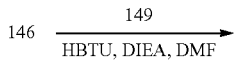

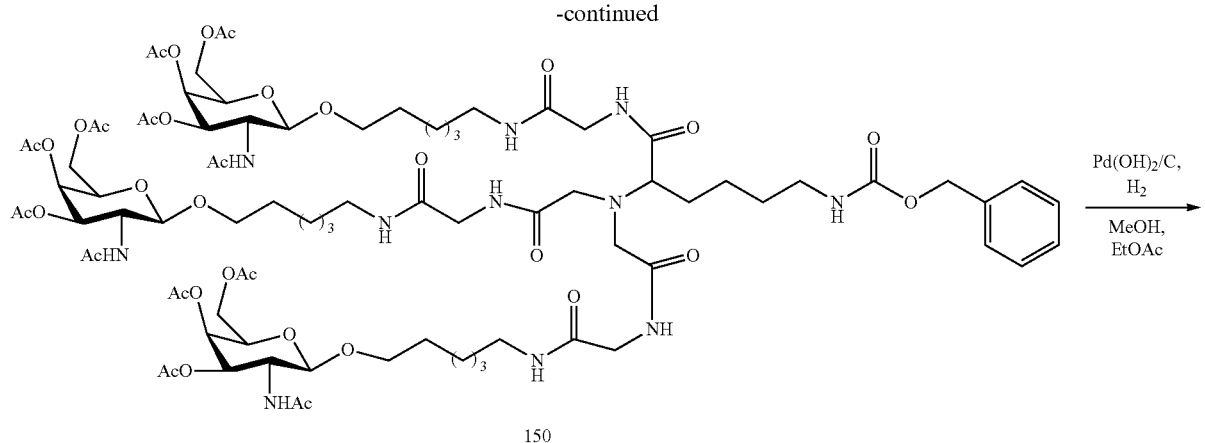

150

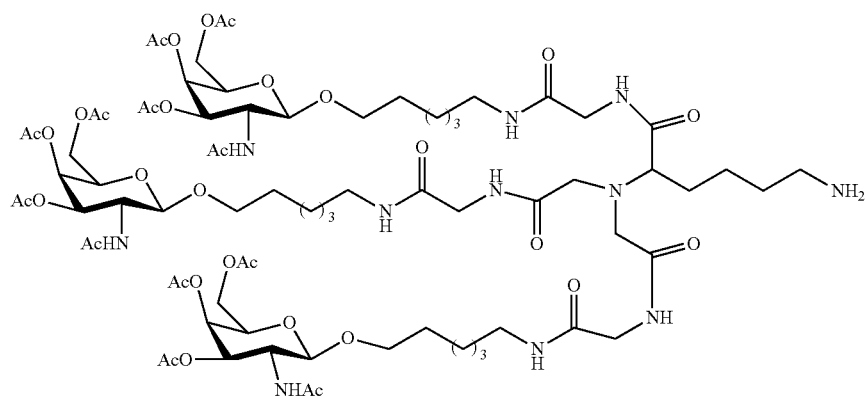

151

Compound 146 (0.68 g, 1.73 mmol) was dissolved in dry DMF (20 ml). To this DIEA (450 µL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous NaHCO$_3$, followed by brine. The organic phase was separated, dried over MgSO$_4$, filtered, and concentrated. The residue was purified by silica gel column chromatography and eluted with 2-10% MeOH in CH$_2$Cl$_2$ to yield Compound 150 (0.62 g, 20%). LCMS and $^1$H NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

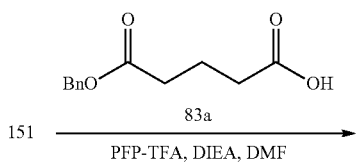

151 $\xrightarrow{\text{PFP-TFA, DIEA, DMF}}$

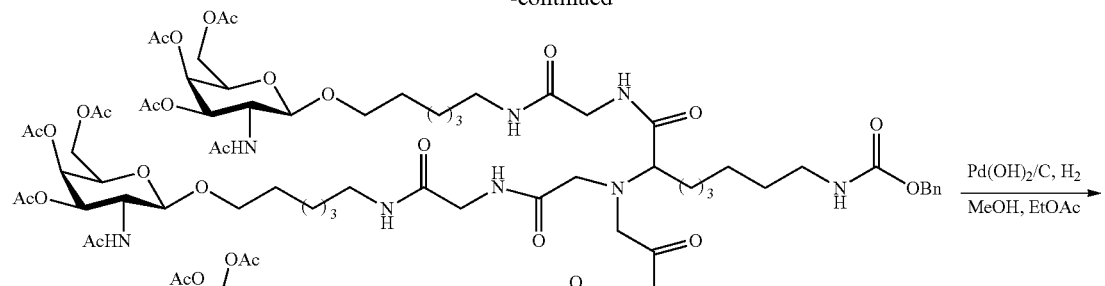

152

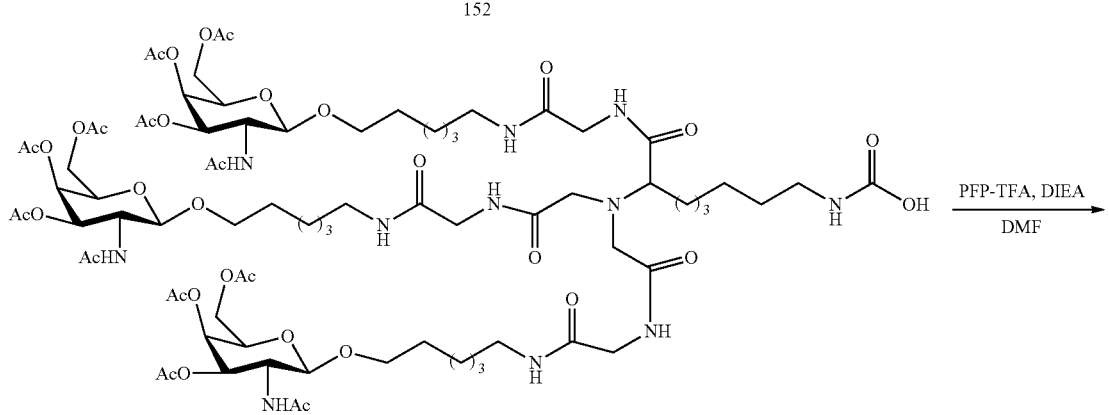

153

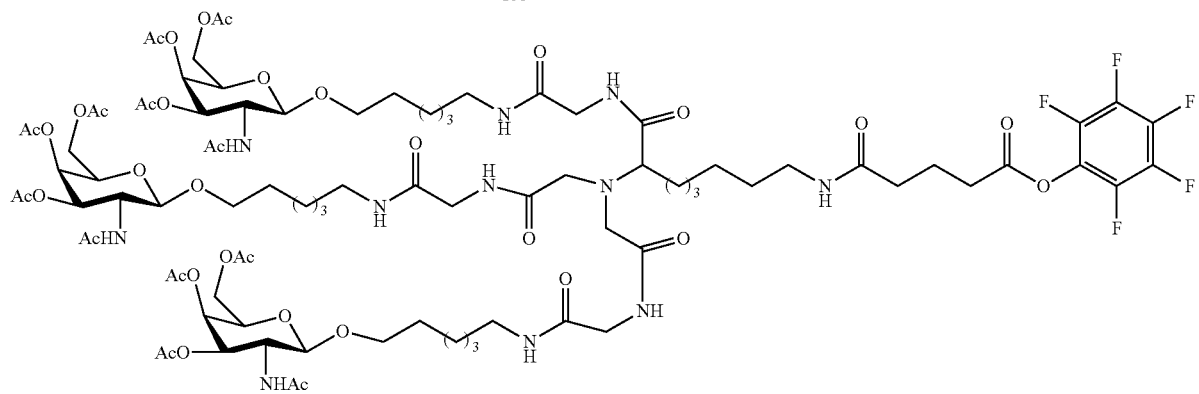

154

Compound 83a (0.11 g, 0.33 mmol) was dissolved in anhydrous DMF (5 mL) and N,N-Diisopropylethylamine (75 µL, 1 mmol) and PFP-TFA (90 µL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min Upon completion, the majority of the solvent was removed under reduced pressure. The residue was diluted with CH$_2$Cl$_2$ and washed with aqueous saturated NaHCO$_3$, followed by brine. The organic phase separated, dried over MgSO$_4$, filtered, and concentrated to an orange syrup. The residue was purified by silica gel column chromatography (2-10% MeOH in CH$_2$Cl$_2$) to yield Compound 152 (0.35 g, 55%). LCMS and $^1$H NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 µm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 µL, 0.37 mmol) and PFP-TFA (35 µL, 0.28 mmol) were added. The reaction mixture was stirred under nitrogen for ~30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with CH$_2$Cl$_2$ (50 mL), and washed with saturated aqueous NaHCO$_3$, followed by brine. The organic layer was dried over MgSO$_4$, filtered, and concentrated to an orange syrup. The residue was purified by column chromatography and eluted with 2-10% MeOH in CH$_2$Cl$_2$ to yield Compound 154 (0.29 g, 79%). LCMS and $^1$H NMR were consistent with the desired product.

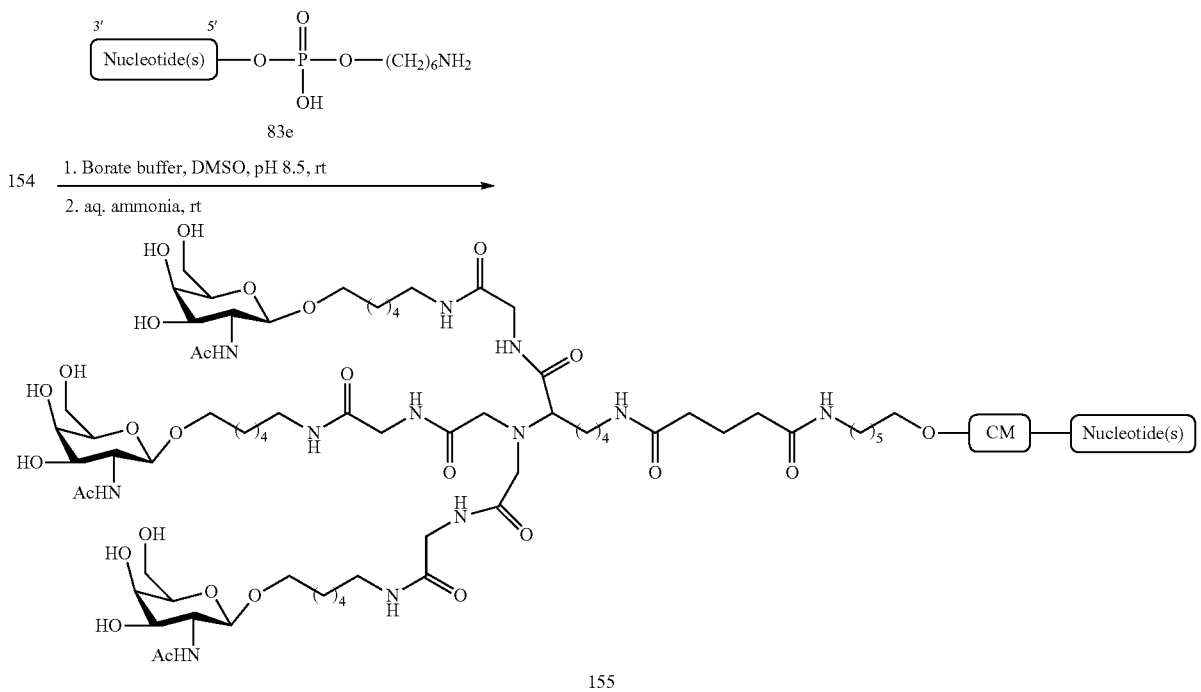

Compound 155, comprising a GalNAc$_3$-6 targeting group, is prepared using the general procedures illustrated in Example 32. The GalNAc$_3$ cluster portion of the targeting group GalNAc$_3$-6 (GalNAc$_3$-6$_a$) can be combined with any cleavable moiety. In a certain embodiment, the cleavable moiety is —P(=O)(OH)-A$_d$-P(=O)(OH)—.

The structure of GalNAc$_3$-6 (GalNAc$_3$-6$_a$-CM-) is shown below:

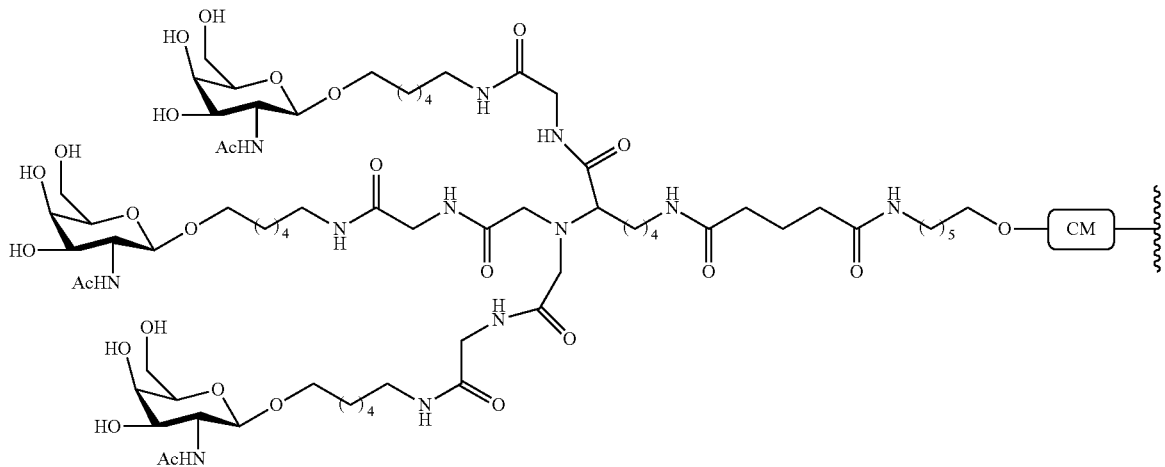

Example 38: Preparation of Therapeutic Agent 160 Comprising GalNAc₃-9

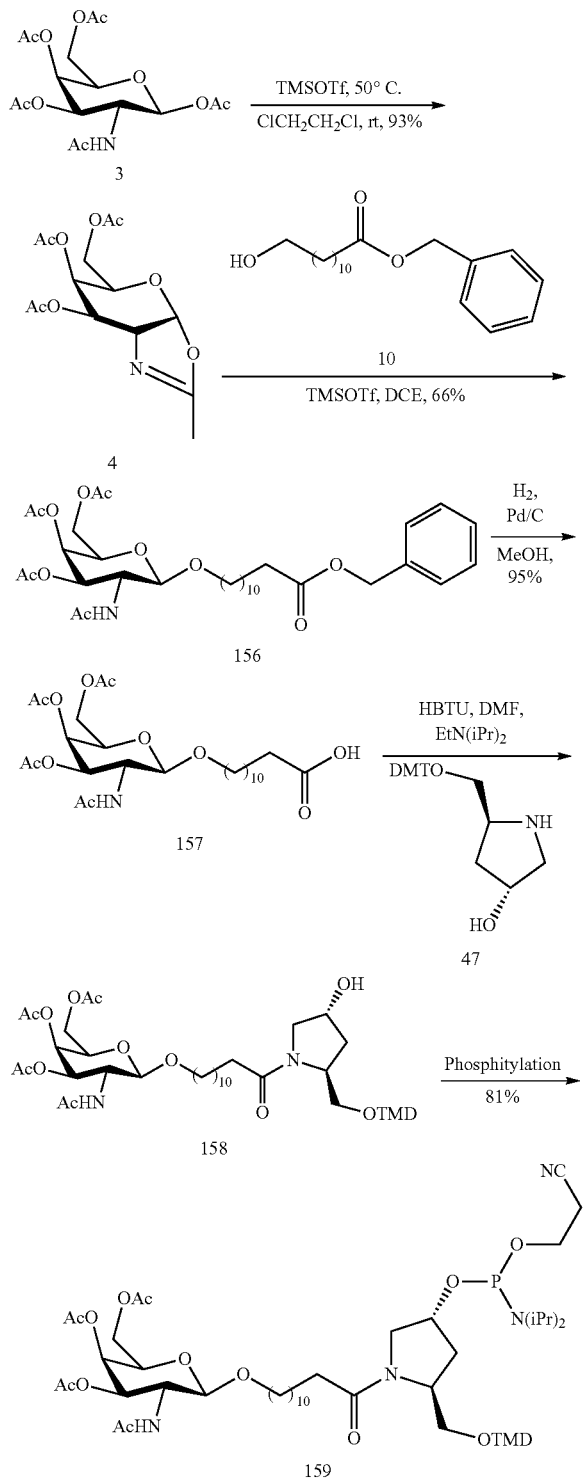

Compound 156 was synthesized following the procedure described in the literature (*J. Med. Chem.* 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 [M−H]⁻.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated NaHCO₃ aqueous solution. The mixture was extracted with ethyl acetate and the organic layer was washed with brine and dried (Na₂SO₄), filtered and evaporated. The residue obtained was purified by silica gel column chromatography and eluted with 50% ethyl acetate in hexane to yield compound 158 (8.25 g, 73.3%). The structure was confirmed by MS and ¹H NMR analysis.

Compound 158 (7.2 g, 7.61 mmol) was dried over P₂O₅ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidate (3.65 mL, 11.50 mmol) were added. The reaction mixture was stirred t under an argon atmosphere for 4 h. The reaction mixture was diluted with ethyl acetate (200 mL). The reaction mixture was washed with saturated NaHCO₃ and brine. The organic phase was separated, dried (Na₂SO₄), filtered and evaporated. The residue was purified by silica gel column chromatography and eluted with 50-90% ethyl acetate in hexane to yield Compound 159 (7.82 g, 80.5%). The structure was confirmed by LCMS and ³¹P NMR analysis.

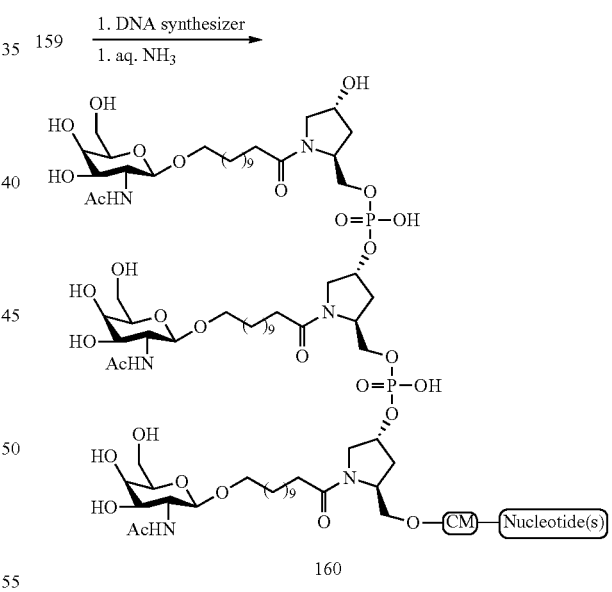

Compound 160, comprising a GalNAc₃-9 targeting group, is prepared using standard oligonucleotide synthesis procedures. Three units of compound 159 are coupled to the solid support, followed by nucleotide phosphoramidite(s). Treatment of the protected compound with aqueous ammonia yields compound 160. The GalNAc₃ cluster portion of the targeting group GalNAc₃-9 (GalNAc₃-9ₐ) can be combined with any cleavable moiety. In a certain embodiment, the cleavable moiety is —P(=O)(OH)-Aₐ-P(=O)(OH)—. The structure of GalNAc₃-9 (GalNAc₃-9ₐ-CM) is shown below:

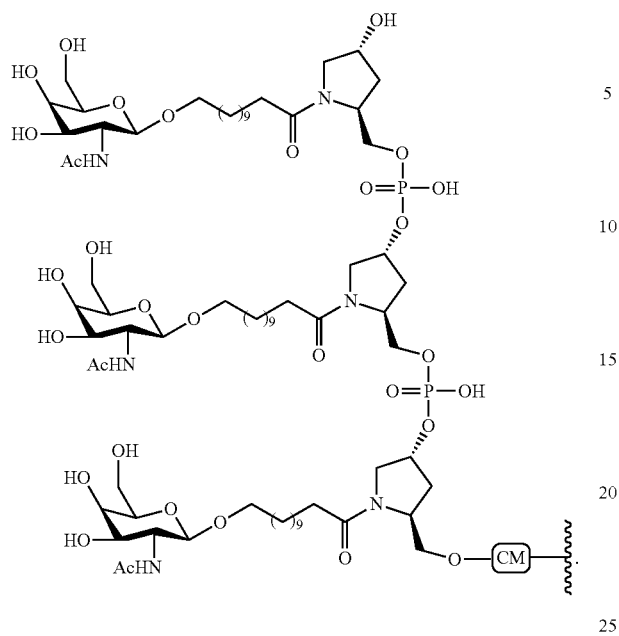
Example 39: Alternate Procedure for Preparation of Compound 18 (GalNAc$_3$—1a and GalNAc$_3$-3a)
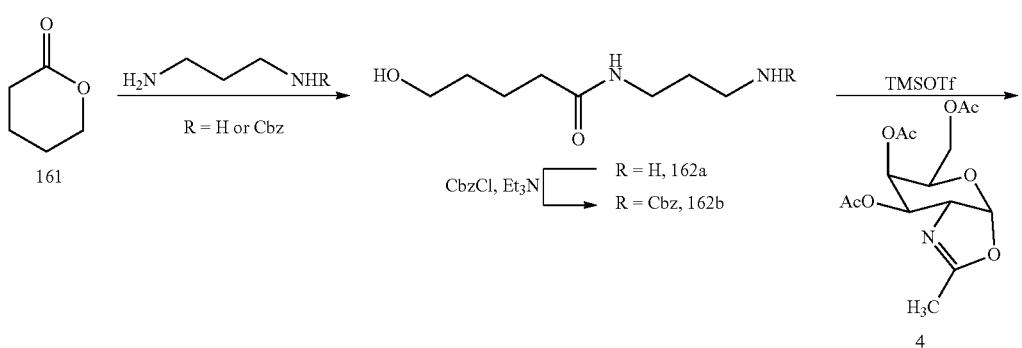
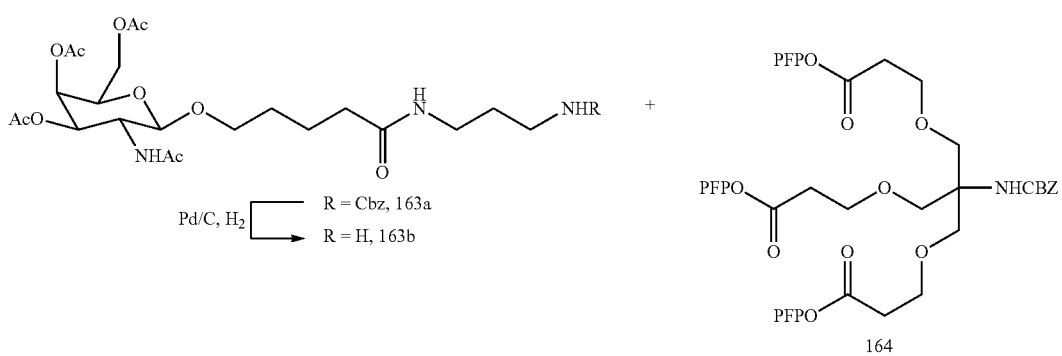

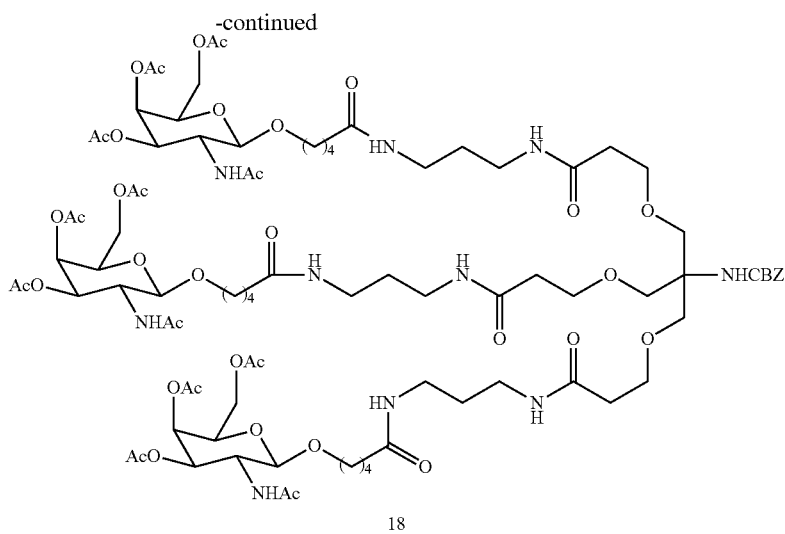

18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b is further reacted with compound 4 in the presence of TMSOTf to provide 163a which is converted to 163b by removal of the Cbz group using catalytic hydrogenation. The pentafluorophenyl (PFP) ester 164 was prepared by reacting triacid 113 with PFPTFA (3.5 eq) and pyridine (3.5 eq) in DMF (0.1 to 0.5 M). The triester 164 is directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 40: Alternate Procedure for Preparation of Compound 18 (GalNAc$_3$—La and GalNAc$_3$-3a)

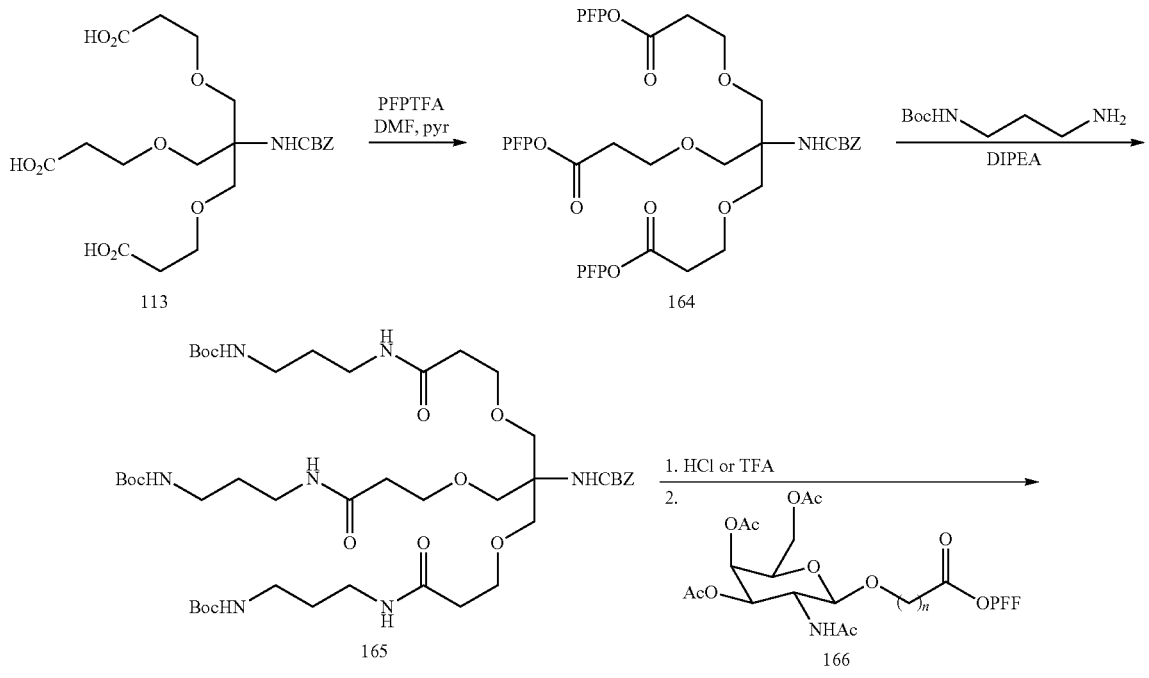

1. 1,6-hexanediol or 1,5-pentane-diol
   TMSOTf + compound 4
2. TEMPO
3. PFPTFA, pyr

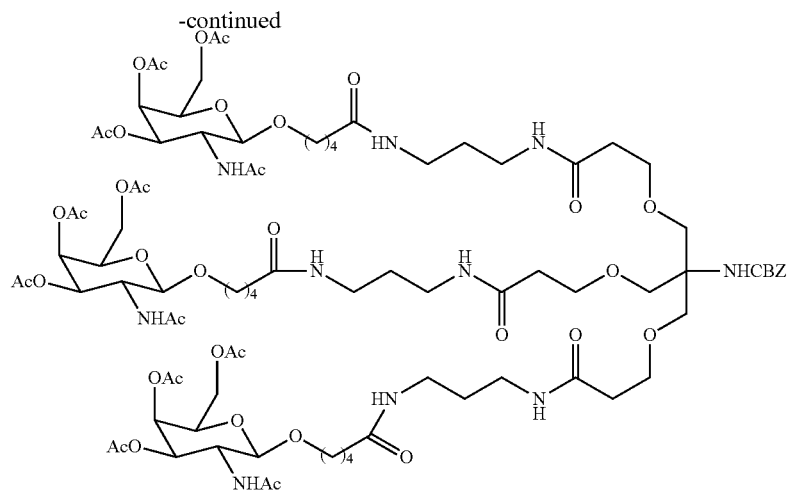

18

The triPFP ester 164 was prepared from acid 113 using the procedure outlined in example 31 and reacted with mono-Boc protected diamine to provide 165 in essentially quantitative yield. The Boc groups are removed with hydrochloric acid or trifluoroacetic acid to provide the triamine which is reacted with the PFP activated acid 166 in the presence of a suitable base such as DIPEA to provide Compound 18.

The PFP protected Gal-NAc acid 166 is prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using the conditions described previously in example 47.

Example 41: Preparation of Therapeutic Agent 175 Comprising GalNAc$_3$-12

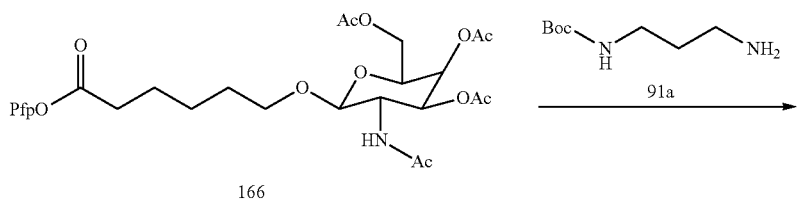

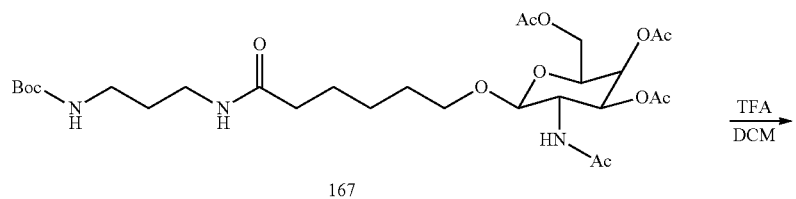

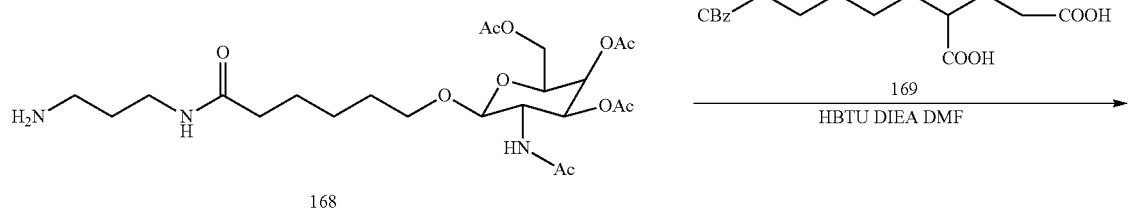

-continued
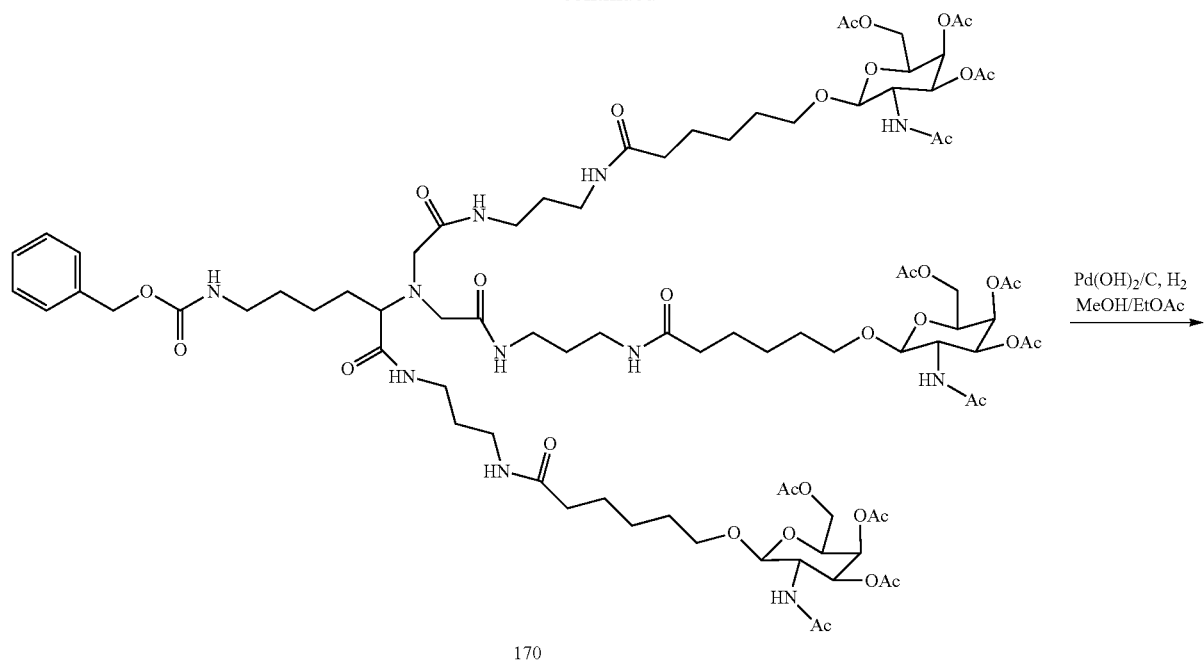
170
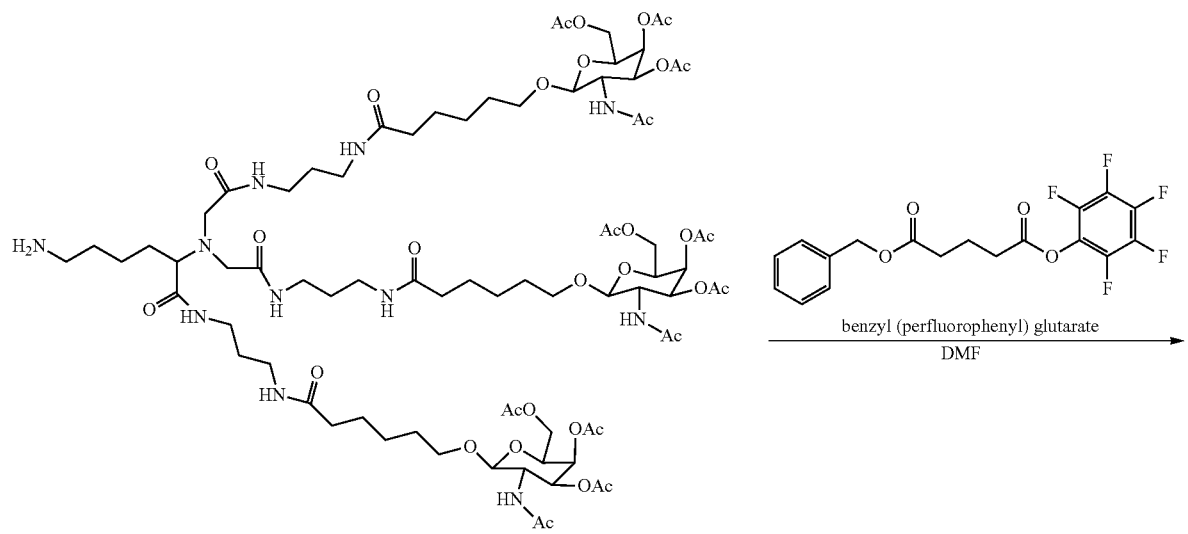
171

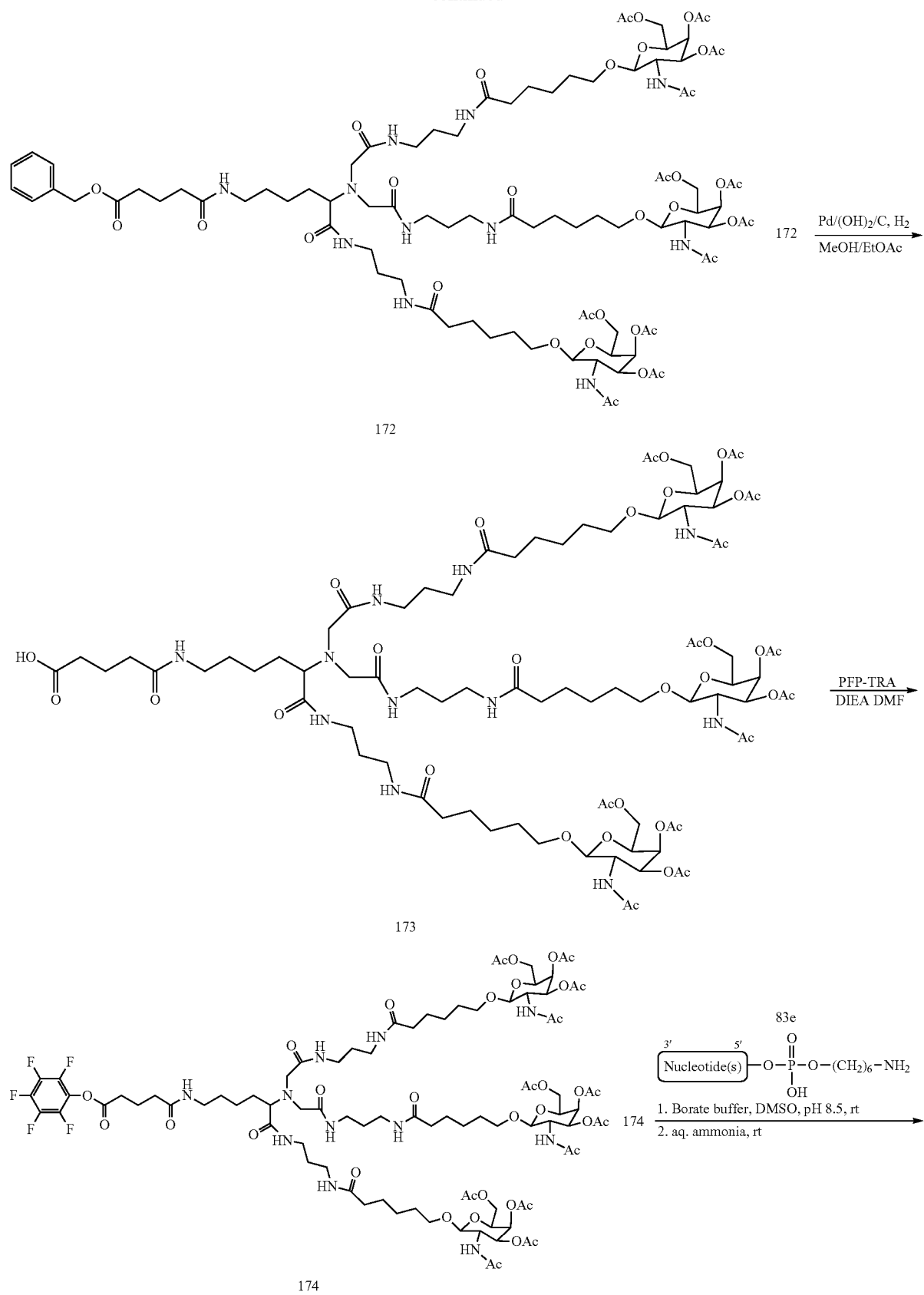

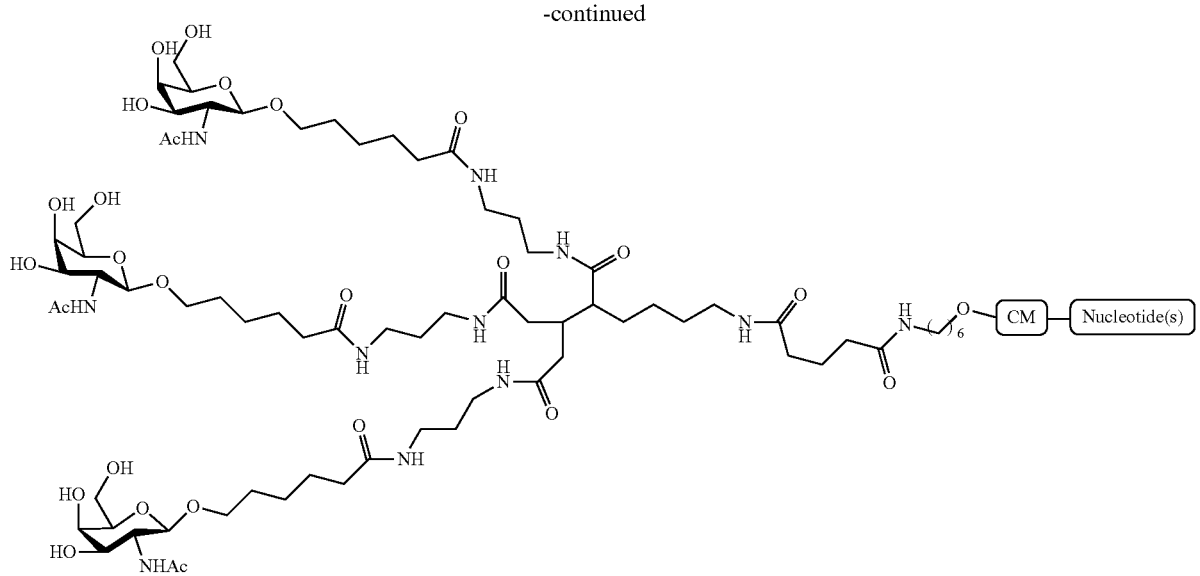

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Compound 175, comprising a GalNAc$_3$-12 targeting group, is prepared from compound 174 using the general procedures illustrated in Example 32. The GalNAc$_3$ cluster portion of the targeting group GalNAc$_3$-12 (GalNAc$_3$-12$_a$) can be combined with any cleavable moiety. In a certain embodiment, the cleavable moiety is —P(=O)(OH)-A$_d$-P(=O)(OH)—. The structure of GalNAc$_3$-12 (GalNAc$_3$-12$_a$-CM-) is shown below:

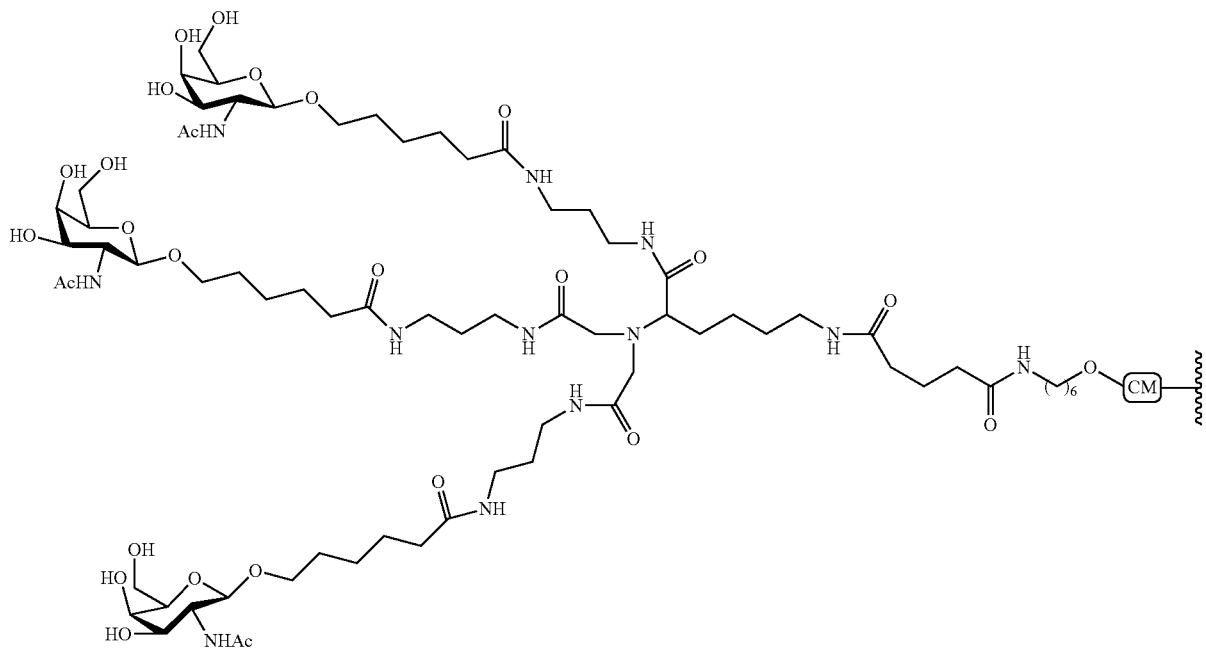

Example 42: Preparation of Therapeutic Agent 180 Comprising GalNAc$_3$-13
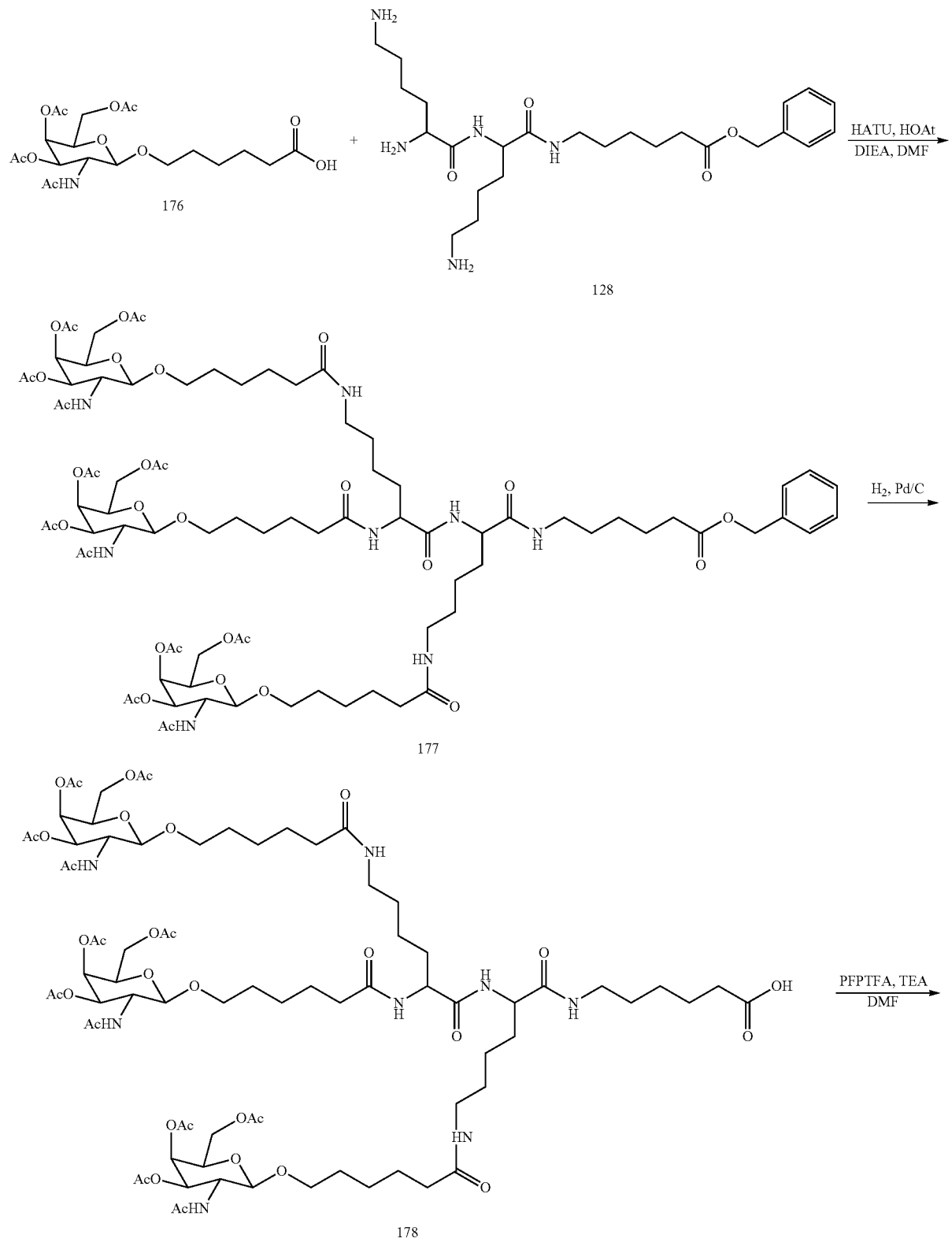

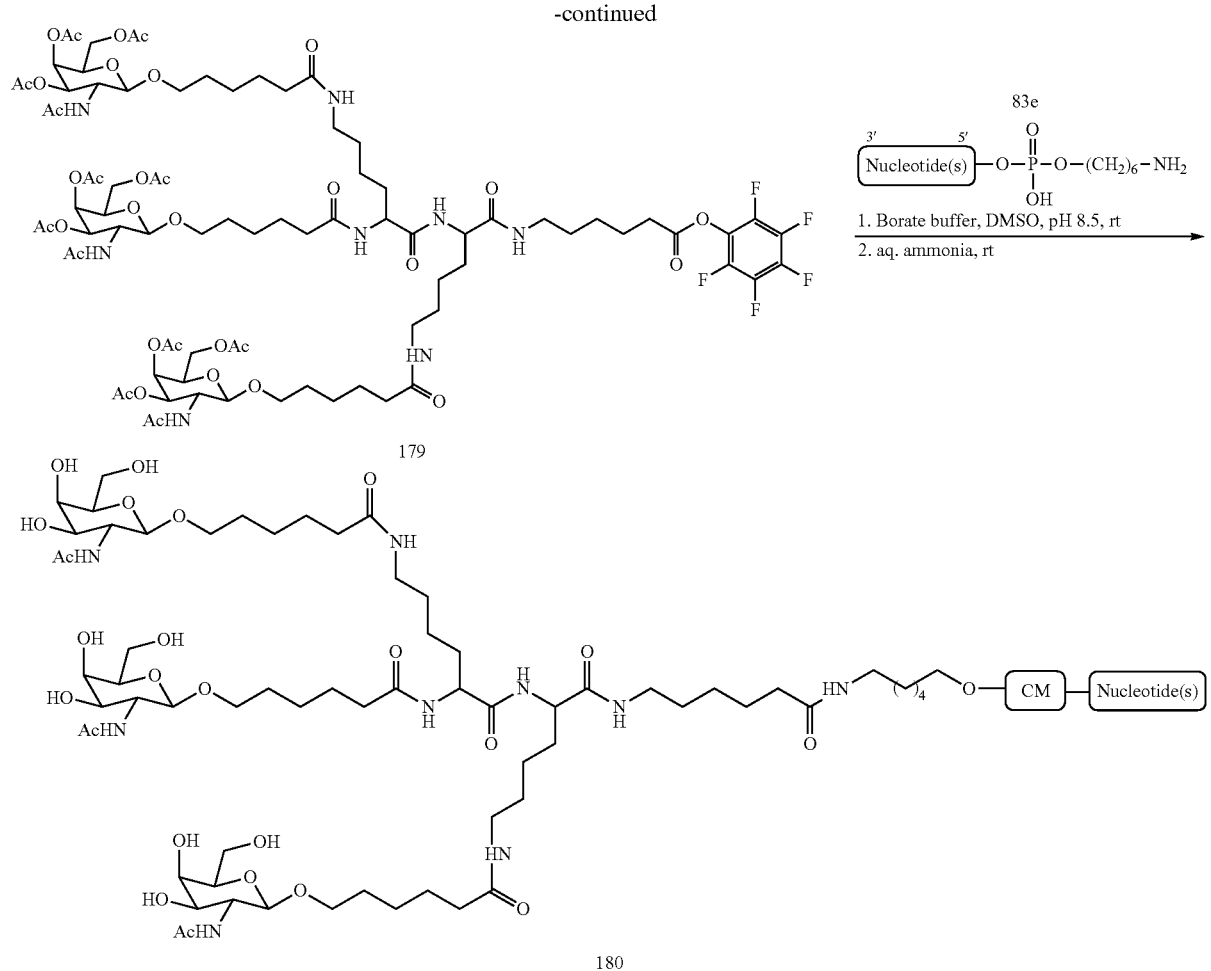

Compound 176 was prepared using the general procedure described in Example 40. Compound 180, comprising a GalNAc₃-13 targeting group, is prepared from compound 177 using the general procedures illustrated in Example 35. The GalNAc₃ cluster portion of the targeting group Gal-NAc₃-13 (GalNAc₃-13$_a$) can be combined with any cleavable moiety. In a certain embodiment, the cleavable moiety is —P(=O)(OH)-A$_d$-P(=O)(OH)—. The structure of GalNAc₃-13 (GalNAc₃-13$_a$-CM-) is shown below:

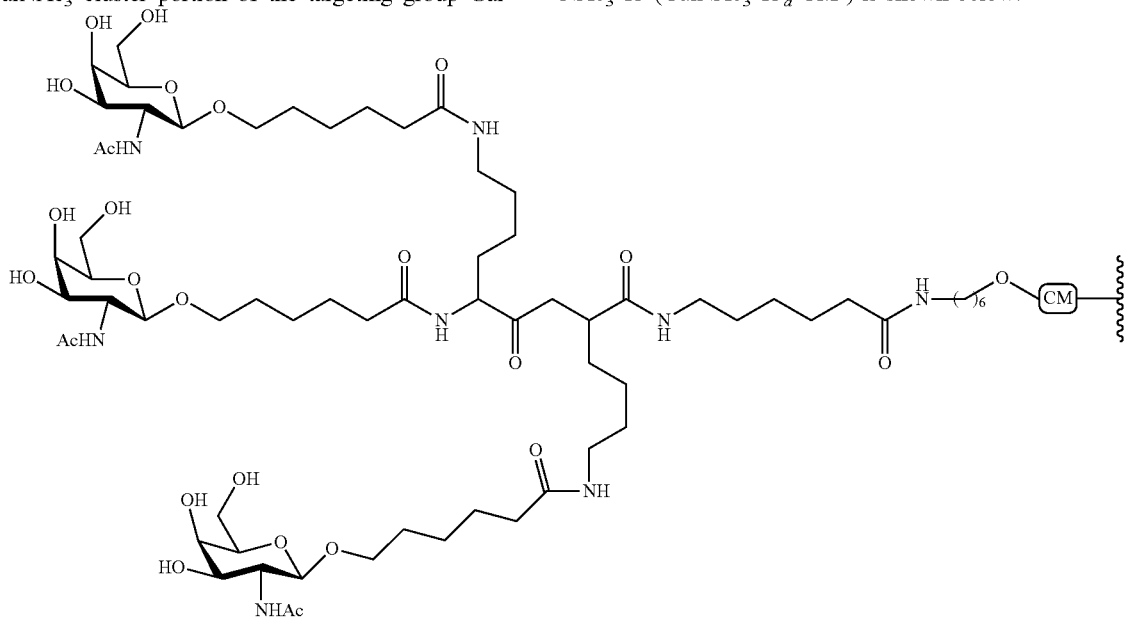

Example 43: Preparation of Therapeutic Agent 188 Comprising GalNAc$_3$-14
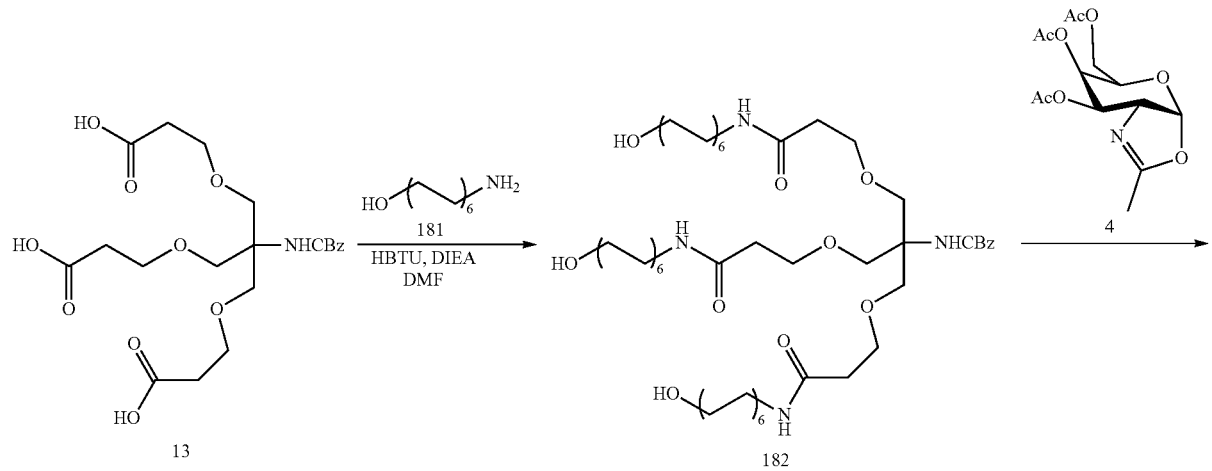
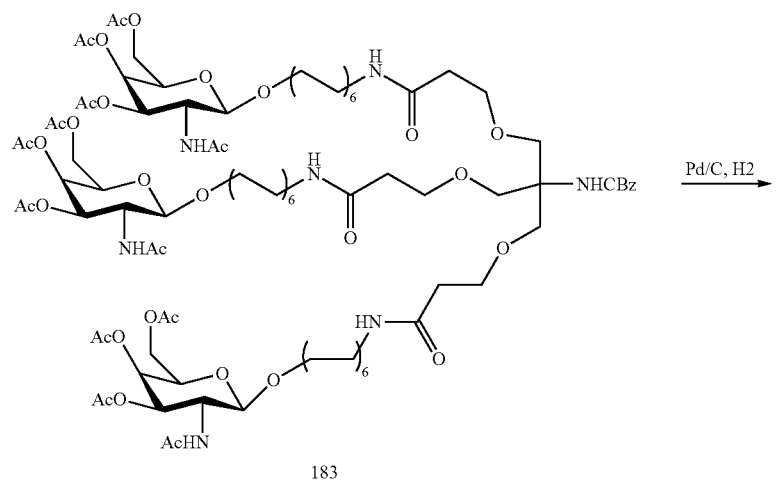
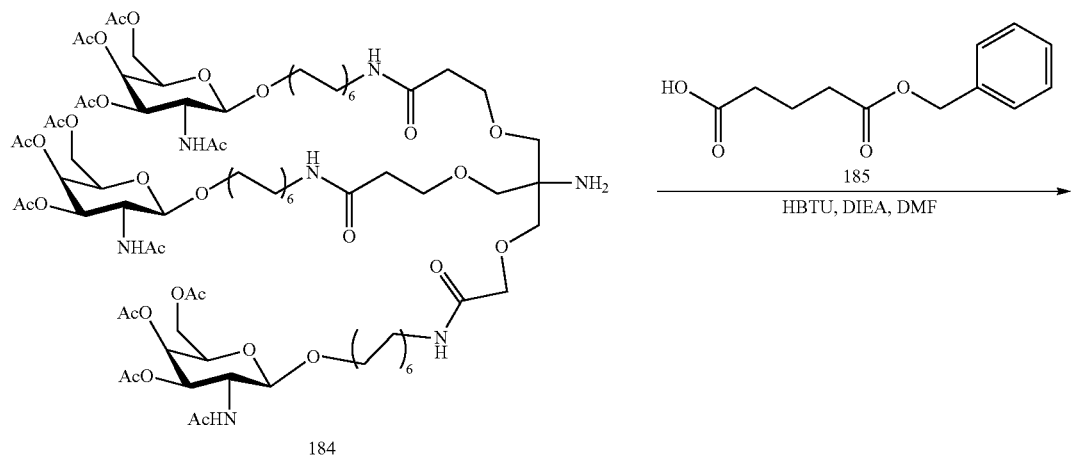

-continued

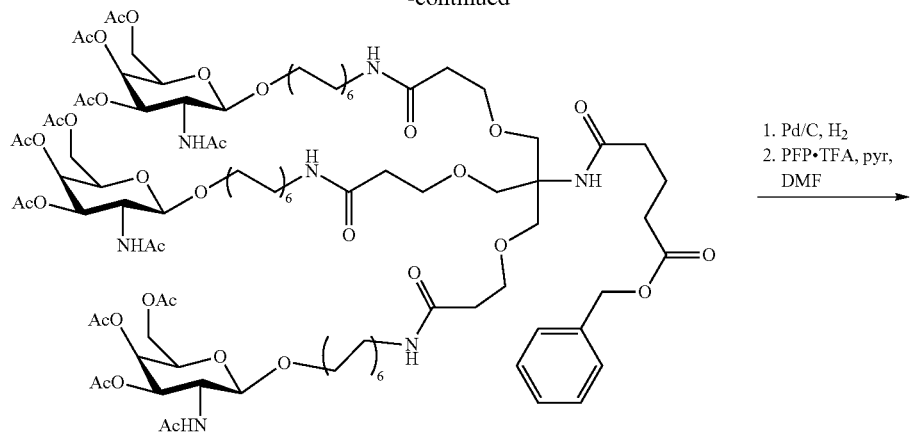

186

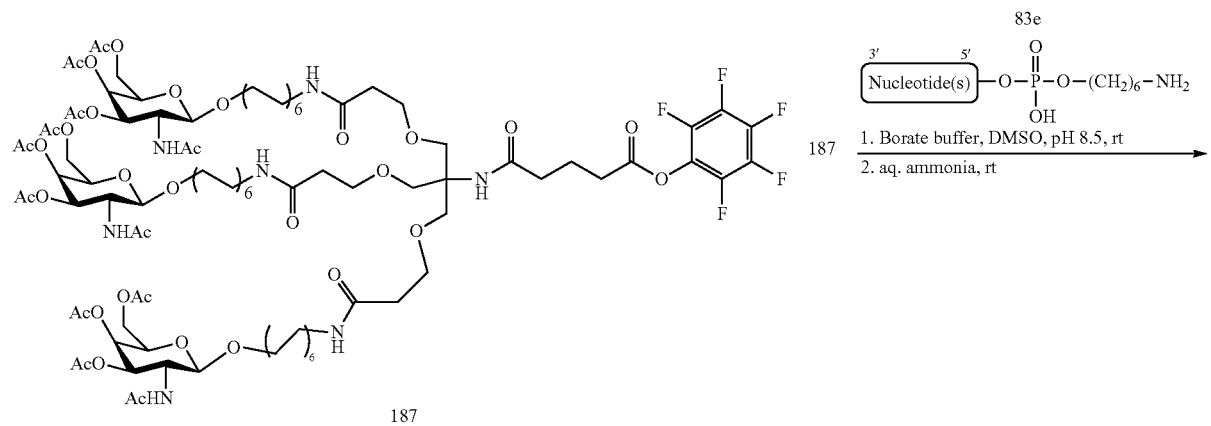

187

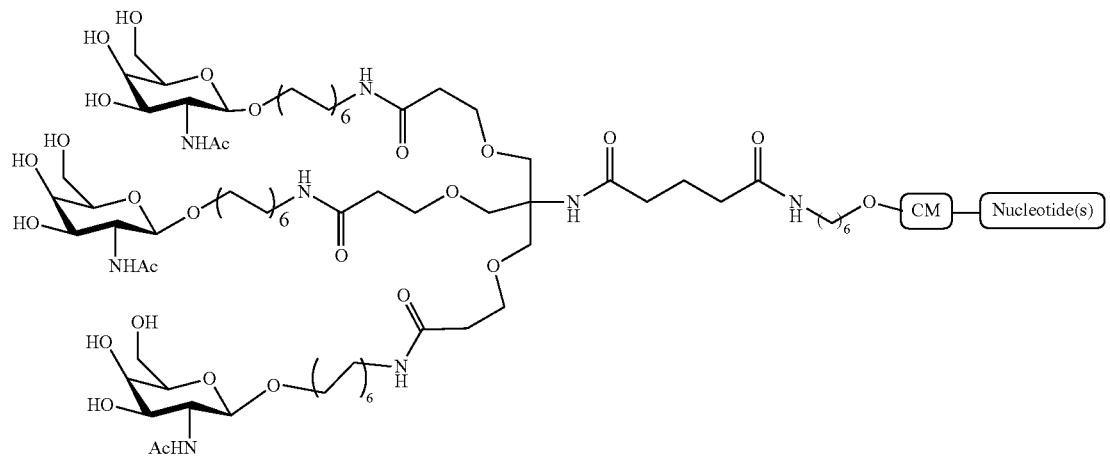

188

Compounds 181 and 185 are commercially available. Compound 188, comprising a GalNAc$_3$-14 targeting group, is prepared from compound 186 using the general procedures illustrated in Example 32. The GalNAc$_3$ cluster portion of the targeting group GalNAc$_3$-14 (GalNAc$_3$-14$_a$) can be combined with any cleavable moiety. In a certain embodiment, the cleavable moiety is —P(=O)(OH)-A$_d$-P(=O)(OH)—. The structure of GalNAc$_3$-14 (GalNAc$_3$-14$_a$-CM-) is shown below:

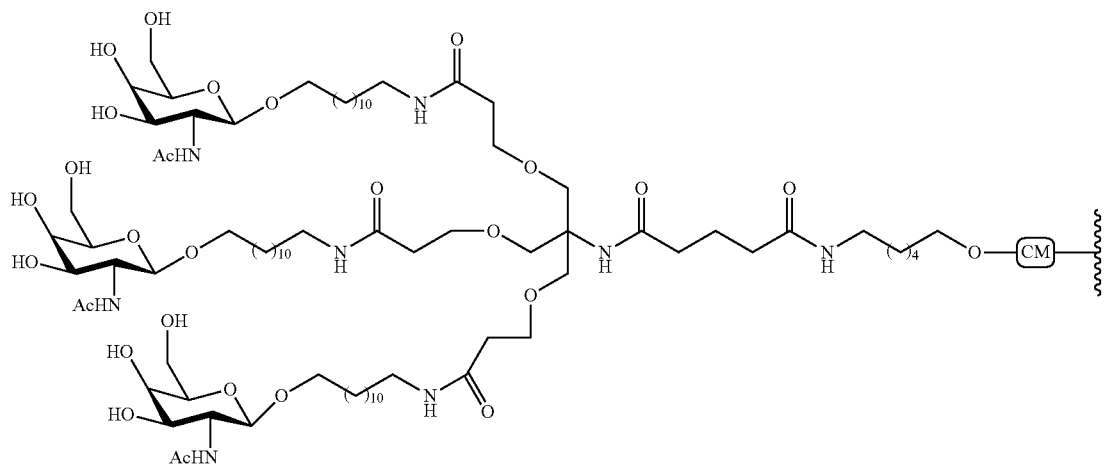
Example 44: Preparation of Therapeutic Agent 197 Comprising GalNAc₃-15
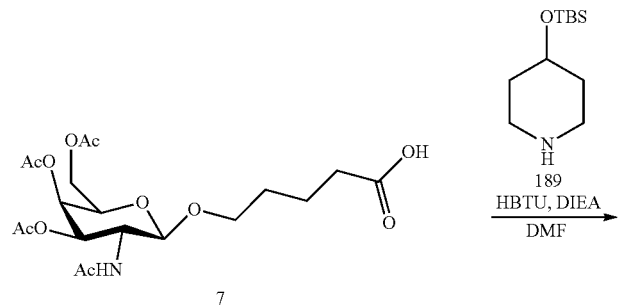
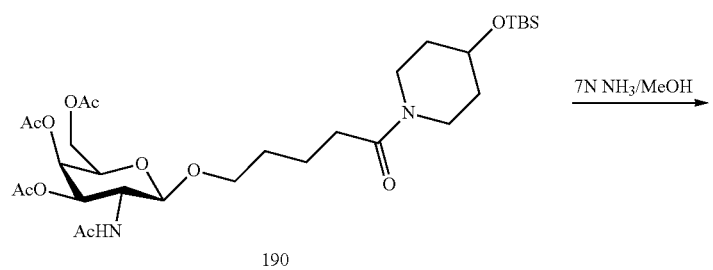
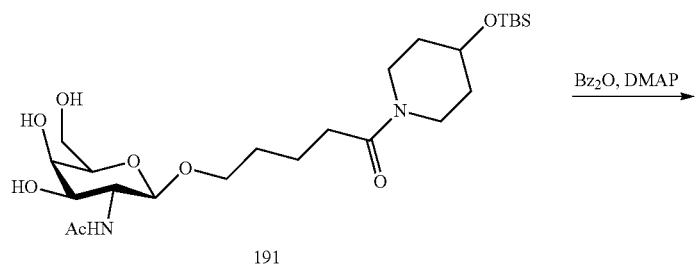

-continued
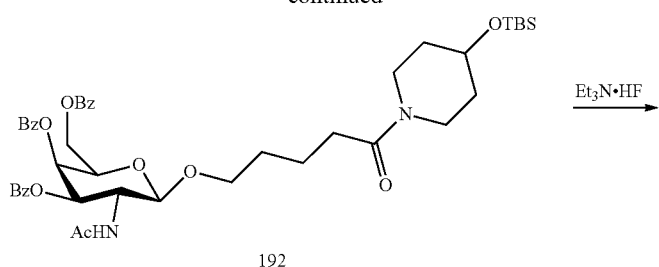

-continued

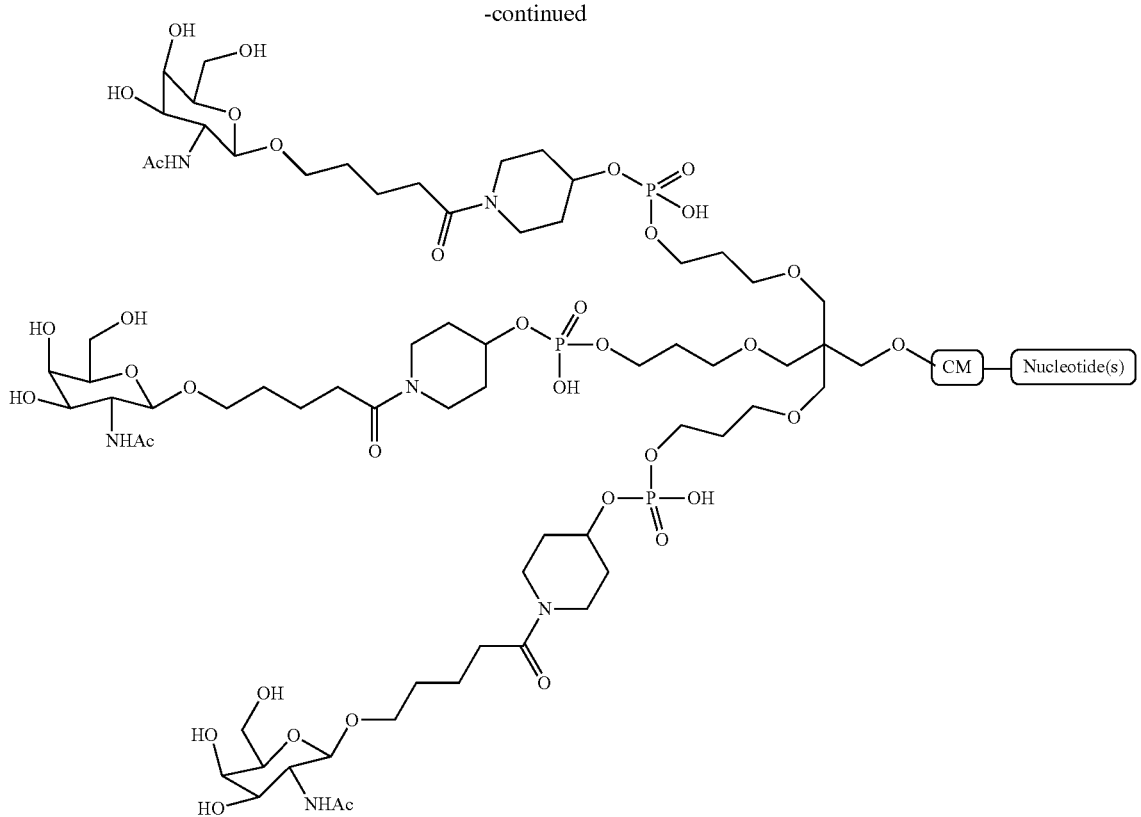

197

Compound 189 is commercially available. Compound 195 was prepared using the general procedure shown in Example 21. Compound 197, comprising a GalNAc$_3$-15 targeting group, is prepared from compounds 194 and 195 using standard oligonucleotide synthesis procedures. The GalNAc$_3$ cluster portion of the targeting group GalNAc$_3$-15 (GalNAc$_3$-15$_a$) can be combined with any cleavable moiety. In a certain embodiment, the cleavable moiety is —P(=O)(OH)-A$_d$-P(=O)(OH)—. The structure of GalNAc$_3$-15 (GalNAc$_3$-15$_a$-CM-) is shown below:

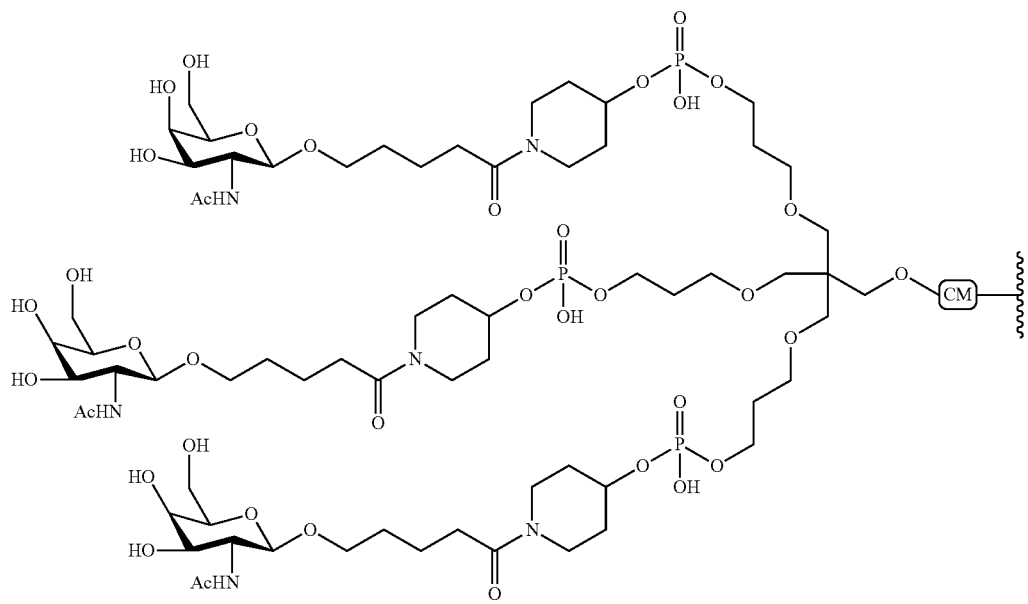

Example 45: Preparation of Therapeutic Agent 199 Comprising GalNAc$_3$-16
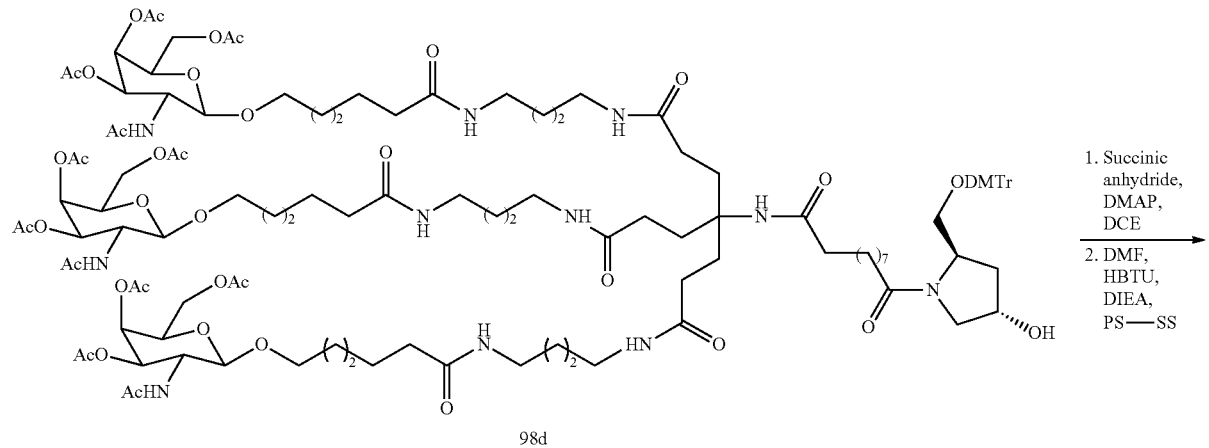
98d
1. Succinic anhydride, DMAP, DCE
2. DMF, HBTU, DIEA, PS—SS
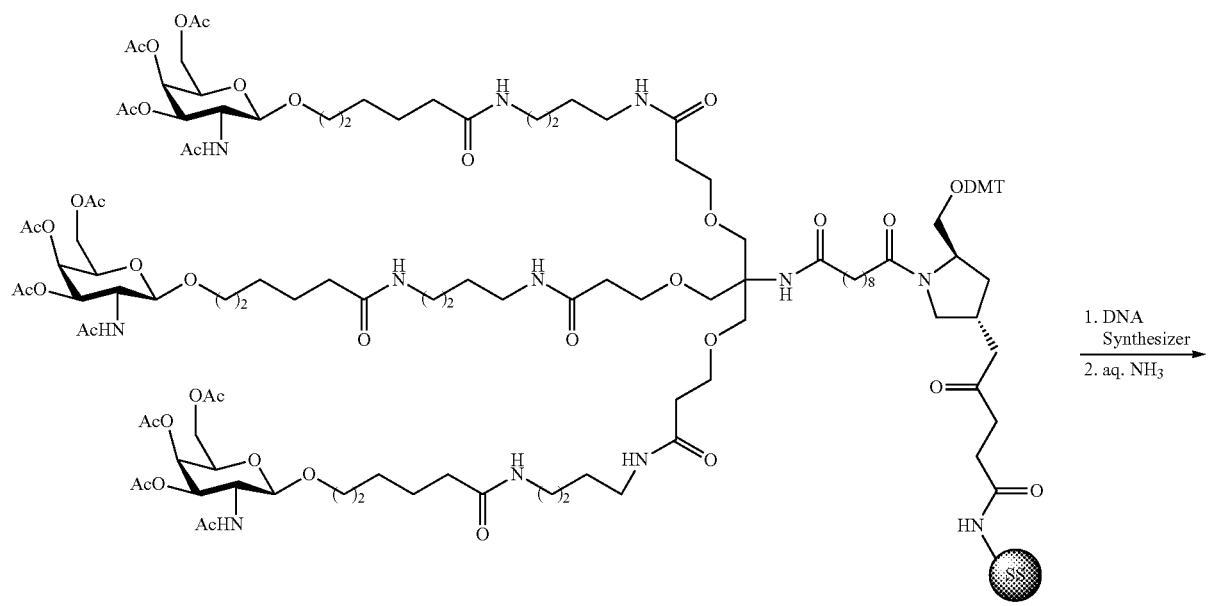
198
1. DNA Synthesizer
2. aq. NH$_3$

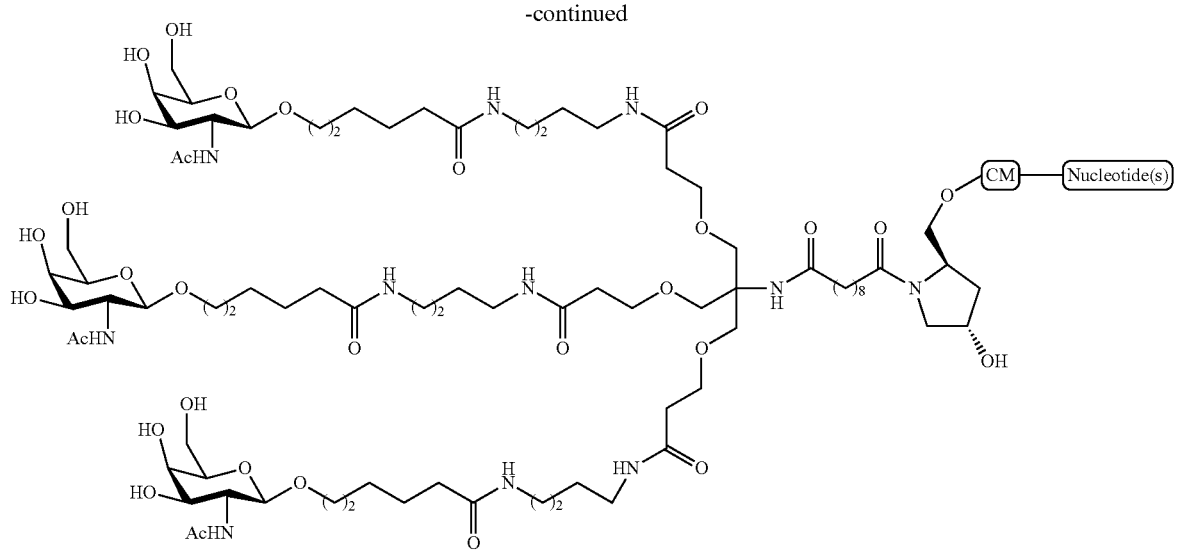

199

Compound 199, comprising a GalNAc$_3$-16 targeting group, is prepared using the general procedures illustrated in Examples 7 and 9. The GalNAc$_3$ cluster portion of the targeting group GalNAc$_3$-16 (GalNAc$_3$-16$_a$) can be combined with any cleavable moiety. In a certain embodiment, the cleavable moiety is —P(=O)(OH)-A$_d$-P(=O)(OH)—. The structure of GalNAc$_3$-16 (GalNAc$_3$-16$_a$-CM-) is shown below:

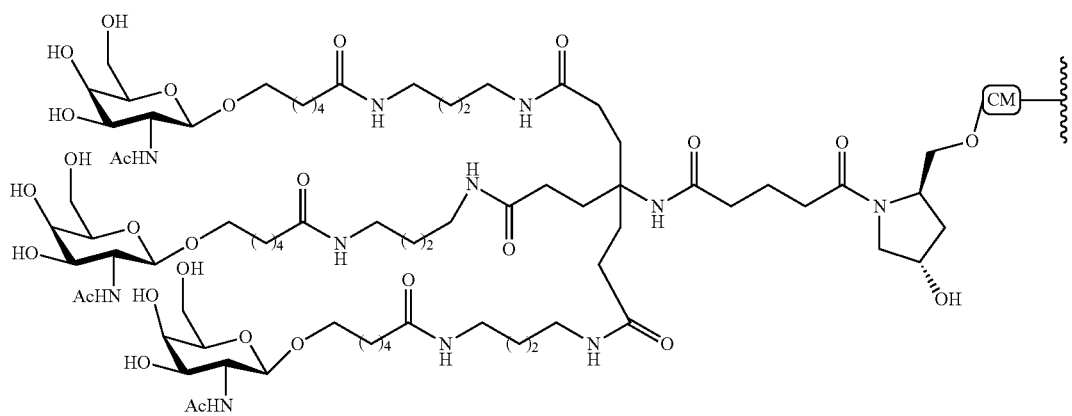

Example 46: Preparation of Therapeutic Agent 200 Comprising GalNAc$_3$-17

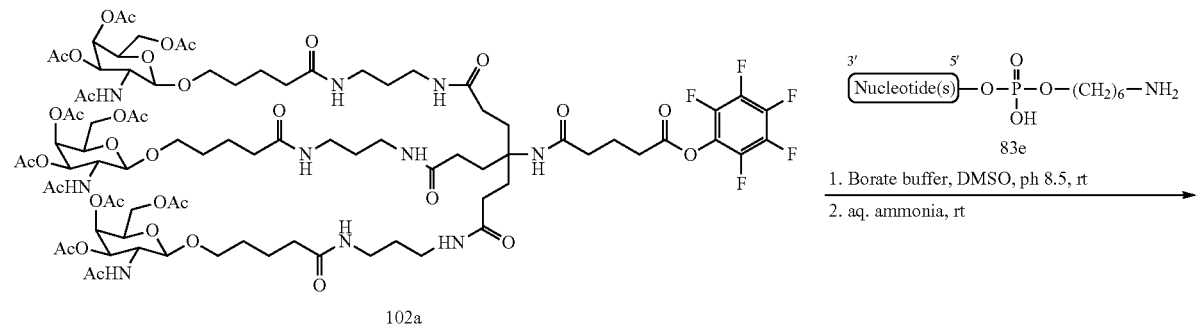

102a

1. Borate buffer, DMSO, ph 8.5, rt
2. aq. ammonia, rt

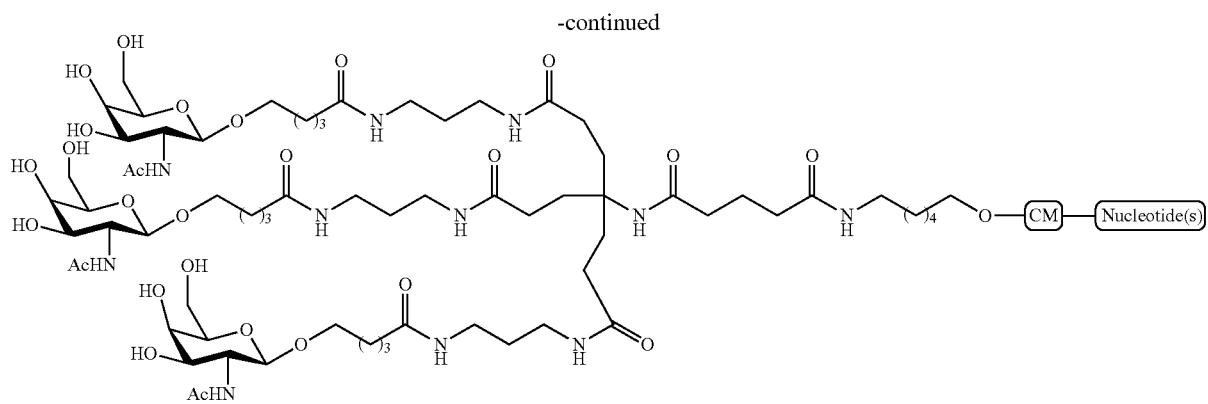

200

Compound 200, comprising a GalNAc$_3$-17 targeting group, is prepared using the general procedures illustrated in Example 32. The GalNAc$_3$ cluster portion of the targeting group GalNAc$_3$-17 (GalNAc$_3$-17$_a$) can be combined with any cleavable moiety. In a certain embodiment, the cleavable moiety is —P(=O)(OH)-A$_d$-P(=O)(OH)—. The structure of GalNAc$_3$-17 (GalNAc$_3$-17$_a$-CM-) is shown below:

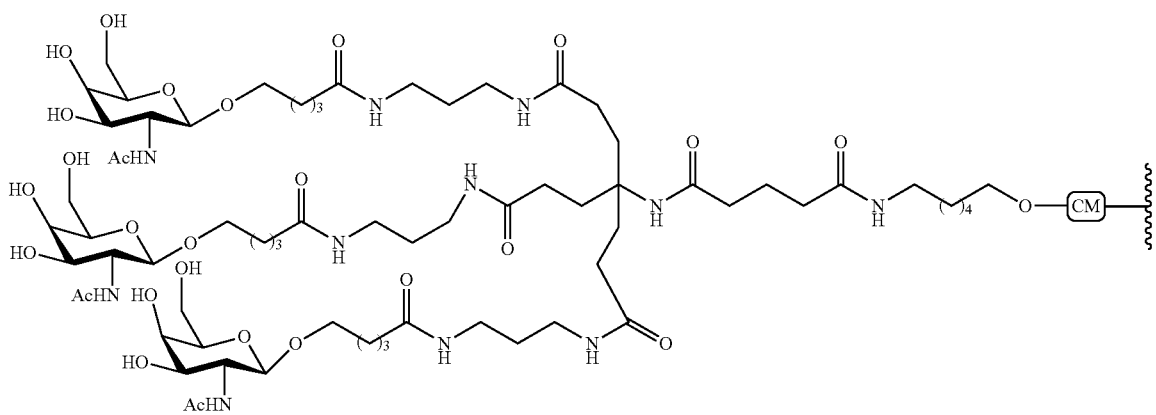

Example 47: Preparation of Therapeutic Agent 201 Comprising GalNAc$_3$-18

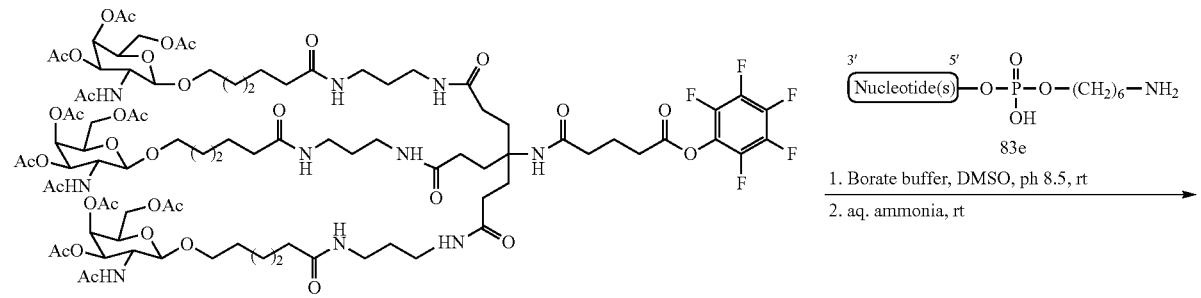

102b

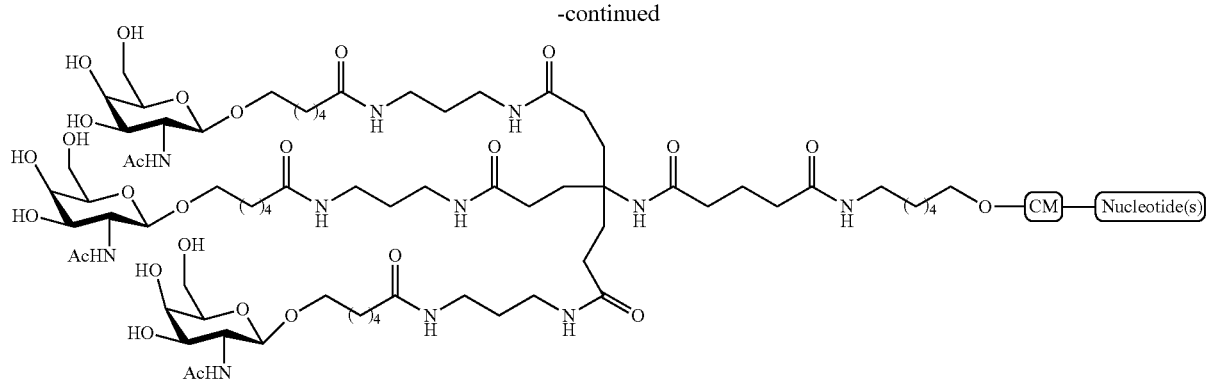

201

Compound 201, comprising a GalNAc$_3$-18 targeting group, is prepared using the general procedures illustrated in Example 32. The GalNAc$_3$ cluster portion of the targeting group GalNAc$_3$-18 (GalNAc$_3$-18$_a$) can be combined with any cleavable moiety. In a certain embodiment, the cleavable moiety is —P(=O)(OH)-A$_d$-P(=O)(OH)—. The structure of GalNAc$_3$-18 (GalNAc$_3$-18$_a$-CM-) is shown below:

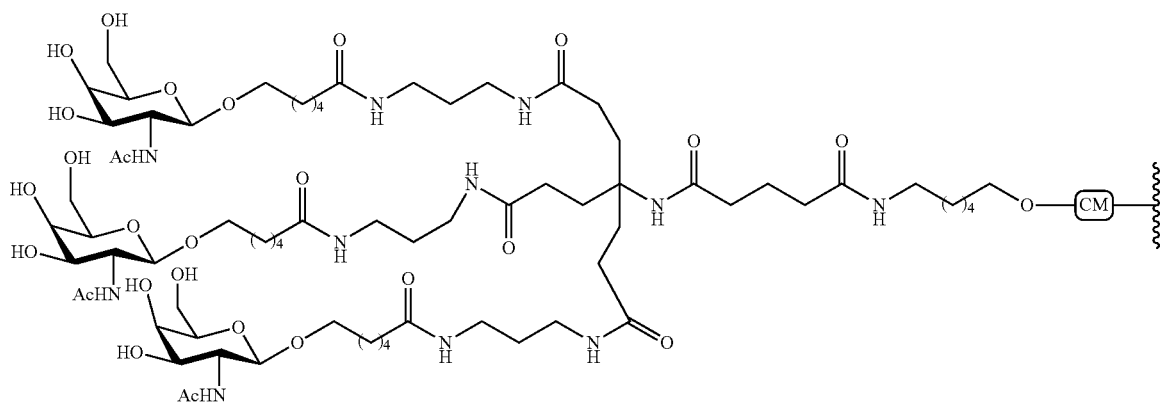

Example 48: Preparation of Therapeutic Agent 204 Comprising GalNAc$_3$-19

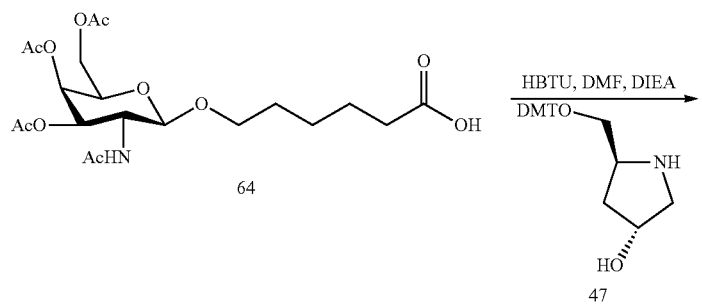

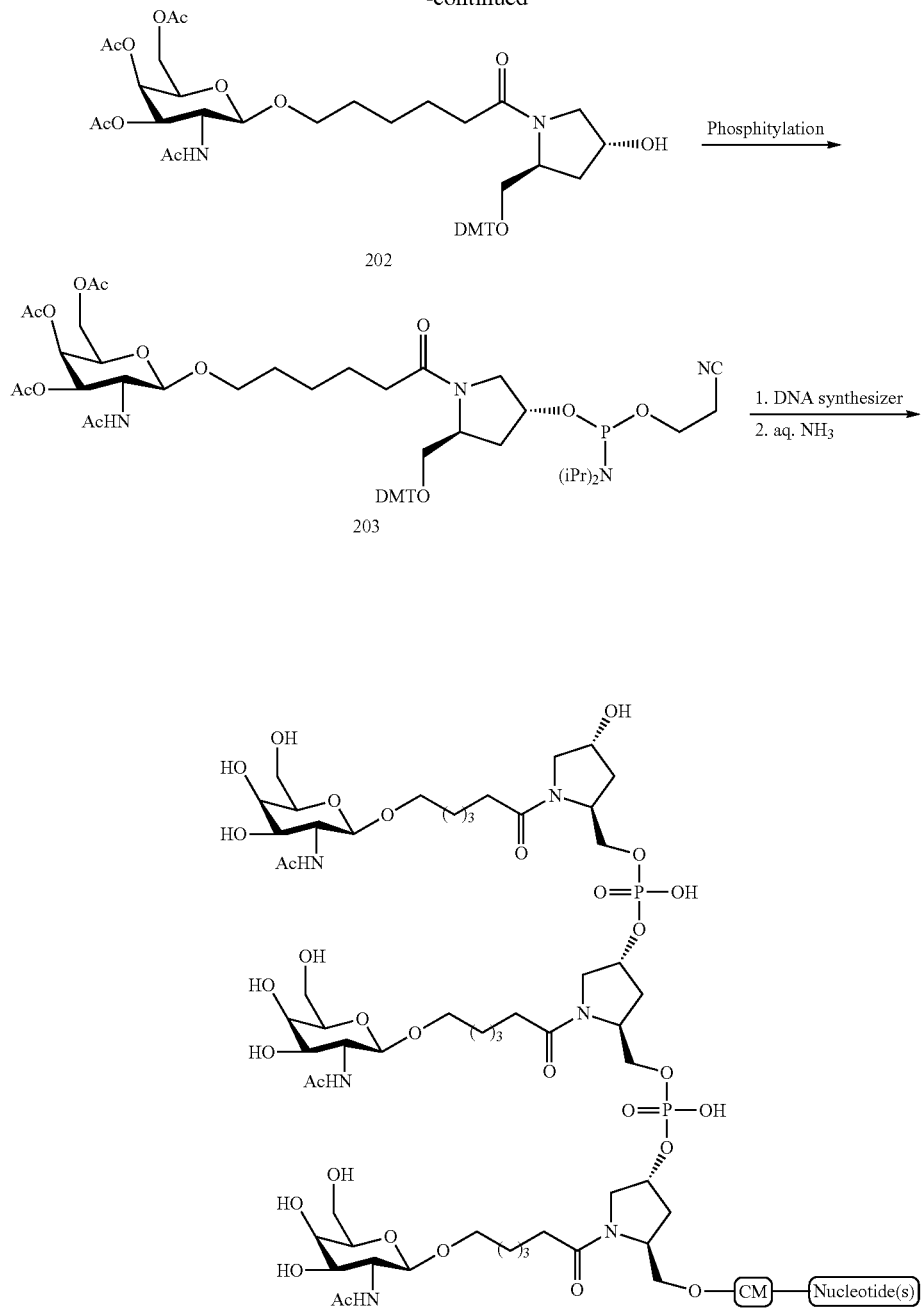

Compound 204, comprising a GalNAc$_3$-19 targeting group, is prepared from compound 64 using the general procedures illustrated in Example 38. The GalNAc$_3$ cluster portion of the targeting group GalNAc$_3$-19 (GalNAc$_3$-19$_a$) can be combined with any cleavable moiety. In a certain embodiment, the cleavable moiety is —P(=O)(OH)-A$_d$-P(=O)(OH)—. The structure of GalNAc$_3$-19 (GalNAc$_3$-19$_a$-CM-) is shown below:

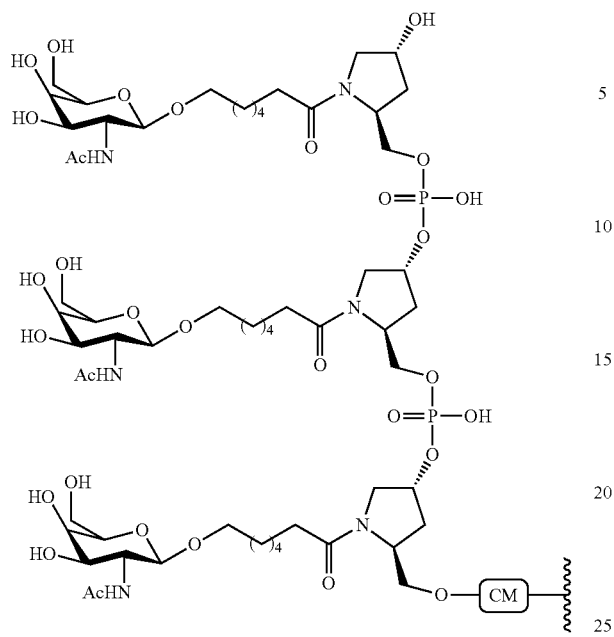
Example 49: Preparation of Therapeutic Agent 210 Comprising GalNAc$_3$-20
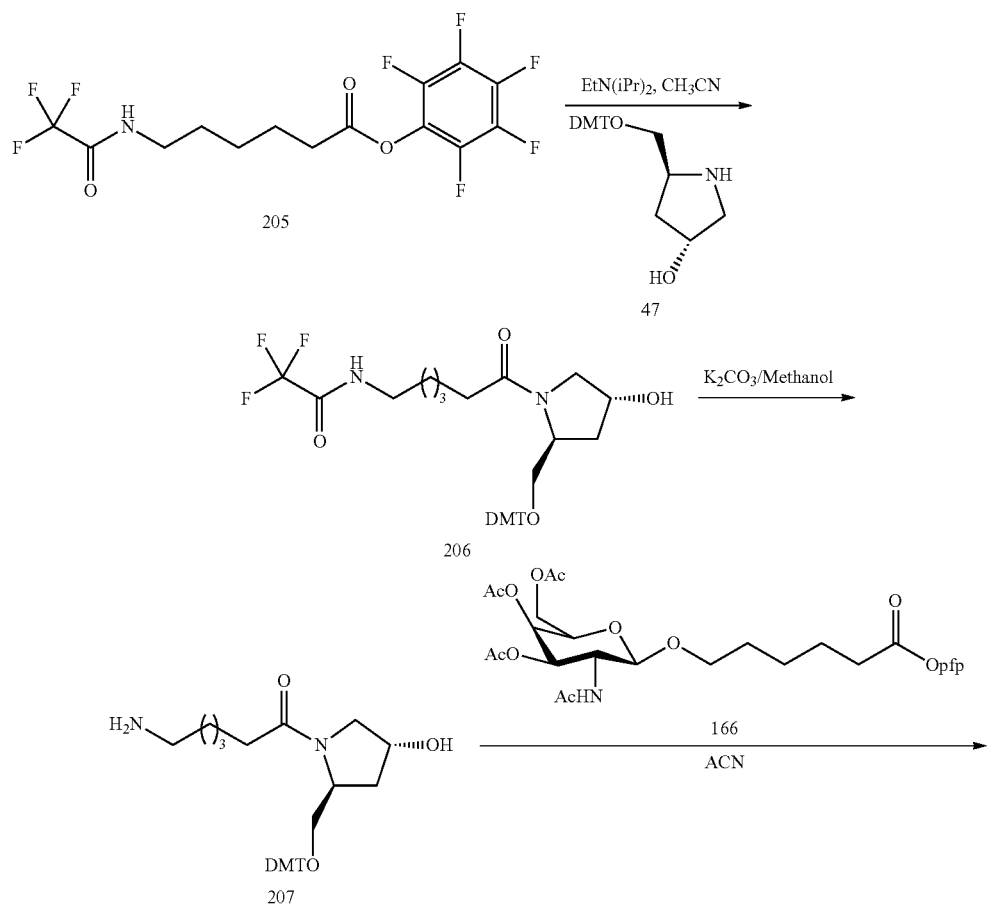

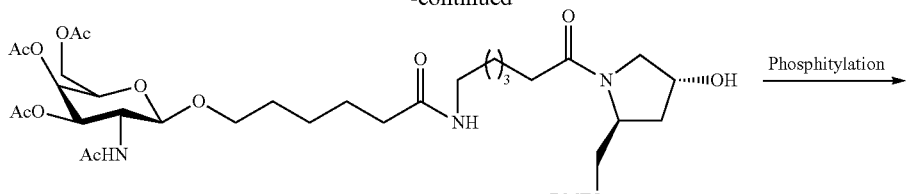

208

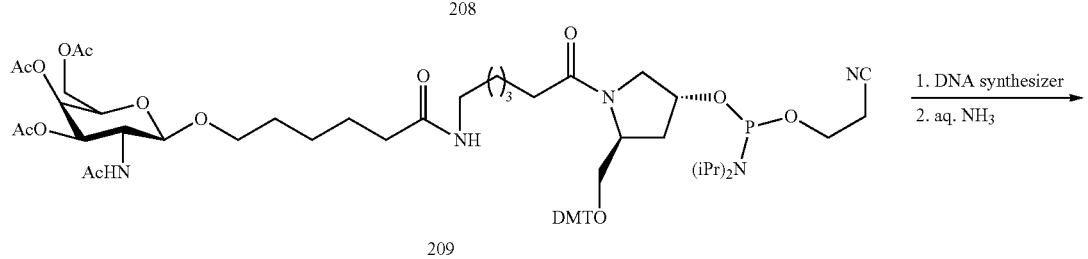

209

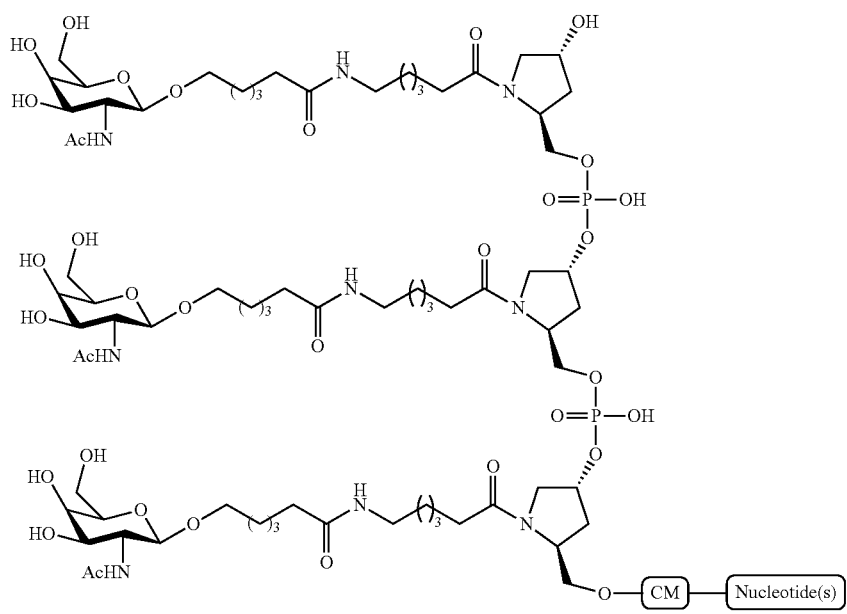

210

Compound 205 was prepared by adding PFP-TFA and DIEA to 6-(2,2,2-trifluoroacetamido)hexanoic acid in acetonitrile. The 6-(2,2,2-trifluoroacetamido)hexanoic acid was prepared by adding triflic anhydride to 6-aminohexanoic acid. The reaction mixture was heated to 80° C., then lowered to rt. Compound 210, comprising a GalNAc$_3$-20 targeting group, is prepared from compound 208 using the general procedures illustrated in Example 38. The GalNAc$_3$ cluster portion of the targeting group GalNAc$_3$-20 (GalNAc$_3$-20$_a$) can be combined with any cleavable moiety. In a certain embodiment, the cleavable moiety is —P(=O)(OH)-A$_d$-P(=O)(OH)—. The structure of GalNAc$_3$-20 (GalNAc$_3$-20$_a$-CM-) is shown below:

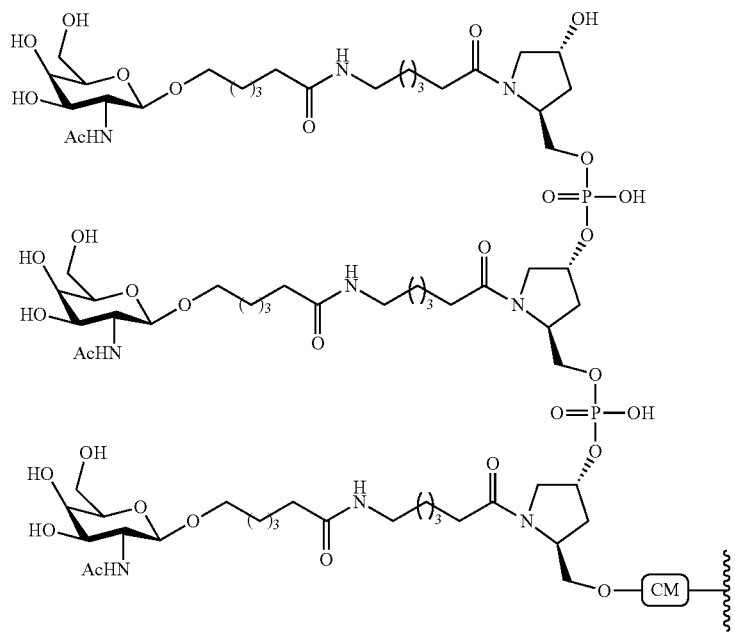
Example 50: Preparation of Therapeutic Agent 215 Comprising GalNAc₃-21
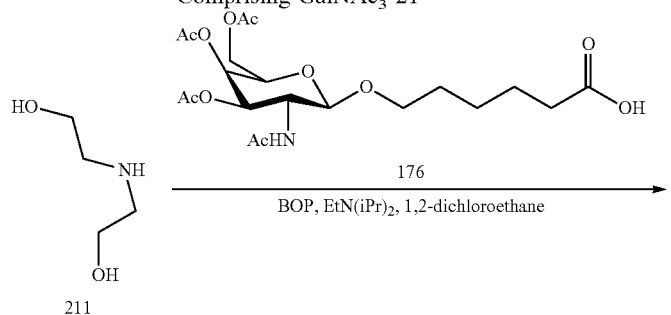
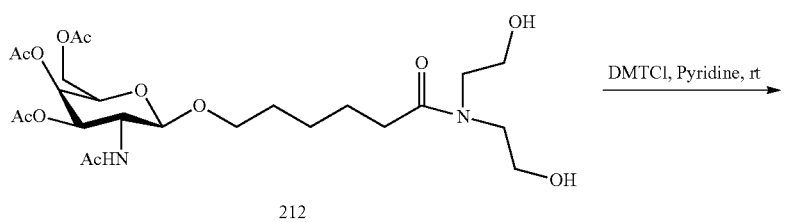
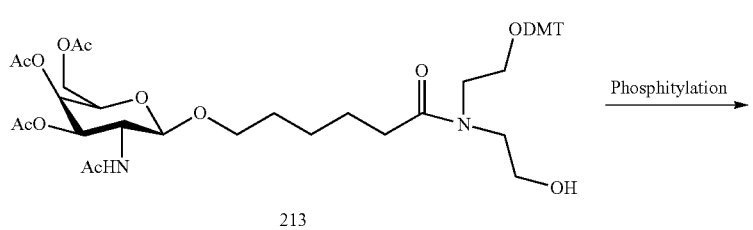

-continued

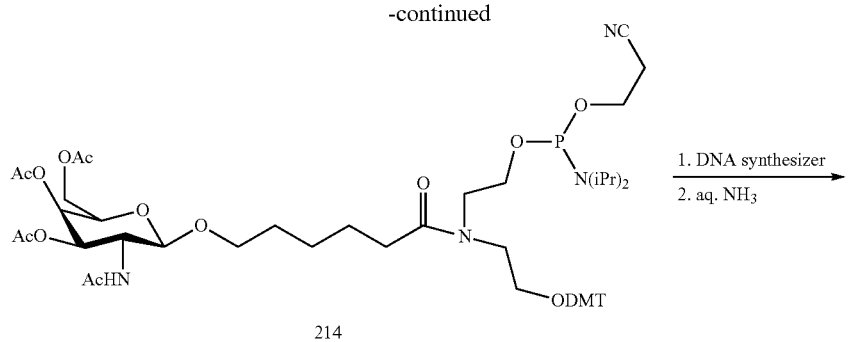

214

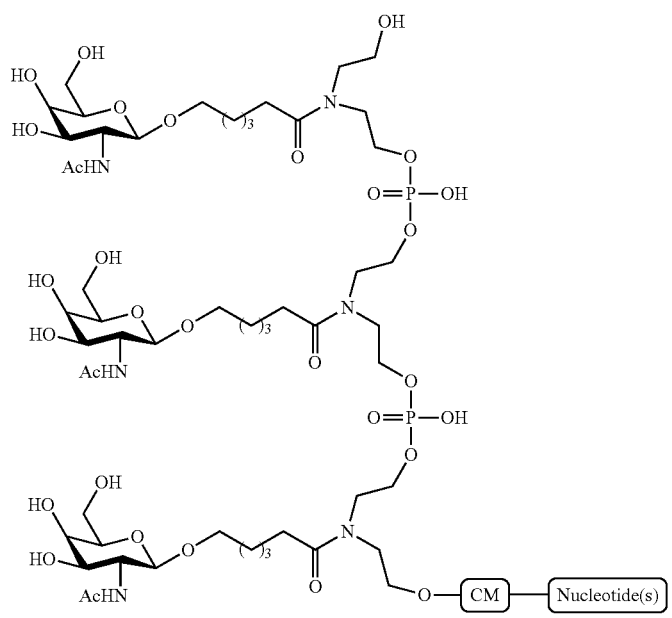

215

Compound 211 is commercially available. Compound 215, comprising a GalNAc$_3$-21 targeting group, is prepared from compound 213 using the general procedures illustrated in Example 38. The GalNAc$_3$ cluster portion of the targeting group GalNAc$_3$-21 (GalNAc$_3$-21$_a$) can be combined with any cleavable moiety. In a certain embodiment, the cleavable moiety is —P(=O)(OH)-A$_d$-P(=O)(OH)—. The structure of GalNAc$_3$-21 (GalNAc$_3$-21$_a$-CM-) is shown below:

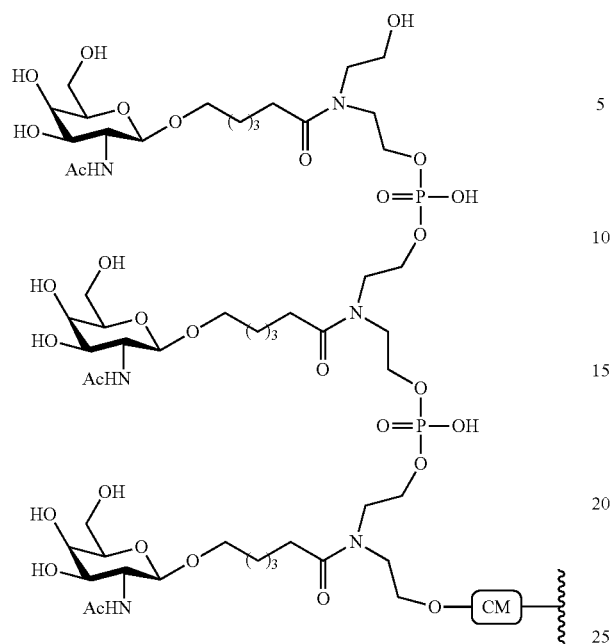
Example 51: Preparation of Therapeutic Agent 221 Comprising GalNAc$_3$-22
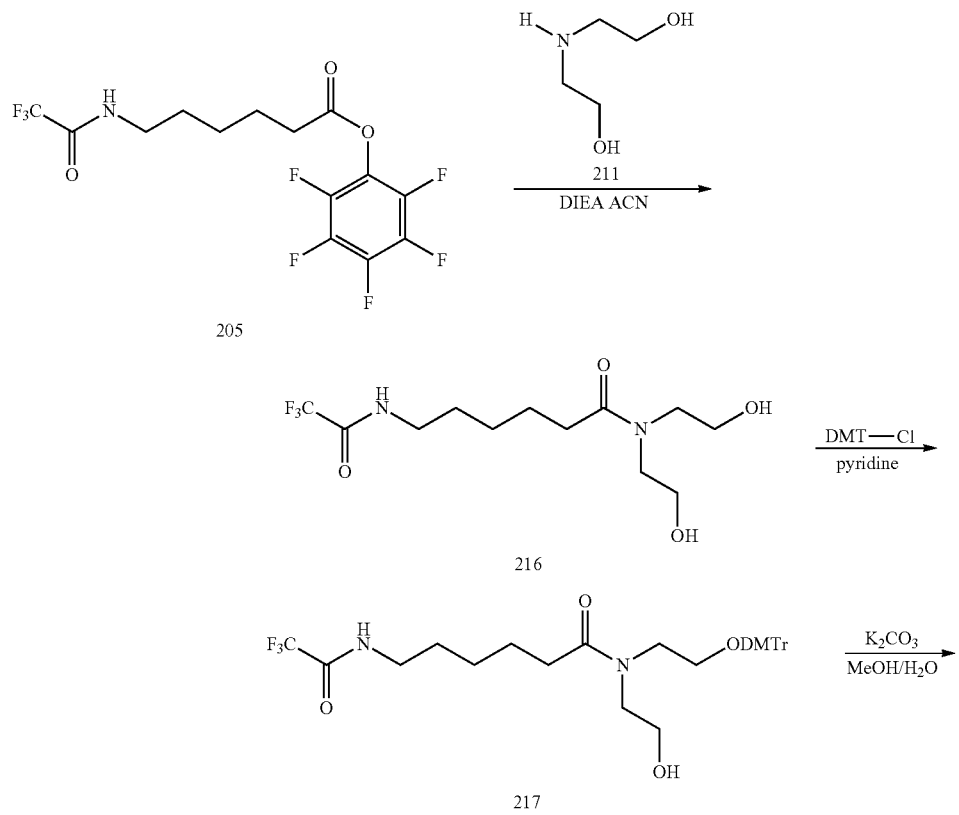

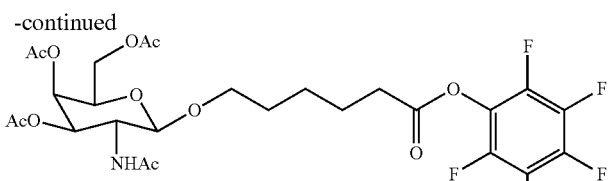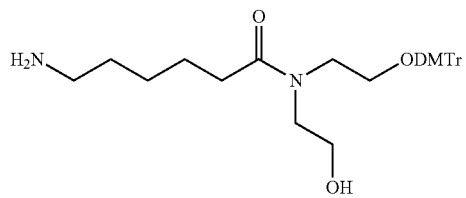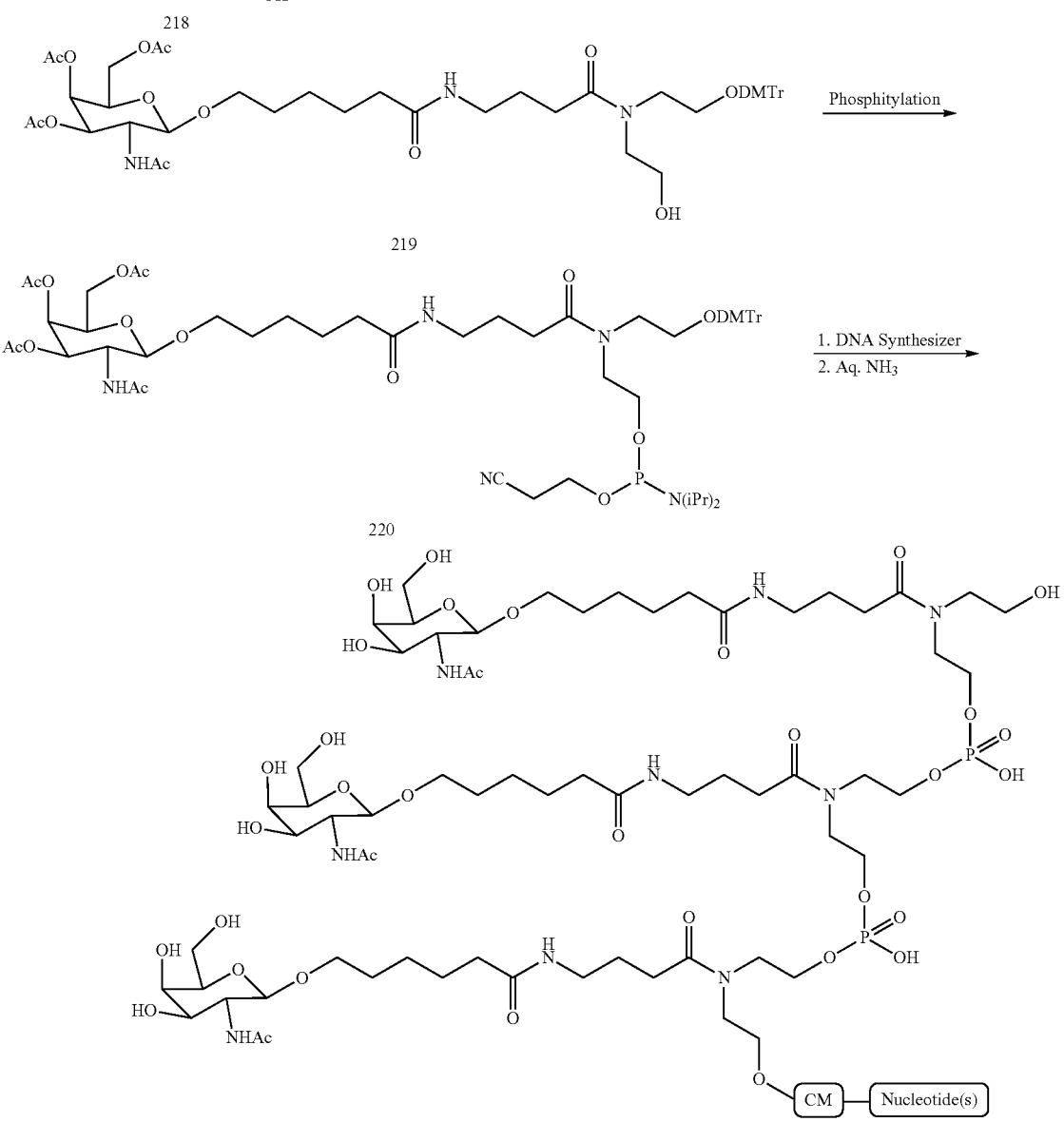

Compound 220 was prepared from compound 219 using diisopropylammonium tetrazolide. Compound 221, comprising a GalNAc₃-21 targeting group, is prepared from compound 220 using the general procedure illustrated in Example 38. The GalNAc₃ cluster portion of the targeting group GalNAc₃-22 (GalNAc₃-22$_a$) can be combined with any cleavable moiety. In a certain embodiment, the cleavable moiety is —P(=O)(OH)-A$_d$-P(=O)(OH)—. The structure of GalNAc₃-22 (GalNAc₃-22$_a$-CM-) is shown below:

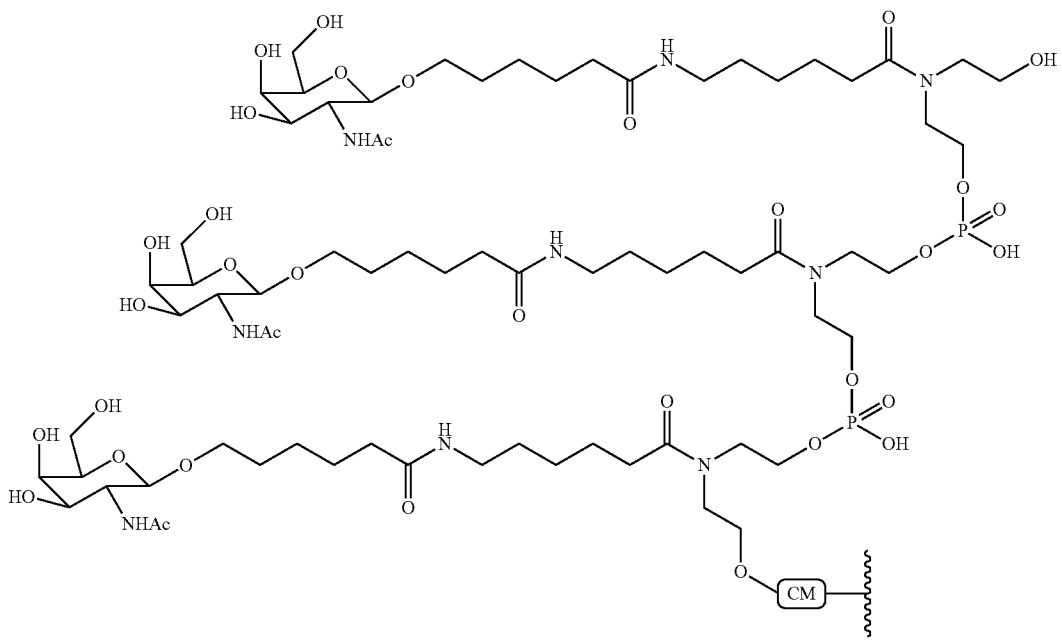
Example 52: Preparation of Therapeutic Agent 230 Comprising GalNAc$_3$-23
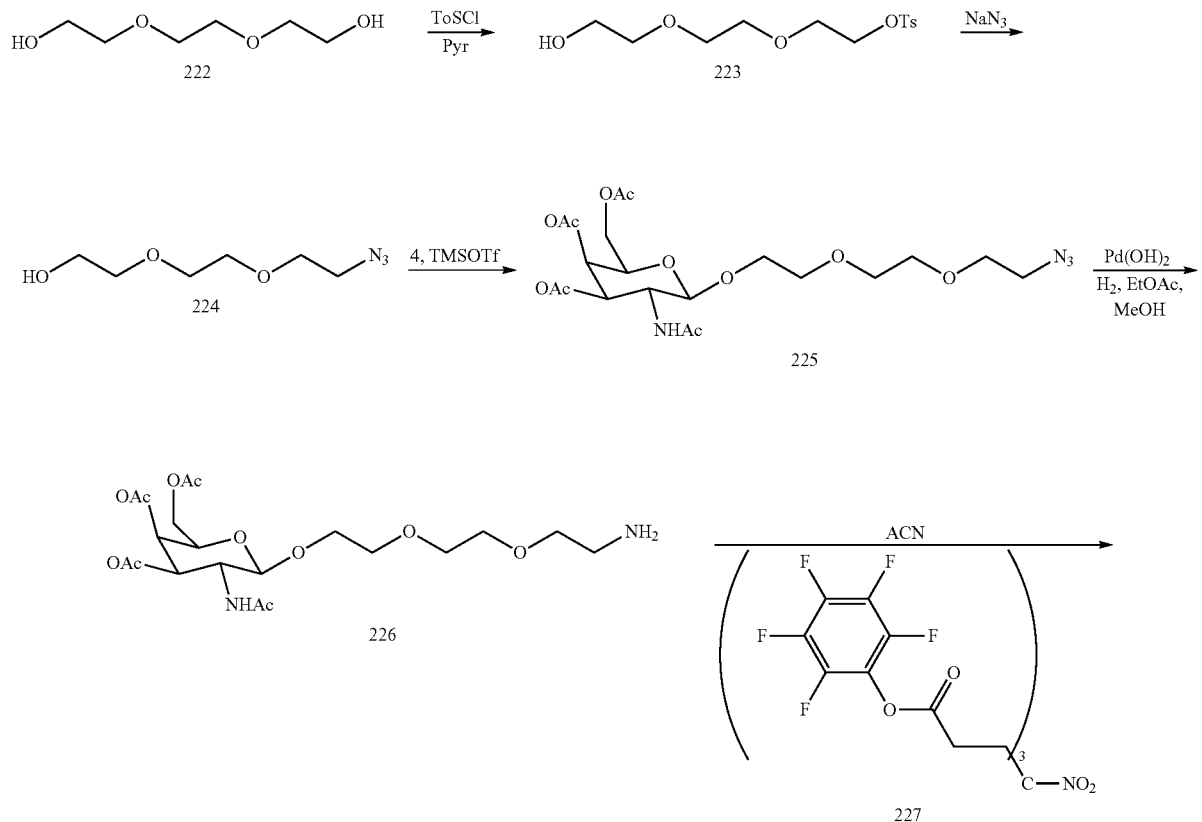

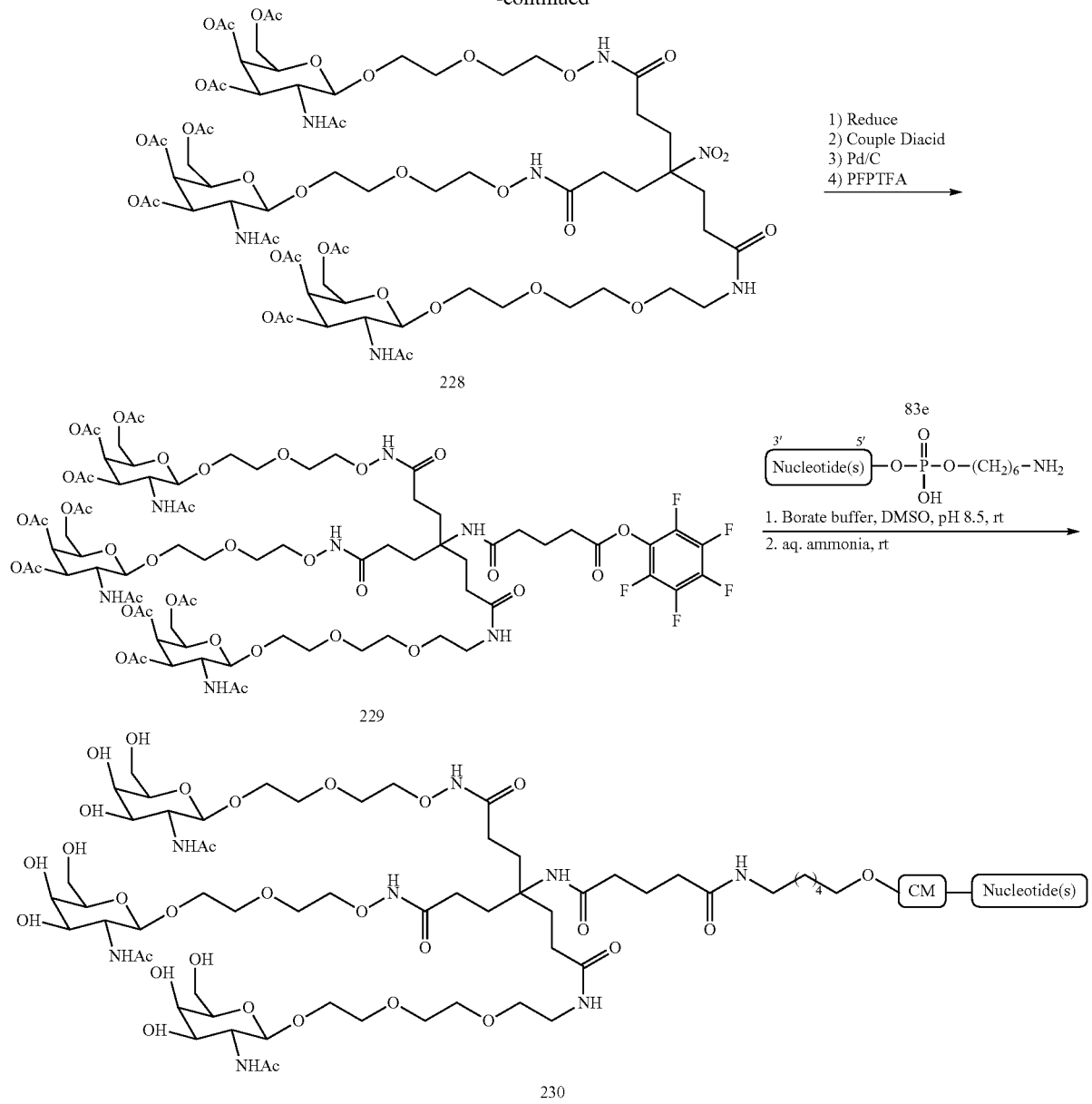

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. NaHCO$_3$, brine, and dried over Na$_2$SO$_4$. The ethyl acetate was concentrated to dryness and purified by column chromatography, eluted with EtOAc/hexanes (1:1) followed by 10% methanol in CH$_2$Cl$_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over Na$_2$SO$_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4 Å molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. NaHCO$_3$, water, brine, and dried over Na$_2$SO$_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over Na₂SO₄. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 µl, 1.6 mmol) in DMF (5 mL). After 16 hours, the DMF was removed under reduced pressure at 65° C. to an oil, and the oil was dissolved in dichloromethane. The organic layer was washed with sat. NaHCO₃, brine, and dried over Na₂SO₄. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 µl, 0.66 mmol) was added and the reaction was purged with argon. Pentaflourotriflouro acetate (46.39 µl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N NaHSO₄, brine, saturated sodium bicarbonate and brine again. The organics were dried over Na₂SO₄, filtered, and were concentrated to dryness to give 225 mg of compound 229 as a brittle yellow foam. LCMS and NMR were consistent with the structure.

Compound 230, comprising a GalNAc₃-23 conjugate group, is prepared from compound 229 using the general procedure illustrated in Example 32. The GalNAc₃ cluster portion of the GalNAc₃-23 conjugate group (GalNAc₃-23$_a$) can be combined with any cleavable moiety to provide a variety of conjugate groups. The structure of GalNAc₃-23 (GalNAc₃-23$_a$-CM) is shown below:

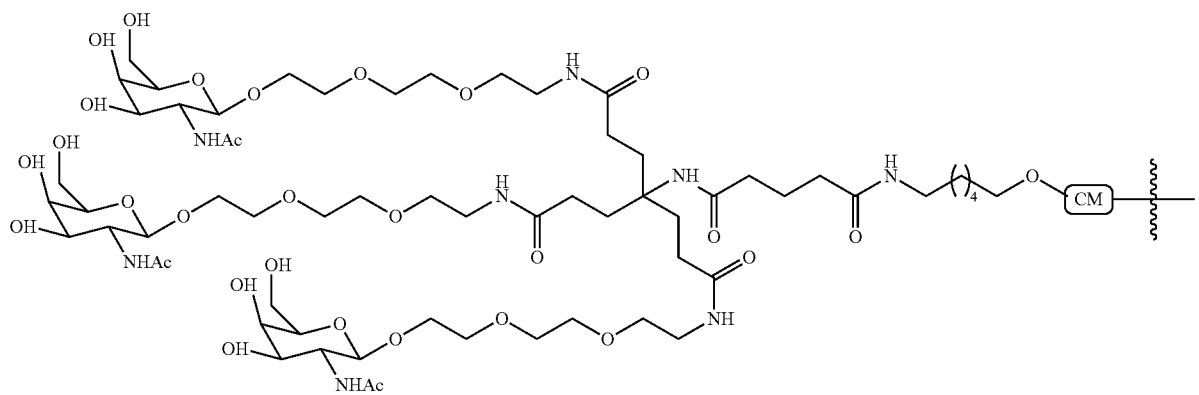

Example 53: Preparation of Therapeutic Agents Comprising a 5'-GalNAc₂ Conjugate

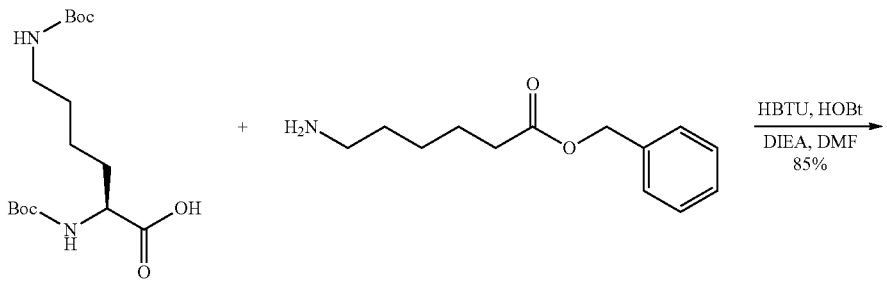

-continued
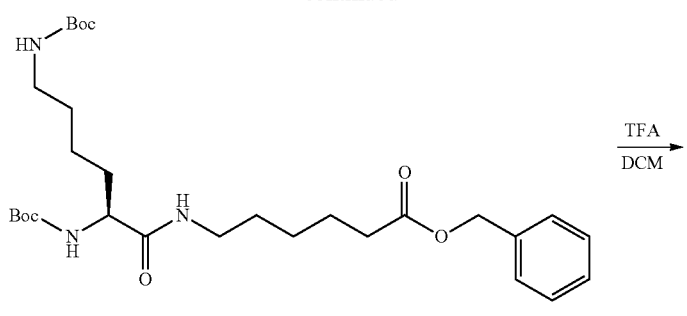
231
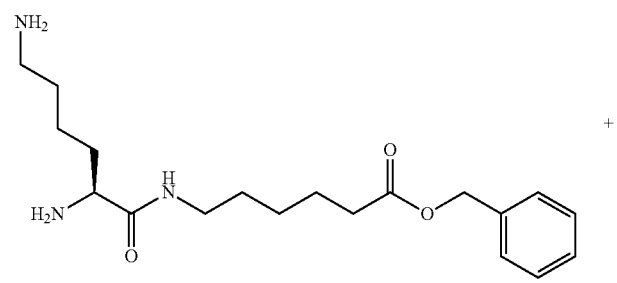
232
+
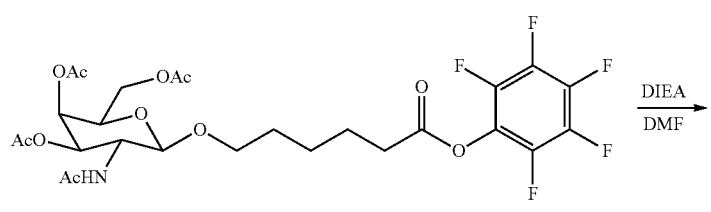
166
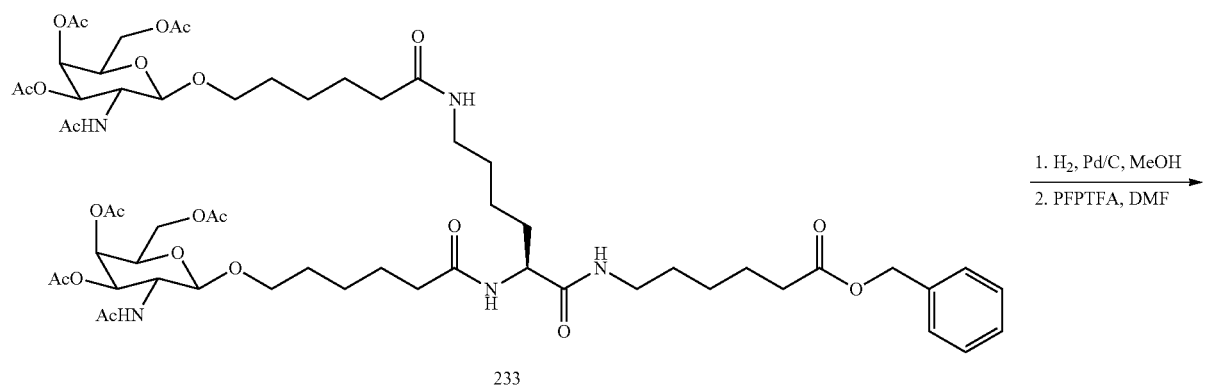
233
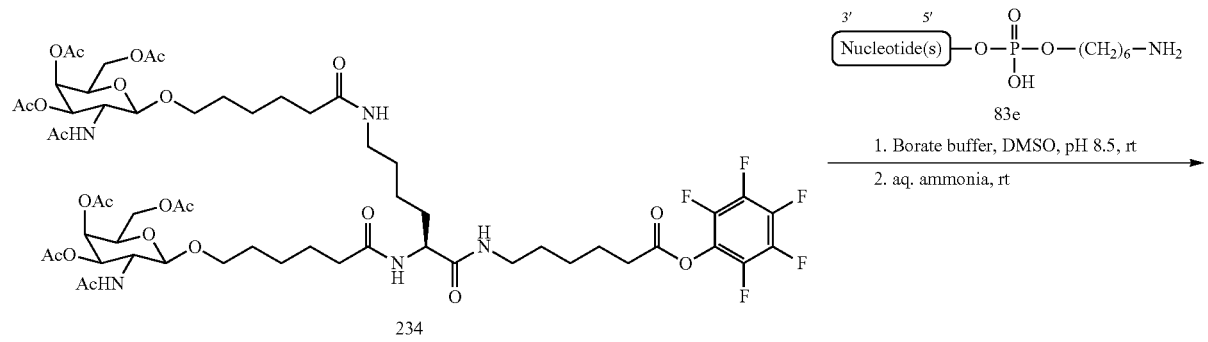
234

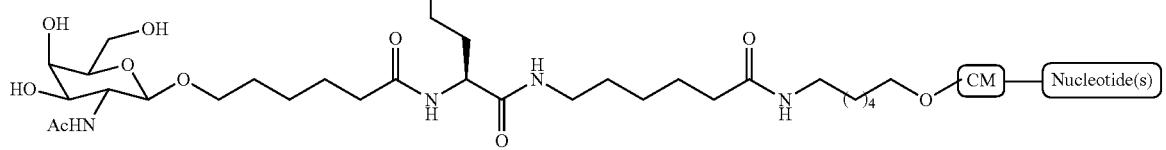

235

Compound 120 is commercially available, and the synthesis of compound 126 is described in Example 35. Compound 120 (1 g, 2.89 mmol), HBTU (0.39 g, 2.89 mmol), and HOBt (1.64 g, 4.33 mmol) were dissolved in DMF (10 mL) and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO4 and extracted with 2×50 mL ethyl acetate. Organic layers were combined and washed with 3×40 mL sat NaHCO$_3$ and 2× brine, dried with Na$_2$SO$_4$, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifluoracetate salt. The synthesis of compound 166 is described in Example 40. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat. aqueous NaHCO$_3$ (3×80 mL), 1 M NaHSO$_4$ (3×80 mL) and brine (2×80 mL), then dried (Na$_2$SO$_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylethylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Compound 235 is prepared using the general procedure described in Example 32. The GalNAc$_2$ cluster portion (GalNAc$_2$-24$_a$) of the conjugate group GalNAc$_2$-24 can be combined with any cleavable moiety present on the therapeutic agent to provide a variety of conjugate groups. The structure of GalNAc$_2$-24 (GalNAc$_2$-24$_a$-CM) is shown below:

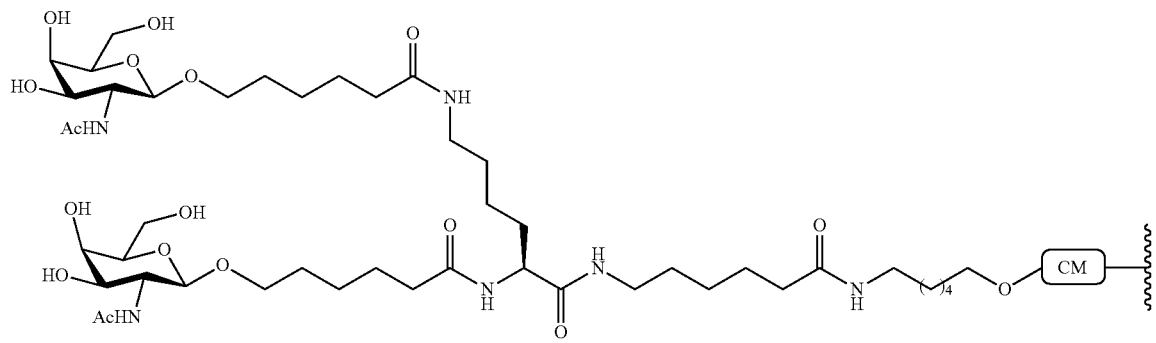

Example 54: Preparation of Therapeutic Agents Comprising a GalNAc$_1$-25 Conjugate

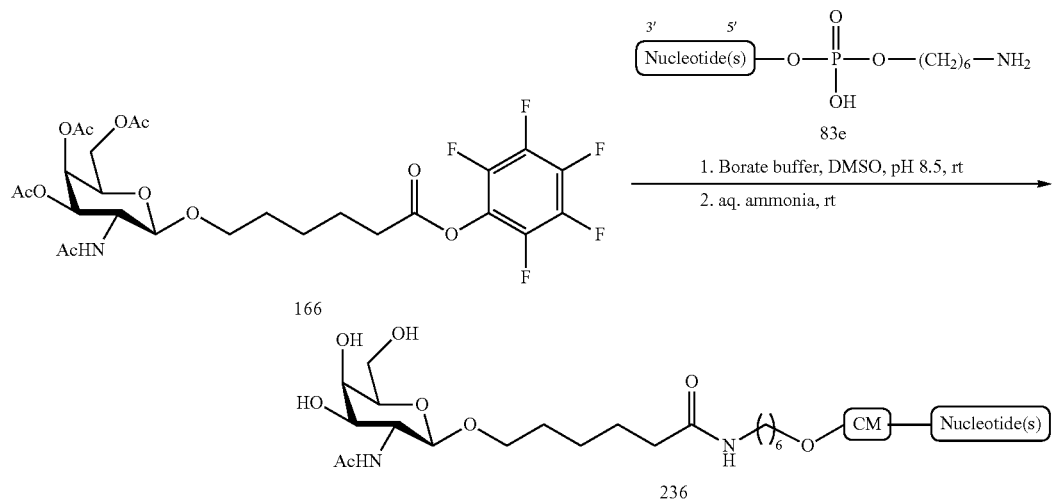

The synthesis of compound 166 is described in Example 40. Compound 236 is prepared using the general procedure described in Example 32.

Alternatively, compound 236 is synthesized using the scheme shown below, and compound 238 is used to form compound 236.

The GalNAc$_1$ cluster portion (GalNAc$_1$-25$_a$) of the conjugate group GalNAc$_1$-25 can be combined with any cleavable moiety present on the therapeutic agent to provide a variety of conjugate groups. The structure of GalNAc$_1$-25 (GalNAc$_1$-25$_a$-CM) is shown below:

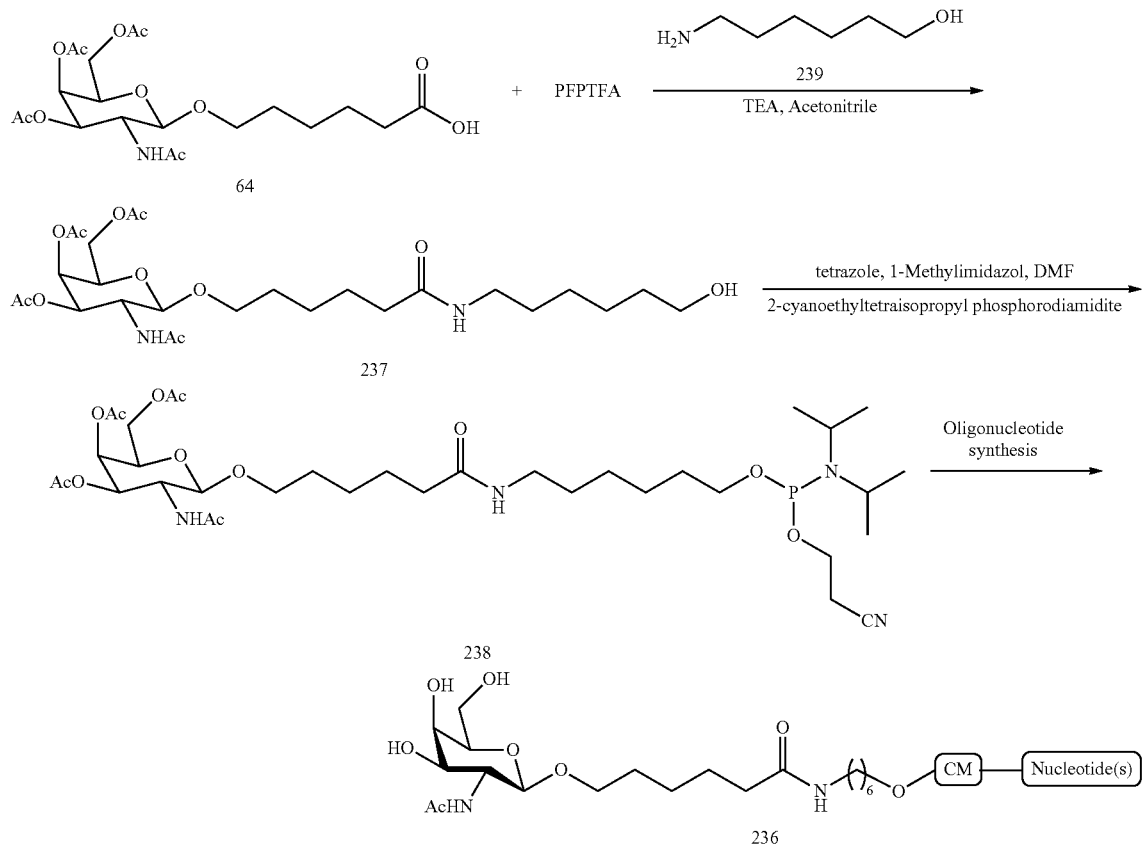

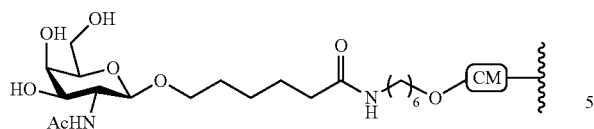

Example 55: Preparation of Therapeutic Agents Comprising a GalNAc$_1$-26 or GalNAc$_1$-27 Conjugate

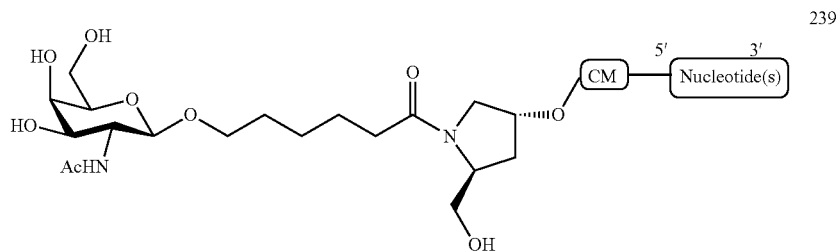

239

Compound 239 is synthesized via coupling of compound 47 (see Example 14) to acid 64 (see Example 23) using HBTU and DIEA in DMF. The resulting amide containing compound is phosphitylated, then added to the 5'-end of a nucleotide(s). The GalNAc$_1$ cluster portion (GalNAc$_1$-26$_a$) of the conjugate group GalNAc$_1$-26 can be combined with any cleavable moiety present on the therapeutic agent to provide a variety of conjugate groups. The structure of GalNAc$_1$-26 (GalNAc$_1$-26$_a$-CM) is shown below:

The GalNAc$_1$ cluster portion (GalNAc$_1$-27$_a$) of the conjugate group GalNAc$_1$-27 can be combined with any cleavable moiety present on the therapeutic agent to provide a variety of conjugate groups. The structure of GalNAc$_1$-27 (GalNAc$_1$-27$_a$-CM) is shown below:

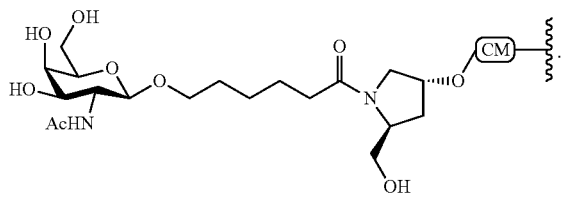

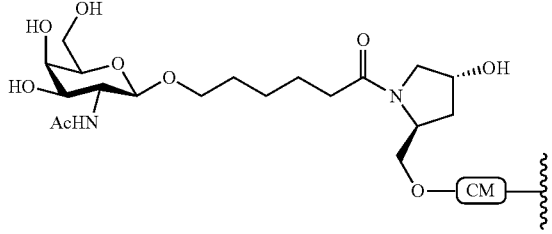

In order to add the GalNAc$_1$ conjugate group to the 3'-end of a nucleotide(s), the amide formed from the reaction of compounds 47 and 64 is added to a solid support. The oligonucleotide synthesis is then completed in order to form compound 240.

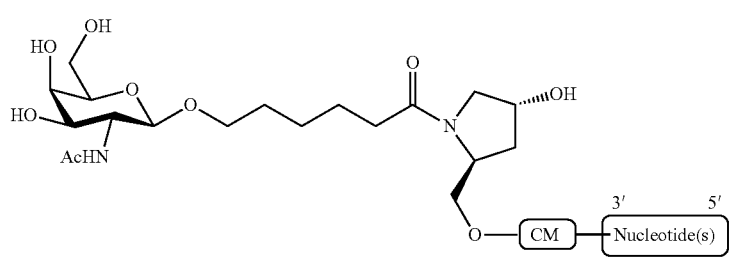

240

Example 56: Preparation of Therapeutic Agents Comprising a GalNAc$_1$-28 or GalNAc$_1$-29 Conjugate

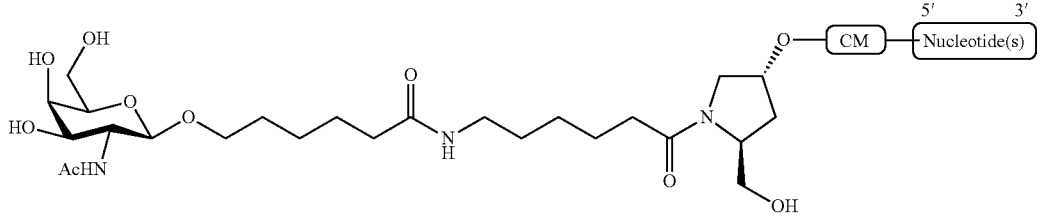

241

Compound 241 is synthesized using procedures similar to those described in Example 49 to form the phosphoramidite intermediate, which is then linked to the nucleotide(s). The GalNAc$_1$ cluster portion (GalNAc$_1$-28$_a$) of the conjugate group GalNAc$_1$-28 can be combined with any cleavable moiety present on the therapeutic agent to provide a variety of conjugate groups. The structure of GalNAc$_1$-28 (GalNAc$_1$-28$_a$-CM) is shown below:

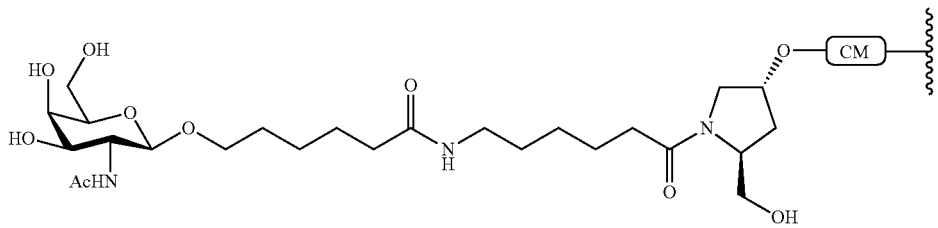

In order to add the GalNAc$_1$ conjugate group to the 3'-end of a nucleotide(s), procedures similar to those described in Example 49 are used to form the hydroxyl intermediate, which is then added to the solid support. Standard oligonucleotide synthesis is then completed in order to form compound 242.

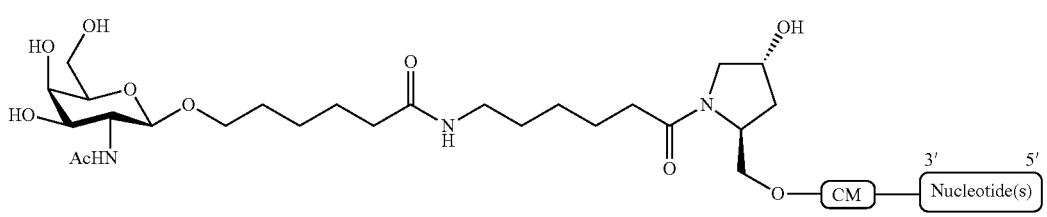

242

The GalNAc$_1$ cluster portion (GalNAc$_1$-29$_a$) of the conjugate group GalNAc$_1$-29 can be combined with any cleavable moiety present on the nucleotide(s) to provide a variety of conjugate groups. The structure of GalNAc$_1$-29 (GalNAc$_1$-29$_a$-CM) is shown below:

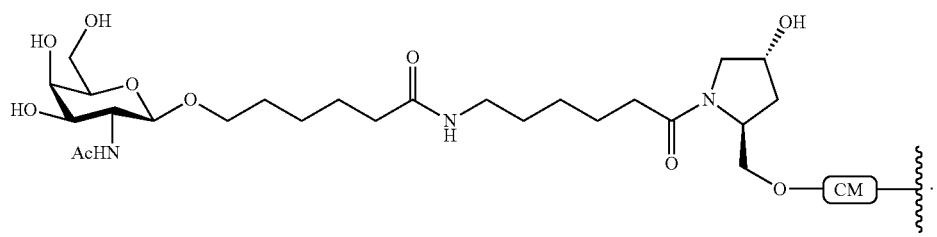

Example 57: Preparation of Therapeutic Agents Comprising a GalNAc$_1$-30 Conjugate

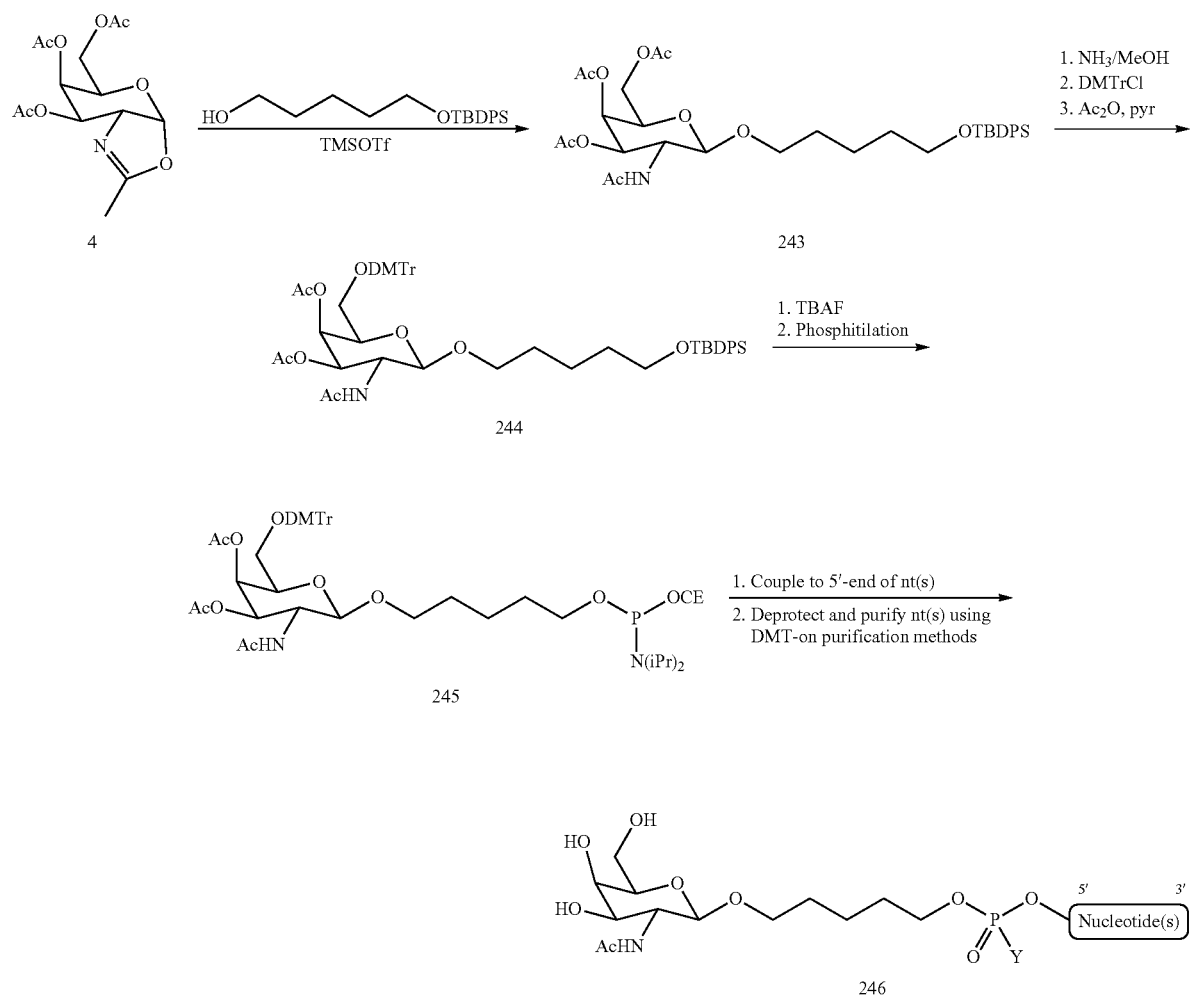

Compound 246 comprising a GalNAc$_1$-30 conjugate group, wherein Y is selected from O, S, a substituted or unsubstituted C$_1$-C$_{10}$ alkyl, amino, substituted amino, azido, alkenyl or alkynyl, is synthesized as shown above. The GalNAc$_1$ cluster portion (GalNAc$_1$-30$_a$) of the conjugate group GalNAc$_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of GalNAc$_1$-30$_a$ is shown below:

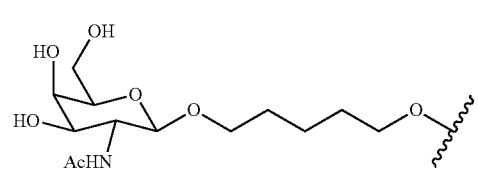 [SMILES: *OCCCCCOC1OC(CO)C(O)C(O)C1NC(C)=O]

Example 58: Synthesis of Oligonucleotides Comprising a GalNAc$_2$-31 or GalNAc$_2$-32 Conjugate

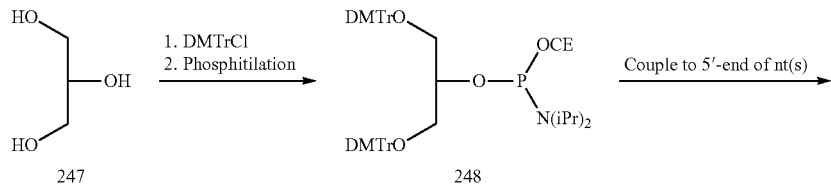

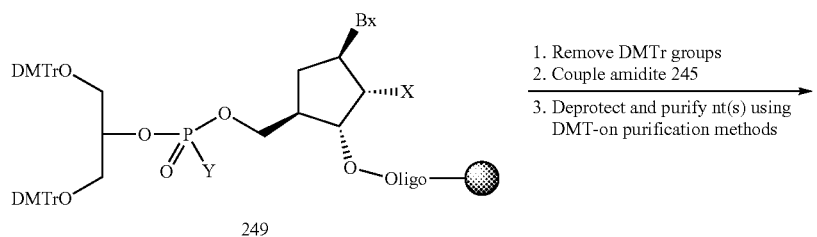

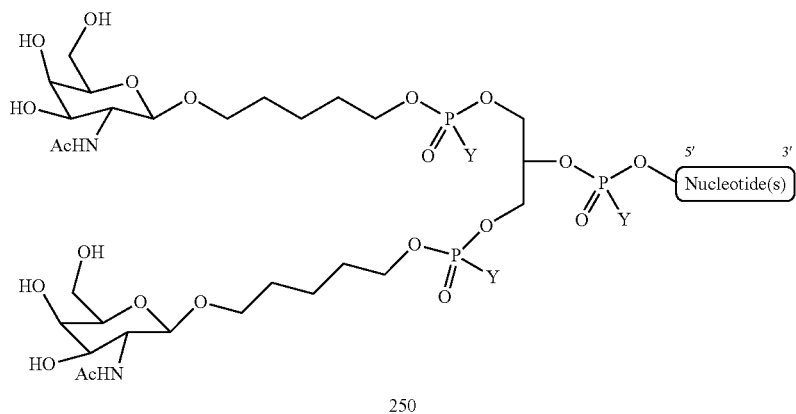

250

Compound 250 comprising a GalNAc$_2$-31 conjugate group, wherein Y is selected from O, S, a substituted or unsubstituted C$_1$-C$_{10}$ alkyl, amino, substituted amino, azido, alkenyl or alkynyl, is synthesized as shown above. The GalNAc$_2$ cluster portion (GalNAc$_2$-31$_a$) of the conjugate group GalNAc$_2$-31 can be combined with any cleavable moiety to provide a variety of conjugate groups. In certain embodiments, the Y-containing group directly adjacent to the 5' position of the nucleotide(s) is part of the cleavable moiety. In certain embodiments, the Y-containing group directly adjacent to the 5' position of the nucleotide(s) is part of a stable moiety, and the cleavable moiety is present on the nucleotide(s). The structure of GalNAc$_2$-31$_a$ is shown below:

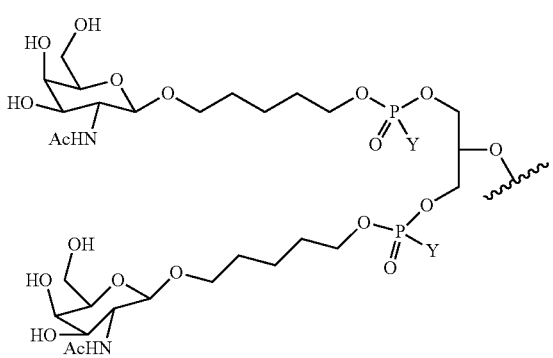

The synthesis of an oligonucleotide comprising a GalNAc$_2$-32 conjugate is shown below.

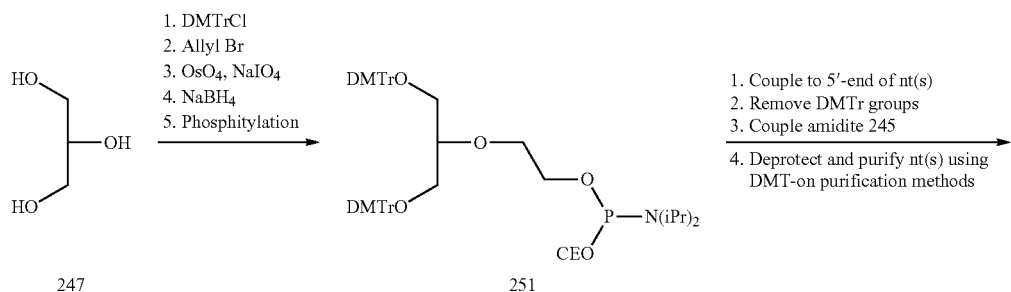

247　　　251

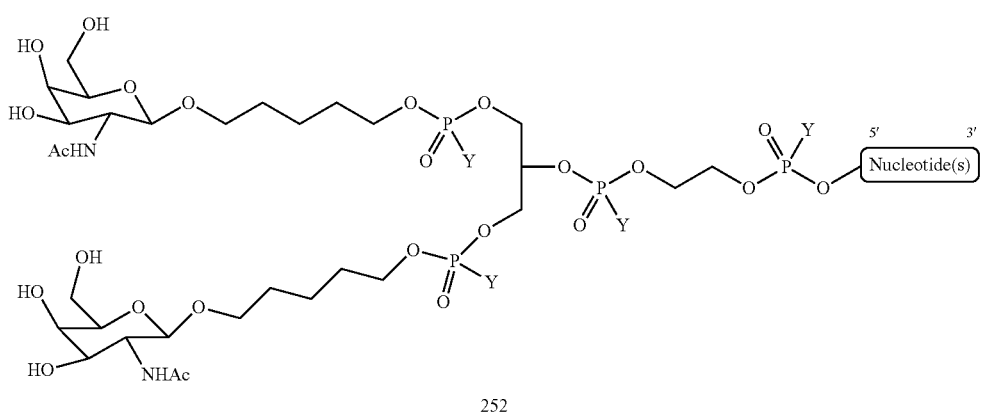

252

Compound 252 comprising a GalNAc$_2$-32 conjugate group, wherein Y is selected from O, S, a substituted or unsubstituted C$_1$-C$_{10}$ alkyl, amino, substituted amino, azido, alkenyl or alkynyl, is synthesized as shown above. The GalNAc$_2$ cluster portion (GalNAc$_2$-32$_a$) of the conjugate group GalNAc$_2$-32 can be combined with any cleavable moiety to provide a variety of conjugate groups. In certain embodiments, the Y-containing group directly adjacent to the 5' position of the nucleotide(s) is part of the cleavable moiety. In certain embodiments, the Y-containing group directly adjacent to the 5' position of the nucleotide(s) is part of a stable moiety, and the cleavable moiety is present on the oligonucleotide. The structure of GalNAc$_2$-32$_a$ is shown below:

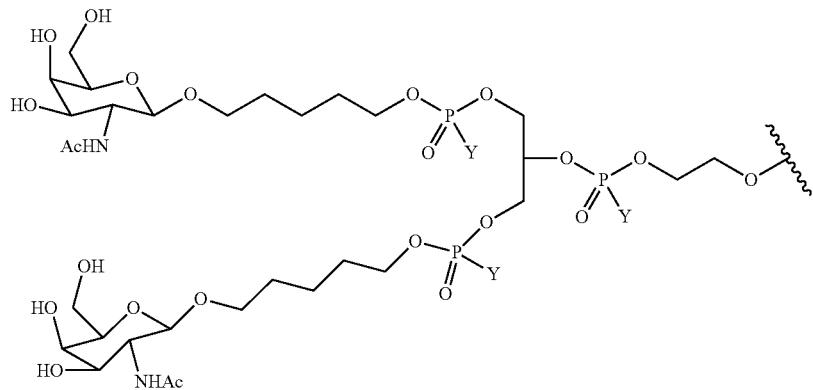

Example 59: Synthesis of Therapeutic Nucleosides Comprising a Targeting Moiety at the 3' Position
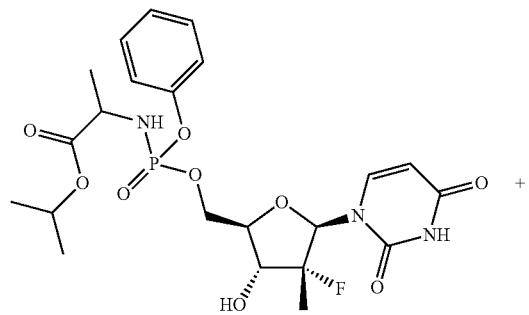
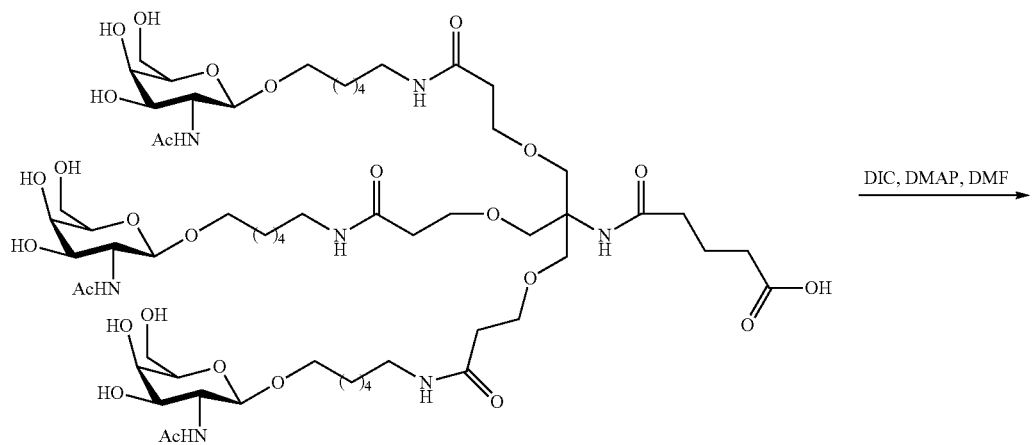
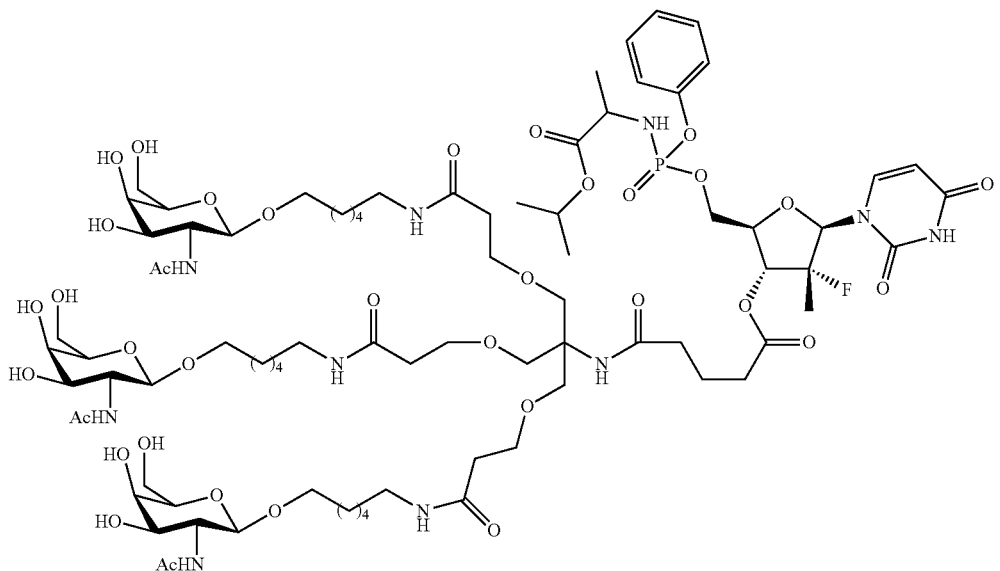
Synthesis of the therapeutic nucleoside is performed as in Cho et al., *Tetrahedron,* 2011, 67, 5498-5493. The carboxylic acid of the targeting group is activated and conjugated to the 3'-hydroxyl group of the therapeutic nucleoside.

Example 60: Synthesis of Therapeutic Nucleosides Comprising a Targeting Moiety at the 5' Position
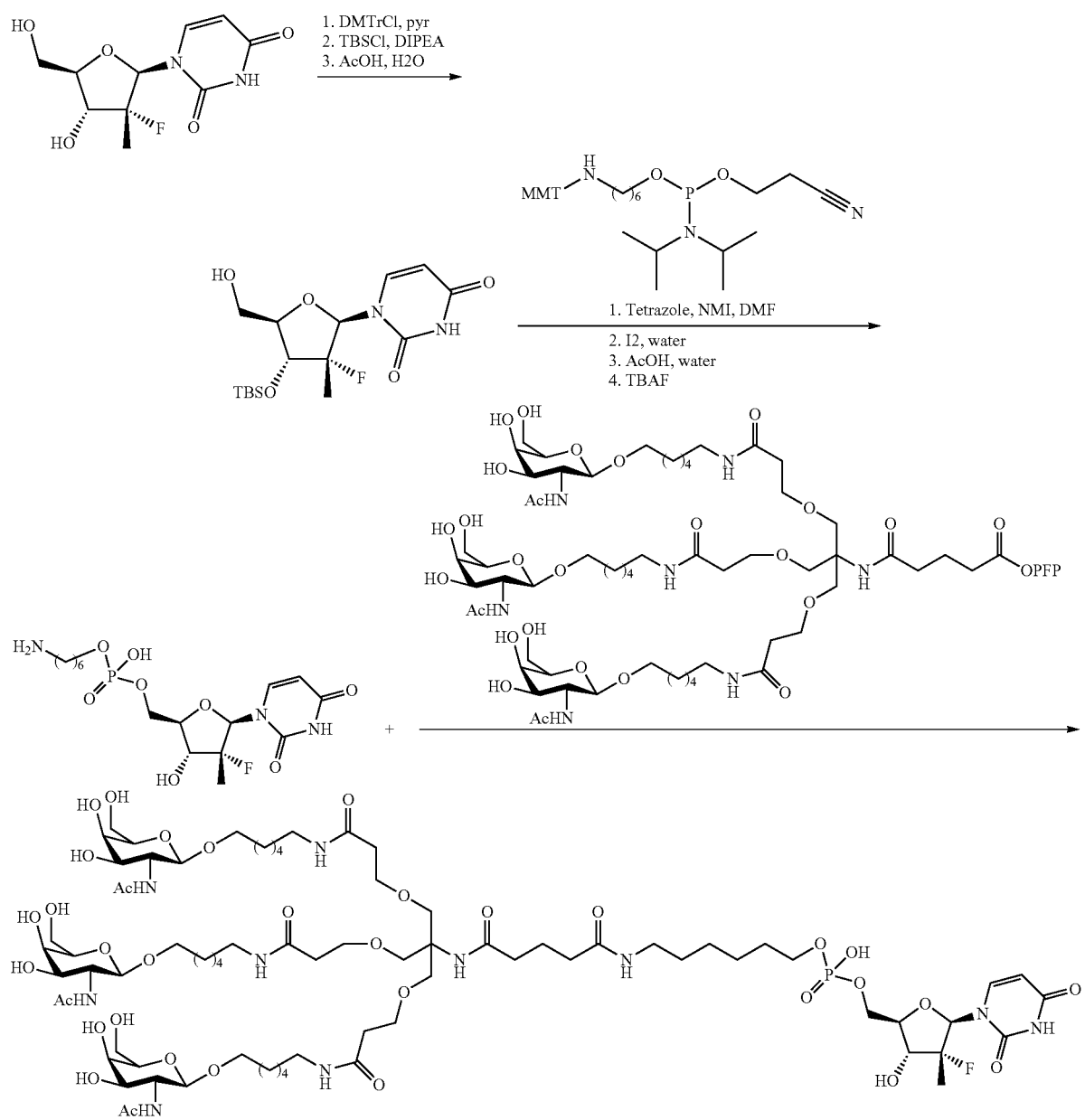
Following addition of a hexylamino linker to a therapeutic nucleoside, the pentafluorophenyl ester of the targeting group is coupled to the amino group of the linker to form the final product.

The invention claimed is:

1. A compound consisting of a targeting group and one therapeutic nucleoside, wherein the targeting group comprises at least one cell-targeting ligand, wherein each cell-targeting ligand is N-acetylgalactosamine.

2. The compound of claim 1, wherein the targeting group comprises 3 cell-targeting ligands.

3. The compound of claim 1, wherein the targeting group comprises a cleavable moiety.

4. The compound of claim 1, wherein the targeting group comprises a structure represented by formula I below:

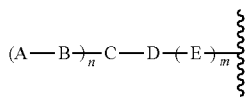

wherein:
A is a cell-targeting ligand;
B is a tether;
C is a branching group;
D is a targeting group linker;
E is a cleavable moiety;
n is 1, 2, 3, 4, or 5; and
m is 0 or 1.

5. The compound of claim 1, wherein the therapeutic nucleoside comprises a furanosyl ring.

6. The compound of claim 5, wherein the furanosyl ring of the therapeutic nucleoside comprises a 2' or 3' substituent independently selected from hydrogen, halogen, hydroxyl, amino, alkyl, alkenyl, alkynyl, alkoxy, $CF_3$, and ester, wherein if the 3' substituent is hydroxyl, the 2' substituent is not hydrogen or hydroxyl.

7. The compound of claim 1, wherein the compound has the following structure:

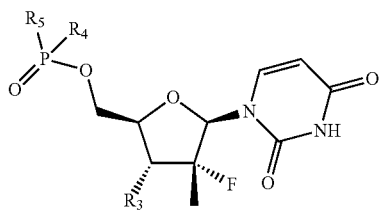

wherein $R_3$ is hydroxyl or the targeting group; and
$R_4$ and $R_5$ are each independently selected from phenoxy, $NHCH(CH_3)C(O)OiPr$, alkoxy, alkylamino, hydroxyl, and the targeting group;
provided that one and only one of $R_3$, $R_4$, and $R_5$ is a targeting group.

8. The compound of claim 1, wherein the compound comprises the following structure:

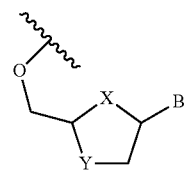

wherein B is a modified or unmodified nucleobase;
X is O or $CCH_2$;
Y is S or $CR_6R_7$; and
$R_6$ and $R_7$ are each independently selected from hydrogen, hydroxyl, O-L-valinyl ester, and the targeting group,
provided that if either of $R_6$ or $R_7$ is the targeting group, the structure is attached to a hydrogen; and provided that if neither $R_6$ nor $R_7$ is the targeting group, the structure is attached to the targeting group.

9. The compound of claim 1, wherein the therapeutic nucleoside is an antiviral nucleoside.

10. The compound of claim 9, wherein the antiviral nucleoside inhibits a viral polymerase.

11. The compound of claim 9, wherein the antiviral nucleoside is selected from among an anti-HCV nucleoside and an anti-HBV nucleoside.

12. A pharmaceutical composition comprising a compound of claim 1 or a pharmaceutically acceptable salt thereof and a pharmaceutically acceptable carrier or diluent.

13. A method of treating an RNA-dependent virus infection comprising administering to a mammal in need of such treatment a therapeutically effective amount of a compound of claim 9.

14. The compound of claim 1, wherein the targeting group comprises 1 N-acetylgalactosamine.

15. The compound of claim 1, wherein the targeting group comprises 2 N-acetylgalactosamines.

16. The compound of claim 3, wherein the cleavable moiety is a phosphodiester bond.

* * * * *

SEQUENCE LISTING

```
<160> NUMBER OF SEQ ID NOS: 13

<210> SEQ ID NO 1
<211> LENGTH: 3182
<212> TYPE: DNA
<213> ORGANISM: Hepatitis B virus
```

<400> SEQUENCE: 1

```
aattccacaa cctttcacca aactctgcaa gatcccagag tgagaggcct gtatttccct      60
gctggtggct ccagttcagg agcagtaaac cctgttccga ctactgcctc tcccttatcg     120
tcaatcttct cgaggattgg ggaccctgcg ctgaacatgg agaacatcac atcaggattc     180
ctaggacccc ttctcgtgtt acaggcgggg ttttcttgt tgacaagaat cctcacaata      240
ccgcagagtc tagactcgtg gtggacttct ctcaattttc taggggaac taccgtgtgt      300
cttggccaaa attcgcagtc cccaacctcc aatcactcac caacctcctg tcctccaact     360
tgtcctggtt atcgctggat gtgtctgcgg cgttttatca tcttcctctt catcctgctg     420
ctatgcctca tcttcttgtt ggttcttctg gactatcaag gtatgttgcc cgtttgtcct     480
ctaattccag gatcctcaac caccagcacg ggaccatgcc gaacctgcat gactactgct     540
caaggaacct ctatgtatcc ctcctgttgc tgtaccaaac cttcggacgg aaattgcacc     600
tgtattccca tccatcatc ctgggctttc ggaaaattcc tatgggagtg ggcctcagcc      660
cgtttctcct ggctcagttt actagtgcca tttgttcagt ggttcgtagg ctttccccc     720
actgtttggc tttcagttat atggatgatg tggtattggg ggccaagtct gtacagcatc     780
ttgagtccct ttttaccgct gttaccaatt ttcttttgtc tttgggtata catttaaacc     840
ctaacaaaac aaagagatgg ggttactctc tgaattttat gggttatgtc attggaagtt     900
atgggtcctt gccacaagaa cacatcatac aaaaaatcaa agaatgtttt agaaaacttc     960
ctattaacag gcctattgat tggaaagtat gtcaacgaat tgtgggtctt ttgggttttg    1020
ctgccccatt tacacaatgt ggttatcctg cgttaatgcc cttgtatgca tgtattcaat    1080
ctaagcaggc tttcactttc tcgccaactt acaaggcctt tctgtgtaaa caatacctga    1140
accttaccc cgttgcccgg caacggccag gtctgtgcca agtgtttgct gacgcaaccc     1200
ccactggctg gggcttggtc atgggccatc agcgcgtgcg tggaaccttt tcggctcctc    1260
tgccgatcca tactgcggaa ctcctagccg cttgttttgc tcgcagcagg tctggagcaa    1320
acattatcgg gactgataac tctgttgtcc tctcccgcaa atatacatcg tatccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt cccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
cgtgaacgcc caccgaatgt tgcccaaggt cttacataag aggactcttg gactctctgc    1680
aatgtcaacg accgaccttg aggcatactt caaagactgt ttgtttaaag actgggagga    1740
gttggggag gagattagat taaaggtctt tgtactagga ggctgtaggc ataaattggt     1800
ctgcgcacca gcaccatgca actttttcac ctctgcctaa tcatctcttg ttcatgtcct    1860
actgttcaag cctccaagct gtgccttggg tggcttgggg gcatggacat cgacccttat    1920
aaagaatttg gagctactgt ggagttactc tcgttttgc cttctgactt ctttccttca     1980
gtacgagatc ttctagatac cgcctcagct ctgtatcggg aagccttaga gtctcctgag    2040
cattgttcac ctcaccatac tgcactcagg caagcaattc tttgctgggg ggaactaatg    2100
actctagcta cctgggtggg tgttaatttg gaagatccag catctagaga cctagtagtc    2160
agttatgtca acactaatat gggcctaaag ttcaggcaac tcttgtggtt tcacatttct    2220
tgtctcactt ttggaagaga aaccgttata gagtatttgg tgtctttcgg agtgtggatt    2280
```

| | |
|---|---|
| cgcactcctc cagcttatag accaccaaat gccctatcc tatcaacact tccggaaact | 2340 |
| actgttgtta gacgacgagg caggtcccct agaagaagaa ctccctcgcc tcgcagacga | 2400 |
| aggtctcaat cgccgcgtcg cagaagatct caatctcggg aacctcaatg ttagtattcc | 2460 |
| ttggactcat aaggtgggga actttactgg tctttattct tctactgtac ctgtctttaa | 2520 |
| tcctcattgg aaaacaccat cttttcctaa tatacattta caccaagaca ttatcaaaaa | 2580 |
| atgtgaacag tttgtaggcc cacttacagt taatgagaaa agaagattgc aattgattat | 2640 |
| gcctgctagg ttttatccaa aggttaccaa atatttacca ttggataagg gtattaaacc | 2700 |
| ttattatcca gaacatctag ttaatcatta cttccaaact agacactatt tacacactct | 2760 |
| atggaaggcg ggtatattat ataagagaga aacaacacat agcgcctcat tttgtgggtc | 2820 |
| accatattct tgggaacaag atctacagca tggggcagaa tctttccacc agcaatcctc | 2880 |
| tgggattctt tcccgaccac cagttggatc cagccttcag agcaaacaca gcaaatccag | 2940 |
| attgggactt caatcccaac aaggacacct ggccagacgc caacaaggta ggagctggag | 3000 |
| cattcgggct gggtttcacc ccaccgcacg gaggcctttt ggggtggagc cctcaggctc | 3060 |
| agggcatact acaaactttg ccagcaaatc cgcctcctgc ctccaccaat cgccagacag | 3120 |
| gaaggcagcc taccccgctg tctccaccct tgagaaacac tcatcctcag gccatgcagt | 3180 |
| gg | 3182 |

```
<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gcagaggtga agcgaagtgc                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ccaatttatg cctacagcct                                                 20

<210> SEQ ID NO 4
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 4
ggcatagcag caggatg                                                    17

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
aggagttccg cagtatggat                                                 20
```

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gtgaagcgaa gtgcacacgg                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gtgcagaggt gaagcgaagt                                              20

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
aggtgaagcg aagtgc                                                  16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
tccgcagtat ggatcg                                                  16

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
aatttatgcc tacagcct                                                18

<210> SEQ ID NO 11
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 11
uggaguguga caauggguguu ug                                          22

<210> SEQ ID NO 12
<211> LENGTH: 15
<212> TYPE: DNA
<213> ORGANISM: Artificial sequence
<220> FEATURE:

```
<223> OTHER INFORMATION: Synthetic oligonucleotide

<400> SEQUENCE: 12
cctcacactg ttacc                                                    15

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 13
acaaacacca ttgtcacact cca                                           23
```